(12) United States Patent
Nemecek et al.

(10) Patent No.: US 8,188,078 B2
(45) Date of Patent: May 29, 2012

(54) 6-ARYL/HETEROALKYLOXY BENZOTHIAZOLE AND BENZIMIDAZOLE DERIVATIVES, METHOD FOR PREPARING SAME, APPLICATION THEREOF AS DRUGS, PHARMACEUTICAL COMPOSITIONS AND NOVEL USE IN PARTICULAR AS C-MET INHIBITORS

(75) Inventors: Conception Nemecek, Paris (FR); Sylvie Wentzler, Paris (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/761,973

(22) Filed: Apr. 16, 2010

(65) Prior Publication Data

US 2010/0273793 A1 Oct. 28, 2010

Related U.S. Application Data

(63) Continuation of application No. PCT/FR2008/001450, filed on Oct. 16, 2008.

(30) Foreign Application Priority Data

Oct. 19, 2007 (FR) ...................... 07 07314

(51) Int. Cl.
*A61K 31/535* (2006.01)
*C07D 417/12* (2006.01)
*C07D 277/82* (2006.01)

(52) U.S. Cl. ...................... 514/233.8; 544/135; 548/164
(58) Field of Classification Search ............... 514/233.8; 544/135; 548/164
See application file for complete search history.

(56) References Cited

U.S. PATENT DOCUMENTS

| | | |
|---|---|---|
| 7,632,952 B2 | 12/2009 | Deprets et al. |
| 2008/0194555 A1 | 8/2008 | Nemecek et al. |

FOREIGN PATENT DOCUMENTS

| | | | |
|---|---|---|---|
| EP | 1 674 466 A1 | | 6/2006 |
| FR | 2 499 995 | | 8/1982 |
| FR | 2 891 273 | | 3/2007 |
| LT | 4726 | * | 11/2000 |
| WO | WO 01/57008 A1 | | 8/2001 |
| WO | WO 03/028721 A2 | | 4/2003 |
| WO | WO 2005/097787 A2 | | 10/2005 |
| WO | WO 2006/108059 A1 | | 10/2006 |
| WO | WO 2007/036630 A1 | | 4/2007 |

OTHER PUBLICATIONS

Registry No. 944887-62-1, STN file Registry, Aug. 17, 2007.*
Hodgetts, Inter- and intramolecular Mitsunobu reaction based approaches to 2-substituted chromans and chroman-4-ones, Tetrahedron, 2005 (61) pp. 6860-6870.
Desmarteau et al, Easy Preparation of Bioactive Peptides from the Novel Nalpha-Trifluoroethyl Amino Acids, Chemistry Letters, 2000 pp. 1052-1053.

* cited by examiner

*Primary Examiner* — Rebecca Anderson
(74) *Attorney, Agent, or Firm* — Scully, Scott, Murphy & Presser, P.C.

(57) ABSTRACT

The disclosure relates to compounds of formula (I):

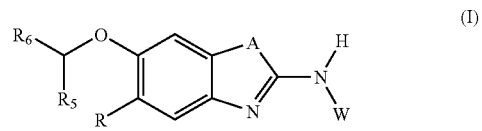

wherein A, W, R, $R_5$, and $R_6$ are as defined in the disclosure, or a salt thereof, and to their use as drugs, in particular as c-Met inhibitors.

15 Claims, No Drawings

6-ARYL/HETEROALKYLOXY BENZOTHIAZOLE AND BENZIMIDAZOLE DERIVATIVES, METHOD FOR PREPARING SAME, APPLICATION THEREOF AS DRUGS, PHARMACEUTICAL COMPOSITIONS AND NOVEL USE IN PARTICULAR AS C-MET INHIBITORS

The present invention relates to novel derivatives of 6-aryl/heteroalkyloxy benzothiazole and benzimidazole, their method of preparation, the novel intermediates obtained, their application as medicinal products, pharmaceutical compositions containing them and the novel use of said derivatives of 6-aryl/heteroalkyloxy benzothiazole and benzimidazole.

The present invention relates more particularly to novel derivatives of 6-aryl/heteroalkyloxy benzothiazole and benzimidazole displaying anticancer activity, via modulation of the activity of proteins, in particular of kinases.

To date, most of the commercial compounds used in chemotherapy are cytotoxics, which pose important problems of side effects and tolerance by the patient. These effects could be limited insofar as the medicinal products used act selectively on the cancerous cells, to the exclusion of the healthy cells. One solution for limiting the undesirable effects of chemotherapy may therefore consist of using medicinal products acting on metabolic pathways or constituent elements of these pathways, expressed predominantly in the cancerous cells, and that would be expressed little if at all in healthy cells. The protein kinases are a family of enzymes that catalyse the phosphorylation of hydroxyl groups of specific protein residues such as tyrosine, serine or threonine residues. Such phosphorylations can extensively modify the function of the proteins: thus, the protein kinases play an important role in the regulation of a great variety of cellular processes, notably including metabolism, cellular proliferation, adhesion and cellular motility, cell differentiation or cell survival, certain protein kinases playing a key role in the initiation, development and completion of the events of the cell cycle.

Among the various cellular functions in which the activity of a protein kinase is involved, certain processes represent attractive targets for treating certain diseases. As an example, we may notably mention angiogenesis and control of the cell cycle, as well as control of cellular proliferation, in which the protein kinases can play an essential role. These processes are notably essential for the growth of solid tumours as well as for other diseases: notably molecules that are inhibitors of said kinases are capable of limiting undesirable cellular proliferations such as those observed in cancers, and can play a part in the prevention, regulation or treatment of neurodegenerative diseases such as Alzheimer's disease or neuronal apoptosis.

The present invention relates to novel derivatives endowed with inhibitory effects with respect to protein kinases. The products according to the present invention can thus notably be used for the prevention or the treatment of diseases that can be modulated by the inhibition of protein kinases.

The products according to the present invention notably display an anticancer activity, via modulation of the activity of kinases. Among the kinases for which modulation of activity is sought, MET and RON as well as mutants of the MET and RON proteins are preferred.

The present invention also relates to the use of said derivatives for the preparation of a medicinal product intended for the treatment of humans.

Thus, one of the aims of the present invention is to propose compositions having anticancer activity, by acting in particular against kinases. Among the kinases for which modulation of activity is sought, MET and RON are preferred.

In the pharmacological section given below, it is shown in biochemical tests and on cell lines that the products of the present application thus notably inhibit the activity of autophosphorylation of MET and of RON and the proliferation of cells whose growth depends on MET and on RON or their mutant forms.

MET, or Hepatocyte Growth Factor Receptor, is a receptor with tyrosine kinase activity expressed in particular by the epithelial and endothelial cells. HGF, Hepatocyte Growth Factor, is described as the MET-specific ligand. HGF is secreted by the mesenchymal cells and activates the receptor MET, which homodimerizes. In consequence, the receptor is autophosphorylated on the catalytic domain tyrosines Y1230, Y1234 and Y1235.

Stimulation of MET by HGF induces proliferation, scattering (or dispersion), cellular motility, resistance to apoptosis, invasion and angiogenesis.

Both MET and HGF are found to be overexpressed in numerous human tumours and a great variety of cancers. MET is also found amplified in gastric tumours and glioblastomas. Numerous point mutations of the MET gene have also been described in tumours, in particular in the kinase domain but also in the juxtamembrane domain and the SEMA domain. Overexpression, amplification or mutations cause constitutive activation of the receptor and deregulation of its functions.

RON (récepteur d'origine nantais) is a receptor with tyrosine kinase activity, a member of the MET proto-oncogenes family. C-MET and RON are the only members of the MET family existing in humans and the only receptor tyrosine kinases possessing a SEMA domain in their extracellular part. The protein RON is of ubiquitous expression in various cellular types but principally in the cells of epithelial origin.

The ligand of RON is the hepatocyte growth factor-like protein (HGFL), also known by the name macrophage-stimulating protein (MSP). MSP is mainly produced in inactive form by the hepatocytes. On attaching to its receptor, MSP activates RON by autophosphorylation of two catalytic domain tyrosines Y1238 and Y1239 and of two tyrosines in the C-terminal portion (Y1353 and Y1360). Activation of RON induces a group of pleiotropic effects including proliferation, tubular morphogenesis, angiogenesis, cellular motility, invasion and resistance to apoptosis and to anoikis.

The overexpression of RON and its mutations seem to play a potential role in tumorigenesis and the formation of metastases. Overexpression of the receptor and alternative transcripts have both been identified in breast, colon and ovarian cancers. Both RON and MSP are overexpressed in non-small-cell lung cancers and pancreatic cancers.

The present invention also relates to novel inhibitors of the protein kinases MET and RON and of their mutants, which can be used for anti-proliferative and anti-metastatic treatment, notably in oncology.

The present invention also relates to novel inhibitors of the protein kinases MET and RON and of their mutants, which can be used for anti-angiogenic treatment, notably in oncology.

The present invention relates to the products of formula (I):

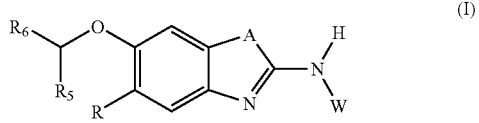

in which
R represents a hydrogen atom, a halogen atom or an alkyl radical,
A represents NH or S;
R5 represents a hydrogen atom or else an alkyl group optionally substituted with one or more halogen atoms;
R6 represents an aryl or heteroaryl radical optionally substituted with one or more radicals, which may be identical or different, selected from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals;
W represents a hydrogen atom or the radical COR7 in which R7 represents:
   a cycloalkyl radical or an alkyl radical optionally substituted with an alkoxy, hydroxyl, phenyl, heteroaryl, NR3R4, CONR3R4 or heterocycloalkyl radical, themselves optionally substituted as indicated below;
   an alkoxy radical optionally substituted with a hydroxyl, alkoxy, phenyl, heteroaryl, NR3R4, CONR3R4 or heterocycloalkyl radical, themselves optionally substituted as indicated below;
   or the radical NR1R2 in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, selected from the hydroxyl, alkoxy, phenylalkoxy, cycloalkylalkoxy radicals and the heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains being optionally substituted as indicated below;
with NR3R4, whatever R3 and R4, identical or different, being such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from the hydroxyl, alkoxy, NH2, NHalk, N(alk)2 radicals and the heteroaryl, heterocycloalkyl, and phenyl radicals optionally substituted with one or more radicals selected from the halogen atoms and the hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains being optionally substituted as indicated below;
the heterocycloalkyl, heteroaryl, aryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl radicals and the alkyl, cycloalkyl, heterocycloalkyl, phenyl, heteroaryl, (heterocycloalkyl)alkyl, (phenyl)alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from the halogen atoms and the hydroxyl, oxo, alkyl and alkoxy radicals containing from 1 to 4 carbon atoms, NH2, NHalk and N(alk)2;
it being understood that:
   R6 bears at least one halogen atom;
   when R6 represents a heteroaryl radical and R5 represents hydrogen, then the heteroaryl that R6 represents is monocyclic
   R7 does not represent the methoxy radical
said products of formula (I) being in all possible isomeric forms: racemic, enantiomeric and diastereoisomeric, as well as the salts of addition of said products of formula (I) with mineral and organic acids or with mineral and organic bases.
The present invention thus relates to the products of formula (I) as defined above in which
R represents a hydrogen atom, a halogen atom or an alkyl radical,
A represents NH or S;
R5 represents a hydrogen atom or else an alkyl group optionally substituted with one or more halogen atoms;
R6 represents an aryl or heteroaryl radical optionally substituted with one or more radicals, which may be identical or different, selected from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals;
W represents a hydrogen atom or the radical COR7 in which R7 represents:
   a cycloalkyl radical or an alkyl radical optionally substituted with an alkoxy, hydroxyl, phenyl, heteroaryl, NR3R4 or heterocycloalkyl radical, themselves optionally substituted as indicated below;
   an alkoxy radical optionally substituted with an alkoxy, phenyl, heteroaryl,
   NR3R4 or heterocycloalkyl radical, themselves optionally substituted as indicated below;
   or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from the hydroxyl, alkoxy, phenylalkoxy, cycloalkylalkoxy radicals, and the heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains being optionally substituted as indicated below;
with NR3R4, whatever R3 and R4, identical or different, being such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from the hydroxyl, alkoxy, NH2, NHalk, N(alk)2 radicals and the heteroaryl, heterocycloalkyl, and phenyl radicals optionally substituted with one or more radicals selected from the halogen atoms and the hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains being optionally substituted as indicated below;

the heterocycloalkyl, heteroaryl, aryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl radicals and the alkyl, cycloalkyl, heterocycloalkyl, phenyl, heteroaryl, (heterocycloalkyl)alkyl, (phenyl)alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radical, such that in these last-mentioned radicals, the heterocycloalkyl, phenyl and heteroaryl radicals are themselves optionally substituted with one or more radicals selected from the halogen atoms and the hydroxyl, oxo, alkyl and alkoxy radicals containing from 1 to 4 carbon atoms, NH2, NHalk and N(alk)2;

it being understood that:
  R6 bears at least one halogen atom;
  when R6 represents a heteroaryl radical and R5 represents hydrogen, then the heteroaryl that R6 represents is monocyclic
  R7 does not represent the methoxy radical
said products of formula (I) being in all possible isomeric forms: racemic, enantiomeric and diastereoisomeric, as well as the salts of addition of said products of formula (I) with mineral and organic acids or with mineral and organic bases.

The present invention thus relates to the products of formula (I) as defined above in which
R represents a hydrogen atom, a halogen atom or an alkyl radical,
A represents NH or S;
R5 represents a hydrogen atom or else an alkyl group optionally substituted with one or more halogen atoms;
R6 represents an aryl or heteroaryl radical optionally substituted with one or more radicals, which may be identical or different, selected from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals;
W represents a hydrogen atom or the radical COR7 in which R7 represents:
  a cycloalkyl radical or an alkyl radical optionally substituted with an alkoxy, hydroxyl, phenyl, heteroaryl, NR3R4 or heterocycloalkyl radical, themselves optionally substituted as indicated below;
  an alkoxy radical optionally substituted with a phenyl, heteroaryl, NR3R4 or heterocycloalkyl radical, themselves optionally substituted as indicated below;
  or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from the hydroxyl, alkoxy, phenylalkoxy, cycloalkylalkoxy radicals, and the heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains being optionally substituted as indicated below;

with NR3R4, whatever R3 and R4, identical or different, being such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from the hydroxyl, alkoxy, NH2, NHalk, N(alk)2 radicals and the heteroaryl, heterocycloalkyl, and phenyl radicals optionally substituted with one or more radicals selected from the halogen atoms and the hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains being optionally substituted as indicated below;

the heterocycloalkyl, heteroaryl, aryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl radicals and the alkyl, cycloalkyl, heterocycloalkyl, phenyl, heteroaryl, (heterocycloalkyl)alkyl, (phenyl)alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from the halogen atoms and the hydroxyl, oxo, alkyl and alkoxy radicals containing from 1 to 4 carbon atoms, NH2, NHalk and N(alk)2;

it being understood that:
  R6 bears at least one halogen atom;
  when R6 represents a heteroaryl radical and R5 represents hydrogen, then the heteroaryl that R6 represents is monocyclic
  R7 does not represent the methoxy radical
said products of formula (I) being in all possible isomeric forms: racemic, enantiomeric and diastereoisomeric, as well as the salts of addition of said products of formula (I) with mineral and organic acids or with mineral and organic bases.

The present invention thus relates to the products of formula (I) as defined above in which:
R represents a hydrogen atom, a halogen atom or an alkyl radical,
A represents NH or S;
R5 represents a hydrogen atom or else an alkyl group optionally substituted with one or more halogen atoms;
R6 represents a phenyl or heteroaryl radical optionally substituted with one or more radicals, which may be identical or different, selected from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals;

W represents a hydrogen atom or the radical COR7 in which R7 represents:
 a cycloalkyl radical or an alkyl radical optionally substituted with a phenyl, heteroaryl, NR3R4 or heterocycloalkyl radical, themselves optionally substituted as indicated below;
 an alkoxy radical optionally substituted with NR3R4;
 or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from the hydroxyl, alkoxy, phenylalkoxy, cycloalkylalkoxy, heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O and NH, said radical including the NH that it possibly contains being optionally substituted as indicated below;
with NR3R4, whatever R3 and R4, identical or different, being such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from the hydroxyl, alkoxy, NH2, NHalk, N(alk)2 and phenyl radical itself optionally substituted with one or more radicals selected from the halogen atoms and the hydroxyl, alkyl and alkoxy radicals; or alternatively R3 and R4 form with the nitrogen atom to which they are attached a cyclic radical optionally containing one or more other heteroatoms selected from O and NH, said radical including the NH that it possibly contains being optionally substituted as indicated below;
the heterocycloalkyl, heteroaryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl radicals and the alkyl, cycloalkyl, heterocycloalkyl, phenyl, phenylalkyl and heteroaryl radicals, these last-mentioned heterocycloalkyl, phenyl, phenylalkyl and heteroaryl radicals themselves being optionally substituted with one or more radicals selected from the halogen atoms and the hydroxyl, oxo, alkyl and alkoxy radicals containing from 1 to 4 carbon atoms, NH2, NHalk and N(alk)2;
said products of formula (I) being in all possible isomeric forms: racemic, enantiomeric and diastereoisomeric, as well as the salts of addition of said products of formula (I) with mineral and organic acids or with mineral and organic bases.

The present invention thus relates to the products of formula (I) as defined above in which:
R represents a hydrogen atom, a halogen atom or an alkyl radical;
A represents NH or S;
R5 represents a hydrogen atom or an alkyl radical optionally substituted with one or more fluorine atoms;
R6 represents a phenyl or pyridyl radical optionally substituted with one or more radicals, which may be identical or different, selected from the halogen atoms and the hydroxyl, alkoxy, NH2, NHalk, N(alk)2, alkyl or phenyl radicals optionally substituted with one or more radicals selected from the halogen atoms and the hydroxyl, alkyl, alkoxy, NH2, NHalk and N(alk)2 radicals;

W represents a hydrogen atom or the radical COR7 in which R7 represents a cycloalkyl radical or the radical NR1R2 in which R1 and R2 are such that one of R1 and R2 represents a hydrogen atom or an alkyl radical and the other of R1 and R2 represents an alkyl radical optionally substituted with one or more radicals, which may be identical or different, selected from the hydroxyl, alkoxy, phenylalkoxy, cycloalkylalkoxy, heteroaryl, heterocycloalkyl, NR3R4, CONR3R4 and phenyl radicals optionally substituted as indicated below; or alternatively R1 and R2 form with the nitrogen atom to which they are attached a radical selected from the pyrrolidinyl, pyrazolidinyl, pyrazolinyl, piperidyl, azepinyl, morpholino or piperazinyl radicals, optionally substituted as indicated below;
with NR3R4, whatever R3 and R4, identical or different, being such that one of R3 and R4 represents a hydrogen atom or an alkyl radical and the other of R3 and R4 represents a hydrogen atom, a CO2Alk radical or an alkyl radical optionally substituted with one or more radicals, which may be identical or different, selected from the hydroxyl, alkoxy, NH2, NHalk, N(alk)2 and phenyl radicals optionally substituted as indicated below; or alternatively R3 and R4 form with the nitrogen atom to which they are attached a radical selected from the pyrrolidinyl, pyrazolidinyl, pyrazolinyl, piperidyl, azepinyl, morpholino or piperazinyl radicals, optionally substituted as indicated below;
all the heterocycloalkyl, heteroaryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl, alkyl, phenyl and phenylalkyl radicals in which the phenyl radical is itself optionally substituted with one or more radicals selected from the halogen atoms and the hydroxyl, alkyl, alkoxy, NH2, NHalk and N(alk)2 radicals;
said products of formula (I) being in all possible isomeric forms: racemic, enantiomeric and diastereoisomeric, as well as the salts of addition of said products of formula (I) with mineral and organic acids or with mineral and organic bases.
the substituents Ra, X and W being selected from all the values defined for these radicals in any one of the other claims, said products of formula (I) being in all possible isomeric forms: racemic, enantiomeric and diastereoisomeric, as well as the salts of addition of said products of formula (I) with mineral and organic acids or with mineral and organic bases.

The present invention relates to the products of formula (I):

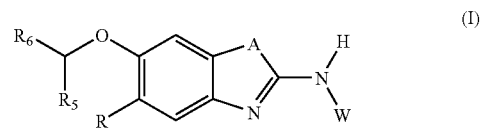

in which
R represents a hydrogen atom or else a halogen atom,
A represents NH or S;
R5 represents a hydrogen atom or else an alkyl group optionally substituted with one or more halogen atoms;
R6 represents an aryl or heteroaryl radical optionally substituted with one or more radicals, which may be identical or different, selected from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals;

W represents a hydrogen atom or the radical COR7 in which R7 represents:
  a cycloalkyl radical or an alkyl radical optionally substituted with an alkoxy, hydroxyl, phenyl, heteroaryl, NR3R4 or heterocycloalkyl radical, themselves optionally substituted as indicated below;
  an alkoxy radical optionally substituted with a phenyl, heteroaryl, NR3R4 or heterocycloalkyl radical, themselves optionally substituted as indicated below;
  or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from the hydroxyl, alkoxy radicals and the heteroaryl, heterocycloalkyl, NR3R4, and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains being optionally substituted as indicated below;

with NR3R4, whatever R3 and R4, identical or different, being such that one of R3 and R4 represents a hydrogen atom or an alkyl radical and the other of R3 and R4 represents a hydrogen atom, a cycloalkyl radical or an alkyl radical optionally substituted with one or more radicals, which may be identical or different, selected from the hydroxyl, alkoxy, NH2, NHalk, N(alk)2 radicals and the heteroaryl, heterocycloalkyl, and phenyl radicals optionally substituted with one or more radicals selected from the halogen atoms and the hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains being optionally substituted as indicated below;

the heterocycloalkyl, heteroaryl, aryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl radicals and the alkyl, cycloalkyl, heterocycloalkyl, phenyl, heteroaryl, (heterocycloalkyl)alkyl, (phenyl)alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from the halogen atoms and the hydroxyl, oxo, alkyl and alkoxy radicals containing from 1 to 4 carbon atoms, NH2, NHalk and N(alk)2;

it being understood that:
  R6 bears at least one halogen atom;
  when R6 represents a heteroaryl radical and R5 represents hydrogen, then the heteroaryl that R6 represents is monocyclic
  R7 does not represent the methoxy radical
said products of formula (I) being in all possible isomeric forms: racemic, enantiomeric and diastereoisomeric, as well as the salts of addition of said products of formula (I) with mineral and organic acids or with mineral and organic bases.

The present invention relates to the products of formula (I) as defined above in which:
R represents a hydrogen atom or else a halogen atom,
A represents NH or S;
R5 represents a hydrogen atom or else an alkyl group optionally substituted with one or more halogen atoms;
R6 represents a phenyl or heteroaryl radical optionally substituted with one or more radicals, which may be identical or different, selected from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals;

W represents a hydrogen atom or the radical COR7 in which R7 represents:
  a cycloalkyl radical or an alkyl radical optionally substituted with a phenyl, heteroaryl, NR3R4 or heterocycloalkyl radical, themselves optionally substituted as indicated below;
  an alkoxy radical optionally substituted with NR3R4;
  or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from the hydroxyl, alkoxy, heteroaryl, heterocycloalkyl, NR3R4 and phenyl radicals optionally substituted as indicated below; or alternatively R1 and R2 form with the nitrogen atom to which they are attached a cyclic radical optionally containing one or more other heteroatoms selected from O and NH, said radical including the NH that it possibly contains being optionally substituted as indicated below;

with NR3R4, whatever R3 and R4, identical or different, being such that one of R3 and R4 represents a hydrogen atom or an alkyl radical and the other of R3 and R4 represents a hydrogen atom, a cycloalkyl radical or an alkyl radical optionally substituted with one or more radicals, which may be identical or different, selected from the hydroxyl, alkoxy, NH2, NHalk, N(alk)2 and phenyl radical itself optionally substituted with one or more radicals selected from the halogen atoms and the hydroxyl, alkyl and alkoxy radicals; or alternatively R3 and R4 form with the nitrogen atom to which they are attached a cyclic radical optionally containing one or more other heteroatoms selected from O and NH, said radical including the NH that it possibly contains being optionally substituted as indicated below;

the heterocycloalkyl, heteroaryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl radicals and the alkyl, cycloalkyl, heterocycloalkyl, phenyl, phenylalkyl and heteroaryl radicals, these last-mentioned heterocycloalkyl, phenyl, phenylalkyl and heteroaryl radicals themselves being optionally substituted with one or more radicals selected from the halogen atoms and the hydroxyl, oxo, alkyl and alkoxy radicals containing from 1 to 4 carbon atoms, NH2, NHalk and N(alk)2;

said products of formula (I) being in all possible isomeric forms: racemic, enantiomeric and diastereoisomeric, as well as the salts of addition of said products of formula (I) with mineral and organic acids or with mineral and organic bases.

The present invention relates to the products of formula (I) as defined above in which:
R represents a hydrogen atom or a halogen atom;
A represents NH or S;
R5 represents a hydrogen atom or an alkyl radical optionally substituted with one or more fluorine atoms;
R6 represents a phenyl or pyridyl radical optionally substituted with one or more radicals, which may be identical or different, selected from the halogen atoms and the hydroxyl, alkoxy, NH2, NHalk, N(alk)2, alkyl or phenyl radicals optionally substituted with one or more radicals selected from the halogen atoms and the hydroxyl, alkyl, alkoxy, NH2, NHalk and N(alk)2 radicals;
W represents a hydrogen atom or the radical COR7 in which R7 represents a cycloalkyl radical or the radical NR1R2 in which R1 and R2 are such that one of R1 and R2 represents a hydrogen atom or an alkyl radical and the other of R1 and R2 represents an alkyl radical optionally substituted with one or more radicals, which may be identical or different, selected from the hydroxyl, alkoxy, heteroaryl, heterocycloalkyl, NR3R4 and phenyl radicals optionally substituted as indicated below; or alternatively R1 and R2 form with the nitrogen atom to which they are attached a radical selected from the pyrrolidinyl, pyrazolidinyl, pyrazolinyl, piperidyl, azepinyl, morpholino or piperazinyl radicals, optionally substituted as indicated below;
with NR3R4, whatever R3 and R4, identical or different, being such that one of R3 and R4 represents a hydrogen atom or an alkyl radical and the other of R3 and R4 represents a hydrogen atom or an alkyl radical optionally substituted with one or more radicals, which may be identical or different, selected from the hydroxyl, alkoxy, NH2, NHalk, N(alk)2 and phenyl radicals optionally substituted as indicated below; or alternatively R3 and R4 form with the nitrogen atom to which they are attached a radical selected from the pyrrolidinyl, pyrazolidinyl, pyrazolinyl, piperidyl, azepinyl, morpholino or piperazinyl radicals, optionally substituted as indicated below;
all the heterocycloalkyl, heteroaryl and phenyl radicals defined above as well as the cyclic radicals that R1 and R2 or R3 and R4 can form with the nitrogen atom to which they are attached, being optionally substituted with one or more radicals selected from the halogen atoms, the hydroxyl, oxo, alkoxy, NH2, NHalk, N(alk)2, free or esterified carboxyl, alkyl, phenyl and phenylalkyl radicals in which the phenyl radical is itself optionally substituted with one or more radicals selected from the halogen atoms and the hydroxyl, alkyl, alkoxy, NH2, NHalk and N(alk)2 radicals;
said products of formula (I) being in all possible isomeric forms: racemic, enantiomeric and diastereoisomeric, as well as the salts of addition of said products of formula (I) with mineral and organic acids or with mineral and organic bases.

The present invention thus relates to the products of formula (I) as defined above in which
R represents a hydrogen atom, a fluorine atom or a methyl radical;
A represents NH or S;
R5 represents a hydrogen atom or a methyl radical optionally substituted with 1 to 3 fluorine atoms;
R6 represents a phenyl or pyridyl radical optionally substituted with 1 to 3 substituents, which may be identical or different, selected from the halogen atoms and the alkyl radicals themselves optionally substituted with one or more halogen atoms;
W represents a hydrogen atom or the radical COR7 in which R7 represents:

a cycloalkyl radical or an alkyl radical optionally substituted with NR3R4;
an alkoxy radical optionally substituted with an alkoxy radical, or NR3R4;
or the radical NR1R2 in which R1 and R2 are such that one of R1 and R2 represents a hydrogen atom or an alkyl radical and the other of R1 and R2 represents an alkyl radical optionally substituted with a radical selected from the radicals hydroxyl; alkoxy; phenylalkoxy optionally substituted on phenyl; cycloalkylalkoxy; CONR3R4; and the pyrrolyl, pyridyl, morpholinyl, piperazinyl, pyrrolidinyl, piperidyl, or azepanyl radicals, these radicals themselves being optionally substituted on carbon or nitrogen atoms with one or more radicals selected from the radicals oxo =O, free or esterified carboxyl, alkyl or phenylalkyl with phenyl optionally substituted;
with NR3R4, whatever R3 and R4, identical or different, being such that one of R3 and R4 represents a hydrogen atom or an alkyl radical and the other of R3 and R4 represents a hydrogen atom, a CO2Alk radical or an alkyl radical optionally substituted with a phenyl radical itself optionally substituted; or alternatively R3 and R4 form with the nitrogen atom to which they are attached a radical selected from the pyrrolidinyl, pyrazolidinyl, pyrazolinyl, piperidyl, azepinyl, morpholino or piperazinyl radicals, these radicals themselves being optionally substituted on carbon or nitrogen atoms with one or more radicals selected from the radicals oxo =O, free or esterified carboxyl, alkyl or phenylalkyl with phenyl optionally substituted;
the phenyl radicals defined above being optionally substituted with one or more radicals selected from the halogen atoms and the hydroxyl, alkoxy, alkyl; NH2, NHalk, N(alk)2 and free or esterified carboxyl radicals;
said products of formula (I) being in all possible isomeric forms: racemic, enantiomeric and diastereoisomeric, as well as the salts of addition of said products of formula (I) with mineral and organic acids or with mineral and organic bases.

The present invention relates to the products of formula (I) as defined above in which:
R represents a hydrogen atom or else a fluorine atom
A represents NH or S;
R5 represents a hydrogen atom or a methyl radical optionally substituted with 1 to 3 fluorine atoms;
R6 represents a phenyl or pyridyl radical optionally substituted with 1 to 3 substituents, which may be identical or different, selected from the halogen atoms and the alkyl radicals themselves optionally substituted with one or more halogen atoms;
W represents a hydrogen atom or the radical COR7 in which R7 represents a cycloalkyl radical or a radical NR1R2 in which R1 and R2 are such that one of R1 and R2 represents a hydrogen atom or an alkyl radical and the other of R1 and R2 represents an alkyl radical optionally substituted with a pyrrolyl, pyridyl, morpholinyl, piperazinyl, pyrrolidinyl, piperidyl, or azepanyl radical, these radicals themselves being optionally substituted on carbon or nitrogen atoms with one or more radicals selected from the radicals oxo =O, free or esterified carboxyl, alkyl or phenylalkyl with phenyl optionally substituted with one or more radicals selected from the halogen atoms and the hydroxyl, alkyl, alkoxy, NH2, NHalk and N(alk)2 radicals;
said products of formula (I) being in all possible isomeric forms: racemic, enantiomeric and diastereoisomeric, as well as the salts of addition of said products of formula (I) with mineral and organic acids or with mineral and organic bases.

The present invention relates to the products of formula (I) as defined above corresponding to the formula (Ia):

in which R, A, R6 and W have any one of the definitions indicated above,
said products of formula (I) being in all possible isomeric forms: racemic, enantiomeric and diastereoisomeric, as well as the salts of addition of said products of formula (I) with mineral and organic acids or with mineral and organic bases.

The products of formula (Ia) therefore correspond to the products of formula (I) as defined above in which R5 represents a methyl radical.

The present invention relates to the products of formula (I) as defined above corresponding to the formula (Ib):

in which R, A and W have any one of the definitions indicated above and X1, X2 and X3, which may be identical or different, are such that one represents a halogen atom and the other two, identical or different, are selected from the hydrogen atom and the optional substituents of R6 as defined above,
said products of formula (I) being in all possible isomeric forms: racemic, enantiomeric and diastereoisomeric, as well as the salts of addition of said products of formula (I) with mineral and organic acids or with mineral and organic bases.

The products of formula (Ib) therefore correspond to the products of formula (I) as defined above in which R5 represents methyl and R6 represents a phenyl radical bearing X1, X2 and X3 as defined above.

Thus, in the products of formula (Ib), X1, X2 and X3, which may be identical or different, are such that one represents a halogen atom and the other two, identical or different, are selected from the hydrogen atom and the optional substituents of the phenyl radical that R6 can represent, as defined above, and notably from the halogen atoms, the hydroxyl, alkoxy, NR3R4 radicals and the alkyl, phenyl and phenylalkyl radicals, these last three radicals themselves being optionally substituted with one or more radicals selected from the halogen atoms and the hydroxyl, alkyl, alkoxy, NH2, NHalk and N(alk)2 radicals, with NR3R4 as defined above.

The present invention thus notably relates to the products of formula (I) as defined above corresponding to the formula (Ib) defined above in which R, A and W have any one of the definitions indicated above and X1, X2 and X3, which may be identical or different, are such that one represents a halogen atom and the other two, identical or different, are selected from the hydrogen atom and the halogen atoms,
said products of formula (I) being in all possible isomeric forms: racemic, enantiomeric and diastereoisomeric, as well as the salts of addition of said products of formula (I) with mineral and organic acids or with mineral and organic bases.

In the products of formula (I) and hereinafter:
the term alkyl radical denotes the following radicals, linear and in particular cases branched: methyl, ethyl, propyl, isopropyl, butyl, isobutyl, sec-butyl, tert-butyl, pentyl, isopentyl, hexyl, isohexyl as well as heptyl, octyl, nonyl and decyl as well as their linear or branched positional isomers: the alkyl radicals containing from 1 to 6 carbon atoms and more particularly the alkyl radicals containing from 1 to 4 carbon atoms, from the above list, are preferred;
the term alkoxy radical denotes the following radicals, linear and in particular cases branched: methoxy, ethoxy, propoxy, isopropoxy, butoxy linear, secondary or tertiary, pentoxy or hexoxy as well as their linear or branched positional isomers: the alkoxy radicals containing from 1 to 4 carbon atoms are preferred, from the above list;
the term halogen atom denotes the chlorine, bromine, iodine or fluorine atoms and preferably the chlorine, bromine or fluorine atom;
the term cycloalkyl radical denotes a saturated carbocyclic radical containing 3 to 10 carbon atoms and thus notably denotes the cyclopropyl, cyclobutyl, cyclopentyl and cyclohexyl radicals and quite particularly the cyclopropyl, cyclopentyl and cyclohexyl radicals;
the term heterocycloalkyl radical thus denotes a monocyclic or bicyclic carbocyclic radical, containing from 3 to 10 ring members interrupted by one or more heteroatoms, identical or different, selected from the oxygen, nitrogen or sulphur atoms: we may mention for example the morpholinyl, thiomorpholinyl, aziridyl, azetidyl, azepanyl, piperidyl, pyrrolidinyl, piperazinyl, homopiperazinyl, imidazolidinyl, pyrazolidinyl, tetrahydrofuryl, tetrahydrothienyl, hexahydropyran, oxodihydropyridazinyl radicals, all these radicals being optionally substituted;
The heterocycloalkyl radicals as defined above notably represent the morpholinyl, azepanyl, piperidyl, pyrrolidinyl and piperazinyl radicals themselves optionally substituted, as defined above or below.
the terms aryl and heteroaryl denote unsaturated or partially unsaturated radicals, respectively carbocyclic and heterocyclic, monocyclic or bicyclic, containing at most 12 ring members, which can optionally contain a ring member —C(O), the heterocyclic radicals containing one or more heteroatoms, identical or different, selected from O, N, or S with N, if necessary, optionally substituted;
the term aryl radical thus denotes monocyclic or bicyclic radicals containing 6 to 12 ring members such as for example the phenyl, naphthyl, biphenyl, indenyl, fluorenyl and anthracenyl radicals, more particularly the phenyl and naphthyl radicals and even more particularly the phenyl radical. It may be noted for example that the tetralone radical is a carbocyclic radical containing a ring member —C(O);
the term heteroaryl radical thus denotes monocyclic or bicyclic radicals containing 5 to 12 ring members: monocyclic heteroaryl radicals such as for example the thienyl radicals such as 2-thienyl and 3-thienyl, furyl such as 2-furyl, 3-furyl, pyranyl, pyrrolyl, pyrrolinyl, pyrazolinyl, imidazolyl, pyrazolyl, pyridyl such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl such as 3- or 4-isoxazolyl, furazannyl, tetrazolyl free or salified, all these radicals being optionally substituted, among which more particularly the thienyl radicals such as 2-thienyl and 3-thienyl, furyl such as 2-furyl, pyrrolyl, pyrrolinyl, pyrazolinyl, imidazolyl, pyrazolyl, oxazolyl, isoxazolyl, pyridyl, pyridazinyl, these radicals being optionally substituted; bicyclic heteroaryl radicals such as for example the benzothienyl radicals such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted;

As examples of monocyclic heteroaryl radicals, we may mention more particularly the pyrimidinyl, pyridyl, pyrrolyl, or pyrazolyl radicals, optionally substituted with one or more substituents, identical or different, as indicated above.

The carboxyl radical or radicals of the products of formula (I) can be salified or esterified with the various groups known by a person skilled in the art.

It may be recalled that stereoisomerism can be defined in its broad sense as the isomerism of compounds having the same structural formulae, but whose various groups are arranged differently in space, such as notably in monosubstituted cyclohexanes where the substituent can be in an axial or equatorial position, and the various possible rotational conformations of the derivatives of ethane. However, there is another type of stereoisomerism, due to different spatial arrangements of fixed substituents, either on double bonds, or on rings, which is often called geometric isomerism or cis-trans isomerism. The term stereoisomers is used in the present application in its broadest sense and therefore relates to the set of compounds indicated above.

The present invention notably relates to the products of formula (I) as defined above in which A represents NH, the other substituents R, R5, R6 and W being selected from all the values defined for these radicals above or below, said products of formula (I) being in all possible isomeric forms: racemic, enantiomeric and diastereoisomeric, as well as the salts of addition of said products of formula (I) with mineral and organic acids or with mineral and organic bases.

The present invention notably relates to the products of formula (I) as defined above in which A represents S, the other substituents R, R5, R6 and W being selected from all the values defined for these radicals above or below, said products of formula (I) being in all possible isomeric forms: racemic, enantiomeric and diastereoisomeric, as well as the salts of addition of said products of formula (I) with mineral and organic acids or with mineral and organic bases.

The present invention relates quite particularly to the products of formula (I) as defined above corresponding to the following formulae:

1-{6-[1-(2,6-dichlorophenyl)ethoxy]-1H-benzimidazol-2-yl}-3-(2-morpholin-4-ylethyl)urea
1-{6-[1-(2,6-dichloro-3-fluorophenyl)ethoxy]-1H-benzimidazol-2-yl}-3-(2-morpholin-4-ylethyl)urea trifluoroacetate
1-{6-[1-(2,6-dichloro-3-fluorophenyl)ethoxy]-5-fluoro-1H-benzimidazol-2-yl}-3-(2-morpholin-4-ylethyl)urea
1-{6-[1-(2,6-dichlorophenyl)ethoxy]-1,3-benzothiazol-2-yl}-3-(2-morpholin-4-ylethyl)urea
1-{6-[1-(2,6-dichloro-3-fluorophenyl)ethoxy]-1,3-benzothiazol-2-yl}-3-(2-morpholin-4-ylethyl)urea
1-{6-[(1R*)-(2,6-dichloro-3-fluorophenyl)ethoxy]-1,3-benzothiazol-2-yl}-3-(2-morpholin-4-ylethyl)urea
1-{6-[1-(2,6-dichlorophenyl)ethoxy]-5-fluoro-1,3-benzothiazol-2-yl}-3-(2-morpholin-4-ylethyl)urea
1-{6-[1-(2,6-dichloro-3-fluorophenyl)ethoxy]-5-fluoro-1,3-benzothiazol-2-yl}-3-(2-morpholin-4-ylethyl)urea
1-{6-[(1R*)-(2,6-dichloro-3-fluorophenyl)ethoxy]-5-fluoro-1,3-benzothiazol-2-yl}-3-(2-morpholin-4-ylethyl)urea
1-{6-[1-(2,6-dichloro-3-fluorophenyl)ethoxy]-1,3-benzothiazol-2-yl}-3-(3-morpholin-4-ylpropyl)urea
1-{6-[1-(2,6-dichloro-3-fluorophenyl)ethoxy]-1,3-benzothiazol-2-yl}-3-[3-(dimethylamino)propyl]urea
1-{6-[1-(2,6-dichloro-3-fluorophenyl)ethoxy]-1,3-benzothiazol-2-yl}-3-(3-piperidin-1-ylpropyl)urea
1-{3-[4-(2-chloro-6-fluorobenzyl)piperazin-1-yl]propyl}-3-{6-[1-(2,6-dichloro-3-fluorophenyl)ethoxy]-1,3-benzothiazol-2-yl}urea
1-(3-azepan-1-ylpropyl)-3-{6-[1-(2,6-dichloro-3-fluorophenyl)ethoxy]-1,3-benzothiazol-2-yl}urea
1-{6-[1-(2,6-dichloro-3-fluorophenyl)ethoxy]-1,3-benzothiazol-2-yl}-3-(2-piperidin-1-ylethyl)urea
1-{6-[1-(2,6-dichloro-3-fluorophenyl)ethoxy]-1,3-benzothiazol-2-yl}-3-(2-pyrrolidin-1-ylethyl)urea
1-[2-(1-benzylpiperidin-4-yl)ethyl]-3-{6-[1-(2,6-dichloro-3-fluorophenyl)ethoxy]-1,3-benzothiazol-2-yl}urea
1-{6-[1-(2,6-dichloro-3-fluorophenyl)ethoxy]-1,3-benzothiazol-2-yl}-3-[2-(1-methyl pyrrolidin-2-yl)ethyl]urea
1-{6-[1-(2,6-dichloro-3-fluorophenyl)ethoxy]-1,3-benzothiazol-2-yl}-3-[2-(4-methylpiperazin-1-yl)ethyl]urea
1-{6-[1-(2,6-dichloro-3-fluorophenyl)ethoxy]-1,3-benzothiazol-2-yl}-3-[2-(2,6-dimethylpiperidin-1-yl)ethyl]urea
1-{6-[1-(2,3-dichloro-6-fluorophenyl)ethoxy]-1,3-benzothiazol-2-yl}-3-(2-morpholin-4-ylethyl)urea,
1-{6-[(1R*)-1-(2,6-dichloro-3-fluorophenyl)ethoxy]-5-fluoro-1,3-benzothiazol-2-yl}-3-[2-(4-methylpiperazin-1-yl)ethyl]urea
1-{6-[(1R*)-1-(2,6-dichloro-3-fluorophenyl)ethoxy]-5-fluoro-1,3-benzothiazol-2-yl}-3-[2-(pyrrolidin-1-yl)ethyl]urea
1-{6-[1-(2,6-dichloro-3-fluorophenyl)ethoxy]-5-fluoro-1,3-benzothiazol-2-yl}-3-(2-hydroxyethyl)urea
1-{6-[(1R*)-1-(2,6-dichloro-3-fluorophenyl)ethoxy]-5-fluoro-1,3-benzothiazol-2-yl}-3-(2-hydroxyethyl)urea
1-{6-[1-(2,6-dichloro-3-fluorophenyl)ethoxy]-5-fluoro-1,3-benzothiazol-2-yl}-3-[2-(4-ethylpiperazin-1-yl)ethyl]urea
1-{6-[(1R*)-1-(2,6-dichloro-3-fluorophenyl)ethoxy]-5-fluoro-1,3-benzothiazol-2-yl}-3-[2-(4-ethylpiperazin-1-yl)ethyl]urea
1-{6-[(1R*)-1-(2,3-dichloro-6-fluorophenyl)ethoxy]-1,3-benzothiazol-2-yl}-3-[2-(4-methylpiperazin-1-yl)ethyl]urea
1-{6-[1-(2,3-dichloro-6-fluorophenyl)ethoxy]-5-fluoro-1,3-benzothiazol-2-yl}-3-[2-(morpholin-4-yl)ethyl]urea
1-{6-[(1R*)-1-(2,3-dichloro-6-fluorophenyl)ethoxy]-5-fluoro-1,3-benzothiazol-2-yl}-3-[2-(morpholin-4-yl)ethyl]urea
1-{6-[1-(2,3-dichloro-6-fluorophenyl)ethoxy]-5-fluoro-1,3-benzothiazol-2-yl}-3-[2-(4-methylpiperazin-1-yl)ethyl]urea
1-{6-[(1R*)-1-(2,3-dichloro-6-fluorophenyl)ethoxy]-5-fluoro-1,3-benzothiazol-2-yl}-3-[2-(4-methylpiperazin-1-yl)ethyl]urea 1-{6-[(1R*)-1-(2,3-dichloro-6-fluorophenyl)ethoxy]-5-fluoro-1,3-benzothiazol-2-yl}-3 [2-(pyrrolidin-1-yl)ethyl]urea as well as the salts of addition of said products of formula (I) with pharmaceutically acceptable mineral and organic acids or with pharmaceutically acceptable mineral and organic bases.

The present invention further relates to any method of preparation of the products of formula (I) as defined above.

The present invention thus relates to any method of preparation of the products of formula (I) as defined above in which A represents NH.

The present invention thus relates to any method of preparation of the products of formula (I) as defined above in which A represents S.

The products according to the invention can be prepared using conventional methods of organic chemistry. Schemes 1 and 2 given below illustrate the methods used for the preparation of the products of formula (I). In this connection, it should not constitute a restriction of the scope of the invention, with respect to the methods of preparation of the claimed compounds.

The products of formula (I) as defined above according to the present invention can thus notably be prepared according to the methods described in schemes 1 and 2 given below.

The present invention thus also relates to the method of preparation of the products of formula (I) according to scheme 1 as defined below.

The present invention thus also relates to the method of preparation of the products of formula (I) according to scheme 2 as defined below.

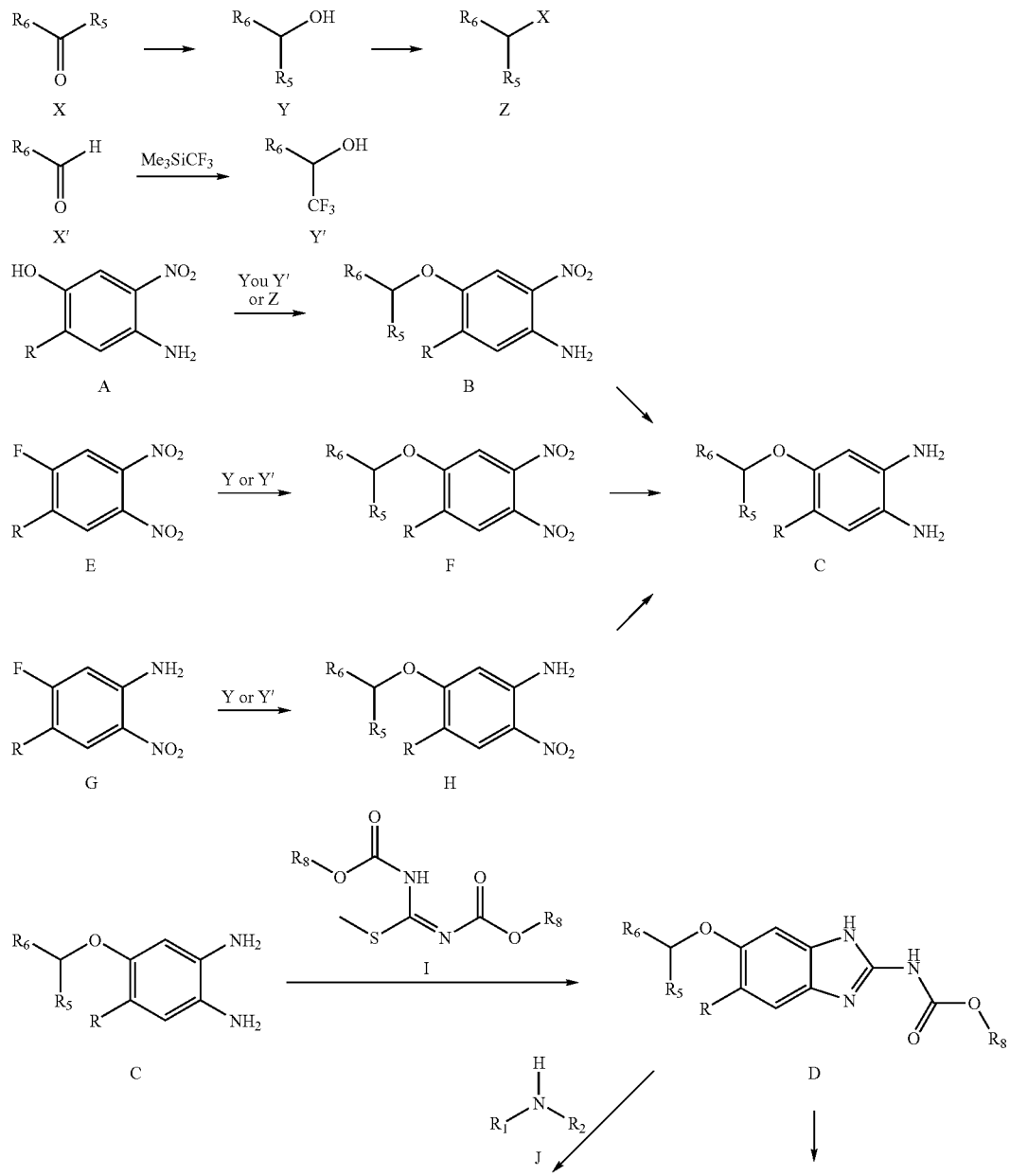

Scheme 1: syntheses of benzimidazole derivatives of formulae 1a, 1b, 1c

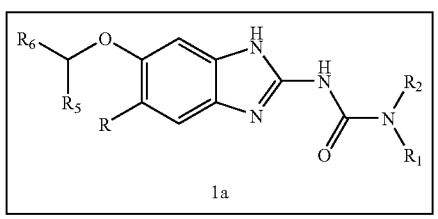

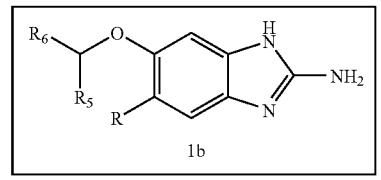

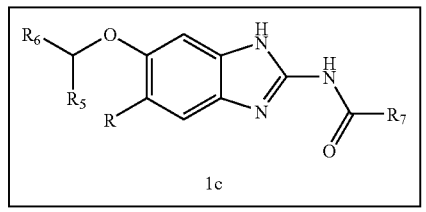

In scheme 1 above, the substituents R, R5, R6, R7, R1 and R2 have the meanings given above for the products of formula (I) and CO2R8 representing an amine protecting group selected from those known by a person skilled in the art such as for example R8 which represents an alkyl or aryl radical and notably phenyl.

In scheme 1 above, the benzimidazoles of general formula (1a), (1b) and (1c) can be prepared from derivatives of 4-amino-3-nitrophenol (A) or alternatively from derivatives of 4-fluoro-1,2-dinitrobenzene (E) or alternatively from derivatives of 4-fluoro-1,2-nitroaniline (G).

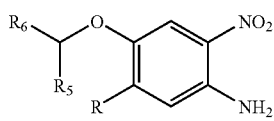

B

The compounds (B) with R, R5 and R6 as defined above, can be obtained from derivatives of 4-amino-3-nitrophenol (A) for example by reaction:
- with an alcohol of formula (Y) or (Y') with R5 and R6 as defined above, in the conditions described for example by K. J. HODGETTS (Tetrahedron 2005, 61 (28), 6860-6870), in the presence of triphenylphosphine and of bis(1-methylethyl) (E)-diazene-1,2-dicarboxylate, in a solvent such as tetrahydrofuran at a temperature close to 20° C.
- with a halide of formula (Z) with R5 and R6 as defined above, in a solvent such as N,N-dimethylformamide in the presence of a base such as potassium hydroxide and at a temperature close to 20° C.

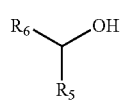

Y

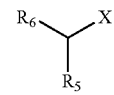

X

The alcohols of formula (Y) can be obtained from ketones of formula (X) for example by reduction by aluminium lithium hydride in a solvent such as tetrahydrofuran and at a temperature close to 20° C.

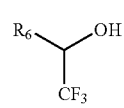

Z

The halides of formula (Z) can be obtained from alcohols of formula (Y) for example by reaction with 2,4,6-trichloro-1,3,5-triazine in a solvent such as N,N-dimethylformamide at a temperature close to 20° C.

Y'

The alcohols of formula (Y') can be obtained from aldehydes of formula (X') for example by reaction of trimethyl (trifluoromethyl)silane in a solvent such as dimethoxyethane in the presence of caesium fluoride and at a temperature close to 20° C.

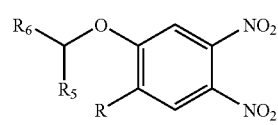

F

The compounds (F) can be obtained from derivatives of 4-fluoro-1,2-dinitrobenzene (E) for example by reaction with the alcohols of formula (Y) or (Y') in the presence of sodium hydride in a solvent such as N,N-dimethylformamide at a temperature close to 20° C.

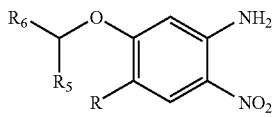
H

The compounds (H) can be obtained from derivatives of 4-fluoro-1,2-nitroaniline (G) for example by reaction with the alcohols of formula (Y) or (Y') in the presence of sodium hydride in a solvent such as N,N-dimethylformamide at a temperature close to 20° C.

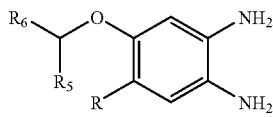
C

The diamines (C) with R, R5 and R6 as defined above, can be obtained for example by reduction of derivatives (B) or alternatively (F) or alternatively (H) in the presence of hydrogen and platinum oxide in a solvent such as ethanol and at a temperature close to 20° C.

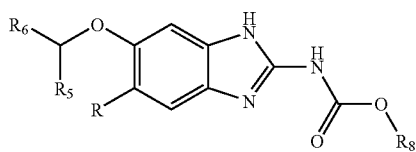
D

More particularly, the carbamates (D) with R, R5, R6 and R8 as defined above, can notably be prepared as described in patent WO03028721A2, but from diamines of formula (C) and from a pseudo-thiourea of formula (I) in the presence of acetic acid and in a protic solvent such as methanol, at a temperature close to 80° C.

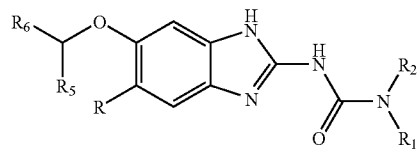
1a

More particularly, the benzimidazoles of general formula (Ia) can be prepared, for example, by reaction of an amine NHR1R2 of formula (J) (with R1 and R2 as defined above) on a carbamate of formula (D) in the presence of an aprotic solvent such as 1-methyl-pyrrolidin-2-one. The reaction can be carried out for example at a temperature close to 120° C. in a sealed tube under microwaves.

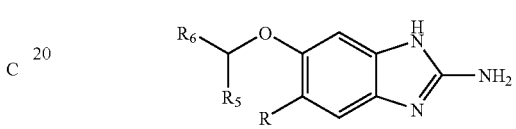
1b

More particularly, the 2-amino benzimidazoles of general formula (Ib) can be prepared, for example, by hydrolysis of carbamates of formula (D) with, for example, potassium hydroxide in a solvent such as N,N-dimethylformamide at a temperature close to 20° C.

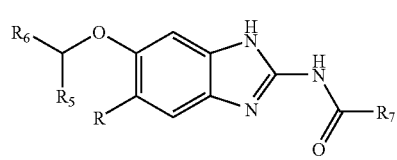
1c

More particularly, the benzimidazoles of general formula (Ic) can be obtained for example:
  by reaction of an acid chloride of formula (K') on the 2-aminobenzimidazoles of formula (Ib) in the presence for example of a solvent such as pyridine at a temperature close to 20° C.
  by coupling of the 2-amino-1,3-benzothiazol-6-yl with an acid of formula (K) in the conditions described for example by D. D. DesMarteau; V. Montanari (Chem Lett, 2000 (9), 1052) in the presence of 1-hydroxybenzotriazole and 1-(3-dimethylaminopropyl)-3-ethylcarbodiimide and in the presence of a base such as triethylamine at a temperature close to 40° C.

Scheme 2: syntheses of benzothiazole derivatives of formulae 2a, 2b, 2c

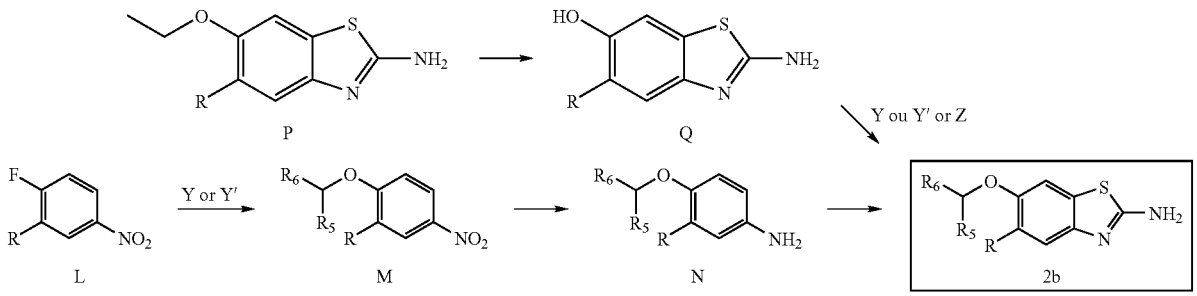

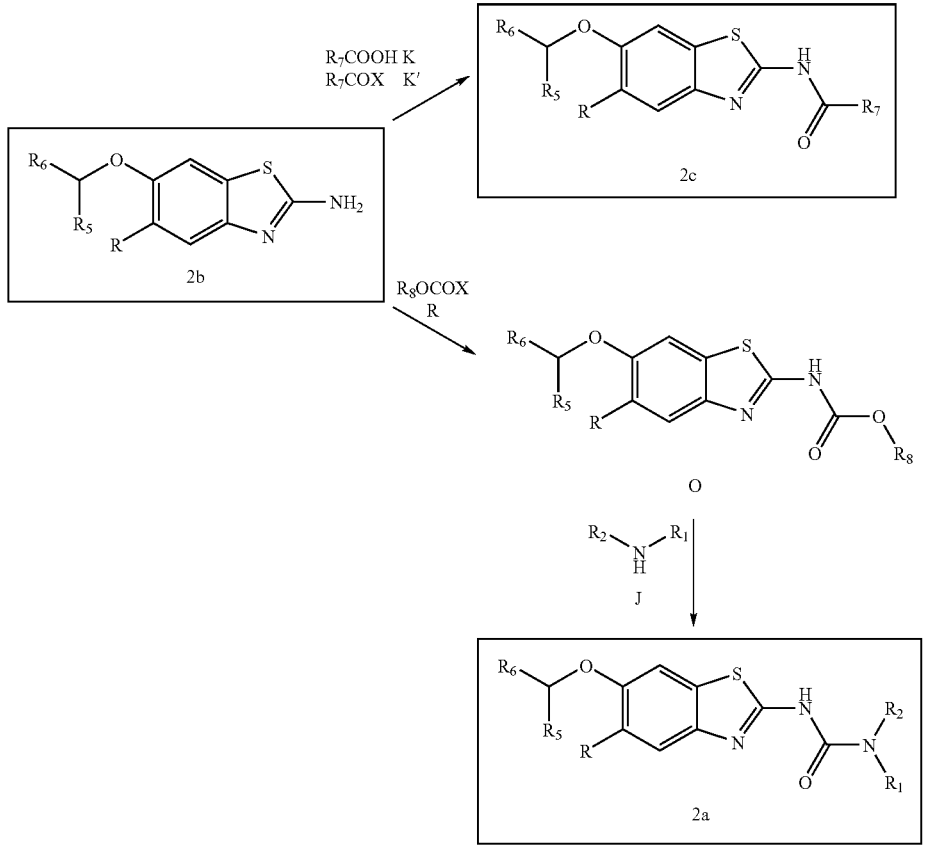

In scheme 2 above, the substituents R, R5, R6, R7, R1 and R2 have the meanings given above for the products of formula (I) and CO2R8 representing an amine protecting group as indicated above.

In scheme 2 above, the benzothiazoles of general formula (2a), (2b), (2c) can be prepared either from 2-aminobenzothiazole derivatives of formula (P) prepared as described in patent WO2007/036630A1 or from 1-fluoro-4-nitrobenzene derivatives of formula (L).

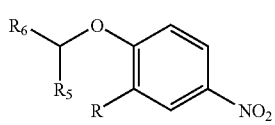

M

The compounds of general formula (M) can be obtained from compounds of formula L, for example by reaction with the alcohols of formula (Y) or (Y') in the presence of sodium hydride in a solvent such as N,N-dimethylformamide at a temperature close to 20° C.

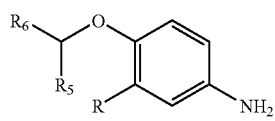

N

The anilines of formula (N) with R, R5 and R6 as defined above, can be obtained for example by reduction of the derivatives (M) in the presence of hydrogen and platinum oxide in a solvent such as ethanol and at a temperature close to 20° C.

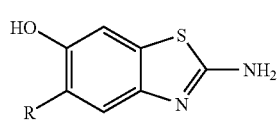

Q

The 2-aminobenzothiazol-6-ol of formula (O) can be prepared for example as described in patent WO2007/036630A1, by dealkylation of compounds of formula (P) with aqueous hydrobromic acid in solution in acetic acid.

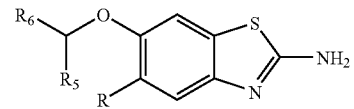

2b

More particularly the 2-aminobenzothiazoles of formula (2b) can be obtained, for example, by reaction of the 2-aminobenzothiazol-6-ol of formula (Q) with:
- the alcohols of formula (Y) or (Y') with R5 and R6 as defined above, in the conditions described for example by K. J. HODGETTS, (Tetrahedron 2005, 61 (28), 6860-

6870) in the presence of triphenylphosphane and bis(1-methylethyl) (E)-diazene-1,2-dicarboxylate, in a solvent such as tetrahydrofuran at a temperature close to 20° C.

halides of formula (Z) with R5 and R6 as defined above, in a solvent such as N,N-dimethylformamide in the presence of a base such as potassium hydroxide and at a temperature close to 20° C.

The 2-aminobenzothiazoles of formula (2b) can also be obtained, for example, by reaction of anilines of formula (N) with potassium thiocyanate and dibromine in the presence of acetic acid at a temperature close to 20° C.

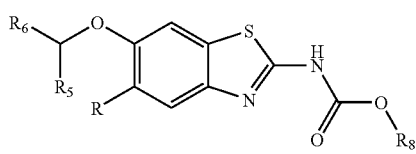

O

More particularly, the carbamates (O) with R, R5, R6 and R8 as defined above, can be obtained for example by reaction with a chlorocarbonate of formula (R) on the 2-aminobenzothiazoles of formula (2b) in a solvent such as tetrahydrofuran in the presence of a base such as sodium hydrogen carbonate at a temperature close to 20° C.

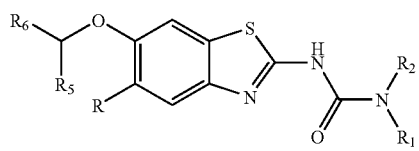

2a

More particularly, the benzothiazoles of general formula (2a) can be prepared, for example, by reaction of an amine NHR1R2 of formula (J) (with R1 and R2 as defined above) on a carbamate of formula (O) in the presence of an aprotic solvent such as 1-methyl-pyrrolidin-2-one. The reaction can be carried out, for example, at a temperature close to 120° C. in a sealed tube under microwaves.

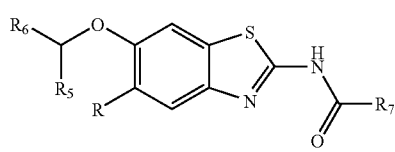

2c

The benzothiazoles of general formula (2c) can be obtained for example by reaction on the 2-amino benzothiazoles of formula (2b):
of an acid chloride of formula (K') in the presence, for example of a solvent such as pyridine at a temperature close to 20° C.
by coupling with an acid of formula (K) in the conditions described for example by D. D. DesMarteau; V. Montanari (Chem Lett, 2000 (9), 1052) in the presence of 1-hydroxybenzotriazole and 1-(3-dimethylaminopropyl)-3-ethylcarbodiimide and in the presence of a base such as triethylamine at a temperature close to 40° C.

Scheme 3: syntheses of derivatives of formulae 2d

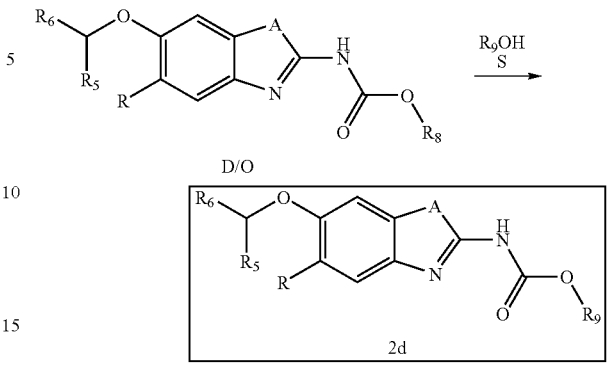

The carbamates of general formula (2d) can be obtained for example by reaction of alcohols of formula (S) on the benzimidazoles of formula D or alternatively on the benzothiazoles of formula (O) in a solvent such as tetrahydrofuran at a temperature close to 65° C.

Among the starting products of formula A, E, G, I, J, K, L, P, R, S, X, X', some are known and can be obtained either commercially or according to the usual methods known by a person skilled in the art, for example from commercial products.

A person skilled in the art will be aware that for applying the methods according to the invention described previously it may be necessary to introduce protecting groups of the amino, carboxyl and alcohol functions in order to avoid side reactions.

The following non-exhaustive list of examples of protection of reactive functions may be mentioned:
the hydroxyl groups can be protected for example by the alkyl radicals such as tert-butyl, trimethylsilyl, tert-butyldimethylsilyl, methoxymethyl, tetrahydropyranyl, benzyl or acetyl,
the amino groups can be protected for example by the acetyl, trityl, benzyl, tert-butoxycarbonyl, BOC, benzyloxycarbonyl, phthalimido or other radicals known in peptide chemistry.

The acid functions can be protected for example in the form of esters formed with the readily cleavable esters such as the benzyl or tert-butyl esters or esters known in peptide chemistry.

A list of various protecting groups that can be used will be found in the manuals known by a person skilled in the art and for example in patent BF 2 499 995.

It may be noted that, if desired and if necessary, intermediates or products of formula (I) thus obtained by the methods indicated above, can be submitted, in order to obtain other intermediates or other products of formula (I), to one or more transformation reactions known by a person skilled in the art, for example:
a) a reaction of esterification of an acid function,
b) a reaction of saponification of an ester function to an acid function,
c) a reaction of reduction of the free or esterified carboxyl function to an alcohol function,
d) a reaction of transformation of an alkoxy function to a hydroxyl function, or alternatively of a hydroxyl function to an alkoxy function,
e) a reaction of elimination of the protecting groups that may be carried by the protected reactive functions, f) a reaction of salification by a mineral or organic acid or by a base to obtain the corresponding salt,
g) a reaction of resolution of the racemic forms into resolved products,
said products of formula (I) thus obtained being in all possible racemic, enantiomeric and diastereoisomeric isomeric forms.

Reactions a) to g) can be performed in the usual conditions known by a person skilled in the art, such as, for example, those indicated below.

a) The products described above can, if desired, be submitted, on the carboxyl functions if present, to reactions of esterification, which can be carried out by the usual methods known by a person skilled in the art.

b) Any transformations of ester functions to acid function of the products described above can, if desired, be carried out in the usual conditions known by a person skilled in the art, notably by acid or alkaline hydrolysis for example by sodium hydroxide or potassium hydroxide in an alcoholic medium, for example in methanol, or by hydrochloric acid or sulphuric acid.

The reaction of saponification can be carried out by the usual methods known by a person skilled in the art, for example in a solvent such as methanol or ethanol, dioxan or dimethoxyethane, in the presence of sodium hydroxide or potassium hydroxide.

c) Any free or esterified carboxyl functions of the products described above can, if desired, be reduced to an alcohol function by the methods known by a person skilled in the art: any esterified carboxyl functions can, if desired, be reduced to an alcohol function by the methods known by a person skilled in the art and notably by lithium aluminium hydride in a solvent such as for example tetrahydrofuran or dioxan or ethyl ether.

Any free carboxyl functions of the products described above can, if desired, be reduced to an alcohol function notably by boron hydride.

d) Any alkoxy functions such as notably methoxy of the products described above can, if desired, be converted to a hydroxyl function in the usual conditions known by a person skilled in the art, for example by boron tribromide in a solvent such as for example methylene chloride, by pyridine hydrobromide or hydrochloride or by hydrobromic or hydrochloric acid in water or trifluoroacetic acid under reflux.

e) The elimination of protecting groups such as for example those indicated above can be effected in the usual conditions known by a person skilled in the art notably by acid hydrolysis carried out with an acid such as hydrochloric, benzenesulphonic or para-toluenesulphonic, formic or trifluoroacetic acid or alternatively by catalytic hydrogenation.

The phthalimido group can be eliminated by hydrazine.

f) The products described above can, if desired, be submitted to reactions of salification for example by a mineral or organic acid or by a mineral or organic base according to the usual methods known by a person skilled in the art: said reaction of salification can be carried out for example in the presence of hydrochloric acid for example or alternatively tartaric, citric or methanesulphonic acid, in an alcohol such as for example ethanol or methanol.

g) Any optically active forms of the products described above can be prepared by resolution of the racemates according to the usual methods known by a person skilled in the art or by separation by preparative chiral-phase HPLC.

The products of formula (I) as defined above, as well as their salts of addition with acids, display interesting pharmacological properties notably by virtue of their kinase inhibiting properties as stated above.

The products of the present invention can notably be used for tumour therapy.

The products of the invention can also thus enhance the therapeutic effects of antitumour agents currently used.

These properties justify their application in therapeutics and the invention relates in particular to, as medicinal products, the products of formula (I) as defined above, said products of formula (I) being in all possible isomeric forms: racemic, enantiomeric and diastereoisomeric, as well as the salts of addition of said products of formula (I) with pharmaceutically acceptable mineral and organic acids or with pharmaceutically acceptable mineral and organic bases.

The invention relates quite particularly to, as medicinal products, the products corresponding to the following formulae:

1-{6-[1-(2,6-dichlorophenyl)ethoxy]-1H-benzimidazol-2-yl}-3-(2-morpholin-4-ylethyl)urea 1-{6-[1-(2,6-dichloro-3-fluorophenyl)ethoxy]-1H-benzimidazol-2-yl}-3-(2-morpholin-4-ylethyl)urea trifluoroacetate 1-{6-[1-(2,6-dichloro-3-fluorophenyl)ethoxy]-5-fluoro-1H-benzimidazol-2-yl}-3-(2-morpholin-4-ylethyl)urea 1-{6-[1-(2,6-dichlorophenyl)ethoxy]-1,3-benzothiazol-2-yl}-3-(2-morpholin-4-ylethyl)urea 1-{6-[1-(2,6-dichloro-3-fluorophenyl)ethoxy]-1,3-benzothiazol-2-yl}-3-(2-morpholin-4-ylethyl)urea 1-{6-[(1R*)-(2,6-dichloro-3-fluorophenyl)ethoxy]-1,3-benzothiazol-2-yl}-3-(2-morpholin-4-ylethyl)urea 1-{6-[1-(2,6-dichlorophenyl)ethoxy]-5-fluoro-1,3-benzothiazol-2-yl}-3-(2-morpholin-4-ylethyl)urea 1-{6-[1-(2,6-dichloro-3-fluorophenyl)ethoxy]-5-fluoro-1,3-benzothiazol-2-yl}-3-(2-morpholin-4-ylethyl)urea 1-{6-[(1R*)-(2,6-dichloro-3-fluorophenyl)ethoxy]-5-fluoro-1,3-benzothiazol-2-yl}-3-(2-morpholin-4-ylethyl)urea 1-{6-[1-(2,6-dichloro-3-fluorophenyl)ethoxy]-1,3-benzothiazol-2-yl}-3-(3-morpholin-4-ylpropyl)urea 1-{6-[1-(2,6-dichloro-3-fluorophenyl)ethoxy]-1,3-benzothiazol-2-yl}-3-[3-(dimethylamino)propyl]urea 1-{6-[1-(2,6-dichloro-3-fluorophenyl)ethoxy]-1,3-benzothiazol-2-yl}-3-(3-piperidin-1-ylpropyl)urea 1-{3-[4-(2-chloro-6-fluorobenzyl)piperazin-1-yl]propyl}-3-{6-[1-(2,6-dichloro-3-fluorophenyl)ethoxy]-1,3-benzothiazol-2-yl}urea 1-(3-azepan-1-ylpropyl)-3-{6-[1-(2,6-dichloro-3-fluorophenyl)ethoxy]-1,3-benzothiazol-2-yl}urea 1-{6-[1-(2,6-dichloro-3-fluorophenyl)ethoxy]-1,3-benzothiazol-2-yl}-3-(2-piperidin-1-ylethyl)urea 1-{6-[1-(2,6-dichloro-3-fluorophenyl)ethoxy]-1,3-benzothiazol-2-yl}-3-(2-pyrrolidin-1-ylethyl)urea 1-[2-(1-benzylpiperidin-4-yl)ethyl]-3-{6-[1-(2,6-dichloro-3-fluorophenyl)ethoxy]-1,3-benzothiazol-2-yl}urea 1-{6-[1-(2,6-dichloro-3-fluorophenyl)ethoxy]-1,3-benzothiazol-2-yl}-3-[2-(1-methyl pyrrolidin-2-yl)ethyl]urea 1-{6-[1-(2,6-dichloro-3-fluorophenyl)ethoxy]-1,3-benzothiazol-2-yl}-3-[2-(4-methylpiperazin-1-yl)ethyl]urea 1-{6-[1-(2,6-dichloro-3-fluorophenyl)ethoxy]-1,3-benzothiazol-2-yl}-3-[2-(2,6-dimethylpiperidin-1-yl)ethyl]urea 1-{6-[1-(2,3-dichloro-6-fluorophenyl)ethoxy]-1,3-benzothiazol-2-yl}-3-(2-morpholin-4-ylethyl)urea 1-{6-[(1R*)-1-(2,6-dichloro-3-fluorophenyl)ethoxy]-5-fluoro-1,3-benzothiazol-2-yl}-3-[2-(4-methylpiperazin-1-yl)ethyl]urea 1-{6-[(1R*)-1-(2,6-dichloro-3-fluorophenyl)ethoxy]-5-fluoro-1,3-benzothiazol-2-yl}-3-[2-(pyrrolidin-1-yl)ethyl]urea 1-{6-[1-(2,6-dichloro-3-fluorophenyl)ethoxy]-5-fluoro-1,3-benzothiazol-2-yl}-3-(2-hydroxyethyl)urea 1-{6-[(1R*)-1-(2,6-dichloro-3-fluorophenyl)ethoxy]-5-fluoro-1,3-benzothiazol-2-yl}-3-(2-hydroxyethyl)urea 1-{6-[1-(2,6-dichloro-3-fluorophenyl)ethoxy]-5-fluoro-1,3-benzothiazol-2-yl}-3-[2-(4-ethylpiperazin-1-yl)ethyl]urea 1-{6-[(1R*)-1-(2,6-dichloro-3-fluorophenyl)ethoxy]-5-fluoro-1,3-benzothiazol-2-yl}-3-[2-(4-ethylpiperazin-1-yl)ethyl]urea 1-{6-[(1R*)-1-(2,3-dichloro-6-fluorophenyl)ethoxy]-1,3-benzothiazol-2-yl}-3-[2-(4-methylpiperazin-1-yl)ethyl]urea 1-{6-[1-(2,3-dichloro-6-fluorophenyl)ethoxy]-5-fluoro-1,3-benzothiazol-2-yl}-3-[2-(morpholin-4-yl)ethyl]urea 1-{6-[(1R*)-1-(2,3-dichloro-6-fluorophenyl)ethoxy]-5-fluoro-1,3-benzothiazol-2-yl}-3-[2-(morpholin-4-yl)ethyl]urea 1-{6-[1-(2,3-dichloro-6-fluorophenyl)ethoxy]-5-fluoro-1,3-benzothiazol-2-yl}-3-[2-(4-methylpiperazin-1-yl)ethyl]urea 1-{6-[(1R*)-1-(2,3-dichloro-6-fluorophenyl)ethoxy]-5-fluoro-1,3-benzothiazol-2-yl}-3-[2-(4-methylpiperazin-1-yl)ethyl]urea 1-{6-[(1R*)-1-(2,3-dichloro-6-fluorophenyl)ethoxy]-5-fluoro-1,3-benzothiazol-2-yl}-3-[2-(pyrrolidin-1-yl)ethyl]urea as well as the salts of addition of said products of formula (I) with pharmaceutically acceptable mineral and organic acids or with pharmaceutically acceptable mineral and organic bases.

The invention also relates to pharmaceutical compositions containing as active principle at least one of the products of formula (I) as defined above or a pharmaceutically acceptable salt of said product or a prodrug of said product and, if applicable, a pharmaceutically acceptable support.

The invention thus extends to pharmaceutical compositions containing as active principle at least one of the medicinal products as defined above.

Said pharmaceutical compositions of the present invention can also, if applicable, contain the active principles of other antimitotic medicinal products such as notably those based on taxol, cisplatin, DNA intercalating agents and others.

Said pharmaceutical compositions can be administered by the buccal route, by the parenteral route or locally in topical application on the skin and the mucosae or by intravenous or intramuscular injection.

Said compositions can be solid or liquid and can be in all the pharmaceutical forms currently used in human medicine, for example, plain or coated tablets, pills, lozenges, capsules, drops, granules, injectable preparations, ointments, creams or gels; they are prepared according to the usual methods. The active principle can be incorporated in them with the excipients usually employed in these pharmaceutical compositions, such as talc, gum arabic, lactose, starch, magnesium stearate, cocoa butter, aqueous or non-aqueous vehicles, fats of animal or vegetable origin, paraffinic derivatives, glycols, various wetting agents, dispersants or emulsifiers, and preservatives.

The usual posology, which varies according to the product used, the subject treated and the disorder in question, can be for example from 0.05 to 5 g per day in adults, or preferably from 0.1 to 2 g per day.

The present invention also relates to the use of the products of formula (I) as defined above or of pharmaceutically acceptable salts of these products for the preparation of a medicinal product intended for inhibiting the activity of a protein kinase.

The present invention also relates to the use of products of formula (I) as defined above for the preparation of a medicinal product intended for the treatment or the prevention of a disease characterized by disturbance of the activity of a protein kinase.

Said medicinal product can notably be intended for the treatment or the prevention of a disease in a mammal.

The present invention also relates to the use defined above in which the protein kinase is a protein-tyrosine kinase.

The present invention also relates to the use defined above in which the protein-tyrosine kinases are MET and RON or their mutant forms.

The present invention also relates to the use defined above in which the protein kinase is in a cell culture.

The present invention also relates to the use defined above in which the protein kinase is in a mammal.

The present invention notably relates to the use of a product of formula (I) as defined above for the preparation of a medicinal product intended for the prevention or the treatment of diseases connected with uncontrolled proliferation.

The present invention relates in particular to the use of a product of formula (I) as defined above for the preparation of a medicinal product intended for the treatment or the prevention of a disease selected from the following group: disorders of blood vessel proliferation, fibrotic disorders, disorders of "mesangial" cell proliferation, metabolic disorders, allergies, asthmas, thromboses, diseases of the nervous system, retinopathy, psoriasis, rheumatoid arthritis, diabetes, muscular degeneration and cancers.

The present invention thus relates quite particularly to the use of a product of formula (I) as defined above for the preparation of a medicinal product intended for the treatment or the prevention of diseases in oncology and notably intended for the treatment of cancers.

Among said cancers, there is interest in the treatment of solid or liquid tumours, and the treatment of cancers that are resistant to cytotoxic agents.

The aforementioned products of the present invention can notably be used for the treatment of primary tumours and/or of metastases in particular in gastric, hepatic, renal, ovarian, colon, and prostate cancers, lung cancers (NSCLC and SCLC), glioblastomas, cancers of the thyroid, of the bladder, of the breast, in melanomas, in haematopoietic lymphoid or myeloid tumours, in sarcomas, in cancers of the brain, of the larynx, of the lymphatic system, bone cancer and pancreatic cancer.

The present invention also relates to the use of the products of formula (I) as defined above for the preparation of medicinal products intended for cancer chemotherapy.

Said medicinal products intended for cancer chemotherapy can be used alone or in combination.

The products of the present application can notably be administered alone or in combination with chemotherapy or with radiotherapy or alternatively in combination for example with other therapeutic agents.

The present invention thus notably relates to the pharmaceutical compositions as defined above additionally containing active principles of other medicinal products for cancer chemotherapy.

Said therapeutic agents can be antitumour agents that are commonly used.

As examples of known inhibitors of protein kinases, we may notably mention butyrolactone, flavopiridol, 2-(2-hydroxyethylamino)-6-benzylamino-9-methylpurine, olomucine, Glivec and Iressa.

The products of formula (I) according to the present invention can thus also be used advantageously in combination with antiproliferative agents: as examples of said antiproliferative agents, though without being limited to this list, we may mention aromatase inhibitors, anti-oestrogens, topoisomerase inhibitors, agents that act on the microtubules, alkylating agents, farnesyl transferase inhibitors, COX-2 inhibitors, MMP inhibitors, mTOR inhibitors, antineoplastic antimetabolites, platinum compounds, proteasome inhibitors, Histone Deacetylase inhibitors (HDACs), and notably HDAC6 inhibitors, compounds causing a decrease in activity of protein kinases as well as anti-angiogenic compounds, gonadorelin agonists, anti-androgens.

The following examples, which are products of formula (I), illustrate the invention but without limiting it.

EXPERIMENTAL SECTION

The naming of the compounds of the present invention was carried out with the software ACDLABS version 10.0 and ACD name version 11.

Microwave oven used: Biotage, Initiator EXP-EU, 300W max, 2450 MHz

Stem-type parallel synthesis reactor (25 stations)

The 1H NMR spectra at 400 MHz and 1H NMR spectra at 300 MHz were recorded on a BRUKER AVANCE DRX-400 or BRUKER AVANCE DPX-300 spectrometer with the chemical shifts (δ in ppm) in the solvent dimethylsulphoxide-d6 (DMSO-d6) referred to 2.5 ppm at a temperature of 303K.

The mass spectra were obtained either by analysis:
LC-MS-DAD-ELSD (MS=Waters ZQ)
LC-MS-DAD-ELSD (MS=Platform II Waters Micromass)
HPLC-MS-DAD-ELSD (MS=Quattro Premier XE Waters)

DAD wavelength considered λ=210-400 nm

ELSD: Sedere SEDEX 85; atomization temperature=35° C.; atomization pressure=3.7 bar The chiral separations were performed by the Prochrom 2 technique on stationary phases of the Chiracel OJ type, Chiralpak The melting points were measured on Köfler or Büchi benches.

Example 1

1-{6-[(2,6-dichlorobenzyl)oxy]-1H-benzimidazol-2-yl}-3-(2-morpholin-4-ylethyl)urea a) 1-{6-[(2,6-Dichlorobenzyl)oxy]-1H-benzimidazol-2-yl}-3-(2-morpholin-4-ylethyl)urea can be prepared as follows:

put a solution of 250 mg of methyl {6-[(2,6-dichlorobenzyl)oxy]-1H-benzimidazol-2-yl}carbamate and 178 mg of 2-morpholin-4-ylethanamine in 3 cm³ of 1-methylpyrrolidin-2-one in a microwave reactor. After the reactor has been sealed, it is put in the microwave cavity for 25 minutes at 125° C. The reaction mixture is then evaporated to dryness under reduced pressure (0.2 kPa) with a bath temperature of 85° C. The residue is taken up in 30 cm³ of water, then extracted three times with 180 cm³ of ethyl acetate. The combined organic phases are washed three times with 30 cm³ of water, dried over magnesium sulphate, filtered and evaporated under reduced pressure (2 kPa). After purification of the residue by silica-column flash chromatography [eluent: dichloromethane/methanol (90/10 by volume)], the product obtained is solidified in 20 cm³ of diethyl oxide, filtered, washed three times with 3 cm³ of diethyl oxide and dried under reduced pressure in the presence of potassium hydroxide. We obtain 241 mg of 1-{6-[(2,6-dichlorobenzyl)oxy]-1H-benzimidazol-2-yl}-3-(2-morpholin-4-ylethyl)urea in the form of a pink powder, which has the following characteristics:

Melting point: 256-259° C. (Köfler)

1H NMR spectrum (400 MHz, DMSO-d6) δ ppm: 2.37-2.47 (m, 6H) 3.23-3.33 (m partially masked, 2H) 3.61 (m, 4H) 5.20 (s, 2H) 6.73 (d broad, J=8.5 Hz, 1H) 7.07 (s broad, 1H) 7.25 (d, J=8.5 Hz, 1H) 7.39 (m spread-out, 1H) 7.45 (dd, J=9.0, 7.5 Hz, 1H) 7.52-7.57 (m, 2H) 9.86 (m spread-out, 1H) 11.35 (m spread-out, 1H)

Mass spectrum: LC-MS-DAD-ELSD: 464(+)=(M+H)(+)

b) Methyl {6-[(2,6-dichlorobenzyl)oxy]-1H-benzimidazol-2-yl}carbamate can be prepared as follows:

add 728 mg of dimethyl[(Z)-(methylsulphanyl)methylylidene]biscarbamate to a solution of 1 g of 4-[(2,6-dichlorobenzyl)oxy]benzene-1,2-diamine in a mixture of 60 cm³ of methanol and 212 mg of glacial acetic acid. The mixture is refluxed for 5.5 hours then concentrated under reduced pressure (0.2 kPa). The residue is taken up in 80 cm³ of a saturated aqueous solution in sodium hydrogen carbonate and the mixture obtained is extracted five times with 150 cm³ of ethyl acetate. The combined organic phases are dried over magnesium sulphate, filtered and evaporated under reduced pressure. The residue is taken up in 25 cm³ of acetonitrile, washed twice with 5 cm³ of acetonitrile, then dried under reduced pressure over sodium hydroxide. We obtain 834 mg of methyl {6-[(2,6-dichlorobenzyl)oxy]-1H-benzimidazol-2-yl}carbamate in the form of a white powder, which has the following characteristics:

Melting point: 210° C. (Köfler)

Mass spectrum: LC-MS-DAD-ELSD: 366(+)=(M+H)(+)

c) 4-[(2,6-Dichlorobenzyl)oxy]benzene-1,2-diamine can be prepared as follows:

add 1.75 g of iron powder to a solution of 1.4 g of 4-[(2,6-dichlorobenzyl)oxy]-2-nitroaniline in 80 cm³ of methanol and 7 cm³ of glacial acetic acid. The reaction mixture is refluxed for three hours. The mixture is concentrated under reduced pressure (0.2 kPa). The residue is taken up in 30 cm³ of water and the pH of the suspension thus obtained is adjusted to 10-11 by adding 2N aqueous solution of sodium hydroxide; 350 cm³ of dichloromethane is then added. After vigorous stirring for 15 min, the insoluble matter is filtered. The filtrate is decanted, then the organic phase is dried over magnesium sulphate, filtered and concentrated under reduced pressure (0.2 kPa). We obtain 1.11 g of 4-[(2,6-dichlorobenzyl)oxy]benzene-1,2-diamine in the form of a black resin, which has the following characteristics:

Rf CCM silica=0.37 [eluent: dichloromethane/methanol (95/5 by volume)]

Mass spectrum: LC-MS-DAD-ELSD: 283(+)=(M+H)(+)

d) 4-[(2,6-Dichlorobenzyl)oxy]-2-nitroaniline can be prepared as follows:

add 561 mg of anhydrous potassium hydroxide to a solution of 1.54 g of 4-amino-3-nitrophenol in 6 cm³ of N,N-dimethylformamide. Add dropwise, to the purple solution obtained, 2.4 g of 2-(bromomethyl)-1,3-dichlorobenzene in solution in 2 cm³ of N,N-dimethylformamide, without exceeding 20° C. After stirring the reaction mixture for about twenty hours at a temperature around 20° C., the reaction mixture is poured into 200 cm³ of water. The mixture obtained is extracted three times with 100 cm³ of ethyl acetate. The combined organic phases are washed five times with 50 cm³ of water, dried over magnesium sulphate, filtered and concentrated under reduced pressure (0.2 kPa). The residue is taken up successively in a 50/50 mixture of diethyl oxide and diisopropyl oxide, and finally drained, washed three times with 2 cm³ of diisopropyl oxide, then dried under reduced pressure in the presence of potassium hydroxide. We obtain 2.4 g of 4-[(2,6-dichlorobenzyl)oxy]-2-nitroaniline in the form of a white powder, which has the following characteristics:

Melting point: 155° C. (Köfler)
Mass spectrum: LC-MS-DAD-ELSD: 313(+)=(M+H)(+)

Example 2

1-{6-[1-(2,6-dichlorophenyl)ethoxy]-1H-benzimidazol-2-yl}-3-(2-morpholin-4-ylethyl)urea a) 1-{6-[1-(2,6-Dichlorophenyl)ethoxy]-1H-benzimidazol-2-yl}-3-(2-morpholin-4-ylethyl)urea can be prepared as in Example 1a but from 300 mg of methyl {6-[1-(2,6-dichlorophenyl)ethoxy]-1H-benzimidazol-2-yl}carbamate and 308 mg of 2-morpholin-4-ylethanamine. After purification of the residue by silica-column flash chromatography [eluent: dichloromethane/methanol (92/8 by volume)], we obtain 243 mg of 1-{6-[1-(2,6-dichlorophenyl)ethoxy]-1H-benzimidazol-2-yl}-3-(2-morpholin-4-ylethyl)urea in the form of a beige solid, which has the following characteristics:

Melting point: 215-220° C. (Köfler)
1H NMR spectrum (400 MHz, DMSO-$d_6$) δ ppm: 1.71 (d, J=6.8 Hz, 3H) 2.41 (m, 6H) 3.39 (m partially masked, 2H) 3.59 (m, 4H) 5.98 (q, J=6.8 Hz, 1H) 6.62 (dd, J=8.3, 2.4 Hz, 1H) 6.79 (m spread-out, 1H) 7.15 (d broad, J=8.3 Hz, 1H) 7.27 (t, J=8.0 Hz, 1H) 7.41 (d, J=8.0 Hz, 2H) 7.47 (m spread-out, 1H) 9.83 (m spread-out, 1H) 11.35 (m spread-out, 1H)
Mass spectrum: LC-MS-DAD-ELSD: 478(+)=(M+H)(+)

b) Methyl {6-[1-(2,6-dichlorophenyl)ethoxy]-1H-benzimidazol-2-yl}carbamate can be prepared as in Example 1b but from 1 g of 4-[1-(2,6-dichlorophenyl)ethoxy]benzene-1,2-diamine and 580 mg of dimethyl [(Z)-(methylsulphanyl)methylylidene]biscarbamate. We thus obtain 1.06 g of methyl {6-[1-(2,6-dichlorophenyl)ethoxy]-1H-benzimidazol-2-yl}carbamate in the form of a cream-colored solid, which has the following characteristics:

Rf CCM silica=0.36 [eluent: dichloromethane/methanol (95/5 by volume)]
Mass spectrum: MS (EI): LC-MS-DAD-ELSD: 380(+)=(M+H)(+)

c) 4-[1-(2,6-Dichlorophenyl)ethoxy]benzene-1,2-diamine can be prepared as follows: in an autoclave, 70 mg of platinum oxide is covered with 5 cm³ of glacial acetic acid; a solution of 920 mg of 4-[1-(2,6-dichlorophenyl)ethoxy]-2-nitroaniline in 130 cm³ of glacial acetic acid is added. The mixture obtained is hydrogenated under 300 kPa of hydrogen and at a temperature close to 22° C. After reaction for 20 h, the reaction mixture is filtered and then concentrated under vacuum under reduced pressure (0.2 kPa). We obtain 1 g of 4-[1-(2,6-dichlorophenyl)ethoxy]benzene-1,2-diamine in the form of a dark orange resin, which has the following characteristics:

Rf CCM silica=0.10 [eluent: dichloromethane/methanol (98/2 by volume)]
Mass spectrum: MS (EI): LC-MS-DAD-ELSD: 297(+)=(M+H)(+)

d) 4-[1-(2,6-Dichlorophenyl)ethoxy]-2-nitroaniline can be prepared as in Example 1d but from 1 g of 4-amino-3-nitrophenol and 1.36 g of 1,3-dichloro-2-(1-chloroethyl)benzene. After purification of the residue by silica-column flash chromatography (eluent: dichloromethane), we obtain 724 mg of 4-[1-(2,6-dichlorophenyl)ethoxy]-2-nitroaniline in the form of a red solid, which has the following characteristics:

Melting point: 135° C. (Köfler)
Mass spectrum LC-MS-DAD-ELSD: 327(+)=(M+H)(+)

e) 1,3-Dichloro-2-(1-chloroethyl)benzene can be obtained as follows:

a solution of 5 g of 2,4,6-trichloro-1,3,5-triazine in 5.5 cm³ of N,N-dimethylformamide is stirred for about 3 hours at a temperature close to 20° C. A white precipitate forms. A solution of 5 g of 1-(2,6-dichlorophenyl)-ethanol in 72 cm³ of dichloromethane is added dropwise without exceeding 25° C. After about 48 hours at a temperature close to 20° C., the suspension is solubilized by adding 150 cm³ of dichloromethane. The solution obtained is washed five times with 40 cm³ of water, then dried over magnesium sulphate, filtered and concentrated under reduced pressure. After filtration of the residue on 100 cm³ of silica [eluent: cyclohexane/ethyl acetate (75/25 by volume)], we obtain 5.5 g of 1,3-dichloro-2-(1-chloroethyl)benzene in the form of a colorless oil, which has the following characteristics:

Rf CCM silica=0.80 [eluent: cyclohexane/ethyl acetate (75/25 by volume)]
Mass spectrum: MS (EI): LC-MS-DAD-ELSD: 209(+)=(M+H)(+)

Example 3

1-{6-[1-(2-chloro-5-fluorophenyl)ethoxy]-1H-benzimidazol-2-yl}-3-(2-morpholin-4-ylethyl)urea a) 1-{6-[1-(2-Chloro-5-fluorophenyl)ethoxy]-1H-benzimidazol-2-yl}-3-(2-morpholin-4-ylethyl)urea can be prepared as in Example 1a but from 300 mg of methyl {6-[1-(2-chloro-5-fluorophenyl)ethoxy]-1H-benzimidazol-2-yl}carbamate and 215 mg of 2-morpholin-4-ylethanamine. We obtain 309 mg of 1-{6-[1-(2-chloro-5-fluorophenyl)ethoxy]-1H-benzimidazol-2-yl}-3-(2-morpholin-4-ylethyl)urea as a beige solid, which has the following characteristics:

Melting point: 210° C. (Köfler)
1H NMR spectrum (400 MHz, DMSO-d6) δ ppm: 1.56 (d, J=6.6 Hz, 3H) 2.41 (m, 6H) 3.30 (m partially masked, 2H) 3.59 (m, 4H) 5.59 (q, J=6.6 Hz, 1H) 6.64 (dd, J=8.3, 2.4 Hz, 1H) 6.77 (m spread-out, 1H) 7.11-7.49 (m, 4H) 7.52 (dd, J=8.8, 5.4 Hz, 1H) 9.79 (m, 1H) 11.3 (m, 1H)
Mass spectrum: LC-MS-DAD-ELSD: 462(+)=(M+H)(+)

b) Methyl {6-[1-(2-chloro-5-fluorophenyl)ethoxy]-1H-benzimidazol-2-yl}carbamate can be prepared as in Example 1b but from 2.5 g of 4-[1-(2-chloro-5-fluorophenyl)ethoxy]benzene-1,2-diamine and 1.2 g of [(Z)-(methylsulphanyl)methylylidene]biscarbamate. We obtain 1.6 g of methyl {6-[1-(2-chloro-5-fluorophenyl)ethoxy]-1H-benzimidazol-2-yl}carbamate in the form of a light ochre solid, which has the following characteristics:

Melting point: 162-165° C. (Köfler)
Mass spectrum: LC-MS-DAD-ELSD: 364(+)=(M+H)(+)

c) 4-[1-(2-Chloro-5-fluorophenyl)ethoxy]benzene-1,2-diamine can be prepared as in Example 2c but from 2 g of 4-[1-(2,6-dichloro-5-fluorophenyl)ethoxy]-2-nitroaniline. We obtain 2.5 g of 4-[1-(2-chloro-5-fluorophenyl)ethoxy]benzene-1,2-diamine in the form of a resin which has the following characteristics:

Mass spectrum: LC-MS-DAD-ELSD: 281(+)=(M+H)(+)

d) 4-[1-(2,6-Dichloro-5-fluorophenyl)ethoxy]-2-nitroaniline can be prepared as follows:

at a temperature close to 20° C., add 1.62 g of 4-amino-3-nitrophenol to a solution of 2 g of 1-(2,6-dichloro-3-fluorophenyl)-ethanol in 70 cm³ of tetrahydrofuran, and then after it has dissolved completely, add 3.7 g of triphenylphosphane. After stirring for one hour at a temperature close to 20° C., the brownish-orange solution is cooled to about 0° C. and 2.9 g of bis(1-methylethyl) (E)-diazene-1,2-dicarboxylate is added dropwise, keeping the temperature between 0 and 3° C. The mixture is stirred for 20 hours, allowing the temperature to rise slowly to about 20° C.

After concentration of the reaction mixture to dryness under reduced pressure (0.2 kPa) and flash chromatography of the residue on silica (eluent: dichloromethane), we obtain 2.07 g of 4-[1-(2-chloro-5-fluorophenyl)ethoxy]-2-nitroaniline in the form of a dark pink solid, which has the following characteristics:

Melting point: 110° C. (Köfler)
1H NMR spectrum (400 MHz, DMSO-$d_6$) δ ppm: 1.55 (d, J=6.4 Hz, 3H) 5.58 (q, J=6.4 Hz, 1H) 6.97 (d, J=8.5 Hz, 1H) 7.15-7.27 (m, 5H) 7.29 (dd, J=9.0, 3.2 Hz, 1H) 7.54 (dd, J=9.0, 5.4 Hz, 1H)
Mass spectrum: LC-MS-DAD-ELSD: 311(+)=(M+H)(+)

e) 1-(2,6-Dichloro-3-fluorophenyl)ethanol can be prepared as follows:

add dropwise, keeping the temperature at about 20° C., 50 cm³ of a 1M solution of aluminium lithium hydride in tetrahydrofuran to a solution of 10.28 g of 1-(2,6-dichloro-3-fluorophenyl)-ethanone in 100 cm³ of tetrahydrofuran. After stirring the reaction mixture for about twenty hours at the same temperature, cool this mixture to about 0° C. and successively add dropwise 2.5 cm³ of water, 2.5 cm³ of a 5N aqueous solution of sodium hydroxide, then after about 30 min, 7.5 cm³ of the 5N solution of sodium hydroxide. Add 100 cm³ of tetrahydrofuran to the resultant suspension, and after stirring for about 10 min, also add 5 g of magnesium sulphate.

After filtration of the mixture and concentration of the filtrate under reduced pressure (0.2 kPa), we obtain 6.29 g of 1-(2,6-dichloro-3-fluoro-phenyl)ethanol in the form of an oil, which has the following characteristics:

Rf CCM silica=0.30 (eluent: dichloromethane)
Mass spectrum: LC-MS-DAD-ELSD: 209(+)=(M+H)(+)

Example 4

4-{2-[({6-[1-(2,6-Dichloro-3-fluorophenyl)ethoxy]-1H-benzimidazol-2-yl}carbamoyl)amino]ethyl}morpholin-4-ium trifluoroacetate a) 4-{2-[({6-[1-(2,6-Dichloro-3-fluorophenyl)ethoxy]-1H-benzimidazol-2-yl}carbamoyl)amino]ethyl}morpholin-4-ium trifluoroacetate can be prepared as in Example 1a but from 180 mg of methyl {6-[1-(2,6-dichloro-3-fluorophenyl)ethoxy]-1H-benzimidazol-2-yl}carbamate and 118 mg of 2-morpholin-4-ylethanamine. The mixture obtained is purified by preparative LCMS chromatography (liquid chromatography+mass spectroscopy), Waters system; reverse-phase column C18 SunFire (Waters) with an acetonitrile gradient (+0.07% TFA) in water (+0.07% TFA). After lyophilization of the mixture, we thus obtain 158 mg of 4-{2-[({6-[1-(2,6-dichloro-3-fluorophenyl)ethoxy]-1H-benzimidazol-2-yl}carbamoyl)amino]ethyl}morpholin-4-ium trifluoroacetate in the form of a white lyophilizate, which has the following characteristics:

1H NMR spectrum (400 MHz, DMSO-$d_6$) δ ppm: 1.73 (d, J=6.8 Hz, 3H) 3.00-4.10 (m spread-out, partially masked, 8H) 3.26 (t, J=5.9 Hz, 2H) 3.57 (q, J=5.9 Hz, 2H) 6.00 (q, J=6.8 Hz, 1H) 6.78 (d broad, J=8.0 Hz, 1H) 6.88 (d, J=2.0 Hz, 1H) 7.31 (d, J=8.0 Hz, 1H) 7.40 (t, J=8.6 Hz, 1H) 7.51 (dd, J=8.6, 4.9 Hz, 1H) 7.72 (m spread-out, 1H) 9.10-11.5 (m very spread-out, 2H)
Mass spectrum: LC-MS-DAD-ELSD: 496(+)=(M+H)(+)

b) Methyl {6-[1-(2,6-dichloro-3-fluorophenyl)ethoxy]-1H-benzimidazol-2-yl}carbamate can be prepared as in Example 1a but from 300 mg of 4-[1-(2,6-dichloro-3-fluorophenyl)ethoxy]benzene-1,2-diamine and 196 mg of dimethyl[(Z)-(methylsulphanyl)methylylidene]biscarbamate.

We obtain 205 mg of methyl {6-[1-(2,6-dichloro-3-fluorophenyl)ethoxy]-1H-benzimidazol-2-yl}carbamate in the form of a pink powder, which has the following characteristics:

Melting point: 210-215° C. (Köfler)
Mass spectrum: LC-MS-DAD-ELSD: 398(+)=(M+H)(+)

c) 4-[1-(2,6-Dichloro-3-fluorophenyl)ethoxy]benzene-1,2-diamine can be prepared as follows:

In an autoclave, cover 36 mg of platinum oxide with 5 cm³ of ethanol; add a solution of 600 mg of 4-[1-(2,6-dichloro-3-fluorophenyl)ethoxy]-1,2-dinitrobenzene in 67 cm³ of ethanol. This mixture is hydrogenated under 200 kPa of hydrogen and at a temperature close to 20° C. After reaction for about twenty hours, the mixture is filtered and concentrated under vacuum under reduced pressure (0.2 kPa). After filtration on silica [eluent: dichloromethane/methanol (98/2 by volume)], we obtain 316 mg of 4-[1-(2,6-dichloro-3-fluorophenyl)ethoxy]benzene-1,2-diamine in the form of a brown resin, which has the following characteristics:

1H NMR spectrum (400 MHz, DMSO-$d_6$) δ ppm: 1.63 (d, J=6.8 Hz, 3H) 3.98 (s broad, 2H) 4.45 (s, 2H) 5.79 (q, J=6.8 Hz, 1H) 5.88 (dd, J=8.3, 2.9 Hz, 1H) 6.14 (d, J=2.9 Hz, 1H) 6.29 (d, J=8.3 Hz, 1H) 7.36 (t, J=8.9 Hz, 1H) 7.47 (dd, J=8.9, 5.1 Hz, 1H)
Mass spectrum: MS (EI): LC-MS-DAD-ELSD: 315(+)=(M+H)(+)

d) 4-[1-(2,6-Dichloro-3-fluorophenyl)ethoxy]-1,2-dinitrobenzene can be prepared as follows:

add dropwise, at a temperature of about 20° C., a solution of 547 mg of 1-(2,6-dichloro-3-fluorophenyl)-ethanol in 5 cm³ of N,N-dimethylformamide to a suspension of 115 mg of sodium hydride (at 60% in the oil) in 2 cm³ of N,N-dimethylformamide. Stir the resultant mixture for 30 minutes at about 20° C.

Then pour the solution obtained dropwise, keeping the temperature at about 20° C., into a solution of 536 mg of 4-fluoro-1,2-dinitrobenzene in 8 cm³ of N,N-dimethylformamide. After stirring for about twenty hours at a temperature close to 20° C., 5 cm³ of water is added and the mixture obtained is concentrated under reduced pressure (0.2 kPa). The residue is taken up in 20 cm³ of water then extracted three times with 40 cm³ of dichloromethane, dried over magnesium sulphate, filtered and concentrated under reduced pressure (0.2 kPa). After purification of the residue by silica-column flash chromatography [eluent: cyclohexane/ethyl acetate (75/25 by volume)], we obtain 600 mg of 4-[1-(2,6-dichloro-3-fluorophenyl)ethoxy]-1,2-dinitrobenzene in the form of a thick yellow oil, which has the following characteristics:

1H NMR spectrum (400 MHz, DMSO-$d_6$) δ ppm: 1.78 (d, J=6.8 Hz, 3H) 6.27 (q, J=6.8 Hz, 1H) 7.18 (dd, J=8.5.2.4 Hz, 1H) 7.49 (t, J=9.1 Hz, 1H) 7.59 (dd, J=9.1, 4.9 Hz, 1H) 7.64 (d, J=2.4 Hz, 1H) 8.22 (d, J=8.5 Hz, 1H)
Mass spectrum: LC-MS-DAD-ELSD: 375(+)=(M+H)(+)

Example 5

1-{6-[1-(2,6-dichlorophenyl)ethoxy]-5-fluoro-1H-benzimidazol-2-yl}-3-(2-morpholin-4-ylethyl)urea a) 1-{6-[1-(2,6-Dichlorophenyl)ethoxy]-5-fluoro-1H-benzimidazol-2-yl}-3-(2-morpholin-4-ylethyl)urea can be prepared as in Example 1a but from 300 mg of methyl {6-[1-(2,6-dichlorophenyl)ethoxy]-5-fluoro-1H-benzimidazol-2-yl}carbamate and 196 mg of 2-morpholin-4-ylethanamine.

We obtain 333 mg of 1-{6-[1-(2,6-dichlorophenyl)ethoxy]-5-fluoro-1H-benzimidazol-2-yl}-3-(2-morpholin-4-ylethyl)urea in the form of a pink solid, which has the following characteristics:

Melting point: 210-216° C. (Köfler)

1H NMR spectrum (400 MHz, DMSO-$d_6$) δ ppm 1.75 (d, J=6.6 Hz, 3H) 2.40 (m, 6H) 3.27 (q, J=5.9 Hz, 2H) 3.59 (m, 4H) 5.96 (q, J=6.6 Hz, 1H) 6.68-7.27 (m spread-out, 2H) 7.14 (d, J=10.3 Hz, 1H) 7.32 (t, J=7.5 Hz, 1H) 7.44 (d, J=7.5 Hz, 2H) 9.83 (m spread-out, 1H) 11.44 (m spread-out, 1H)

Mass spectrum: LC-MS-DAD-ELSD: 494(−)=(M−H)(−); 496(+)=(M+H)(+)

b) Methyl {6-[1-(2,6-dichlorophenyl)ethoxy]-5-fluoro-1H-benzimidazol-2-yl}carbamate can be prepared as in Example 1b but from 1 g of 4-[1-(2,6-dichlorophenyl)ethoxy]-5-fluorobenzene-1,2-diamine and 561 mg of dimethyl [(Z)-(methylsulphanyl)methylylidene]biscarbamate. We thus obtain 397 g of methyl {6-[1-(2,6-dichlorophenyl)ethoxy]-5-fluoro-1H-benzimidazol-2-yl}carbamate in the form of a pink powder, which has the following characteristics:

Melting point: 240-245° C. (Köfler)

Mass spectrum: LC-MS-DAD-ELSD: 396(−)=(M−H)(−); 398(+)=(M+H)(+)

c) 4-[1-(2,6-Dichlorophenyl)ethoxy]-5-fluorobenzene-1,2-diamine can be prepared as in Example 2c but from 940 mg of 5-[1-(2,6-dichlorophenyl)ethoxy]-4-fluoro-2-nitroaniline. We obtain 1 g of 4-[1-(2,6-dichlorophenyl)ethoxy]-5-fluorobenzene-1,2-diamine in the form of a dark orange resin which is used as it is for the next stage.

d) 5-[1-(2,6-Dichlorophenyl)ethoxy]-4-fluoro-2-nitroaniline can be prepared as follows:

pour dropwise, at a temperature close to 20° C., a solution of 500 mg of 1-(2,6-dichlorophenyl)-ethanol in 10 cm$^3$ of tetrahydrofuran into a suspension of 115 mg of sodium hydride (at 60% in the oil) in 4 cm$^3$ of tetrahydrofuran. Stir the suspension obtained for 2.5 hours at about 20° C. A solution of 456 mg of 4,5-difluoro-2-nitroaniline in 15 cm$^3$ of tetrahydrofuran is then poured in dropwise at about 20° C. After stirring for about 1.5 h at a temperature close to 20° C., 150 cm$^3$ of a saturated aqueous solution of sodium chloride is added to the reaction mixture. The resultant mixture is extracted five times with 50 cm$^3$ of ethyl acetate, then the organic phases are dried over magnesium sulphate, filtered and then concentrated under reduced pressure (0.2 kPa). We thus obtain 953 mg of 5-[1-(2,6-dichlorophenyl)ethoxy]-4-fluoro-2-nitroaniline in the form of a dark orange solid, which has the following characteristics:

Melting point: 188° C. (Köfler)

Mass spectrum: LC-MS-DAD-ELSD: 343(−)=(M−H)(−); 345(+)=(M+H)(+)

Example 6

1-{6-[1-(2,6-dichloro-3-fluorophenyl)ethoxy]-5-fluoro-1H-benzimidazol-2-yl}-3-(2-morpholin-4-ylethyl)urea a) 1-{6-[1-(2,6-Dichloro-3-fluorophenyl)ethoxy]-5-fluoro-1H-benzimidazol-2-yl}-3-(2-morpholin-4-ylethyl)urea can be prepared as in Example 1a but from 300 mg of methyl {6-[1-(2,6-dichloro-3-fluorophenyl)ethoxy]-5-fluoro-1H-benzimidazol-2-yl}carbamate and 188 mg of 2-morpholin-4-ylethanamine. After purification of the residue by flash chromatography on silica [eluent: dichloromethane/methanol (90/10 by volume)], we obtain 224 mg of 1-{6-[1-(2,6-dichloro-3-fluorophenyl)ethoxy]-5-fluoro-1H-benzimidazol-2-yl}-3-(2-morpholin-4-ylethyl)urea in the form of a pink solid, which has the following characteristics:

Melting point: 190-192° C. (Köfler)

1H NMR spectrum (400 MHz, DMSO-$d_6$) δ ppm: 1.76 (d, J=6.7 Hz, 3H) 2.40 (m, 6H) 3.28 (m, 2H) 3.59 (m, 4H) 5.94 (q, J=6.7 Hz, 1H) 6.81 (s broad, 1H) 7.15 (d, J=11.7 Hz, 1H) 7.30 (m spread-out, 1H) 7.42 (t, J=8.8 Hz, 1H) 7.51 (dd, J=8.8, 4.9 Hz, 1H) 9.85 (m spread-out, 1H) 11.5 (m spread-out, 1H)

Mass spectrum: LC-MS-DAD-ELSD: 512(−)=(M−H)(−); 514(+)=(M+H)(+)

b) Methyl {6-[1-(2,6-dichloro-3-fluorophenyl)ethoxy]-5-fluoro-1H-benzimidazol-2-yl}carbamate can be prepared as in Example 1b but from 468 mg of 4-[1-(2,6-dichloro-3-fluorophenyl)ethoxy]-5-fluoro-benzene-1,2-diamine and 290 mg of dimethyl [(Z)-(methylthio)methylylidene]biscarbamate. We obtain 400 mg of methyl {6-[1-(2,6-dichloro-3-fluorophenyl)ethoxy]-5-fluoro-1H-benzimidazol-2-yl}carbamate in the form of a pale pink solid, which has the following characteristics:

Melting point: 245-250° C. (Köfler)

Mass spectrum: LC-MS-DAD-ELSD: 414(−)=(M−H)(−); 416(+)=(M+H)(+)

c) 4-[1-(2,6-Dichloro-3-fluorophenyl)ethoxy]-5-fluoro-benzene-1,2-diamine can be prepared as follows:

In an autoclave, cover 32 mg of platinum oxide with 5 cm$^3$ of methanol and add a solution of 510 mg of 5-[1-(2,6-dichloro-3-fluorophenyl)ethoxy]-4-fluoro-2-nitroaniline. The mixture is hydrogenated under 300 kPa of pressure of hydrogen and at a temperature close to 20° C. for about twenty hours. The mixture is filtered and the filtrate containing the expected compound is used as it is for the next stage.

Rf CCM silica=0.21 (eluent: toluene)

d) 5-[1-(2,6-Dichloro-3-fluorophenyl)ethoxy]-4-fluoro-2-nitroaniline can be prepared as in Example 5d but from 600 mg of 1-(2,6-dichloro-3-fluorophenyl)ethanol and 550 mg of 4,5-difluoro-2-nitroaniline. We obtain 520 mg of 5-[1-(2,6-dichloro-3-fluorophenyl)ethoxy]-4-fluoro-2-nitroaniline in the form of an orange powder, which has the following characteristics:

Melting point: 163° C. (Köfler)

Mass spectrum: LC-MS-DAD-ELSD: 361(−)=(M−H)(−); 363(+)=(M+H)(+)

Example 7

N-{6-[(2,6-dichlorobenzyl)oxy]-1H-benzimidazol-2-yl}cyclopropane carboxamide a) N-{6-[(2,6-Dichlorobenzyl)oxy]-1H-benzimidazol-2-yl}cyclopropane carboxamide can be prepared as follows:

a solution of 270 mg of 1-[bis(dimethylamino)methylidene]-2,3-dihydro-1H-[1,2,3]triazolo[4,5-b]pyridin-1-ium-3-oxide hexafluorophosphate, 61 mg of cyclopropanecarboxylic acid and 176 mg of diisopropylethylamine in 40 cm$^3$ of N,N-dimethylformamide is stirred for one hour at a temperature close to 20° C. Then 250 mg of 6-[(2,6-dichlorobenzyl)oxy]-1H-benzimidazol-2-aminium trifluoroacetate is added and the orange solution obtained is stirred for about twenty hours at about 20° C. After concentration under reduced pressure (0.2 kPa), the residue is taken up in 40 cm$^3$ of water and the mixture obtained is extracted three times with 40 cm$^3$ of ethyl acetate. The combined organic phases are washed three times with 40 cm$^3$ of water, then dried over magnesium sulphate, filtered and concentrated under reduced pressure. After purification of the residue by flash chromatography on silica [eluent: dichloromethane/methanol (95/5 by volume)], we obtain 64 mg of N-{6-[(2,6-dichlorobenzyl)oxy]-1H-benzimidazol-2-yl}cyclopropanecarboxamide in the form of a white powder, which has the following characteristics:

Melting point: 133-135° C. (Köfler)

1H NMR spectrum (400 MHz, DMSO-$d_6$) δ ppm: 0.91 (d, J=6.1 Hz, 4H) 1.97 (quin, J=6.1 Hz, 1H) 5.21 (s broad, 2H) 6.79 (m spread-out, 1H) 7.13 (s broad, 1H) 7.32 (d, J=8.6 Hz, 1H) 7.46 (dd, J=8.8, 7.1 Hz, 1H) 7.57 (m, 2H) 11.67-11.90 (m spread-out, 2H)

Mass spectrum: LC-MS-DAD-ELSD: 376(+)=(M+H)(+)

b) 6-[(2,6-Dichlorobenzyl)oxy]-1H-benzimidazol-2-aminium trifluoroacetate can be prepared as follows:

add 1.95 g of trifluoroacetic acid to a solution of 580 mg of 1,1-dimethylethyl {6-[(2,6-dichlorobenzyl)oxy]-1H-benzimidazol-2-yl}carbamate in 30 cm³ of dichloromethane. Stir the solution obtained for about twenty hours at about 20° C. After concentration of the reaction mixture to dryness under reduced pressure (0.2 kPa), the residue is taken up in 25 cm³ of diethyl ether, drained and then washed three times with 5 cm³ of diethyl ether. We thus obtain 546 mg of 6-[(2,6-dichlorobenzyl)oxy]-1H-benzimidazol-2-aminium trifluoroacetate in the form of grey powder, which has the following characteristics:

Melting point: 193° C. (Köfler)

Mass spectrum: LC-MS-DAD-ELSD: 422(+)=(M+H)(+)

c) 1,1-Dimethylethyl {6-[(2,6-dichlorobenzyl)oxy]-1H-benzimidazol-2-yl}carbamate can be prepared as follows:

add 615 mg of bis(1,1-dimethylethyl) [(Z)-(methylsulphanyl)methylylidene]biscarbamate to a solution of 600 mg of 4-[(2,6-dichlorobenzyl)oxy]benzene-1,2-diamine in a mixture of 30 cm³ of methanol and 127 mg of pure acetic acid. The mixture is refluxed for about 3 hours then concentrated under reduced pressure (0.2 kPa). The residue is taken up in 20 cm³ of a saturated aqueous solution of potassium carbonate and the mixture is extracted three times with 100 cm³ of dichloromethane. The combined organic phases are dried over magnesium sulphate, then filtered and evaporated under reduced pressure. After purification of the residue by silica-column flash chromatography [eluent: dichloromethane/methanol (98/2 by volume)], we obtain 586 mg of 1,1-dimethylethyl {6-[(2,6-dichlorobenzyl)oxy]-1H-benzimidazol-2-yl}carbamate in the form of an orange resin, which has the following characteristics:

Rf CCM silica=0.50 [eluent: dichloromethane/methanol (95/5 by volume)]

Mass spectrum: LC-MS-DAD-ELSD: 408(+)=(M+H)(+)

Example 8

6-[(2-chloro-6-fluorobenzyl)oxy]-1,3-benzothiazol-2-amine

6-[(2-Chloro-6-fluorobenzyl)oxy]-1,3-benzothiazol-2-amine can be prepared as follows:

add 337 mg of anhydrous potassium hydroxide to a solution of 1 g of 2-amino-1,3-benzothiazol-6-ol in 5 cm³ of N,N-dimethylformamide. After stirring for one hour at a temperature close to 20° C., a solution of 1.08 g of 1-chloro-2-(chloromethyl)-3-fluorobenzene in 2 cm³ of N,N-dimethylformamide is added dropwise. Stir the resultant mixture for about twenty hours at about 20° C. The reaction mixture is poured into 30 cm³ of water, and extracted three times with 50 cm³ of dichloromethane. The organic phases are combined and washed three times with 50 cm³ of a 0.1N aqueous solution of sodium hydroxide, then dried over magnesium sulphate, filtered and concentrated under reduced pressure (0.2 kPa). The residue is taken up in 10 cm³ of a dichloromethane/methanol mixture (98/2 by volume), drained and then washed twice with 5 cm³ of the same mixture, stove-dried under reduced pressure (0.2 kPa) and at a temperature close to 35° C. We obtain 339 mg of 6-[(2-chloro-6-fluorobenzyl)oxy]-1,3-benzothiazol-2-amine in the form of a white solid, which has the following characteristics:

Melting point: 175° C. (Köfler)

1H NMR spectrum (400 MHz, DMSO-$d_6$) δ ppm: 5.12 (d, J=2.0 Hz, 2H) 6.90 (dd, J=8.5, 2.7 Hz, 1H) 7.24 (m, 3H) 7.31 (t, J=8.8 Hz, 1H) 7.41 (m, 2H) 7.51 (td, J=8.8, 6.4 Hz, 1H)

Mass spectrum: LC-MS-DAD-ELSD: 309(+)=(M+H)(+)

2-Amino-1,3-benzothiazol-6-ol is prepared as described in patent WO 2007/036630 A1.

Example 9

N-{6-[(2,6-dichlorobenzyl)oxy]-1,3-benzothiazol-2-yl}cyclopropane carboxamide a) N-{6-[(2,6-Dichlorobenzyl)oxy]-1,3-benzothiazol-2-yl}cyclopropane carboxamide can be prepared as follows:

add 23 mg of cyclopropanecarboxylic acid to a solution of 70 mg of 6-[(2,6-dichlorobenzyl)oxy]-1,3-benzothiazol-2-amine in 1.5 cm³ of anhydrous pyridine. After stirring for one hour at around 20° C., the reaction mixture is concentrated to dryness under reduced pressure (0.2 kPa). The residue is taken up in 25 cm³ of water, then the mixture obtained is extracted three times with 20 cm³ of dichloromethane. The combined organic phases are washed twice with 20 cm³ of water, dried over magnesium sulphate, filtered and concentrated to dryness under reduced pressure. After purification of the residue by silica-column flash chromatography [eluent: dichloromethane/methanol (92/8 by volume)], we obtain 51 mg of N-{6-[(2,6-dichlorobenzyl)oxy]-1,3-benzothiazol-2-yl}cyclopropanecarboxamide in the form of a cream-coloured powder, which has the following characteristics:

Melting point: 178° C. (Köfler)

1H NMR spectrum (400 MHz, DMSO-$d_6$) δ ppm: 0.94 (d, J=5.9 Hz, 4H) 1.98 (quin, J=5.9 Hz, 1H) 5.27 (s, 2H) 7.10 (dd, J=8.8, 2.0 Hz, 1H) 7.49 (dd, J=8.5, 7.7 Hz, 1H) 7.58 (m, 2H) 7.64 (d, J=8.8 Hz, 1H) 7.73 (d, J=2.0 Hz, 1H) 12.5 (m spread-out, 1H)

Mass spectrum: LC-MS-DAD-ELSD: 392(+)=(M+H)(+)

b) 6-[(2,6-Dichlorobenzyl)oxy]-1,3-benzothiazol-2-amine can be prepared as follows:

add 289 mg of 2-(bromomethyl)-1,3-dichlorobenzene to a solution of 200 mg of 2-amino-1,3-benzothiazol-6-ol in 12.1 cm³ of a 0.1N aqueous solution of sodium hydroxide. The suspension obtained is stirred for 24 hours at about 20° C. The pH is then adjusted to the range 4-5 by adding glacial acetic acid then to 6-7 by adding solid sodium hydrogen carbonate. The mixture obtained is extracted 3 times with 40 cm³ of dichloromethane. The organic phases are combined, dried over magnesium sulphate, treated with vegetable black, then filtered and concentrated under reduced pressure (0.2 kPa). After purification of the residue by filtration on silica [eluent: dichloromethane/methanol (95/5 by volume)], we obtain 70 mg of 6-[(2,6-dichlorobenzyl)oxy]-1,3-benzothiazol-2-amine in the form of a grey meringue, which has the following characteristics:

1H NMR spectrum (300 MHz, DMSO-$d_6$) δ ppm 5.20 (s, 2H) 6.91 (dd, J=8.8, 2.6 Hz, 1H) 7.25 (m, 3H) 7.45 (m, 2H) 7.55 (m, 2H)

Example 10

1-{6-[(2,6-dichlorobenzyl)oxy]-1,3-benzothiazol-2-yl}-3-(2-morpholin-4-ylethyl)urea a) 1-{6-[(2,6-Dichlorobenzyl)oxy]-1,3-benzothiazol-2-yl}-3-(2-morpholin-4-ylethyl)urea can be prepared as follows:

a solution of 300 mg of {6-[(2,6-dichlorobenzyl)oxy]-1,3-benzothiazol-2-yl}phenyl carbamate and 0.088 cm³ of 2-morpholin-4-ylethanamine in 7 cm³ of tetrahydrofuran is stirred for about twenty hours at around 20° C. The mixture is diluted with 10 cm³ of dichloromethane. The solution obtained is washed twice with 10 cm³ of a 0.1N aqueous solution of sodium hydroxide, then twice with 10 cm³ of water before being dried over magnesium sulphate, filtered and concentrated to dryness under reduced pressure (0.2 kPa). After purification of the residue by silica-column flash chromatography [eluent: dichloromethane/methanol (95/5 by volume)], we obtain 171 mg of 1-{6-[(2,6-dichlorobenzyl)oxy]-1,3-benzothiazol-2-yl}-3-(2-morpholin-4-ylethyl)urea in the form of a white solid, which has the following characteristics:

Melting point: 268-271° C. (Büchi)

1H NMR spectrum (400 MHz, DMSO-$d_6$) δ ppm: 2.38-2.46 (m, 6H) 3.29 (m partially masked, 2H) 3.60 (m. 4H) 5.26 (s, 2H) 6.79 (t broad, J=5.6 Hz 1H) 7.04 (dd, J=8.5, 2.9 Hz, 1H) 7.47 (dd, J=8.8, 7.8 Hz, 1H) 7.52 (d, J=8.5 Hz, 1H) 7.58 (m, 2H) 7.65 (d, J=2.9 Hz, 1H) 10.7 (m spread-out, 1H)

Mass spectrum: LC-MS-DAD-ELSD: 481(+)=(M+H)(+)

b) {6-[(2,6-Dichlorobenzyl)oxy]-1,3-benzothiazol-2-yl}phenyl carbamate can be prepared as follows:

a mixture of 1.88 g of 6-[(2,6-dichlorobenzyl)oxy]-1,3-benzothiazol-2-amine, 1.81 g of phenyl chlorocarbonate, 0.97 g of sodium hydrogen carbonate in 25 cm³ of tetrahydrofuran and 2.5 cm³ of water is stirred at around 20° C. for about 70 hours. The grey suspension obtained is filtered, the filter cake is washed twice with 5 cm³ of water, then dried in a ventilated stove at about 50° C. We obtain 608 mg of {6-[(2,6-dichlorobenzyl)oxy]-1,3-benzothiazol-2-yl}phenyl carbamate in the form of a white solid, which has the following characteristics:

Rf CCM silica=0.57 [eluent: dichloromethane/methanol (98/2 by volume)]

Mass spectrum: LC-MS-DAD-ELSD: 445(+)=(M+H)(+)

Example 11

1-{6-[(2,6-dichlorobenzyl)oxy]-1,3-benzothiazol-2-yl}-3-(3-morpholin-4-ylpropyl)urea 1-{6-[(2,6-Dichlorobenzyl)oxy]-1,3-benzothiazol-2-yl}-3-(3-morpholin-4-ylpropyl)urea can be prepared as in Example 10a but from 0.3 g of {6-[(2,6-dichlorobenzyl)oxy]-1,3-benzothiazol-2-yl}phenyl carbamate and 97 mg of 3-morpholin-4-ylpropan-1-amine. After purification of the residue by silica-column flash chromatography [eluent: dichloromethane/methanol (95/5 by volume)], we obtain 182 mg of 1-{6-[(2,6-dichlorobenzyl)oxy]-1,3-benzothiazol-2-yl}-3-(3-morpholin-4-ylpropyl)urea in the form of a white solid, which has the following characteristics:

Melting point: 162-166° C. (Büchi)

1H NMR spectrum (400 MHz, DMSO-$d_6$) δ ppm: 1.63 (m, 2H) 2.28-2.37 (m, 6H) 3.19 (q, J=6.4 Hz, 2H) 3.58 (m, 4H) 5.25 (s, 2H) 6.80 (t broad, J=6.4 Hz, 1H) 7.03 (dd, J=8.8, 2.4 Hz, 1H) 7.47 (dd, J=8.8, 7.5 Hz, 1H) 7.51 (d, J=8.8 Hz, 1H) 7.58 (m, 2H) 7.64 (d, J=2.4 Hz, 1H) 10.66 (m spread-out, 1H)

Mass spectrum: LC-MS-DAD-ELSD: 495(+)=(M+H)(+)

Example 12

6-[(2,6-difluorobenzyl)oxy]-1,3-benzothiazol-2-amine

6-[(2,6-Difluorobenzyl)oxy]-1,3-benzothiazol-2-amine can be prepared as in Example 8 but from 1 g of 2-amino-1,3-benzothiazol-6-ol and 1.24 g of 2-(bromomethyl)-1,3-difluorobenzene. After purification of the residue by silica-column flash chromatography [eluent: dichloromethane/methanol (92/8 by volume)], we obtain 317 mg of 6-[(2,6-difluorobenzyl)oxy]-1,3-benzothiazol-2-amine in the form of a white solid, which has the following characteristics:

Melting point: 178° C. (Büchi)

1H NMR spectrum (400 MHz, DMSO-$d_6$) δ ppm: 5.08 (s, 2H) 6.88 (dd, J=8.8, 2.4 Hz, 1H) 7.18 (t, J=7.8 Hz, 2H) 7.23 (m, 3H) 7.40 (d, J=2.4 Hz, 1H) 7.51 (m, 1H)

Mass spectrum: LC-MS-DAD-ELSD: 293(+)=(M+H)(+)

Example 13

1-{6-[(2,6-difluorobenzyl)oxy]-1,3-benzothiazol-2-yl}-3-(2-morpholin-4-ylethyl)urea a) 1-{6-[(2,6-Difluorobenzyl)oxy]-1,3-benzothiazol-2-yl}-3-(2-morpholin-4-ylethyl)urea can be prepared as in Example 10a but from 160 mg of {6-[(2,6-difluorobenzyl)oxy]-1,3-benzothiazol-2-yl}phenyl carbamate and 0.051 cm³ of 2-morpholin-4-ylethanamine. We obtain 225 mg of 1-{6-[(2,6-difluorobenzyl)oxy]-1,3-benzothiazol-2-yl}-3-(2-morpholin-4-ylethyl)urea in the form of a white solid, which has the following characteristics:

Melting point: 219° C. (Büchi)

1H NMR spectrum (400 MHz, DMSO-$d_6$) δ ppm 2.40 (m, 6H) 3.20-3.35 (m partially masked, 2H) 3.58 (m. 4H) 5.11 (s, 2H) 6.76 (t broad, J=6.0 Hz, 1H) 6.99 (dd, J=8.6, 2.7 Hz, 1H) 7.17 (t, J=7.8 Hz, 2H) 7.49 (d, J=8.6 Hz, 1H) 7.51 (m, 1H) 7.58 (d, J=2.7 Hz, 1H) 10.65 (m spread-out, 1H)

Mass spectrum: LC-MS-DAD-ELSD: 449(+)=(M+H)(+)

b) {6-[(2,6-Difluorobenzyl)oxy]-1,3-benzothiazol-2-yl}phenyl carbamate can be prepared as in Example 10b but from 0.25 g of 6-[(2,6-difluorobenzyl)oxy]-1,3-benzothiazol-2-amine and 0.268 g of phenyl chlorocarbonate. We obtain 0.347 g of {6-[(2,6-difluorobenzyl)oxy]-1,3-benzothiazol-2-yl}phenyl carbamate in the form of a white solid, which has the following characteristics:

Melting point: 216° C. (Büchi)

Mass spectrum: LC-MS-DAD-ELSD: 413(+)=(M+H)(+)

Example 14

1-(2-morpholin-4-ylethyl)-3-[6-(1-phenylethoxy)-1,3-benzothiazol-2-yl]urea a) 1-(2-Morpholin-4-ylethyl)-3-[6-(1-phenylethoxy)-1,3-benzothiazol-2-yl]urea can be prepared as described in Example 10a but from 0.34 g of [6-(1-phenylethoxy)-1,3-benzothiazol-2-yl]phenyl carbamate and 0.14 g of 2-morpholin-4-ylethanamine. After purification of the residue by silica-column flash chromatography [eluent: dichloromethane/methanol (92.5/7.5 by volume)], we obtain 0.32 g of 1-(2-morpholin-4-ylethyl)-3-[6-(1-phenylethoxy)-1,3-benzothiazol-2-yl]urea in the form of a white powder, which has the following characteristics:

Melting point: 161° C. (Köfler)

1H NMR spectrum (400 MHz, DMSO-d$_6$) δ ppm: 1.55 (d, J=6.4 Hz, 3H) 2.40 (m, 6H) 3.25 (q, J=5.9 Hz, 2H) 3.59 (m, 4H) 5.51 (q, J=6.4 Hz, 1H) 6.81 (t broad, J=5.9 Hz, 1H) 6.94 (dd, J=8.8, 2.4 Hz, 1H) 7.25 (t, broad, J=7.6 Hz, 1H) 7.34 (t, J=7.6 Hz, 2H) 7.42 (m, 4H) 10.65 (m spread-out, 1H)

Mass spectrum: LC-MS-DAD-ELSD: 427(+)=(M+H)(+)

b) [6-(1-Phenylethoxy)-1,3-benzothiazol-2-yl]phenyl carbamate can be prepared as in Example 10b but from 0.3 g of 6-(1-phenylethoxy)-1,3-benzothiazol-2-amine and 0.695 g of phenyl chlorocarbonate. We obtain 0.344 g of [6-(1-phenylethoxy)-1,3-benzothiazol-2-yl]phenyl carbamate in the form of beige powder, which has the following characteristics:

Melting point: 173-175° C. (Köfler)

Mass spectrum: LC-MS-DAD-ELSD: 391(+)=(M+H)(+)

c) 6-(1-Phenylethoxy)-1,3-benzothiazol-2-amine can be prepared as in Example 8 but from 0.5 g of 2-amino-1,3-benzothiazol-6-ol and 0.555 g of (1-bromoethyl)benzene. After purification of the residue by silica-column flash chromatography [eluent: dichloromethane/methanol (95/5 by volume)], we obtain 0.308 g of 641-phenylethoxy)-1,3-benzothiazol-2-amine in the form of a thick brown oil, which has the following characteristics:

Rf CCM silica=0.22 [eluent: dichloromethane/methanol (95/5 by volume)]

Mass spectrum: LC-MS-DAD-ELSD: 271(+)=(M+H)(+)

Example 15

1-{6-[(2-chloro-6-fluorobenzyl)oxy]-1,3-benzothiazol-2-yl}-3-(2-morpholin-4-ylethyl)urea a) 1-{6-[(2-Chloro-6-fluorobenzyl)oxy]-1,3-benzothiazol-2-yl}-3-(2-morpholin-4-ylethyl)urea can be prepared as in Example 10a but from 0.2 g of {6-[(2-chloro-6-fluorobenzyl)oxy]-1,3-benzothiazol-2-yl}phenyl carbamate and 0.061 cm$^3$ of 2-morpholin-4-ylethanamine. We obtain 0.196 g of 1-{6-[(2-chloro-6-fluorobenzyl)oxy]-1,3-benzothiazol-2-yl}-3-(2-morpholin-4-ylethyl)urea in the form of a white solid, which has the following characteristics:

Melting point: 210° C. (Büchi)

1H NMR spectrum (400 MHz, DMSO-d$_6$) δ ppm: 2.42 (m, 6H) 3.18-3.42 (m masked, 2H) 3.60 (m, 4H) 5.17 (s. 2H) 6.79 (s broad, 1H) 7.02 (dd, J=8.8, 2.4 Hz, 1H) 7.32 (t, J=8.8 Hz, 1H) 7.43 (d, J=8.8 Hz, 1H) 7.51 (m, 2H) 7.62 (d, J=2.4 Hz, 1H) 10.67 (m spread-out, 1H)

Mass spectrum: LC-MS-DAD-ELSD: 465(+)=(M+H)(+)

b) {6-[(2-Chloro-6-fluorobenzyl)oxy]-1,3-benzothiazol-2-yl}phenyl carbamate can be prepared as in Example 10b but from 0.374 g of 6-[(2-chloro-6-fluorobenzyl)oxy]-1,3-benzothiazol-2-amine and 0.379 g of phenyl chlorocarbonate. We obtain 0.375 g of {6-[(2-chloro-6-fluorobenzyl)oxy]-1,3-benzothiazol-2-yl}phenyl carbamate in the form of a white solid, which has the following characteristics:

Melting point: 227° C. (Büchi)

1H NMR spectrum (500 MHz, DMSO-d$_6$) δ ppm: 5.19 (s, 2H) 7.10 (dd, J=8.8, 2.0 Hz, 1H) 7.24-7.37 (m, 4H) 7.46 (m, 3H) 7.53 (m, 1H) 7.65 (d, J=8.8 Hz, 1H) 7.75 (d, J=2.0 Hz, 1H) 12.52 (s broad, 1H)

Mass spectrum: LC-MS-DAD-ELSD: 429(+)=(M+H)(+)

Example 16

1-{6-[(2,6-dichloropyridin-4-yl)methoxy]-1,3-benzothiazol-2-yl}-3-(2-morpholin-4-ylethyl)urea a) 1-{6-[(2,6-Dichloropyridin-4-yl)methoxy]-1,3-benzothiazol-2-yl}-3-(2-morpholin-4-ylethyl)urea can be prepared as in Example 10a but from 0.4 g of {6-[1-(2,6-dichloropyridin-4-yl)ethoxy]-1,3-benzothiazol-2-yl}phenyl carbamate and 0.14 g of 2-morpholin-4-ylethanamine. We obtain 0.338 g of 1-{6-[(2,6-dichloropyridin-4-yl)methoxy]-1,3-benzothiazol-2-yl}-3-(2-morpholin-4-ylethyl)urea in the form of a white solid, which has the following characteristics:

Melting point: 193° C. (Köfler)

1H NMR spectrum (400 MHz, DMSO-d$_6$) δ ppm: 2.42 (m, 6H) 3.28 (m partially masked, 2H) 3.60 (m, 4H) 5.24 (s, 2H) 6.79 (s broad, 1H) 7.07 (dd, J=8.8, 2.6 Hz, 1H) 7.53 (d, J=8.8 Hz, 1H) 7.57 (d, J=2.6 Hz, 1H) 7.62 (s, 2H) 10.75 (m spread-out, 1H)

Mass spectrum: LC-MS-DAD-ELSD: 482(+)=(M+H)(+)

b) {6-[1-(2,6-Dichloropyridin-4-yl)ethoxy]-1,3-benzothiazol-2-yl}phenyl carbamate can be prepared as in Example 10b but from 0.30 g of 6-[1-(2,6-dichloropyridin-4-yl)ethoxy]-1,3-benzothiazol-2-amine and 0.309 g of phenyl chlorocarbonate. We obtain 0.406 g of 6-[1-(2,6-dichloropyridin-4-yl)ethoxy]-1,3-benzothiazol-2-yl}phenyl carbamate in the form of a beige solid, which has the following characteristics:

Melting point: 210-215° C. (Köfler)

Mass spectrum: LC-MS-DAD-ELSD: 446(+)=(M+H)(+)

c) 6-[1-(2,6-Dichloropyridin-4-yl)ethoxy]-1,3-benzothiazol-2-amine can be prepared as in Example 8 but from 0.50 g of 2-amino-1,3-benzothiazol-6-ol and 0.723 g of 4-(bromomethyl)-2,6-dichloropyridine. After purification of the residue by silica-column flash chromatography [eluent: dichloromethane/methanol (95/5 by volume)], we obtain 306 mg of -[1-(2,6-dichloropyridin-4-yl)ethoxy]-1,3-benzothiazol-2-amine in the form of a beige solid, which has the following characteristics:

Melting point: 165-170° C. (Köfler)

Mass spectrum: LC-MS-DAD-ELSD: 326(+)=(M+H)(+)

Example 17

1-{6-[1-(2,6-dichlorophenyl)ethoxy]-1,3-benzothiazol-2-yl}-3-(2-morpholin-4-ylethyl)urea a) 1-{6-[1-(2,6-Dichlorophenyl)ethoxy]-1,3-benzothiazol-2-yl}-3-(2-morpholin-4-ylethyl)urea can be prepared as in Example 10a but from 0.36 g of {6-[1-(2,6-dichlorophenyl)ethoxy]-1,3-benzothiazol-2-yl}phenyl carbamate and 0.112 mg of 2-morpholin-4-ylethanamine. We obtain 0.187 g of 1-{6-[1-(2,6-dichlorophenyl)ethoxy]-1,3-benzothiazol-2-yl}-3-(2-morpholin-4-ylethyl)urea in the form of a white solid, which has the following characteristics:

Melting point: 165-168° C. (Köfler)

1H NMR spectrum (400 MHz, DMSO-d$_6$) δ ppm: 1.73 (d, J=6.7 Hz, 3H) 2.40 (m, 6H) 3.26 (m, 2H) 3.59 (m, 4H) 6.06 (q, J=6.7 Hz, 1H) 6.76 (s broad, 1H) 6.88 (dd, J=8.8, 2.4 Hz, 1H) 7.22-7.33 (m, 2H) 7.43 (d, J=7.8 Hz, 3H) 10.5 (m spread-out, 1H)

Mass spectrum: LC-MS-DAD-ELSD: 493(+)=(M−H)(−); 495(+)=(M+H)(+)

b) {6-[1-(2,6-Dichlorophenyl)ethoxy]-1,3-benzothiazol-2-yl}phenyl carbamate can be prepared as in Example 10b but from 0.35 g of 6-[1-(2,6-dichlorophenyl)ethoxy]-1,3-benzothiazol-2-amine and 0.646 g of phenyl chlorocarbonate. We obtain 0.460 g of {6-[1-(2,6-dichlorophenyl)ethoxy]-1,3-benzothiazol-2-yl}phenyl carbamate in the form of a white powder, which has the following characteristics:

Melting point: 230° C. (Köfler)

Mass spectrum: LC-MS-DAD-ELSD: 459(+)=(M+H)(+)

c) 6-[1-(2,6-Dichlorophenyl)ethoxy]-1,3-benzothiazol-2-amine can be prepared as in Example 8 but from 0.5 g of 2-amino-1,3-benzothiazol-6-ol and 1.24 g of 1,3-dichloro-2-(1-chloroethyl)benzene. After purification of the residue by silica-column flash chromatography [eluent: dichloromethane/methanol (95/5 by volume)], we obtain 362 mg of 6-[1-(2,6-dichlorophenyl)ethoxy]-1,3-benzothiazol-2-amine in the form of a pink solid, which has the following characteristics:

Melting point: 188° C. (Köfler)

Mass spectrum: LC-MS-DAD-ELSD: 339(+)=(M+H)(+)

Example 18

1-{6-[1-(2,6-difluorophenyl)ethoxy]-1,3-benzothiazol-2-yl}-3-(2-morpholin-4-ylethyl)urea a) 1-{6-[1-(2,6-Difluorophenyl)ethoxy]-1,3-benzothiazol-2-yl}-3-(2-morpholin-4-ylethyl)urea can be prepared as in Example 10a but from 0.26 g of {6-[1-(2,6-difluorophenyl)ethoxy]-1,3-benzothiazol-2-yl}phenyl carbamate and 0.873 mg of 2-morpholin-4-ylethanamine. After purification of the residue by silica-column flash chromatography [eluent: dichloromethane/methanol (92/8 by volume)], we obtain 0.260 g de1-{6-[1-(2,6-difluorophenyl)ethoxy]-1,3-benzothiazol-2-yl}-3-(2-morpholin-4-ylethyl)urea in the form of a white meringue, which has the following characteristics:

Rf CCM silica=0.18 [eluent: dichloromethane/methanol (95/5 by volume)]

1H NMR spectrum (400 MHz, DMSO-$d_6$) δ ppm: 1.71 (d, J=6.6 Hz, 3H) 2.40 (m, 6H) 3.26 (q, J=5.9 Hz, 2H) 3.58 (m, 4H) 5.79 (q, J=6.6 Hz, 1H) 6.76 (t broad, J=5.9 Hz 1H) 6.93 (dd, J=8.6, 2.7 Hz, 1H) 7.06 (t, J=8.3 Hz, 2H) 7.37 (m, 1H) 7.42 (m, 2H) 10.64 (m spread-out, 1H)

Mass spectrum: LC-MS-DAD-ELSD: 463(+)=(M+H)(+)

b) {6-[1-(2,6-Difluorophenyl)ethoxy]-1,3-benzothiazol-2-yl}phenyl carbamate can be prepared as in Example 10b but from 0.22 g of 6-[1-(2,6-difluorophenyl)ethoxy]-1,3-benzothiazol-2-amine and 0.241 g of phenyl chlorocarbonate. We obtain 0.266 g of {6-[1-(2,6-difluorophenyl)ethoxy]-1,3-benzothiazol-2-yl}phenyl carbamate in the form of a cream-coloured powder, which has the following characteristics:

Melting point: 190-195° C. (Köfler)

Mass spectrum: LC-MS-DAD-ELSD: 427(+)=(M+H)(+)

c) 6-[1-(2,6-Difluorophenyl)ethoxy]-1,3-benzothiazol-2-amine can be prepared as in Example 8 but from 0.5 g of 2-amino-1,3-benzothiazol-6-ol and 1.24 g of 2-(1-chloroethyl)-1,3-difluorobenzene. After purification of the residue by silica-column flash chromatography [eluent: dichloromethane/methanol (92/8 by volume)], we obtain 222 mg of 6-[1-(2,6-difluorophenyl)ethoxy]-1,3-benzothiazol-2-amine in the form of a pink solid, which has the following characteristics:

Mass spectrum: LC-MS-DAD-ELSD: 307(+)=(M+H)(+)

d) 2-(1-Chloroethyl)-1,3-difluorobenzene can be prepared as in Example 2e but from 2.45 g of 2,4,6-trichloro-1,3,5-triazine and 2 g of 1-(2,6-difluoro-phenyl)ethanol. After filtration on 150 cm$^3$ of silica (eluent: dichloromethane), we obtain 1.92 g of 2-(1-chloroethyl)-1,3-difluorobenzene in the form of a colorless oil, which has the following characteristics:

1H NMR spectrum (500 MHz, DMSO-$d_6$) δ ppm: 1.90 (d, J=6.9 Hz, 3H) 5.58 (q, J=6.9 Hz, 1H) 7.16 (t, J=8.9 Hz, 2H) 7.48 (m, 1H)

Mass spectrum: SM-EI: 176(+)=M(+)

Example 19

1-(2-morpholin-4-ylethyl)-3-(6-{1-[2-(trifluoromethyl)phenyl]ethoxy}-1,3-benzothiazol-2-yl)urea a) 1-(2-Morpholin-4-ylethyl)-3-(6-{1-[2-(trifluoromethyl)phenyl]ethoxy}-1,3-benzothiazol-2-yl)urea can be prepared as in Example 10a but from 0.28 g of (6-{1-[2-(trifluoromethyl)phenyl]ethoxy}-1,3-benzothiazol-2-yl)phenyl carbamate and 0.875 mg of 2-morpholin-4-ylethanamine. After purification of the residue by silica-column flash chromatography [eluent: dichloromethane/methanol (93/7 by volume)], we obtain 0.147 g of 1-(2-morpholin-4-ylethyl)-3-(6-{1-[2-(trifluoromethyl)phenyl]ethoxy}-1,3-benzothiazol-2-yl)urea in the form of a white meringue, which has the following characteristics:

1H NMR spectrum (400 MHz, DMSO-$d_6$) δ ppm: 1.60 (d, J=6.4 Hz, 3H) 2.40 (m, 6H) 3.26 (q, J=6.0 Hz, 2H) 3.58 (m, 4H) 5.70 (q, J=6.4 Hz, 1H) 6.78 (m broad, 1H) 6.90 (dd, J=8.8, 2.4 Hz, 1H) 7.37 (d, J=2.4 Hz, 1H) 7.43 (d, J=8.8 Hz, 1H) 7.49 (t, J=7.8 Hz, 1H) 7.64-7.75 (m, 2H) 7.83 (d, J=7.8 Hz, 1H) 10.7 (m spread-out, 1H)

Mass spectrum: LC-MS-DAD-ELSD: 495(+)=(M+H)(+)

b) (6-{1-[2-(Trifluoromethyl)phenyl]ethoxy}-1,3-benzothiazol-2-yl)phenyl carbamate can be prepared as in Example 10b but from 0.21 g of 6-{1-[2-(trifluoromethyl)phenyl]ethoxy}-1,3-benzothiazol-2-amine and 0.388 g of phenyl chlorocarbonate. We obtain 0.280 g of (6-{1-[2-(trifluoromethyl)phenyl]ethoxy}-1,3-benzothiazol-2-yl)phenyl carbamate in the form of a white powder, which has the following characteristics:

Melting point: 200-205° C. (Köfler)

Mass spectrum: LC-MS-DAD-ELSD: 459(+)=(M+H)(+)

c) 6-{1-[2-(Trifluoromethyl)phenyl]ethoxy}-1,3-benzothiazol-2-amine can be prepared as in Example 8 but from 0.5 g of 2-amino-1,3-benzothiazol-6-ol and 0.761 g of 1-(1-bromoethyl)-2-(trifluoromethyl)benzene. After purification of the residue by silica-column flash chromatography [eluent: dichloromethane/methanol (95/5 by volume)], we obtain 223 mg of 6-{1-[2-(trifluoromethyl)phenyl]ethoxy}-1,3-benzothiazol-2-amine in the form of a pink solid, which has the following characteristics:

Mass spectrum: LC-MS-DAD-ELSD: 339(+)=(M+H)(+)

Example 20

1-{6-[(1,3-dimethyl-1H-pyrazol-5-yl)methoxy]-1,3-benzothiazol-2-yl}-3-(2-morpholin-4-ylethyl)urea a) 1-{6-[(1,3-Dimethyl-1H-pyrazol-5-yl)methoxy]-1,3-benzothiazol-2-yl}-3-(2-morpholin-4-ylethyl)urea can be prepared as in Example 10a but from 0.240 g of {6-[(1,3-dimethyl-1H-pyrazol-5-yl)methoxy]-1,3-benzothiazol-2-yl}phenyl carbamate and 0.158 g of 2-morpholin-4-ylethanamine. After purification of the residue by silica-column flash chromatography [eluent: dichloromethane/methanol (90/10 by volume)], we obtain 0.240 g of 1-{6-[(1,3-dimethyl-1H-pyrazol-5-yl)methoxy]-1,3-benzothiazol-2-yl}-3-(2-morpholin-4-ylethyl)urea in the form of a beige powder, which has the following characteristics:

Melting point: 160° C. (Köfler)

1H NMR spectrum (400 MHz, DMSO-$d_6$) δ ppm: 2.11 (s, 3H) 2.42 (m, 6H) 3.28 (q, J=6.0 Hz, 2H) 3.60 (m, 4H) 3.74 (s, 3H) 5.11 (s, 2H) 6.14 (s, 1H) 6.85 (m broad, 1 H) 7.03 (dd, J=8.8, 2.4 Hz, 1H) 7.51 (d, J=8.8 Hz, 1H) 7.59 (d, J=2.4 Hz, 1H) 10.67 (m spread-out, 1H)

Mass spectrum: LC-MS-DAD-ELSD: 431(+)=(M+H)(+)

b) {6-[(1,3-Dimethyl-1H-pyrazol-5-yl)methoxy]-1,3-benzothiazol-2-yl}phenyl carbamate can be prepared as in Example 10b but from 0.445 g of 6-[(1,3-dimethyl-1H-pyrazol-5-yl)methoxy]-1,3-benzothiazol-2-amine and 1.016 g of phenyl chlorocarbonate. After purification of the residue by silica-column flash chromatography [eluent: dichloromethane/methanol (98/2 by volume)], we obtain 0.250 g of {6-[(1,3-dimethyl-1H-pyrazol-5-yl)methoxy]-1,3-benzothiazol-2-yl}phenyl carbamate in the form of a white powder, which has the following characteristics:

Melting point: 215° C. (Köfler)

Mass spectrum: LC-MS-DAD-ELSD: 393(−)=(M−H)(−); 395(+)=(M+H)(+)

d) 6-[(1,3-Dimethyl-1H-pyrazol-5-yl)methoxy]-1,3-benzothiazol-2-amine can be prepared as follows:

add, dropwise, a solution of 0.103 cm$^3$ of dibromine in 3 cm$^3$ of glacial acetic acid at around 20° C. to a solution of 0.44 g of 4-[(1,3-dimethyl-1H-pyrazol-5-yl)methoxy]aniline and 0.787 g of potassium thiocyanate in 6 cm$^3$ of glacial acetic acid. After stirring for about twenty hours, the reaction mixture is poured into 50 cm$^3$ of water. The pH of the solution obtained is adjusted to 8-9 by adding solid potassium carbonate. A gum forms. After stirring for about an hour, the beige solid that formed is drained, washed three times with 20 cm$^3$ of water, then dried in a desiccator under reduced pressure (0.2 kPa) in the presence of phosphoric anhydride. We obtain 0.448 g of 6-[(1,3-dimethyl-1H-pyrazol-5-yl)methoxy]-1,3-benzothiazol-2-amine in the form of a beige powder, which has the following characteristics:

Melting point: 208° C. (Köfler)

Mass spectrum: LC-MS-DAD-ELSD: 275(+)=(M+H)(+)

e) 4-[(1,3-Dimethyl-1H-pyrazol-5-yl)methoxy]aniline can be prepared as follows: in an autoclave, cover 0.046 g of platinum oxide with 10 cm$^3$ of methanol; add a solution of 0.5 g of 1,3-dimethyl-5-[(4-nitrophenoxy)methyl]-1H-pyrazole in 60 cm$^3$ of methanol. The mixture is hydrogenated under 300 kPa of hydrogen and at a temperature close to 20° C. for about 14 hours.

After the reaction mixture has been filtered and evaporated to dryness under reduced pressure, we obtain 0.44 g of 4-[(1,3-dimethyl-1H-pyrazol-5-yl)methoxy]aniline in the form of a pink solid, which has the following characteristics:

Melting point: 145° C. (Köfler)

Mass spectrum: LC-MS-DAD-ELSD: 218(+)=(M+H)(+)

f) 1,3-Dimethyl-5-[(4-nitrophenoxy)methyl]-1H-pyrazole can be prepared as follows:

add dropwise, at about 20° C., a solution of 0.894 g of (1,3-dimethyl-1H-pyrazol-5-yl)methanol in 8 cm$^3$ of tetrahydrofuran to a suspension of 0.312 g of sodium hydride (at 60% in the oil) in 10 cm$^3$ of tetrahydrofuran. The reaction mixture is then stirred for about three hours at about 20° C. The solution obtained is added dropwise to a solution of 1.1 g of 1-fluoro-4-nitrobenzene in 10 cm$^3$ of tetrahydrofuran. The resultant reaction mixture is stirred for about 60 hours then poured into 50 cm$^3$ of water. The mixture obtained is extracted three times with 50 cm$^3$ of ethyl acetate. The organic phases are combined, dried over magnesium sulphate, then filtered and concentrated under reduced pressure. The residue is taken up in 10 cm$^3$ of diisopropyl oxide, drained and then washed three times with 5 cm$^3$ of diisopropyl oxide and finally dried. We thus obtain 1.12 g of 1,3-dimethyl-5-[(4-nitrophenoxy)methyl]-1H-pyrazole in the form of a cream-coloured powder, which has the following characteristics:

Melting point: 141° C. (Köfler)

Mass spectrum: LC-MS-DAD-ELSD: 248(+)=(M+H)(+)

Example 21

1-{6-[(2,6-dichlorobenzyl)oxy]-5-fluoro-1,3-benzothiazol-2-yl}-3-(2-morpholin-4-ylethyl)urea a) 1-{6-[(2,6-Dichlorobenzyl)oxy]-5-fluoro-1,3-benzothiazol-2-yl}-3-(2-morpholin-4-ylethyl)urea can be prepared as in Example 10a but from 0.18 g of {6-[(2,6-dichlorobenzyl)oxy]-5-fluoro-1,3-benzothiazol-2-yl}phenyl carbamate and 0.056 mg of 2-morpholin-4-ylethanamine. We obtain 0.159 g of 1-{6-[(2,6-dichlorobenzyl)oxy]-5-fluoro-1, 3-benzothiazol-2-yl}-3-(2-morpholin-4-ylethyl)urea in the form of a white solid, which has the following characteristics:

Melting point: 206° C. (Köfler)

1H NMR spectrum (400 MHz, DMSO-d$_6$) δ ppm: 2.40 (m, 6H) 3.20-3.37 (m masked, 2H) 3.60 (m, 4H) 5.32 (s, 2H) 6.83 (m broad, 1H) 7.35-7.52 (m, 2H) 7.58 (m, 2H) 7.90 (d, J=8.9 Hz, 1H) 10.8 (m spread-out, 1H)

Mass spectrum: LC-MS-DAD-ELSD: 499(+)=(M+H)(+)

b) {6-[(2,6-Dichlorobenzyl)oxy]-5-fluoro-1,3-benzothiazol-2-yl}phenyl carbamate can be prepared as in Example 10b but from 0.165 g of 6-[(2,6-dichlorobenzyl)oxy]-5-fluoro-1,3-benzothiazol-2-amine and 0.301 g of phenyl chlorocarbonate. We obtain 0.188 g of {6-[(2,6-dichlorobenzyl)oxy]-5-fluoro-1,3-benzothiazol-2-yl}phenyl carbamate in the form of a white solid, which has the following characteristics:

Melting point: 245-250° C. (Büchi)

Mass spectrum: LC-MS-DAD-ELSD: 463(+)=(M+H)(+)

d) 6-[(2,6-Dichlorobenzyl)oxy]-5-fluoro-1,3-benzothiazol-2-amine can be prepared as in Example 8 but from 0.30 g of 2-amino-5-fluoro-1,3-benzothiazol-6-ol and 0.391 g of 2-(bromomethyl)-1,3-dichlorobenzene. After purification of the residue by silica-column flash chromatography [eluent: dichloromethane/methanol (95/5 by volume)], we obtain 0.165 g of 6-[(2,6-dichlorobenzyl)oxy]-5-fluoro-1,3-benzothiazol-2-amine in the form of a grey solid, which has the following characteristics:

Rf CCM silica=0.56 [eluent: dichloromethane/methanol (90/10 by volume)]

Mass spectrum: LC-MS-DAD-ELSD: 343(+)=(M+H)(+)

2-Amino-5-fluoro-1,3-benzothiazol-6-ol can be prepared as described in J. Med. Chem 1991, 34, 7, 1975

Example 22

N-{6-[(2,6-dichlorobenzyl)oxy]-5-fluoro-1,3-benzothiazol-2-yl}cyclopropanecarboxamide N-{6-[(2,6-Dichlorobenzyl)oxy]-5-fluoro-1,3-benzothiazol-2-yl}cyclopropanecarboxamide can be prepared as in Example 9a but from 0.35 g of 6-[(2,6-dichlorobenzyl)oxy]-5-fluoro-1,3-benzothiazol-2-amine and 0.107 g of cyclopropanecarboxylic acid. We obtain 0.302 g of N-{6-[(2,6-dichlorobenzyl)oxy]-5-fluoro-1,3-benzothiazol-2-yl}cyclopropanecarboxamide in the form of a cream-coloured powder, which has the following characteristics:

Melting point: 215° C. (Köfler)

1H NMR spectrum (400 MHz, DMSO-d$_6$) δ ppm: 0.94 (m, 4H) 1.99 (m, 1H) 5.35 (s, 2H) 7.50 (dd, J=8.8, 7.5 Hz, 1H) 7.59 (m, 2H) 7.62 (d, J=12.0 Hz, 1H) 8.00 (d, J=8.2 Hz, 1H) 12.6 (m spread-out, 1H)

Mass spectrum: LC-MS-DAD-ELSD: 411(+)=(M+H)(+)

Example 23

6-[1-(2,6-dichloro-3-fluorophenyl)ethoxy]-1,3-benzothiazol-2-amine a) 6-[1-(2,6-Dichloro-3-fluorophenyl)ethoxy]-1,3-benzothiazol-2-amine can be prepared as in Example 20d but from 2.9 g of 4-[1-(2,6-dichloro-3-fluorophenyl)ethoxy]aniline, 3.75 g of potassium thiocyanate and 0.494 cm$^3$ of dibromine. After purification of the residue by silica-column flash chromatography [eluent: dichloromethane/methanol (98/2 by volume)], we obtain 0.964 g of 6-[1-(2,6-dichloro-3-fluorophenyl)ethoxy]-1,3-benzothiazol-2-amine in the form of a beige powder, which has the following characteristics:

Melting point: 186-194° C. (Büchi)
Mass spectrum: LC-MS-DAD-ELSD: 357(+)/=(M+H)(+)
1H NMR spectrum (400 MHz, DMSO-d$_6$) δ ppm: 1.72 (d, J=6.6 Hz, 3H) 5.99 (q, J=6.6 Hz, 1H) 6.74 (dd, J=8.6, 2.7 Hz, 1H) 7.17 (d, J=8.6 Hz, 1H) 7.20 (d, J=2.7 Hz, 1H) 7.24 (s, 2H) 7.40 (t, J=8.8 Hz, 1H) 7.51 (dd, J=8.8, 5.4 Hz, 1H)

b) 4-[1-(2,6-Dichloro-3-fluorophenyl)ethoxy]aniline can be prepared as in Example 20e but from 0.129 g of platinum oxide and 1.88 g of 1,3-dichloro-4-fluoro-2-[1-(4-nitrophenoxy)ethyl]benzene in 160 cm$^3$ of ethanol. We thus obtain 1.63 g of 4-[1-(2,6-dichloro-3-fluorophenyl)ethoxy]aniline in the form of a brown oil, which has the following characteristics:

Rf CCM silica=0.42 [eluent: dichloromethane/methanol (98/2 by volume)]
Mass spectrum: LC-MS-DAD-ELSD: 300(+)/=(M+H)(+)

c) 1,3-Dichloro-4-fluoro-2-[1-(4-nitrophenoxy)ethyl]benzene can be prepared as in Example 20f but from 1.92 g of sodium hydride (at 60% in the oil), 9.13 g of 1-(2,6-dichloro-3-fluorophenyl)-ethanol and 6.8 g of 1-fluoro-4-nitrobenzene. After purification of the residue by silica-column flash chromatography [eluent: cyclohexane/ethyl acetate (75/25 by volume)], we obtain 12.85 g of 1,3-dichloro-4-fluoro-2-[1-(4-nitrophenoxy)ethyl]benzene in the form of a yellow oil which crystallizes, and which has the following characteristics:

Rf CCM silica=0.60 [eluent: cyclohexane/ethyl acetate (75/25 by volume)]
Mass spectrum: LC-MS-DAD-ELSD: 331(+)/=(M+H)(+)

Example 24

1-{6-[1-(2,6-dichloro-3-fluorophenyl)ethoxy]-1,3-benzothiazol-2-yl}-3-(2-morpholin-4-ylethyl)urea a) 1-{6-[1-(2,6-Dichloro-3-fluorophenyl)ethoxy]-1,3-benzothiazol-2-yl}-3-(2-morpholin-4-ylethyl)urea can be prepared as in Example 10a but from 0.160 g of {6-[1-(2,6-dichloro-3-fluorophenyl)ethoxy]-1,3-benzothiazol-2-yl}phenyl carbamate and 0.048 g of 2-morpholin-4-ylethanamine. We thus obtain 0.160 g of 1-{6-[1-(2,6-dichloro-3-fluorophenyl)ethoxy]-1,3-benzothiazol-2-yl}-3-(2-morpholin-4-ylethyl)urea in the form of a white powder, which has the following characteristics:

Melting point: 110° C. (Köfler)
1H NMR spectrum (400 MHz, DMSO-d$_6$) δ ppm: 1.74 (d, J=6.7 Hz, 3H) 2.40 (m, 6H) 3.20-3.37 (m partially masked, 2H) 3.58 (m, 4H) 6.05 (q, J=6.7 Hz, 1H) 6.80 (m broad, 1H) 6.88 (dd, J=8.8, 2.2 Hz, 1H) 7.33 (d, J=2.2 Hz, 1H) 7.36-7.46 (m, 2H) 7.51 (dd, J=9.0, 5.1 Hz, 1H) 10.65 (m spread-out, 1H)
Mass spectrum: LC-MS-DAD-ELSD: 511(−)=(M−H)(−); 513(+)=(M+H)(+)

b) {6-[1-(2,6-Dichloro-3-fluorophenyl)ethoxy]-1,3-benzothiazol-2-yl}phenyl carbamate can be prepared as in Example 10b but from 0.240 g of 6-[1-(2,6-dichloro-3-fluorophenyl)ethoxy]-1,3-benzothiazol-2-amine and 0.421 g of phenyl chlorocarbonate. We thus obtain 0.168 g of {6-[1-(2,6-dichloro-3-fluorophenyl)ethoxy]-1,3-benzothiazol-2-yl}phenyl carbamate in the form of a white powder, which has the following characteristics:

Rf CCM silica=0.73 [eluent: dichloromethane/methanol (98/2 by volume)]
Mass spectrum: LC-MS-DAD-ELSD: 478(+)=(M+H)(+)

Example 25

1-{6-[(1R)-(2,6-dichloro-3-fluorophenyl)ethoxy]-1,3-benzothiazol-2-yl}-3-(2-morpholin-4-ylethyl)urea or 1-{6-[(1S)-(2,6-dichloro-3-fluorophenyl)ethoxy]-1,3-benzothiazol-2-yl}-3-(2-morpholin-4-ylethyl)urea 0.891 g of 1-{6-[(1R.S)-(2,6-dichloro-3-fluorophenyl)ethoxy]-1,3-benzothiazol-2-yl}-3-(2-morpholin-4-ylethyl)urea was separated by chiral HPLC on Chiralcel OJ 20 µm (8×35 cm). We thus obtain 0.433 g of the dextrorotatory enantiomer 1-{6-[(1R*)-(2,6-dichloro-3-fluorophenyl)ethoxy]-1,3-benzothiazol-2-yl}-3-(2-morpholin-4-ylethyl)urea in the form of a beige powder, which has the following characteristics:

PR=+10.1°+/−0.7° C.=1.799 mg/0.5 ml DMSO on 589 nM
1H NMR spectrum (300 MHz, DMSO-d$_6$) δ ppm 1.74 (d, J=6.8 Hz, 3H) 2.40 (m, 6H) 3.20-3.40 (m partially masked, 2H) 3.58 (m, 4H) 6.05 (q, J=6.8 Hz, 1H) 6.82 (t broad, J=5.8 Hz 1H) 6.89 (dd, J=8.9, 2.6 Hz, 1H) 7.34 (d, J=2.6 Hz, 1H) 7.40 (t, J=9.0 Hz, 1H) 7.45 (d, J=8.9 Hz, 1H) 7.51 (dd, J=9.0, 5.1 Hz, 1H) 10.7 (m spread-out, 1H)
Mass spectrum: LC-MS-DAD-ELSD: 513(+)=(M+H)(+)

Example 26

1-{6-[(1R)-(2,6-dichloro-3-fluorophenyl)ethoxy]-1,3-benzothiazol-2-yl}-3-(2-morpholin-4-ylethyl)urea or 1-{6-[(1S)-(2,6-dichloro-3-fluorophenyl)ethoxy]-1,3-benzothiazol-2-yl}-3-(2-morpholin-4-ylethyl)urea 0.891 g of 1-{6-[(1RS)-(2,6-dichloro-3-fluorophenyl)ethoxy]-1,3-benzothiazol-2-yl}-3-(2-morpholin-4-ylethyl)urea was separated by chiral HPLC on Chiralcel OJ 20 µm (8×35 cm). We thus obtain 0.432 g of the laevorotatory enantiomer 1-{6-[(1S*)-(2,6-dichloro-3-fluorophenyl)ethoxy]-1,3-benzothiazol-2-yl}-3-(2-morpholin-4-ylethyl)urea in the form of a beige powder, which has the following characteristics:

PR=−6.1°+/−0.6° C.=1.916 mg/0.5 ml DMSO on 589 nM
1H NMR spectrum (300 MHz, DMSO-d$_6$) δ ppm 1.74 (d, J=6.6 Hz, 3H) 2.40 (m, 6H) 3.20-3.40 (m partially masked, 2H) 3.58 (m, 4H) 6.05 (q, J=6.6 Hz, 1H) 6.80 (t broad, J=5.6 Hz, 1H) 6.89 (dd, J=8.8, 2.6 Hz, 1H) 7.34 (d, J=2.6 Hz, 1H) 7.40 (t, J=9.0 Hz, 1H) 7.45 (d, J=8.8 Hz, 1H) 7.51 (dd, J=9.0, 5.1 Hz, 1H) 10.7 (m spread-out, 1H)
Mass spectrum: LC-MS-DAD-ELSD: 513(+)=(M+H)(+)

Example 27

6-[1-(2-chloro-6-fluoro-3-methylphenyl)ethoxy]-1,3-benzothiazol-2-amine a) 6-[1-(2-Chloro-6-fluoro-3-methylphenyl)ethoxy]-1,3-benzothiazol-2-amine can be prepared as in Example 20d but from 2 g of 4-[1-(2-chloro-6-fluoro-3-methylphenyl)ethoxy]aniline, 2.78 g of potassium thiocyanate and 0.366 cm³ of dibromine. After purification of the residue by silica-column flash chromatography [eluent: dichloromethane/methanol (98/2 by volume)], we obtain 0.287 g of 6-[1-(2-chloro-6-fluoro-3-methylphenyl)ethoxy]-1,3-benzothiazol-2-amine in the form of a beige powder, which has the following characteristics:

Melting point: 170° C. (Köfler)
Mass spectrum: LC-MS-DAD-ELSD: 337(+)=(M+H)(+)
1H NMR spectrum (400 MHz, DMSO-d$_6$) δ ppm: 1.67 (d, J=6.7 Hz, 3H) 2.29 (s, 3H) 5.87 (q, J=6.7 Hz, 1H) 6.75 (dd, J=8.7, 2.7 Hz, 1H) 7.09 (dd, J=10.8, 8.3 Hz, 1H) 7.15 (d, J=8.7 Hz, 1H) 7.17-7.25 (m, 3H) 7.31 (dd, J=8.3, 5.9 Hz, 1H)

b) 4-[1-(2-Chloro-6-fluoro-3-methylphenyl)ethoxy]aniline can be prepared as in Example 20e but from 0.183 g of platinum oxide and 2.5 g of 2-chloro-4-fluoro-1-methyl-3-[1-(4-nitrophenoxy)ethyl]benzene in 190 cm³ of methanol. We thus obtain 2.2 g of 4-[1-(2-chloro-6-fluoro-3-methylphenyl)ethoxy]aniline in the form of a green resin, which has the following characteristics:

Rf CCM silica=0.26 [eluent: dichloromethane]
Mass spectrum: LC-MS-DAD-ELSD: 280(+)=(M+H)(+)

c) 2-Chloro-4-fluoro-1-methyl-3-[1-(4-nitrophenoxy)ethyl]benzene can be prepared as in Example 20f but from 0.466 g of sodium hydride (at 60% in the oil), 0.5 g of 1-(2-chloro-6-fluoro-3-methylphenyl)ethanol and 0.458 g of 1-fluoro-4-nitrobenzene. We thus obtain 2.56 g of 2-chloro-4-fluoro-1-methyl-3-[1-(4-nitrophenoxy)ethyl]benzene in the form of a cream-coloured powder, which has the following characteristics:

Melting point: 125° C. (Köfler)
Mass spectrum: LC-MS-DAD-ESD: 310(+)=(M+H)(+)

d) 1-(2-Chloro-6-fluoro-3-methylphenyl)ethanol can be prepared as in Example 3e but from 10 g of 1-(2-chloro-6-fluoro-3-methylphenyl)ethanone and 53 cm³ of a 1M solution of aluminium lithium hydride in tetrahydrofuran. We thus obtain 10.1 g of 1-(2-chloro-6-fluoro-3-methylphenyl)ethanol in the form of a colorless oil, which has the following characteristics:

1H NMR spectrum (400 MHz, DMSO-d$_6$) δ ppm: 1.44 (d, J=6.4 Hz, 3H) 2.30 (s, 3H) 5.28 (s broad, 2H) 7.06 (dd, J=10.8, 8.3 Hz, 1H) 7.27 (dd, J=8.3, 5.9 Hz, 1H)
Mass spectrum: SM-EI: 188(+)=M(+)

Example 28

1-{6-[1-(2-chloro-6-fluoro-3-methylphenyl)ethoxy]-1,3-benzothiazol-2-yl}-3-(2-morpholin-4-ylethyl)urea a) 1-{6-[1-(2-Chloro-6-fluoro-3-methylphenyl)ethoxy]-1,3-benzothiazol-2-yl}-3-(2-morpholin-4-ylethyl)urea can be prepared as in Example 10a but from 0.9 g of {6-[1-(2-chloro-6-fluoro-3-methylphenyl)ethoxy]-1,3-benzothiazol-2-yl}phenyl carbamate and 0.513 g of 2-morpholin-4-ylethanamine. We thus obtain 0.884 g of 1-{6-[1-(2-chloro-6-fluoro-3-methylphenyl)ethoxy]-1,3-benzothiazol-2-yl}-3-(2-morpholin-4-ylethyl)urea in the form of a white powder, which has the following characteristics:

Melting point: 165-170° C. (Köfler)
1H NMR spectrum (400 MHz, DMSO-d$_6$) δ ppm: 1.70 (d, J=6.7 Hz, 3H) 2.30 (s, 3H) 2.40 (m, 6H) 3.26 (q, J=5.4 Hz, 2H) 3.59 (m, 4H) 5.94 (q, J=6.7 Hz, 1H) 6.75 (m broad, 1H) 6.90 (dd, J=8.8, 2.4 Hz, 1H) 7.10 (dd, J=10.8, 8.3 Hz, 1H) 7.32 (dd, J=8.3, 5.9 Hz, 1H) 7.37 (d, J=2.4 Hz, 1H) 7.44 (d, J=8.8 Hz, 1H) 10.48 (m spread-out, 1H)
Mass spectrum: HPLC-MS-DAD-ELSD: 491(−)=(M−H)(−); 493(+)=(M+H)(+)

b) {6-[1-(2-Chloro-6-fluoro-3-methylphenyl)ethoxy]-1,3-benzothiazol-2-yl}phenyl carbamate can be prepared as in Example 10b but from 1 g of 6-[1-(2-chloro-6-fluoro-3-methylphenyl)ethoxy]-1,3-benzothiazol-2-amine and 1.86 g of phenyl chlorocarbonate. We thus obtain 0.97 g of {6-[1-(2-chloro-6-fluoro-3-methylphenyl)ethoxy]-1,3-benzothiazol-2-yl}phenyl carbamate in the form of a white powder, which has the following characteristics:

Melting point: 205° C. (Köfler)
Mass spectrum: HPLC-MS-DAD-ELSD: 457(+)=(M+H)(+)

Example 29

1-{6-[1-(2,6-dichlorophenyl)ethoxy]-5-fluoro-1,3-benzothiazol-2-yl}-3-(2-morpholin-4-ylethyl)urea a) 1-{6-[1-(2,6-Dichlorophenyl)ethoxy]-5-fluoro-1,3-benzothiazol-2-yl}-3-(2-morpholin-4-ylethyl)urea can be prepared as in Example 10a but from 0.4 g of {6-[1-(2,6-dichlorophenyl)ethoxy]-5-fluoro-1,3-benzothiazol-2-yl}phenyl carbamate and 0.12 g of 2-morpholin-4-ylethanamine. After purification of the residue by silica-column flash chromatography [eluent: dichloromethane/methanol (95/5 by volume)], we obtain 0.379 g of 1-{6-[1-(2,6-dichlorophenyl)ethoxy]-5-fluoro-1,3-benzothiazol-2-yl}-3-(2-morpholin-4-ylethyl)urea in the form of a beige powder, which has the following characteristics:

Melting point: 200-205° C. (Köfler)
1H NMR spectrum (400 MHz, DMSO-d$_6$) δ ppm: 1.77 (d, J=6.8 Hz, 3H) 2.39 (m, 6H) 3.26 (q, J=5.9 Hz, 2H) 3.58 (m, 4H) 6.07 (q, J=6.8 Hz, 1H) 6.74 (s broad, 1H) 7.25-7.36 (m, 2H) 7.41-7.49 (m, 3H) 10.84 (m, 1H)
Mass spectrum: LC-MS-DAD-ELSD: 511(−)=(M−H)(−); 513(+)=(M+H)(+)

b) {6-[1-(2,6-Dichlorophenyl)ethoxy]-5-fluoro-1,3-benzothiazol-2-yl}phenyl carbamate can be prepared as in Example 10b but from 0.35 g of 6-[1-(2,6-dichlorophenyl)ethoxy]-5-fluoro-1,3-benzothiazol-2-amine and 0.614 g of phenyl chlorocarbonate. We thus obtain 0.46 g of {6-[1-(2,6-dichlorophenyl)ethoxy]-5-fluoro-1,3-benzothiazol-2-yl}phenyl carbamate in the form of a white powder, which has the following characteristics:

Melting point: 250° C. (Köfler)
Mass spectrum: HPLC-MS-DAD-ELSD: 477(+)=(M+H)(+)

d) 6-[1-(2,6-Dichlorophenyl)ethoxy]-5-fluoro-1,3-benzothiazol-2-amine can be prepared as in Example 20d but from 0.566 g of 4-[1-(2,6-dichlorophenyl)ethoxy]-3-fluoroaniline, 0.733 g of potassium thiocyanate and 0.097 cm³ of dibromine. After purification of the residue by silica-column flash chromatography [eluent: dichloromethane/methanol (95/5 by volume)], we obtain 0.39 g of 6-[1-(2-chloro-6-fluoro-3-methylphenyl)ethoxy]-1,3-benzothiazol-2-amine in the form of cream-coloured crystals, which have the following characteristics:

Melting point: melting at 225° C. (Köfler)

Mass spectrum: LC-MS-DAD-ELSD: 357(+)=(M+H)(+)

e) 4-[1-(2,6-Dichlorophenyl)ethoxy]-3-fluoroaniline can be prepared as in Example 20e but from 0.05 g of platinum oxide and 0.73 g of 1,3-dichloro-2-[1-(2-fluoro-4-nitrophenoxy)ethyl]benzene in 190 cm$^3$ of methanol. We thus obtain 0.566 g of 4-[1-(2,6-dichlorophenyl)ethoxy]-3-fluoroaniline in the form of an orange resin, which has the following characteristics:

Rf CCM silica=0.39 [eluent: dichloromethane]

Mass spectrum: LC-MS-DAD-ELSD: 300(+)=(M+H)(+)

f) 1,3-Dichloro-2-[1-(2-fluoro-4-nitrophenoxy)ethyl]benzene can be prepared as in Example 20f but from 0.115 g of sodium hydride (at 60% in the oil), 0.5 g of 1-(2-chloro-6-fluoro-3-methylphenyl)ethanol and 1.5 g of 1,2-difluoro-4-nitrobenzene. We thus obtain 2.56 g of 1,3-dichloro-2-[1-(2-fluoro-4-nitrophenoxy)ethyl]benzene in the form of a beige powder, which has the following characteristics:

Melting point: 120° C. (Köfler)

Mass spectrum: SM-EI: 329(+)=M(+)

Example 30

6-[1-(2,6-dichloro-3-fluorophenyl)ethoxy]-5-fluoro-1,3-benzothiazol-2-amine a) 6-[1-(2,6-Dichloro-3-fluorophenyl)ethoxy]-5-fluoro-1,3-benzothiazol-2-amine can be prepared as in Example 20d but from 2.6 g of 4-[1-(2,6-dichloro-3-fluorophenyl)ethoxy]-3-fluoroaniline, 3.17 g of potassium thiocyanate and 0.418 cm$^3$ of dibromine. After purification of the residue by silica-column flash chromatography [eluent: dichloromethane/methanol (98/2 by volume)], we obtain 0.186 g of 6-[1-(2,6-dichloro-3-fluorophenyl)ethoxy]-5-fluoro-1,3-benzothiazol-2-amine in the form of a beige powder, which has the following characteristics:

Melting point: 223° C. (Köfler)

Mass spectrum: HPLC-MS-DAD-ELSD: 375(+)=(M+H)(+)

1H NMR spectrum (400 MHz, DMSO-d$_6$) δ ppm: 1.76 (d, J=6.6 Hz, 3H) 5.96 (q, J=6.6 Hz, 1H) 7.17 (d, J=12.2 Hz, 1H) 7.22 (d, J=8.3 Hz, 1H) 7.43 (m, 3H) 7.51 (dd, J=8.8, 5.4 Hz, 1H)

b) 4-[1-(2,6-Dichloro-3-fluorophenyl)ethoxy]-3-fluoroaniline can be prepared as in Example 20e but from 0.196 g of platinum oxide and 3 g of 1,3-dichloro-4-fluoro-2-[1-(2-fluoro-4-nitrophenoxy)ethyl]benzene in 200 cm$^3$ of methanol. We thus obtain 2.62 g of 4-[1-(2,6-dichloro-3-fluorophenyl)-3-fluoroaniline in the form of a green oil, which has the following characteristics:

Rf CCM silica=0.31 [eluent: dichloromethane]

Mass spectrum: LC-MS-DAD-ELSD: 318(+)=(M+H)(+)

c) 1,3-Dichloro-4-fluoro-2-[1-(2-fluoro-4-nitrophenoxy)ethyl]benzene can be prepared as in Example 20f but from 2.1 g of sodium hydride (at 60% in the oil), 10 g of 1-(2,6-dichloro-3-fluorophenyl)-ethanol and 8.37 g of 1,2-difluoro-4-nitrobenzene. We thus obtain 16.6 g of 1,3-dichloro-4-fluoro-2-[1-(2-fluoro-4-nitrophenoxy)ethyl]benzene in the form of an orange powder, which has the following characteristics:

Melting point: 110° C. (Köfler)

Mass spectrum: SM-EI: 347(+)=M(+)

Example 31

1-{6-[1-(2,6-dichloro-3-fluorophenyl)ethoxy]-5-fluoro-1,3-benzothiazol-2-yl}-3-(2-morpholin-4-ylethyl)urea a) 1-{6-[1-(2,6-Dichloro-3-fluorophenyl)ethoxy]-5-fluoro-1,3-benzothiazol-2-yl}-3-(2-morpholin-4-ylethyl)urea can be prepared as in Example 10a but from 0.35 g of {6-[1-(2,6-dichloro-3-fluorophenyl)ethoxy]-5-fluoro-1,3-benzothiazol-2-yl}phenyl carbamate and 0.101 g of 2-morpholin-4-ylethanamine. After purification of the residue by silica-column flash chromatography [eluent: dichloromethane/methanol (93/7 by volume)], we obtain 0.318 g of 1-{6-[1-(2,6-dichloro-3-fluorophenyl)ethoxy]-5-fluoro-1,3-benzothiazol-2-yl}-3-(2-morpholin-4-ylethyl)urea in the form of a white powder, which has the following characteristics:

Melting point: 226-228° C. (Köfler)

1H NMR spectrum (400 MHz, DMSO-d$_6$) δ ppm: 1.78 (d, J=6.4 Hz, 3H) 2.40 (m, 6H) 3.25 (q, J=5.9 Hz, 2H) 3.58 (m, 4H) 6.04 (q, J=6.4 Hz, 1H) 6.69 (m broad, 1H) 7.30-7.49 (m, 3H) 7.53 (dd, J=8.8, 5.0 Hz, 1H) 10.78 (m spread-out, 1H)

Mass spectrum: LC-MS-DAD-ELSD: 529(−)=(M−H)(−); 531(+)=(M+H)(+)

b) {6-[1-(2,6-Dichloro-3-fluorophenyl)ethoxy]-5-fluoro-1,3-benzothiazol-2-yl}phenyl carbamate can be prepared as in Example 10b but from 0.35 g of 6-[1-(2,6-dichloro-3-fluorophenyl)ethoxy]-5-fluoro-1,3-benzothiazol-2-amine and 0.584 g of phenyl chlorocarbonate. We thus obtain 0.401 g {6-[1-(2,6-dichloro-3-fluorophenyl)ethoxy]-5-fluoro-1,3-benzothiazol-2-yl}phenyl carbamate in the form of a cream-coloured powder, which has the following characteristics:

Melting point: 240-245° C. (Köfler)

Mass spectrum: HPLC-MS-DAD-ELSD: 495(+)=(M+H)(+)

Example 32

1-{6-[(1R)-(2,6-dichloro-3-fluorophenyl)ethoxy]-5-fluoro-1,3-benzothiazol-2-yl}-3-(2-morpholin-4-ylethyl)urea or 1-{6-[(1S)-(2,6-dichloro-3-fluorophenyl)ethoxy]-5-fluoro-1,3-benzothiazol-2-yl}-3-(2-morpholin-4-ylethyl)urea 0.248 g of 1-{6-[(1RS)-(2,6-dichloro-3-fluorophenyl)ethoxy]-5-fluoro-1,3-benzothiazol-2-yl}-3-(2-morpholin-4-ylethyl)urea was separated by chiral HPLC on Chiralcel OJ 10 μm (20×250 mm). We thus obtain 0.122 g of the dextrorotatory enantiomer 1-{6-[(1R*)-(2,6-dichloro-3-fluorophenyl)ethoxy]-1,3-benzothiazol-2-yl}-3-(2-morpholin-4-ylethyl)urea in the form of a white powder, which has the following characteristics:

PR=+137° C.=2.073 mg/1.5 ml DMSO on 589 nM

1H NMR spectrum (400 MHz, DMSO-d$_6$) δ ppm: 1.78 (d, J=6.8 Hz, 3H) 2.40 (m, 6H) 3.26 (q, J=5.4 Hz, 2H) 3.59 (m, 4H) 6.04 (q, J=6.8 Hz, 1H) 6.70 (m broad, 1H) 7.39 (d, J=8.3 Hz, 1H) 7.43 (t, J=8.8 Hz, 1H) 7.46 (d, J=12.2 Hz, 1H) 7.53 (dd, J=8.8, 5.4 Hz, 1H) 10.76 (m spread-out, 1H)

Mass spectrum: LC-MS-DAD-ELSD: 531(+)=(M+H)(+)

Example 33

1-{6-[(1R)-(2,6-dichloro-3-fluorophenyl)ethoxy]-5-fluoro-1,3-benzothiazol-2-yl}-3-(2-morpholin-4-ylethyl)urea or 1-{6-[(1S)-(2,6-dichloro-3-fluorophenyl)ethoxy]-5-fluoro-1,3-benzothiazol-2-yl}-3-(2-morpholin-4-ylethyl)urea 0.248 g of 1-{6-[(1RS)-(2,6-dichloro-3-fluorophenyl)ethoxy]-5-fluoro-1,3-benzothiazol-2-yl}-3-(2-morpholin-4- ylethyl)urea was separated by chiral HPLC on Chiralcel OJ 20 µm (8×35 cm). We thus obtain 0.12 g of the laevorotatory enantiomer 1-{6-[(1S*)-(2,6-dichloro-3-fluorophenyl)ethoxy]-1,3-benzothiazol-2-yl}-3-(2-morpholin-4-ylethyl)urea in the form of a white powder, which has the following characteristics:

PR=−87.61°+/−1.5° C.=1.854 mg/0.5 ml DMSO on 589 nM

1H NMR spectrum (400 MHz, DMSO-$d_6$) δ ppm: 1.78 (d, J=6.7 Hz, 3H) 2.39 (m, 6H) 3.26 (q, J=5.9 Hz, 2H) 3.59 (m, 4H) 6.04 (q, J=6.7 Hz, 1H) 6.67 (m broad, 1H) 7.34-7.48 (m, 3H) 7.53 (dd, J=8.8, 4.9 Hz, 1H) 10.78 (m spread-out, 1H)

Mass spectrum: LC-MS-DAD-ELSD: 531(+)=(M+H)(+)

Example 34

1-[2-(4-benzylpiperidin-1-yl)ethyl]-3-{6-[1-(2,6-dichloro-3-fluorophenyl)ethoxy]-1,3-benzothiazol-2-yl}urea 1-[2-(4-Benzylpiperidin-1-yl)ethyl]-3-{6-[1-(2,6-dichloro-3-fluorophenyl)ethoxy]-1,3-benzothiazol-2-yl}urea can be prepared as in Example 10a but from 0.2 g of {6-[1-(2,6-dichloro-3-fluorophenyl)ethoxy]-5-fluoro-1,3-benzothiazol-2-yl}phenyl carbamate and 0.091 g of 2-(4-benzylpiperidin-1-yl)ethanamine. After purification of the residue by silica-column flash chromatography [eluent: dichloromethane/methanol (95/5 by volume)], we obtain 0.172 g of 1-[2-(4-benzylpiperidin-1-yl)ethyl]-3-{6-[1-(2,6-dichloro-3-fluorophenyl)ethoxy]-1,3-benzothiazol-2-yl}urea in the form of a white powder, which has the following characteristics:

Melting point: 133-139° C. (Büchi)

1H NMR spectrum (400 MHz, DMSO-$d_6$) δ ppm: 1.20 (m, 2H) 1.43-1.59 (m, 3H) 1.74 (d, J=6.8 Hz, 3H) 1.85 (m, 2H) 2.37 (t, J=5.8 Hz, 2H) 2.84 (m, 2H) 3.22 (m, 2H) 3.29 (m masked, 2H) 6.05 (q, J=6.8 Hz, 1H) 6.69 (m broad, 1H) 6.89 (dd, J=8.8, 2.4 Hz, 1H) 7.12-7.19 (m, 3H) 7.28 (t, J=7.3 Hz, 2H) 7.34 (d, J=2.4 Hz, 1H) 7.40 (t, J=8.8 Hz, 1H) 7.44 (d, J=8.8 Hz, 1H) 7.51 (dd, J=8.8, 4.9 Hz, 1H) 10.64 (m spread-out, 1H)

Mass spectrum: HPLC-MS-DAD-ELSD: 601(+)=(M+H)(+)

Example 35

1-[2-(4-benzylpiperazin-1-yl)ethyl]-3-{6-[1-(2,6-dichloro-3-fluorophenyl)ethoxy]-1,3-benzothiazol-2-yl}urea 1-[2-(4-Benzylpiperazin-1-yl)ethyl]-3-{6-[1-(2,6-dichloro-3-fluorophenyl)ethoxy]-1,3-benzothiazol-2-yl}urea can be prepared as in Example 10a but from 0.2 g of {6-[1-(2,6-dichloro-3-fluorophenyl)ethoxy]-5-fluoro-1,3-benzothiazol-2-yl}phenyl carbamate and 0.092 g of 2-(4-benzylpiperazin-1-yl)ethanamine. After purification of the residue by silica-column flash chromatography [eluent: dichloromethane/methanol (95/5 by volume)], we obtain 0.174 g of 1-[2-(4-benzylpiperazin-1-yl)ethyl]-3-{6-[1-(2,6-dichloro-3-fluorophenyl)ethoxy]-1,3-benzothiazol-2-yl}urea in the form of a white powder, which has the following characteristics:

Melting point: 125-139° C. (Büchi)

1H NMR spectrum (400 MHz, DMSO-$d_6$) δ ppm: 1.74 (d, J=6.8 Hz, 3H) 2.28-2.54 (m partially masked, 10H) 3.24 (q, J=5.4 Hz, 2H) 3.46 (s, 2H) 6.05 (q, J=6.8 Hz, 1H) 6.71 (m broad, 1H) 6.89 (dd, J=8.8, 2.7 Hz, 1H) 7.19-7.33 (m, 5H) 7.34 (d, J=2.7 Hz, 1H) 7.40 (t, J=8.8 Hz, 1H) 7.45 (d, J=8.8 Hz, 1H) 7.51 (dd, J=8.8, 4.9 Hz, 1H) 10.64 (m spread-out, 1H)

Mass spectrum: HPLC-MS-DAD-ELSD: 602(+)=(M+H)(+)

Example 36

1,1-dimethylethyl 4-{2-[({6-[1-(2,6-dichloro-3-fluorophenyl)ethoxy]-1,3-benzothiazol-2-yl}carbamoyl)amino]ethyl}piperazine-1-carboxylate 1,1-Dimethylethyl 4-{2-[({6-[1-(2,6-dichloro-3-fluorophenyl)ethoxy]-1,3-benzothiazol-2-yl}carbamoyl)amino]ethyl}piperazine-1-carboxylate can be prepared as in Example 10a but from 0.4 g of {6-[1-(2,6-dichloro-3-fluorophenyl)ethoxy]-5-fluoro-1,3-benzothiazol-2-yl}phenyl carbamate and 0.192 g of 1,1-dimethylethyl 4-(2-aminoethyl)piperazine-1-carboxylate. After purification of the residue by silica-column flash chromatography [eluent: dichloromethane/methanol (95/5 by volume)], we obtain 0.42 g of 1,1-dimethylethyl 4-{2-[({6-[1-(2,6-dichloro-3-fluorophenyl)ethoxy]-1,3-benzothiazol-2-yl}carbamoyl)amino]ethyl}piperazine-1-carboxylate in the form of a white powder, which has the following characteristics:

Melting point: 87° C. (Büchi)

1H NMR spectrum (400 MHz, DMSO-$d_6$) δ ppm: 1.39 (s, 9H) 1.74 (d, J=6.4 Hz, 3H) 2.36 (m, 4H) 2.42 (t, J=6.1 Hz, 2H) 3.20-3.44 (m partially masked, 6H) 6.05 (q, J=6.4 Hz, 1H) 6.76 (m broad, 1H) 6.88 (dd, J=8.8, 2.4 Hz, 1H) 7.34 (d, J=2.4 Hz, 1H) 7.40 (t, J=8.8 Hz, 1H) 7.44 (d, J=8.8 Hz, 1H) 7.51 (dd, J=8.8, 5.1 Hz, 1H) 10.69 (m spread-out, 1H)

Mass spectrum: HPLC-MS-DAD-ELSD: 610(−)=(M−H)(−); 612(+)=(M+H)(+)

Example 37

1-{6-[1-(2,6-Dichloro-3-fluorophenyl)ethoxy]-1,3-benzothiazol-2-yl}-3-(2-piperazin-1-ylethyl)urea trifluoroacetate 1-{6-[1-(2,6-Dichloro-3-fluorophenyl)ethoxy]-1,3-benzothiazol-2-yl}-3-(2-piperazin-1-ylethyl)urea trifluoroacetate can be prepared as follows:

add 0.376 cm$^3$ of trifluoroacetic acid to a solution of 0.250 g of 1,1-dimethylethyl 4-{2-[({6-[1-(2,6-dichloro-3-fluorophenyl)ethoxy]-1,3-benzothiazol-2-yl}carbamoyl)amino]ethyl}piperazine-1-carboxylate trifluoroacetate in 5 cm$^3$ of dichloromethane. Continue stirring for 4 hours at a temperature close to 20° C. The reaction mixture is then evaporated to dryness under reduced pressure (2 kPa). The residue is taken up in 10 cm$^3$ of water. The mixture obtained is adjusted to pH 9 with a 1N solution of sodium hydroxide and then extracted three times with 20 cm$^3$ of ethyl acetate. The combined organic phases are dried over magnesium sulphate, then filtered and evaporated to dryness under reduced pressure (2 kPa). The white solid obtained is solidified in 5 cm$^3$ of diisopropyl oxide, filtered and then dried under reduced pressure. We obtain 0.117 g of 1-{6-[1-(2,6-dichloro-3-fluorophenyl)ethoxy]-1,3-benzothiazol-2-yl}-3-(2-piperazin-1-ylethyl)urea trifluoroacetate in the form of a white powder, which has the following characteristics:

Melting point: 138-169° C. (Büchi)

1H NMR spectrum (400 MHz, DMSO-$d_6$) δ ppm: 1.74 (d, J=6.8 Hz, 3H) 2.38-2.53 (m partially masked, 6H) 2.87 (m, 4H) 3.18-3.40 (m partially masked, 2H) 6.05 (q, J=6.8 Hz, 1H) 6.71 (t broad, J=5.8 Hz, 1H) 6.89 (dd, J=8.8, 2.4 Hz, 1H)

7.35 (d, J=2.4 Hz, 1H) 7.40 (t, J=8.8 Hz, 1H) 7.45 (d, J=8.8 Hz, 1H) 7.51 (dd, J=8.8, 4.9 Hz, 1H) 10.25 (m very spread-out, 1H)

Mass spectrum: HPLC-MS-DAD-ELSD: 512(+)=(M+H) (+)

Example 38

1,1-dimethylethyl 4-{2-[({6-[1-(2,6-dichloro-3-fluorophenyl)ethoxy]-1,3-benzothiazol-2-yl}carbamoyl)amino]ethyl}piperidine-1-carboxylate 1,1-Dimethylethyl 4-{2-[({6-[1-(2,6-dichloro-3-fluorophenyl)ethoxy]-1,3-benzothiazol-2-yl}carbamoyl)amino]ethyl}piperidine-1-carboxylate can be prepared as in Example 10a but from 0.4 g of {6-[1-(2,6-dichloro-3-fluorophenyl)ethoxy]-5-fluoro-1,3-benzothiazol-2-yl}phenyl carbamate and 0.191 g of 1,1-dimethylethyl 4-(2-aminoethyl)piperidine-1-carboxylate. After purification of the residue by silica-column flash chromatography [eluent: dichloromethane/methanol (95/5 by volume)], we obtain 0.174 g of 1,1-dimethylethyl 4-{2-[({6-[1-(2,6-dichloro-3-fluorophenyl)ethoxy]-1,3-benzothiazol-2-yl}carbamoyl)amino]ethyl}piperidine-1-carboxylate in the form of a white powder, which has the following characteristics:

Melting point: 95-105° C. (Büchi)

1H NMR spectrum (400 MHz, DMSO-$d_6$) δ ppm: 0.98 (m, 2H) 1.23-1.50 (m, 3H) 1.39 (s, 9H) 1.64 (m, 2H) 1.74 (d, J=6.6 Hz, 3H) 2.35-2.75 (m partially masked, 2H) 3.17 (q, J=6.0 Hz, 2H) 3.91 (m, 2H) 6.05 (q, J=6.6 Hz, 1H) 6.74 (m broad, 1H) 6.88 (dd, J=8.8, 2.7 Hz, 1H) 7.33 (d, J=2.7 Hz, 1H) 7.40 (t, J=8.8 Hz, 1H) 7.43 (d, J=8.8 Hz, 1H) 7.51 (dd, J=8.8, 4.9 Hz, 1H) 10.53 (m spread-out, 1H)

Mass spectrum: HPLC-MS-DAD-ELSD: 611(+)=(M+H) (+)

Example 39

1-{6-[1-(2,6-Dichloro-3-fluorophenyl)ethoxy]-1,3-benzothiazol-2-yl}-3-(2-piperidin-4-ylethyl)urea trifluoroacetate 1-{6-[1-(2,6-Dichloro-3-fluorophenyl)ethoxy]-1,3-benzothiazol-2-yl}-3-(2-piperidin-4-ylethyl)urea trifluoroacetate can be prepared as in Example 37 but from 0.250 g of 1-{6-[1-(2,6-dichloro-3-fluorophenyl)ethoxy]-1,3-benzothiazol-2-yl}-3-(2-piperidin-4-ylethyl)urea trifluoroacetate and 0.376 cm³ of trifluoroacetic acid. We thus obtain 0.12 g of 1-{6-[1-(2,6-dichloro-3-fluorophenyl)ethoxy]-1,3-benzothiazol-2-yl}-3-(2-piperidin-4-ylethyl)urea trifluoroacetate in the form of a white powder, which has the following characteristics:

Melting point: 136-152° C. (Büchi)

1H NMR spectrum (400 MHz, DMSO-$d_6$) δ ppm: 1.00 (m, 2H) 1.36 (m, 3H) 1.58 (m, 2H) 1.74 (d, J=6.8 Hz, 3H) 2.38-2.55 (m partially masked, 2H) 2.90 (m, 2H) 3.16 (m, 2H) 6.05 (q, J=6.8 Hz, 1H) 6.72 (m broad, 1H) 6.88 (dd, J=8.8, 2.4 Hz, 1H) 7.34 (d, J=2.4 Hz, 1H) 7.40 (t, J=9.0 Hz, 1H) 7.44 (d, J=8.8 Hz, 1H) 7.51 (dd, J=9.0, 4.9 Hz, 1H)

Mass spectrum: HPLC-MS-DAD-ELSD: 625(+)=(M+H) (+)

Examples 40 to 59 a) The derivatives in Examples 40 to 59 were prepared in parallel synthesis as follows:

In a parallel synthesis reactor of the Stem type (25 stations), a solution of 0.1 g {6-[1-(2,6-dichloro-3-fluorophenyl)ethoxy]-5-fluoro-1,3-benzothiazol-2-yl}phenyl carbamate in 3 cm³ of tetrahydrofuran is put in each tube, with stirring. In each tube, 1 equivalent of amine is added and 0.029 cm³ of triethylamine in case 40. The mixture is then stirred for about 48 hours at a temperature close to 20° C.

| Amine No. | Name | Mass | Volume |
|---|---|---|---|
| L40 | 3-(1H-pyrrol-1-yl)propan-1-amine hydrochloride | 0.026 g | |
| L41 | 3-(4-benzylpiperidin-1-yl)propan-1-amine | 0.0487 g | |
| L42 | 3-morpholin-4-ylpropan-1-amine | 0.0302 g | |
| L43 | N,N-dimethylpropane-1,3-diamine | | 0.0264 cm³ |
| L44 | 3-piperidin-1-ylpropan-1-amine | 0.0298 g | |
| L45 | 1-(3-aminopropyl)pyrrolidin-2-one | 0.0298 g | |
| L46 | 3-[4-(2-chloro-6-fluorobenzyl)piperazin-1-yl]-propan-1-amine | 0.0599 g | |
| L47 | 3-(2,6-dimethylpiperidin-1-yl)propan-1-amine | 0.0357 g | |
| L48 | 3-azepan-1-ylpropan-1-amine | 0.0327 g | |
| L49 | 3-(4-benzylpiperazin-1-yl)propan-1-amine | 0.0489 g | |
| L50 | 2-piperidin-1-ylethanamine | 0.0269 g | |
| L51 | 2-pyrrolidin-1-ylethanamine | 0.0239 g | |
| L52 | 2-(1-benzylpiperidin-4-yl)ethanamine | 0.0457 g | |
| L53 | 2-(1-methylpyrrolidin-2-yl)ethanamine | | 0.0303 cm³ |
| L54 | 2-azepan-1-ylethanamine | 0.0298 g | |
| L55 | 2-(4-methylpiperazin-1-yl)ethanamine | 0.03 g | |
| L56 | 2-(2,6-dimethylpiperidin-1-yl)ethanamine | 0.0327 g | |
| L57 | 1-pyridin-4-ylmethanamine | | 0.0213 cm³ |
| L58 | 1-pyridin-2-ylmethanamine | | 0.0213 cm³ |
| L59 | 1-pyridin-3-ylmethanamine | | 0.0213 cm³ |

Then 5 cm³ of dichloromethane and 5 cm³ of a 0.1N aqueous solution of sodium hydroxide are added to each tube. After stirring for about 2 minutes, the aqueous phases are removed. 3 cm³ of water is added to the residual organic phases and after stirring for 2 minutes, the aqueous phases are removed. This operation is repeated once again for each tube. The organic phases are dried over magnesium sulphate, filtered and concentrated under reduced pressure. The residues are purified by silica-column flash chromatography and the following compounds are obtained:

| EX No. | Name | Quantity | Mass spectrum: LC-MS-DAD-ELSD |
|---|---|---|---|
| 40 | 1-{6-[1-(2,6-dichloro-3-fluorophenyl)ethoxy]-1,3-benzothiazol-2-yl}-3-[3-(1H-pyrrol-1-yl)propyl]urea | 0.0598 g | 505(−) = (M − H)(−); 507(+) = (M + H)(+) |
| 41 | 1-[3-(4-benzylpiperidin-1-yl)propyl]-3-{6-[1-(2,6-dichloro-3-fluorophenyl)ethoxy]-1,3-benzothiazol-2-yl}urea | 0.0834 g | 613(−) = (M − H)(−); 615(+) = (M + H)(+) |
| 42 | 1-{6-[1-(2,6-dichloro-3-fluorophenyl)ethoxy]-1,3-benzothiazol-2-yl}-3-(3-morpholin-4-ylpropyl)urea | 0.0824 g | 525(−) = (M − H)(−); 527(+) = (M + H)(+) |
| 43 | 1-{6-[1-(2,6-dichloro-3-fluorophenyl)ethoxy]-1,3-benzothiazol-2-yl}-3-[3-(dimethylamino)propyl]urea | 0.1364 g | 483(−) = (M − H)(−); 485(+) = (M + H)(+) |
| 44 | 1-{6-[1-(2,6-dichloro-3-fluorophenyl)ethoxy]-1,3-benzothiazol-2-yl}-3-(3-piperidin-1-ylpropyl)urea | 0.0223 g | 523(−) = (M − H)(−); 525(+) = (M + H)(+) |
| 45 | 1-{6-[1-(2,6-dichloro-3-fluorophenyl)ethoxy]-1,3-benzothiazol-2-yl}-3-[3-(2-oxopyrrolidin-1-yl)propyl]urea | 0.09 g | 523(−) = (M − H)(−); 525(+) = (M + H)(+) |
| 46 | 1-{3-[4-(2-chloro-6-fluorobenzyl)piperazin-1-yl]propyl}-3-{6-[1-(2,6-dichloro-3-fluorophenyl)ethoxy]-1,3-benzothiazol-2-yl}urea | 0.1 g | 666(−) = (M − H)(−); 668(+) = (M + H)(+) |
| 47 | 1-{6-[1-(2,6-dichloro-3-fluorophenyl)ethoxy]-1,3-benzothiazol-2-yl}-3-[3-(2,6-dimethylpiperidin-1-yl)propyl]urea | 0.005 g | 551(−) = (M − H)(−); 553(+) = (M + H)(+) |
| 48 | 1-(3-azepan-1-ylpropyl)-3-{6-[1-(2,6-dichloro-3-fluorophenyl)ethoxy]-1,3-benzothiazol-2-yl}urea | 0.005 g | 539(+) = (M + H)(+) |
| 49 | 1-[3-(4-benzylpiperazin-1-yl)propyl]-3-{6-[1-(2,6-dichloro-3-fluorophenyl)ethoxy]-1,3-benzothiazol-2-yl}urea | 0.083 g | 616(+) = (M + H)(+) |
| 50 | 1-{6-[1-(2,6-dichloro-3-fluorophenyl)ethoxy]-1,3-benzothiazol-2-yl}-3-(2-piperidin-1-ylethyl)urea | 0.074 g | 509(−). = (M − H)(−); 511(+) = (M + H)(+)( |
| 51 | 1-{6-[1-(2,6-dichloro-3-fluorophenyl)ethoxy]-1,3-benzothiazol-2-yl}-3-(2-pyrrolidin-1-ylethyl)urea | 0.05 g | 495(−) = (M − H)(−); 497(+) = (M + H)(+) |
| 52 | 1-[2-(1-benzylpiperidin-4-yl)ethyl]-3-{6-[1-(2,6-dichloro-3-fluorophenyl)ethoxy]-1,3-benzothiazol-2-yl}urea | 0.09 g | 601(+) = (M + H)(+) |
| 53 | 1-{6-[1-(2,6-dichloro-3-fluorophenyl)ethoxy]-1,3-benzothiazol-2-yl}-3-[2-(1-methylpyrrolidin-2-yl)ethyl]urea | 0.0184 g | 509(−) = (M − H)(−); 511(+) = (M + H)(+) |
| 54 | 1-(2-azepan-1-ylethyl)-3-{6-[1-(2,6-dichloro-3-fluorophenyl)ethoxy]-1,3-benzothiazol-2-yl}urea | 0.023 g | 525(+) = (M + H)(+) |
| 55 | 1-{6-[1-(2,6-dichloro-3-fluorophenyl)ethoxy]-1,3-benzothiazol-2-yl}-3-[2-(4-methylpiperazin-1-yl)ethyl]urea | 0.009 g | 526(+) = (M + H)(+) |
| 56 | 1-{6-[1-(2,6-dichloro-3-fluorophenyl)ethoxy]-1,3-benzothiazol-2-yl}-3-[2-(2,6-dimethylpiperidin-1-yl)ethyl]urea | 0.035 g | 539(+) = (M + H)(+) |
| 57 | 1-{6-[1-(2,6-dichloro-3-fluorophenyl)ethoxy]-1,3-benzothiazol-2-yl}-3-(pyridin-4-ylmethyl)urea | 0.021 g | 491(+) = (M + H)(+) |
| 58 | 1-{6-[1-(2,6-dichloro-3-fluorophenyl)ethoxy]-1,3-benzothiazol-2-yl}-3-(pyridin-2-ylmethyl)urea | 0.040 g | 489(−) = (M − H)(−); 491(+) = (M + H)(+) |
| 59 | 1-{6-[1-(2,6-dichloro-3-fluorophenyl)ethoxy]-1,3-benzothiazol-2-yl}-3-(pyridin-3-ylmethyl)urea | 0.0435 g | 489(−) = (M − H)(−); 491(+) = (M + H)(+) |

The results obtained by NMR for the products in examples 40 to 59 are presented below:

Example 40

1H NMR spectrum (400 MHz, DMSO-$d_6$) δ ppm: 1.74 (d, J=6.7 Hz, 3H) 1.87 (quin, J=6.8 Hz, 2H) 3.09 (q, J=6.8 Hz, 2H) 3.90 (t, J=6.8 Hz, 2H) 5.98 (t, J=2.0 Hz, 2H) 6.05 (q, J=6.7 Hz, 1H) 6.75 (t, J=2.0 Hz, 2H) 6.77 (m broad, 1H) 6.89 (dd, J=8.8, 2.6 Hz, 1H) 7.34 (d, J=2.6 Hz, 1H) 7.40 (t, J=8.8 Hz, 1H) 7.45 (d, J=8.8 Hz, 1H) 7.51 (dd, J=8.8, 4.9 Hz, 1H) 10.5 (m spread-out, 1H)

Example 41

1H NMR spectrum (400 MHz, DMSO-$d_6$) δ ppm: 1.10-1.70 (m spread-out, 7H) 1.74 (d, J=6.8 Hz, 3H) 2.30-3.50 (m very spread-out, partially masked, 8H) 3.16 (q, J=5.5 Hz, 2H) 6.05 (q, J=6.8 Hz, 1H) 6.76 (m broad, 1H) 6.89 (dd, J=8.8, 2.6 Hz, 1H) 7.17 (m, 3H) 7.27 (t, J=7.3 Hz, 2H) 7.34 (d, J=2.6 Hz, 1H) 7.40 (t, J=8.9 Hz, 1H) 7.45 (d, J=8.8 Hz, 1H) 7.51 (dd, J=8.9, 5.1 Hz, 1H) 10.63 (m, 1H)

Example 42

1H NMR spectrum (400 MHz, DMSO-$d_6$) δ ppm: 1.61 (quin, J=6.9 Hz, 2H) 1.74 (d, J=6.8 Hz, 3H) 2.29 (t, J=6.9 Hz, 2H) 2.33 (m, 4H) 3.17 (q, J=6.9 Hz, 2H) 3.57 (m, 4H) 6.05 (q, J=6.8 Hz, 1H) 6.72 (m broad, 1H) 6.89 (dd, J=8.8, 2.7 Hz, 1H) 7.34 (d, J=2.7 Hz, 1H) 7.40 (t, J=8.8 Hz, 1H) 7.44 (d, J=8.8 Hz, 1H) 7.51 (dd, J=8.8, 5.2 Hz, 1H) 10.56 (m spread-out, 1H)

Example 43

1H NMR spectrum (400 MHz, DMSO-$d_6$) δ ppm: 1.57 (quin, J=6.9 Hz, 2H) 1.74 (d, J=6.7 Hz, 3H) 2.13 (s, 6H) 2.23 (t, J=6.9 Hz, 2H) 3.16 (q, J=6.9 Hz, 2H) 6.05 (q, J=6.7 Hz, 1H) 6.80 (m broad, 1H) 6.88 (dd, J=8.8, 2.7 Hz, 1H) 7.34 (d, J=2.7 Hz, 1H) 7.40 (t, J=8.8 Hz, 1H) 7.45 (d, J=8.8 Hz, 1H) 7.51 (dd, J=8.8, 4.9 Hz, 1H) 10.56 (m spread-out, 1H)

Example 44

1H NMR spectrum (400 MHz, DMSO-d$_6$) δ ppm: 1.10-1.90 (m very spread-out, 8H) 1.74 (d, J=6.8 Hz, 3H) 2.30-3.50 (m very spread-out, partially masked, 6H) 3.19 (m, 2H) 6.05 (q, J=6.8 Hz, 1H) 6.79 (m broad, 1H) 6.89 (dd, J=8.8, 2.4 Hz, 1H) 7.35 (d, J=2.4 Hz, 1H) 7.40 (t, J=8.8 Hz, 1H) 7.46 (d, J=8.8 Hz, 1H) 7.51 (dd, J=8.8.4.9 Hz, 1H) 10.63 (m spread-out, 1H)

Example 45

1H NMR spectrum (400 MHz, DMSO-d$_6$) δ ppm: 1.63 (quin, J=6.5 Hz, 2H) 1.74 (d, J=6.4 Hz, 3H) 1.92 (quin, J=7.5 Hz, 2H) 2.21 (t, J=7.5 Hz, 2H) 3.10 (q, J=6.4 Hz, 2H) 3.20 (t, J=6.4 Hz, 2H) 3.32 (t, J=7.5 Hz, 2H) 6.05 (q, J=6.4 Hz, 1H) 6.76 (m broad, 1H) 6.88 (dd, J=8.8, 2.4 Hz, 1H) 7.34 (d, J=2.4 Hz, 1H) 7.40 (q, J=8.8 Hz, 1H) 7.45 (d, J=8.8 Hz, 1H) 7.51 (dd, J=8.8, 4.9 Hz, 1H) 10.63 (m spread-out, 1H)

Example 46

1H NMR spectrum (400 MHz, DMSO-d$_6$) δ ppm: 1.57 (quin, J=6.5 Hz, 2H) 1.74 (d, J=6.6 Hz, 3H) 2.20-2.52 (m partially masked, 8H) 2.26 (t, J=6.5 Hz, 2H) 3.15 (q, J=6.5 Hz, 2H) 3.58 (d, J=2.0 Hz, 2H) 6.05 (q, J=6.6 Hz, 1H) 6.70 (m broad, 1H) 6.88 (dd, J=8.8, 2.4 Hz, 1H) 7.20 (m, 1H) 7.28-7.36 (m, 3H) 7.39 (t, J=8.8 Hz, 1H) 7.44 (d, J=8.8 Hz, 1H) 7.51 (dd, J=8.8, 4.9 Hz, 1H) 10.52 (m spread-out, 1H)

Example 47

1H NMR spectrum (400 MHz, DMSO-d$_6$) δ ppm: 0.65-1.87 (m, 14H) 1.74 (d, J=6.6 Hz, 3H) 2.90-3.36 (m partially masked, 6H) 6.05 (q, J=6.6 Hz, 1H) 6.90 (dd, J=8.8, 2.4 Hz, 1H) 7.00 (m spread-out, 1H) 7.34 (d, J=2.4 Hz, 1H) 7.40 (t, J=8.8 Hz, 1H) 7.45 (d, J=8.8 Hz, 1H) 7.51 (dd, J=8.8, 4.9 Hz, 1H) 10.74 (m spread-out, 1H)

Example 48

1H NMR spectrum (400 MHz, DMSO-d$_6$) δ ppm: 1.40-1.97 (m, 10H) 1.74 (d, J=6.6 Hz, 3H) 2.35-3.40 (m partially masked, 8H) 6.05 (d, J=6.6 Hz, 1H) 6.75 (m spread-out, 1H) 6.89 (dd, J=8.8, 2.4 Hz, 1H) 7.35 (d, J=2.4 Hz, 1H) 7.41 (t, J=8.8 Hz, 1H) 7.46 (d, J=8.8 Hz, 1H) 7.51 (dd, J=8.8, 4.9 Hz, 1H) 10.73 (m spread-out, 1H)

Example 49

1H NMR spectrum (400 MHz, DMSO-d$_6$) δ ppm: 1.59 (quin, J=6.9 Hz, 2H) 1.74 (d, J=6.6 Hz, 3H) 2.20 2.60 (m partially masked, 8H) 2.28 (t, J=6.9 Hz, 2H) 3.14 (m, 2H) 3.44 (s, 2H) 6.05 (q, J=6.6 Hz, 1H) 6.71 (m spread-out, 1H) 6.88 (dd, J=8.8, 2.4 Hz, 1H) 7.14-7.33 (m, 5H) 7.34 (d, J=2.4 Hz, 1H) 7.40 (t, J=8.8 Hz. 1H) 7.45 (d, J=8.8 Hz, 1H) 7.51 (dd, J=8.8, 5.1 Hz, 1H) 10.53 (m spread-out, 1H)

Example 50

1H NMR spectrum (400 MHz, DMSO-d$_6$) δ ppm: 1.40 (m, 2H) 1.52 (m, 4H) 1.74 (d, J=6.7 Hz, 3H) 2.37 (m, 6H) 3.19-3.36 (m partially masked, 6H) 6.05 (q, J=6.7 Hz, 1H) 6.72 (m broad, 1H) 6.89 (dd, J=8.8, 2.9 Hz, 1H) 7.34 (d, J=2.9 Hz, 1H) 7.40 (t, J=8.8 Hz, 1H) 7.45 (d, J=8.8 Hz, 1H) 7.51 (dd, J=8.8, 4.9 Hz, 1H) 10.63 (m spread-out, 1H)

Example 51

1H NMR spectrum (400 MHz, DMSO-d$_6$) δ ppm: 1.69 (m, 4H) 1.74 (d, J=6.8 Hz, 3H) 2.40-2.57 (m partially masked, 6H) 3.25 (m, 2H) 6.05 (q, J=6.8 Hz, 1H) 6.77 (m broad, 1H) 6.88 (dd, J=8.8, 2.4 Hz, 1H) 7.34 (d, J=2.4 Hz, 1H) 7.40 (t, J=8.8 Hz, 1H) 7.44 (d, J=8.8 Hz, 1H) 7.51 (dd, J=8.8, 5.1 Hz. 1H) 10.53 (m, 1H)

Example 52

1H NMR spectrum (400 MHz, DMSO-d$_6$) δ ppm: 1.16 (m, 2H) 1.33 (m, 1H) 1.39 (q, J=6.8 Hz, 2H) 1.64 (m, 2H) 1.74 (d, J=6.6 Hz, 3H) 1.89 (m, 2H) 2.78 (m, 2H) 3.16 (q, J=6.8 Hz, 2H) 3.43 (m, 2H) 6.05 (q, J=6.6 Hz, 1H) 6.66 (t, J=6.8 Hz, 1H) 6.89 (dd, J=8.8, 2.4 Hz, 1H) 7.18-7.33 (m, 5H) 7.34 (d, J=2.4 Hz, 1H) 7.40 (t, J=8.8 Hz, 1H) 7.44 (d, J=8.8 Hz, 1H) 7.51 (dd, J=8.8, 5.1 Hz, 1H) 10.44 (m spread-out, 1H)

Example 53

1H NMR spectrum (400 MHz, DMSO-d$_6$) δ ppm: 1.33-1.49 (m, 2H) 1.61 (m, 2H) 1.74 (d, J=6.5 Hz, 3H) 1.76 (m, 1H) 1.88 (m, 1H) 2.03 (m, 2H) 2.20 (s, 3H) 2.93 (m, 1H) 3.17 (q, J=6.5 Hz, 2H) 6.05 (q, J=6.5 Hz, 1H) 6.77 (m broad, 1H) 6.88 (dd, J=8.8, 2.6 Hz, 1H) 7.34 (d, J=2.6 Hz, 1H) 7.40 (t, J=8.8 Hz, 1H) 7.44 (d, J=8.8 Hz, 1H) 7.51 (dd, J=8.8, 4.9 Hz, 1H) 10.58 (m spread-out, 1H)

Example 54

1H NMR spectrum (400 MHz, DMSO-d$_6$) δ ppm: 1.40-1.90 (m broad, 8H) 1.73 (d, J=6.8 Hz, 3H) 2.40-3.70 (m partially masked, 8H) 6.06 (q, J=6.8 Hz, 1H) 6.71 (m spread-out, 1H) 6.89 (dd, J=8.8, 2.4 Hz, 1H) 7.35 (d, J=2.4 Hz, 1H) 7.40 (t, J=8.8 Hz, 1H) 7.46 (d, J=8.8 Hz, 1H) 7.51 (dd, J=8.8, 4.9 Hz, 1H) 10.72 (m spread-out, 1 H)

Example 55

1H NMR spectrum (400 MHz, DMSO-d$_6$) δ ppm: 1.74 (d, J=6.7 Hz, 3H) 2.15 (s, 3H) 2.25-2.55 (m partially masked, 10H) 3.23 (m, 2H) 6.05 (q, J=6.7 Hz, 1H) 6.70 (m broad, 1H) 6.89 (dd, J=8.8, 2.4 Hz, 1H) 7.34 (d, J=2.4 Hz, 1H) 7.40 (t, J=8.8 Hz, 1H) 7.45 (d, J=8.8 Hz, 1H) 7.51 (dd, J=8.8, 4.9 Hz, 1H) 10.69 (m spread-out, 1H)

Example 56

1H NMR spectrum (400 MHz, DMSO-d$_6$) δ ppm: 0.80-1.95 (m, 14H) 1.74 (d, J=6.8 Hz, 3H) 3.00-3.55 (m partially masked, 4H) 6.05 (q, J=6.8 Hz, 1H) 6.72 (m spread-out, 1H) 6.90 (dd, J=8.8, 2.0 Hz, 1H) 7.33 (d, J=2.0 Hz, 1H) 7.40 (t, J=8.8 Hz, 1H) 7.46 (d broad, J=8.8 Hz, 1H) 7.51 (dd, J=8.8, 4.9 Hz, 1H) 10.65 (m spread-out, 1H)

Example 57

1H NMR spectrum (400 MHz, DMSO-d$_6$) δ ppm: 1.74 (d, J=6.4 Hz, 3H) 4.39 (d, J=5.9 Hz, 2H) 6.06 (q, J=6.4 Hz, 1H) 6.90 (dd, J=8.8, 2.4 Hz, 1H) 7.28 (d, J=5.9 Hz, 2H) 7.32 (m broad, 1H) 7.35 (d, J=2.4 Hz, 1H) 7.40 (t, J=8.8 Hz, 1H) 7.47 (d, J=8.8 Hz, 1H) 7.51 (dd, J=8.8, 4.9 Hz, 1H) 8.51 (d broad, J=5.9 Hz, 2H) 10.84 (m spread-out, 1H)

Example 58

1H NMR spectrum (400 MHz, DMSO-d$_6$) δ ppm: 1.74 (d, J=6.7 Hz, 3H) 4.47 (d, J=5.4 Hz, 2H) 6.06 (q, J=6.7 Hz, 1H)

6.89 (dd, J=8.8, 2.4 Hz, 1H) 7.30 (dd, J=7.7, 5.5 Hz, 1H) 7.33-7.43 (m, 3H) 7.40 (t, J=8.8 Hz. 1H) 7.47 (d, J=8.8 Hz, 1H) 7.51 (dd, J=8.8, 5.1 Hz, 1H) 7.78 (td, J=7.7, 2.0 Hz, 1H) 8.53 (d broad, J=5.5 Hz, 1H) 10.79 (m spread-out, 1H)

Example 59

1H NMR spectrum (400 MHz, DMSO-d$_6$) δ ppm: 1.74 (d, J=6.6 Hz, 3H) 4.38 (d, J=5.9 Hz, 2H) 6.05 (q, J=6.6 Hz, 1H) 6.89 (dd, J=8.8, 2.4 Hz, 1H) 7.28 (m broad, 1H) 7.32-7.37 (m, 2H) 7.40 (t, J=8.8 Hz, 1H) 7.45 (d, J=8.8 Hz, 1H) 7.51 (dd, J=8.8, 4.9 Hz, 1H) 7.71 (dt, J=7.8, 2.0 Hz, 1H) 8.46 (dd, J=4.9, 2.0 Hz, 1H) 8.53 (d, J=2.0 Hz, 1H) 10.75 (m spread-out, 1H)

Example 60

1-(2-morpholin-4-ylethyl)-3-{6-[1-(2,3,6-trifluorophenyl)ethoxy]-1,3-benzothiazol-2-yl}urea a) 1-(2-Morpholin-4-ylethyl)-3-{6-[1-(2,3,6-trifluorophenyl)ethoxy]-1,3-benzothiazol-2-yl}urea can be prepared as in Example 10a but from 0.26 g of {6-[1-(2,3,6-trifluorophenyl)ethoxy]-1,3-benzothiazol-2-yl}phenyl carbamate and 0.152 g of 2-morpholin-4-ylethanamine. After solidification of the resin obtained in 6 cm$^3$ of acetonitrile, we obtain 0.24 g of 1-(2-morpholin-4-ylethyl)-3-{6-[1-(2,3,6-trifluorophenyl)ethoxy]-1,3-benzothiazol-2-yl}urea in the form of a white powder, which has the following characteristics:

Melting point: 187° C. (Köfler)
1H NMR spectrum (400 MHz, DMSO-d$_6$) δ ppm: 1.73 (d, J=6.5 Hz, 3H) 2.41 (m, 6H) 3.26 (q, J=5.9 Hz, 2H) 3.59 (m, 4H) 5.81 (q, J=6.5 Hz, 1H) 6.77 (t broad, J=5.9 Hz, 1H) 6.94 (dd, J=8.8, 2.4 Hz, 1H) 7.12 (tdd, J=9.6, 3.5, 2.2 Hz, 1H) 7.46 (m, 3H) 10.68 (m spread-out, 1H)
Mass spectrum: LC-MS-DAD-ELSD: 479(−)=(M−H)(−); 481(+)=(M+H)(+)

b) {6-[1-(2,3,6-Trifluorophenyl)ethoxy]-1,3-benzothiazol-2-yl}phenyl carbamate can be prepared as in Example 10b but from 0.9 g of 6-[1-(2,3,6-trifluorophenyl)ethoxy]-1,3-benzothiazol-2-amine and 1.74 g of phenyl chlorocarbonate. We thus obtain 1.26 g of {6-[1-(2,3,6-trifluorophenyl)ethoxy]-1,3-benzothiazol-2-yl}phenyl carbamate in the form of a cream-coloured powder, which has the following characteristics:

Melting point: 190° C. (Köfler)
Mass spectrum: LC-MS-DAD-ELSD: 445(+)=(M+H)(+)

d) 6-[1-(2,3,6-Trifluorophenyl)ethoxy]-1,3-benzothiazol-2-amine can be prepared as in Example 20d but from 0.85 g of 4-[1-(2,3,6-trifluorophenyl)ethoxy]aniline, 1.24 g of potassium thiocyanate and 0.163 cm$^3$ of dibromine. We thus obtain 1 g of 6-[1-(2,3,6-trifluorophenyl)ethoxy]-1,3-benzothiazol-2-amine in the form of orange crystals, which have the following characteristics:

Melting point: 150° C. (Köfler)
Mass spectrum: LC-MS-DAD-ELSD: 325(+)=(M+H)(+)

e) 4-[1-(2,3,6-Trifluorophenyl)ethoxy]aniline can be prepared as in Example 20e but from 0.115 g of platinum oxide and 1.5 g of 1,2,4-trifluoro-3-[1-(4-nitrophenoxy)ethyl]benzene in 150 cm$^3$ of methanol. After purification of the residue by silica-column flash chromatography [eluent: dichloromethane/methanol (98/2 by volume)], we obtain 0.865 g of 4-[1-(2,3,6-trifluorophenyl)ethoxy]aniline in the form of an orange resin, which has the following characteristics:

Rf CCM silica=0.27 [eluent: dichloromethane/methanol (98/2 by volume)]
Mass spectrum: LC-MS-DAD-ELSD: 268(+)=(M+H)(+)

f) 1,2,4-Trifluoro-3-[1-(4-nitrophenoxy)ethyl]benzene can be prepared as in Example 20f but from 0.499 g of sodium hydride (at 60% in the oil), 2 g of 1-(2,3,6-trifluorophenyl)ethanol and 1.6 g of 1-fluoro-4-nitrobenzene. We thus obtain 2.56 g of 1,2,4-trifluoro-3-[1-(4-nitrophenoxy)ethyl]benzene in the form of a beige powder, which has the following characteristics:

Melting point: 120° C. (Köfler)
Mass spectrum: SM-EI: 329(+)=M(+)

g) 1-(2,3,6-Trifluorophenyl)ethanol can be prepared as in Example 3e but from 5 g of 1-(2,3,6-trifluorophenyl)ethanone and 28.7 cm$^3$ of a 1M solution of aluminium lithium hydride in tetrahydrofuran. We thus obtain 4.66 g of 1-(2,3,6-trifluorophenyl)ethanol in the form of a colorless oil, which has the following characteristics:

Rf CCM silica=0.27 [eluent: dichloromethane]
Mass spectrum: LC-MS-DAD-ELSD: 159(+)=(M+H)(+)−H20

Example 61

1-{6-[1-(2,3-dichloro-6-fluorophenyl)ethoxy]-1,3-benzothiazol-2-yl}-3-(2-morpholin-4-ylethyl)urea a) 1-{6-[1-(2,3-Dichloro-6-fluorophenyl)ethoxy]-1,3-benzothiazol-2-yl}-3-(2-morpholin-4-ylethyl)urea can be prepared as in Example 10a but from 0.3 g of {6-[1-(2,3-dichloro-6-fluorophenyl)ethoxy]-1,3-benzothiazol-2-yl}phenyl carbamate and 0.164 g of 2-morpholin-4-ylethanamine. After crystallization of the powder obtained in 60 cm$^3$ of acetonitrile, we obtain 0.213 g of 1-{6-[1-(2,3-dichloro-6-fluorophenyl)ethoxy]-1,3-benzothiazol-2-yl}-3-(2-morpholin-4-ylethyl)urea in the form of a cream-coloured powder, which has the following characteristics:

Melting point: 200° C. (Köfler)
1H NMR spectrum (400 MHz, DMSO-d$_6$) δ ppm: 1.74 (d, J=6.8 Hz, 3H) 2.40 (m, 6H) 3.26 (q, J=5.9 Hz, 2H) 3.58 (m, 4H) 6.05 (q, J=6.8 Hz, 1H) 6.78 (m spread-out, 1H) 6.88 (dd, J=8.8, 2.4 Hz, 1H) 7.33 (d, J=2.4 Hz, 1H) 7.41 (t, J=8.8 Hz, 1H) 7.44 (d, J=8.8 Hz, 1H) 7.51 (dd, J=8.8, 4.9 Hz, 1H) 10.68 (m spread-out, 1H)
Mass spectrum: LC-MS-DAD-ELSD: 511(−)=(M−H)(−); 513(+)=(M+H)(+)

b) {6-[1-(2,3-Dichloro-6-fluorophenyl)ethoxy]-1,3-benzothiazol-2-yl}phenyl carbamate can be prepared as in Example 10b but from 1.7 g of 6-[1-(2,3-dichloro-6-fluorophenyl)ethoxy]-1,3-benzothiazol-2-amine and 2.98 g of phenyl chlorocarbonate. We thus obtain 2.28 g of {6-[1-(2,3-dichloro-6-fluorophenyl)ethoxy]-1,3-benzothiazol-2-yl}phenyl carbamate in the form of a cream-coloured powder, which has the following characteristics:

Melting point: 210-220° C. (Köfler)
Mass spectrum: LC-MS-DAD-ELSD: 477(+)=(M+H)(+)

d) 6-[1-(2,3-Dichloro-6-fluorophenyl)ethoxy]-1,3-benzothiazol-2-amine can be prepared as in Example 20d but from 1.5 g of 4-[1-(2,3-dichloro-6-fluorophenyl)ethoxy]aniline, 1.94 g of potassium thiocyanate and 0.256 cm$^3$ of dibromine. We thus obtain 1.75 g of 6-[1-(2,3-dichloro-6-fluorophenyl)ethoxy]-1,3-benzothiazol-2-amine in the form of ochre crystals, which have the following characteristics:

Melting point: 250° C. (Köfler)
Mass spectrum: HPLC-MS-DAD-ELSD: 357(+)=(M+H)(+)

e) 4-[1-(2,3-Dichloro-6-fluorophenyl)ethoxy]aniline can be prepared as in Example 20e but from 0.117 g of platinum oxide and 1.7 g of 1,2-dichloro-4-fluoro-3-[1-(4-nitrophenoxy)ethyl]benzene in 150 cm$^3$ of methanol. We obtain 1.5 g of 4-[1-(2,3-dichloro-6-fluorophenyl)ethoxy]aniline in the form of an orange resin, which has the following characteristics:

Rf CCM silica=0.59 [eluent: dichloromethane/methanol (98/2 by volume)]

Mass spectrum: LC-MS-DAD-ELSD: 300(+)=(M+H)(+); 341(+)=(M+acetonitrile)(+)

f) 1,2-Dichloro-4-fluoro-3-[1-(4-nitrophenoxy)ethyl]benzene can be prepared as in Example 20f but from 0.499 g of sodium hydride (at 60% in the oil), 2.37 g of 1-(2,3-dichloro-6-fluorophenyl)ethanol and 1.6 g of 1-fluoro-4-nitrobenzene. We thus obtain 1.75 g of 1,2-dichloro-4-fluoro-3-[1-(4-nitrophenoxy)ethyl]benzene in the form of orange crystals, which have the following characteristics:

1H NMR spectrum (400 MHz, DMSO-$d_6$) δ ppm: 1.77 (d, J=6.4 Hz, 3H) 6.18 (q, J=6.4 Hz, 1H) 6.99 (d, J=9.0 Hz, 2H) 7.46 (t, J=8.9 Hz, 1H) 7.56 (dd, J=8.9, 5.4 Hz, 1H) 8.17 (d, J=9.0 Hz, 2H)

Mass spectrum: LC-MS-DAD-ELSD: 330(+)=(M+H)(+)

g) 1-(2,3-Dichloro-6-fluorophenyl)ethanol can be prepared as in Example 3e but from 5 g of 1-(2,3-dichloro-6-fluorophenyl)ethanone and 24.1 cm$^3$ of a 1M solution of aluminium lithium hydride in tetrahydrofuran. We thus obtain 4.8 g of 1-(2,3-dichloro-6-fluorophenyl)ethanol in the form of a colorless oil, which has the following characteristics:

Rf CCM silica=0.61 [eluent: dichloromethane/methanol (98/2 by volume)]

Mass spectrum: SM-EI: 208(+)=M(+)

Example 62

1-{6-[1-(3,5-difluorophenyl)ethoxy]-1,3-benzothiazol-2-yl}-3-(2-morpholin-4-ylethyl)urea a) 1-{6-[1-(3,5-Difluorophenyl)ethoxy]-1,3-benzothiazol-2-yl}-3-(2-morpholin-4-ylethyl)urea can be prepared as in Example 10a but from 2 g of {6-[1-(3,5-difluorophenyl) ethoxy]-1,3-benzothiazol-2-yl}phenyl carbamate and 1.22 g of 2-morpholin-4-ylethanamine. After crystallization of the powder obtained in 35 cm$^3$ of acetonitrile, we obtain 1.6 g of 1-{6-[1-(3,5-difluorophenyl)ethoxy]-1,3-benzothiazol-2-yl}-3-(2-morpholin-4-ylethyl)urea in the form of a white powder, which has the following characteristics:

Melting point: 179° C. (Köfler)

1H NMR spectrum (400 MHz, DMSO-$d_6$) δ ppm: 1.55 (d, J=6.4 Hz, 3H) 2.41 (m, 6H) 3.27 (q, J=5.4 Hz, 2H) 3.59 (m, 4H) 5.55 (q, J=6.4 Hz, 1H) 6.76 (m broad, 1H) 6.97 (dd, J=8.8, 2.4 Hz, 1H) 7.04-7.19 (m, 3H) 7.45 (m, 2H) 10.60 (m spread-out, 1H)

Mass spectrum: LC-MS-DAD-ELSD: 461(−)=(M−H)(−); 463(+)=(M+H)(+)

b) {6-[1-(3,5-Difluorophenyl)ethoxy]-1,3-benzothiazol-2-yl}phenyl carbamate can be prepared as in Example 10b but from 1.7 g of 6-[1-(3,5-difluorophenyl)ethoxy]-1,3-benzothiazol-2-amine and 3.48 g of phenyl chlorocarbonate. We thus obtain 2.28 g of {6-[1-(3,5-difluorophenyl)ethoxy]-1,3-benzothiazol-2-yl}phenyl carbamate in the form of a cream-coloured powder, which has the following characteristics:

Melting point: 175-180° C. (Köfler)

Mass spectrum: LC-MS-DAD-ELSD: 427(+)=(M+H)(+)

d) 6-[1-(3,5-Difluorophenyl)ethoxy]-1,3-benzothiazol-2-amine can be prepared as in Example 20d but from 1.5 g of 4-[1-(3,5-difluorophenyl)ethoxy]aniline, 2.33 g of potassium thiocyanate and 0.308 cm$^3$ of dibromine. We thus obtain 1.85 g 6-[1-(3,5-difluorophenyl)ethoxy]-1,3-benzothiazol-2-amine in the form of a cream-coloured powder, which has the following characteristics:

Melting point: 132° C. (Köfler)

Mass spectrum: LC-MS-DAD-ELSD: 307(+)=(M+H)(+)

e) 4-[1-(3,5-Difluorophenyl)ethoxy]aniline can be prepared as in Example 20e but from 0.147 g of platinum oxide and 1.8 g of 1,3-difluoro-5-[1-(4-nitrophenoxy)ethyl]benzene in 150 cm$^3$ of methanol. We obtain 1.6 g of 4-[1-(3,5-difluorophenyl)ethoxy]aniline in the form of an orange-coloured oil, which has the following characteristics:

1H NMR spectrum (400 MHz, DMSO-$d_6$) δ ppm: 1.47 (d, J=6.4 Hz, 3H) 4.59 (s broad, 2H) 5.28 (q, J=6.4 Hz, 1H) 6.43 (d, J=8.8 Hz, 2H) 6.62 (d, J=8.8 Hz, 2H) 7.07 (m, 3H)

Mass spectrum: LC-MS-DAD-ELSD: 250(+)=(M+H)(+)

f) 1,3-Difluoro-5-[1-(4-nitrophenoxy)ethyl]benzene can be prepared as in Example 20f but from 0.499 g of sodium hydride (at 60% in the oil), 1.8 g of 1-(3,5-difluorophenyl) ethanol and 1.6 g of 1-fluoro-4-nitrobenzene. We thus obtain 1.98 g of 1,3-difluoro-5-[1-(4-nitrophenoxy)ethyl]benzene in the form of a yellow oil, which has the following characteristics:

Rf CCM silica=0.49 [eluent: petroleum ether/ethyl acetate (95/5 by volume)]

Mass spectrum: SM-EI: 279(+)=M(+)

Example 63

1-{6-[1-(3-chloro-2,6-difluorophenyl)ethoxy]-1,3-benzothiazol-2-yl}-3-(2-morpholin-4-ylethyl)urea a) 1-{6-[1-(3-Chloro-2,6-difluorophenyl)ethoxy]-1,3-benzothiazol-2-yl}-3-(2-morpholin-4-ylethyl)urea can be prepared as in Example 10a but from 1.5 g of {6-[1-(3-chloro-2,6-difluorophenyl)ethoxy]-1,3-benzothiazol-2-yl}phenyl carbamate and 0.847 g of 2-morpholin-4-ylethanamine. After crystallization of the resin obtained in 15 cm$^3$ of acetonitrile, we obtain 1.2 g of 1-{6-[1-(3-chloro-2,6-difluorophenyl) ethoxy]-1,3-benzothiazol-2-yl}-3-(2-morpholin-4-ylethyl) urea in the form of a cream-coloured powder, which has the following characteristics:

Melting point: 154° C. (Köfler)

1H NMR spectrum (400 MHz, DMSO-$d_6$) δ ppm: 1.72 (d, J=6.4 Hz, 3H) 2.40 (m, 6H) 3.27 (q, J=5.9 Hz, 2H) 3.59 (m, 4H) 5.82 (q, J=6.4 Hz, 1H) 6.77 (m broad, 1H) 6.94 (dd, J=8.8, 2.4 Hz, 1H) 7.17 (td, J=8.5, 2.0 Hz, 1H) 7.45 (m, 2H) 7.59 (td, J=8.5, 5.6 Hz, 1H) 10.68 (m spread-out, 1H)

Mass spectrum: HPLC-MS-DAD-ELSD: 497(+)=(M+H) (+)

b) {6-[1-(3-Chloro-2,6-difluorophenyl)ethoxy]-1,3-benzothiazol-2-yl}phenyl carbamate can be prepared as in Example 10b but from 3 g of 6-[1-(3-chloro-2,6-difluorophenyl)ethoxy]-1,3-benzothiazol-2-amine and 5.51 g of phenyl chlorocarbonate. We thus obtain 4 g of {6-[1-(3-chloro-2,6-difluorophenyl)ethoxy]-1,3-benzothiazol-2-yl}phenyl carbamate in the form of a cream-coloured powder, which has the following characteristics:

Melting point: 175° C. (Köfler)

Mass spectrum: LC-MS-DAD-ELSD: 461(+)=(M+H)(+)

d) 6-[1-(3-Chloro-2,6-difluorophenyl)ethoxy]-1,3-benzothiazol-2-amine can be prepared as in Example 20d but from 4.5 g of 4-[1-(3-chloro-2,6-difluorophenyl)ethoxy] aniline, 6.17 g of potassium thiocyanate and 0.813 cm$^3$ of dibromine. After coagulation of the solid obtained in 30 cm$^3$ of diisopropyl oxide then filtration and drying, we obtain 3.07 g of 6-[1-(3-chloro-2,6-difluorophenyl)ethoxy]-1,3-benzothiazol-2-amine in the form of cream-coloured crystals, which have the following characteristics:

Melting point: 160° C. (Köfler)

Mass spectrum: LC-MS-DAD-ELSD: 341(+)=(M+H)(+)

e) 4-[1-(3-Chloro-2,6-difluorophenyl)ethoxy]aniline can be prepared as in Example 20e but from 0.362 g of platinum oxide and 5 g of 1-chloro-2,4-difluoro-3-[1-(4-nitrophenoxy)ethyl]benzene in 370 cm³ of methanol. We obtain 4.5 g of 4-[1-(3-chloro-2,6-difluorophenyl)ethoxy]aniline in the form of a beige resin, which has the following characteristics:

Rf CCM silica=0.22 [eluent: dichloromethane]

Mass spectrum: LC-MS-DAD-ELSD: 284(+).=(M+H)(+)

f) 1-Chloro-2,4-difluoro-3-[1-(4-nitrophenoxy)ethyl]benzene can be prepared as in Example 20f but from 1.14 g of sodium hydride (at 60% in the oil), 5 g of 1-(3-chloro-2,6-difluorophenyl)ethanol and 3.66 g of 1-fluoro-4-nitrobenzene. We thus obtain 5 g of 1-chloro-2,4-difluoro-3-[1-(4-nitrophenoxy)ethyl]benzene in the form of a cream-coloured powder, which has the following characteristics:

Rf CCM silica=0.29 [eluent: petroleum ether/ethyl acetate (95/5 by volume)]

Mass spectrum: SM-EI: 313(+)=M(+)

g) 1-(3-Chloro-2,6-difluorophenyl)ethanol can be prepared as in Example 3e but from 5 g of 1-(2,3-dichloro-6-fluorophenyl)ethanone and 27 cm³ of a 1M solution of aluminium lithium hydride in tetrahydrofuran. We thus obtain 5 g of 1-(3-chloro-2,6-difluorophenyl)ethanone in the form of a colorless oil, which has the following characteristics:

Rf CCM silica=0.15 [eluent: dichloromethane/methanol (98/2 by volume)]

Mass spectrum: LC-MS-DAD-ELSD: 216(+)=(M+H)(+)−H2O+CH3CN

Example 64

1-{6-[1-(2,6-dichlorophenyl)-2,2,2-trifluoroethoxy]-1,3-benzothiazol-2-yl}-3-(2-morpholin-4-ylethyl) urea a) 1-{6-[1-(2,6-Dichlorophenyl)-2,2,2-trifluoroethoxy]-1,3-benzothiazol-2-yl}-3-(2-morpholin-4-ylethyl)urea can be prepared as in Example 10a but from 0.5 g of {6-[1-(2,6-dichlorophenyl)-2,2,2-trifluoroethoxy]-1,3-benzothiazol-2-yl}phenyl carbamate and 0.254 g of 2-morpholin-4-ylethanamine. After crystallization of the product obtained in 3 cm³ of acetonitrile and then addition of 30 cm³ of water, we obtain 0.479 g of 1-{6-[1-(2,6-dichlorophenyl)-2,2,2-trifluoroethoxy]-1,3-benzothiazol-2-yl}-3-(2-morpholin-4-ylethyl) urea in the form of a cream-coloured powder, which has the following characteristics:

Melting point: 150-160° C. (Köfler)

1H NMR spectrum (400 MHz, DMSO-d6) δ ppm: 2.40 (m, 6H) 3.26 (q, J=5.4 Hz, 2H) 3.59 (m, 4H) 6.63 (q, J=6.8 Hz, 1H) 6.77 (m broad, 1H) 6.95 (dd, J=8.8, 2.6 Hz, 1H) 7.45-7.67 (m, 5H) 10.77 (m spread-out, 1H)

Mass spectrum: LC-MS-DAD-ELSD: 547(−)=(M−H)(−); 549(+)=(M+H)(+)

b) {6-[1-(2,6-Dichlorophenyl)-2,2,2-trifluoroethoxy]-1,3-benzothiazol-2-yl}phenyl carbamate can be prepared as in Example 10b but from 1.7 g of 6-[1-(2,6-dichlorophenyl)-2,2,2-trifluoroethoxy]-1,3-benzothiazol-2-amine and 2.71 g of phenyl chlorocarbonate. We thus obtain 2 g of {6-[1-(2,6-dichlorophenyl)-2,2,2-trifluoroethoxy]-1,3-benzothiazol-2-yl}phenyl carbamate in the form of a cream-coloured powder, which has the following characteristics:

Melting point: 194° C. (Köfler)

Mass spectrum: LC-MS-DAD-ELSD: 511(−)=(M−H)(−); 513(+)=(M+H)(+)

d) 6-[1-(2,6-Dichlorophenyl)-2,2,2-trifluoroethoxy]-1,3-benzothiazol-2-amine can be prepared as in Example 20d but from 1.5 g of 4-[1-(2,6-dichlorophenyl)-2,2,2-trifluoroethoxy]aniline, 1.74 g of potassium thiocyanate and 0.229 cm³ of dibromine. We thus obtain 1.76 g of 6-[1-(2,6-dichlorophenyl)-2,2,2-trifluoroethoxy]-1,3-benzothiazol-2-amine in the form of cream-coloured crystals, which have the following characteristics:

Rf CCM silica=0.34 [eluent: dichloromethane/methanol (95/5 by volume)]

Mass spectrum: HPLC-MS-DAD-ELSD: 393(+)=(M+H) (+)

e) 4-[1-(2,6-Dichlorophenyl)-2,2,2-trifluoroethoxy] aniline can be prepared as in Example 20e but from 0.105 g of platinum oxide and 1.7 g of 1,3-dichloro-2-[2,2,2-trifluoro-1-(4-nitrophenoxy)ethyl]benzene in 370 cm³ of methanol. We obtain 1.55 g of 4-[1-(2,6-dichlorophenyl)-2,2,2-trifluoroethoxy]aniline in the form of an orange-coloured oil, which has the following characteristics:

Rf CCM silica=0.64 [eluent: dichloromethane/methanol (98/2 by volume)]

Mass spectrum: LC-MS-DAD-ELSD: 336(+)=(M+H)(+)

f) 1,3-Dichloro-2-[2,2,2-trifluoro-1-(4-nitrophenoxy) ethyl]benzene can be prepared as in Example 20f but from 0.269 of sodium hydride (at 60% in the oil), 1.5 g of 1-(2,6-dichlorophenyl)-2,2,2-trifluoroethanol and 0.864 g of 1-fluoro-4-nitrobenzene. We thus obtain 1.75 g of 1,3-dichloro-2-[2,2,2-trifluoro-1-(4-nitrophenoxy)ethyl]benzene in the form of a cream-coloured powder, which has the following characteristics:

Melting point: 108° C. (Köfler)

Mass spectrum: SM-EI: 365(+)=M(+)

g) 1-(2,6-dichlorophenyl)-2,2,2-trifluoroethanol can be prepared as follows:

Add 1.75 g of trimethyl(trifluoromethyl)silane to a solution of 2.1 g of 2,6-dichlorobenzaldehyde in 60 cm³ of dimethoxyethane. The reaction mixture becomes clear with a yellow sheen; it is then cooled on a water/ice bath to about 15° C. Add 0.055 g of caesium fluoride in one go. Stir for 4 hours at a temperature close to 20° C. The reaction mixture is then poured into 7.2 cm³ of a 4N aqueous solution of hydrochloric acid. The aqueous phase is decanted then extracted three times with 40 cm³ of diethyl oxide. The organic phases are combined and then dried over magnesium sulphate, filtered and evaporated to dryness under reduced pressure (2 kPa). We obtain 2.9 g of 1-(2,6-dichlorophenyl)-2,2,2-trifluoroethanol in the form of an oil with a yellow sheen, which has the following characteristics:

Rf CCM silica=0.27 [eluent: petroleum ether/ethyl acetate (95/5 by volume)]

Mass spectrum: SM-EI: 244(+)=M(+)

Example 65

N-{6-[1-(2,6-dichloro-3-fluorophenyl)ethoxy]-1,3-benzothiazol-2-yl}-4-(morpholin-4-yl)butanamide N-{6-[1-(2,6-Dichloro-3-fluorophenyl)ethoxy]-1,3-benzothiazol-2-yl}-4-(morpholin-4-yl)butanamide can be prepared as in Example 7a but from 800 mg of 6-[1-(2,6-dichloro-3-fluorophenyl)ethoxy]-1,3-benzothiazol-2-amine, 1.7 g of 1-[bis(dimethylamino)methylidene]-2,3-dihydro-1H-[1,2,3]triazolo[4,5-b]pyridin-1-ium-3-oxide hexafluorophosphate and 0.939 g of 4-(morpholin-4-yl)butanoic acid.

We thus obtain 0.408 g of N-{6-[1-(2,6-dichloro-3-fluorophenyl)ethoxy]-1,3-benzothiazol-2-yl}-4-(morpholin-4-yl)butanamide in the form of a white solid, which has the following characteristics:

Melting point: 141-145° C. (Büchi)

1H NMR spectrum (400 MHz, DMSO-$d_6$) δ ppm: 1.75 (d, J=6.8 Hz, 3H) 1.81 (m spread-out, 2H) 2.19-2.52 (m spread-out, partially masked, 8H) 3.53 (m spread-out, 4H) 6.08 (q, J=6.8 Hz, 1H) 6.96 (dd, J=8.8, 2.4 Hz, 1H) 7.33-7.46 (m, 2H) 7.51 (dd, J=8.8, 4.9 Hz, 1H) 7.58 (d, J=8.8 Hz, 1H) 12.19 (s broad, 1H)

Mass spectrum: LC-MS-DAD-ELSD: [M+H]+m/z=512

Example 66

N-{6-[1-(2,6-dichloro-3-fluorophenyl)ethoxy]-1,3-benzothiazol-2-yl}cyclopropanecarboxamide N-{6-[1-(2,6-Dichloro-3-fluorophenyl)ethoxy]-1,3-benzothiazol-2-yl}cyclopropanecarboxamide can be prepared as in Example 9a but from 0.5 g of 6-[1-(2,6-dichloro-3-fluorophenyl)ethoxy]-1,3-benzothiazol-2-amine and 0.161 g of cyclopropanecarbonyl chloride.

We thus obtain 0.218 g of a sable-coloured solid, which has the following characteristics:

Melting point: 194-199° C. (Büchi)

1H NMR spectrum (400 MHz, DMSO-$d_6$) δ ppm: 0.84-0.97 (m, 4H) 1.75 (d, J=6.8 Hz, 3H) 1.95 (m, 1H) 6.08 (q, J=6.8 Hz, 1H) 6.96 (dd, J=8.8, 2.9 Hz, 1H) 7.37-7.44 (m, 2H) 7.51 (dd, J=8.8, 4.9 Hz, 1H) 7.58 (d, J=8.8 Hz, 1H) 12.67 (s broad, 1 H)

Mass spectrum: LC-MS-DAD-ELSD: [M+H]+m/z=425; [M-H]+-m/z=423

Example 67

N-{6-[1-(2,6-dichloro-3-fluorophenyl)ethoxy]-5-fluoro-1,3-benzothiazol-2-yl}cyclopropanecarboxamide N-{6-[1-(2,6-Dichloro-3-fluorophenyl)ethoxy]-5-fluoro-1,3-benzothiazol-2-yl}cyclopropanecarboxamide can be prepared as in Example 9a but from 500 mg of 6-[1-(2,6-dichloro-3-fluorophenyl)ethoxy]-5-fluoro-1,3-benzothiazol-2-amine and 139 mg of cyclopropanecarbonyl chloride.

We thus obtain 117 mg of a white solid, which has the following characteristics:

Melting point: 186-189° C. (Büchi)

1H NMR spectrum (400 MHz, DMSO-$d_6$) δ ppm: 0.88-0.98 (m, 4H) 1.79 (d, J=6.8 Hz, 3H) 1.96 (m, 1H) 6.07 (q, J=6.8 Hz, 1H) 7.39-7.48 (m, 2H) 7.53 (dd, J=8.9, 5.0 Hz, 1H) 7.60 (d, J=12.0 Hz, 1H) 12.57 (s broad, 1H)

Mass spectrum: LC-MS-DAD-ELSD: [M+H]+m/z=443; [M-H]-m/z=441

Example 68

N-{6-[1-(2,6-dichloro-3-fluorophenyl)ethoxy]-5-fluoro-1,3-benzothiazol-2-yl}-4-(pyrrolidin-1-yl)butanamide N-{6-[1-(2,6-Dichloro-3-fluorophenyl)ethoxy]-5-fluoro-1,3-benzothiazol-2-yl}-4-(pyrrolidin-1-yl)butanamide can be prepared as in Example 7a but from 500 mg of 6-[1-(2,6-dichloro-3-fluorophenyl)ethoxy]-5-fluoro-1,3-benzothiazol-2-amine, 1 g of 1-[bis(dimethylamino)methylidene]-2,3-dihydro-1H-[1,2,3]triazolo[4,5-b]pyridin-1-ium-3-oxide hexafluorophosphate and 414 mg of 4-(pyrrolidin-1-yl)butanoic acid. We obtain 114 mg of N-{6-[1-(2,6-dichloro-3-fluorophenyl)ethoxy]-5-fluoro-1,3-benzothiazol-2-yl}-4-(pyrrolidin-1-yl)butanamide in the form of a white solid, which has the following characteristics:

Melting point: 153-157° C. (Büchi)

1H NMR spectrum (400 MHz, DMSO-$d_6$) δ ppm: 1.66 (m, 4H) 1.77 (m, 2H) 1.79 (d, J=6.6 Hz, 3H) 2.40-2.54 (m partially masked, 8H) 6.07 (q, J=6.6 Hz, 1H) 7.39-7.48 (m, 2H) 7.53 (dd, J=9.0, 4.9 Hz, 1H) 7.59 (d, J=11.7 Hz, 1H) 12.38 (m spread-out, 1H)

Mass spectrum: LC-MS-DAD-ELSD: [M+H]+m/z=514; [M-H]-m/z=512

Example 69

N-{6-[1-(2,6-dichloro-3-fluorophenyl)ethoxy]-5-fluoro-1,3-benzothiazol-2-yl}-2-(piperazin-1-yl)acetamide a) N-{6-[1-(2,6-Dichloro-3-fluorophenyl)ethoxy]-5-fluoro-1,3-benzothiazol-2-yl}-2-(piperazin-1-yl)acetamide can be prepared as follows:

add 0.73 cm³ of trifluoroacetic acid to a solution of 0.385 g of 1,1-dimethylethyl 4-[2-({6-[1-(2,6-dichloro-3-fluorophenyl)ethoxy]-5-fluoro-1,3-benzothiazol-2-yl}amino)-2-oxoethyl]piperazine-1-carboxylate in 45 cm³ of dichloromethane. Stir for 16 hours at a temperature close to 20° C. The reaction mixture is then evaporated to dryness under reduced pressure (2 kPa). The residue is taken up in 15 cm³ of water. The mixture obtained is adjusted to pH 8-9 with an aqueous solution of sodium hydrogen carbonate and then extracted three times with 40 cm³ of ethyl acetate. The combined organic phases are dried over magnesium sulphate, then filtered and evaporated to dryness under reduced pressure (2 kPa). The white solid obtained is solidified in 5 cm³ of acetonitrile, filtered and then dried under reduced pressure. We obtain 0.178 g N-{6-[1-(2,6-dichloro-3-fluorophenyl)ethoxy]-5-fluoro-1,3-benzothiazol-2-yl}-2-(piperazin-1-yl)acetamide in the form of a cream-coloured powder, which has the following characteristics:

Melting point: 188-190° C. (Köfler)

1H NMR spectrum (400 MHz, DMSO-$d_6$) δ ppm: 1.79 (d, J=6.7 Hz, 3H) 2.43 (m, 4H) 2.71 (m, 4H) 3.25 (s, 2H) 6.07 (q, J=6.7 Hz, 1H) 7.42-7.48 (m, 2H) 7.53 (dd, J=8.9, 5.0 Hz, 1H) 7.60 (d, J=11.7 Hz, 1H)

Mass spectrum: LC-MS-DAD-ELSD: [M+H]+m/z=501 b) 1,1-Dimethylethyl 4-[2-({6-[1-(2,6-dichloro-3-fluorophenyl)ethoxy]-5-fluoro-1,3-benzothiazol-2-yl}amino)-2-oxoethyl]piperazine-1-carboxylate can be prepared as in Example 7a but from 0.5 g of 6-[1-(2,6-dichloro-3-fluorophenyl)ethoxy]-5-fluoro-1,3-benzothiazol-2-amine, 1.01 g of 1-[bis(dimethylamino)methylidene]-2,3-dihydro-1H-[1,2,3]triazolo[4,5-b]pyridin-1-ium-3-oxide hexafluorophosphate and 0.747 g of (4-{[(2-methylpropan-2-yl)oxy]carbonyl}piperazin-1-yl)acetic acid.

We obtain 0.387 g of 1,1-dimethylethyl 4-[2-({6-[1-(2,6-dichloro-3-fluorophenyl)ethoxy]-5-fluoro-1,3-benzothiazol-2-yl}amino)-2-oxoethyl]piperazine-1-carboxylate in the form of an orange-coloured meringue, which has the following characteristics:

Rf CCM silica=0.21 [eluent: dichloromethane/MeOH 98/2]

Mass spectrum: LC-MS-DAD-ELSD: [M+H]+: m/z 601; [M-H]- m/z 599

Example 70

{6-[1-(2,6-dichloro-3-fluorophenyl)ethoxy]-5-fluoro-1,3-benzothiazol-2-yl}3-(diethylamino)propyl carbamate {6-[1-(2,6-Dichloro-3-fluorophenyl)ethoxy]-5-fluoro-1,3-benzothiazol-2-yl}3-(diethylamino)propyl carbamate can be prepared as follows:

Suspend 0.35 g of {6-[1-(2,6-dichloro-3-fluorophenyl)ethoxy]-5-fluoro-1,3-benzothiazol-2-yl}phenyl carbamate in 25 cm$^3$ of tetrahydrofuran and then add 0.185 g of 3-(diethylamino)propan-1-ol. The reaction mixture is refluxed for 16 hours. The insoluble matter is then filtered off, and the filtrate is evaporated to dryness under reduced pressure (2 kPa). The residue is dissolved in 15 cm$^3$ of boiling acetonitrile then the mixture is cooled. The crystals obtained are filtered and then dried under reduced pressure. We obtain 0.279 g of {6-[1-(2,6-dichloro-3-fluorophenyl)ethoxy]-5-fluoro-1,3-benzothiazol-2-yl}3-(diethylamino)propyl carbamate in the form of a cream-coloured powder, which has the following characteristics:

Melting point: 188-190° C. (Köfler)

1H NMR spectrum (400 MHz, DMSO-d$_6$) δ ppm: 0.94 (t, J=7.1 Hz, 6H) 1.73 (m, 2H) 1.78 (d, J=6.6 Hz, 3H) 2.40-2.48 (m, 6H) 4.19 (t, J=6.6 Hz, 2H) 6.06 (q, J=6.6 Hz, 1H) 7.39-7.47 (m, 2H) 7.50-7.56 (m, 2H) 12.20 (m spread-out, 1H)

Mass spectrum: LC-MS-DAD-ELSD: [M+H]+m/z=532; [M−H]−m/z=530

Example 71

{6-[1-(2,6-dichloro-3-fluorophenyl)ethoxy]-5-fluoro-1,3-benzothiazol-2-yl}2-(diethylamino)ethyl carbamate {6-[1-(2,6-Dichloro-3-fluorophenyl)ethoxy]-5-fluoro-1,3-benzothiazol-2-yl}2-(diethylamino)ethyl carbamate can be prepared as in Example 70 but from 0.4 g of {6-[1-(2,6-dichloro-3-fluorophenyl)ethoxy]-5-fluoro-1,3-benzothiazol-2-yl}phenyl carbamate and 0.189 g of 2-(diethylamino)ethanol. We thus obtain 0.213 g of {6-[1-(2,6-dichloro-3-fluorophenyl)ethoxy]-5-fluoro-1,3-benzothiazol-2-yl}2-(diethylamino)ethyl carbamate in the form of a cream-coloured powder, which has the following characteristics:

Melting point: 184-186° C. (Köfler)

1H NMR spectrum (400 MHz, DMSO-d$_6$) δ ppm: 0.95 (t, J=7.1 Hz, 6H) 1.79 (d, J=6.8 Hz, 3H) 2.47-2.55 (m partially masked, 4H) 2.67 (t, J=6.1 Hz, 2H) 4.21 (t, J=6.1 Hz, 2H) 6.06 (q, J=6.8 Hz, 1H) 7.39-7.47 (m, 2H) 7.50-7.60 (m, 2H) 11.97 (m spread-out, 1H)

Mass spectrum: LC-MS-DAD-ELSD: [M+H]+m/z=518; [M−H]−m/z=516

Example 72

{6-[1-(2,6-dichloro-3-fluorophenyl)ethoxy]-5-fluoro-1,3-benzothiazol-2-yl}2-methoxyethyl carbamate {6-[1-(2,6-Dichloro-3-fluorophenyl)ethoxy]-5-fluoro-1,3-benzothiazol-2-yl}2-methoxyethyl carbamate can be prepared as in Example 70 but from 0.35 g of {6-[1-(2,6-dichloro-3-fluorophenyl)ethoxy]-5-fluoro-1,3-benzothiazol-2-yl}phenyl carbamate and 0.107 g of 2-methoxyethanol. We thus obtain 0.214 g of {6-[1-(2,6-dichloro-3-fluorophenyl)ethoxy]-5-fluoro-1,3-benzothiazol-2-yl}2-methoxyethyl carbamate in the form of a white powder, which has the following characteristics:

Melting point: 200-205° C. (Köfler)

1H NMR spectrum (400 MHz, DMSO-d$_6$) δ ppm: 1.78 (d, J=6.8 Hz, 3H) 3.28 (s, 3H) 3.58 (m, 2H) 4.31 (m, 2H) 6.06 (q, J=6.8 Hz, 1H) 7.40-7.48 (m, 2H) 7.53 (dd, J=9.0, 4.9 Hz, 1H) 7.56 (d, J=11.9 Hz, 1H) 12.02 (m spread-out, 1H)

Mass spectrum: LC-MS-DAD-ELSD: [M+H]+m/z=477

Example 73

{6-[1-(2,6-dichloro-3-fluorophenyl)ethoxy]-5-fluoro-1,3-benzothiazol-2-yl}2-(pyrrolidin-1-yl)ethyl carbamate {6-[1-(2,6-Dichloro-3-fluorophenyl)ethoxy]-5-fluoro-1,3-benzothiazol-2-yl}2-(pyrrolidin-1-yl)ethyl carbamate can be prepared as in Example 70 but from 0.5 g of {6-[1-(2,6-dichloro-3-fluorophenyl)ethoxy]-5-fluoro-1,3-benzothiazol-2-yl}phenyl carbamate and 0.232 g of 2-(pyrrolidin-1-yl)ethanol. We thus obtain 0.37 g of {6-[1-(2,6-dichloro-3-fluorophenyl)ethoxy]-5-fluoro-1,3-benzothiazol-2-yl}2-(pyrrolidin-1-yl)ethyl carbamate in the form of an orange-coloured meringue, which has the following characteristics:

1H NMR spectrum (400 MHz, DMSO-d6) δ ppm: 1.69 (d, J=6.7 Hz, 3H) 3.71 (s, 3H) 3.82 (s, 3H) 5.92 (q, J=6.7 Hz, 1H) 6.73 (dd, J=8.8, 2.9 Hz, 1H) 7.11 (s, 1H) 7.13-7.17 (m, 2H) 7.21 (s, 2H)

Mass spectrum: LC-MS-DAD-ELSD: [M+H]+m/z=399

Example 74

{6-[1-(2,6-dichloro-3-fluorophenyl)ethoxy]-1,3-benzothiazol-2-yl}2-(morpholin-4-yl)ethyl carbamate {6-[1-(2,6-Dichloro-3-fluorophenyl)ethoxy]-1,3-benzothiazol-2-yl}2-(morpholin-4-yl)ethyl carbamate can be prepared as in Example 70 but from 0.5 g of {6-[1-(2,6-dichloro-3-fluorophenyl)ethoxy]-1,3-benzothiazol-2-yl}phenyl carbamate and 0.152 g of 2-(morpholin-4-yl)ethanol. We thus obtain 0.23 g of {6-[1-(2,6-dichloro-3-fluorophenyl)ethoxy]-1,3-benzothiazol-2-yl}2-(morpholin-4-yl)ethyl carbamate in the form of a white solid, which has the following characteristics:

1H NMR spectrum (400 MHz, DMSO-d6) δ ppm: 1.74 (d, J=6.5 Hz, 3H) 2.43 (m, 4H) 2.59 (t, J=5.9 Hz, 2H) 3.55 (m, 4H) 4.27 (m, 2H) 6.07 (q, J=6.5 Hz, 1H) 6.93 (d broad, J=8.8 Hz, 1H) 7.35-7.44 (m, 2H) 7.48-7.56 (m, 2H) 11.91 (m spread-out, 1H)

Mass spectrum: LC-MS-DAD-ELSD: [M+H]+m/z=514

The examples described below were synthesized according to the following scheme:

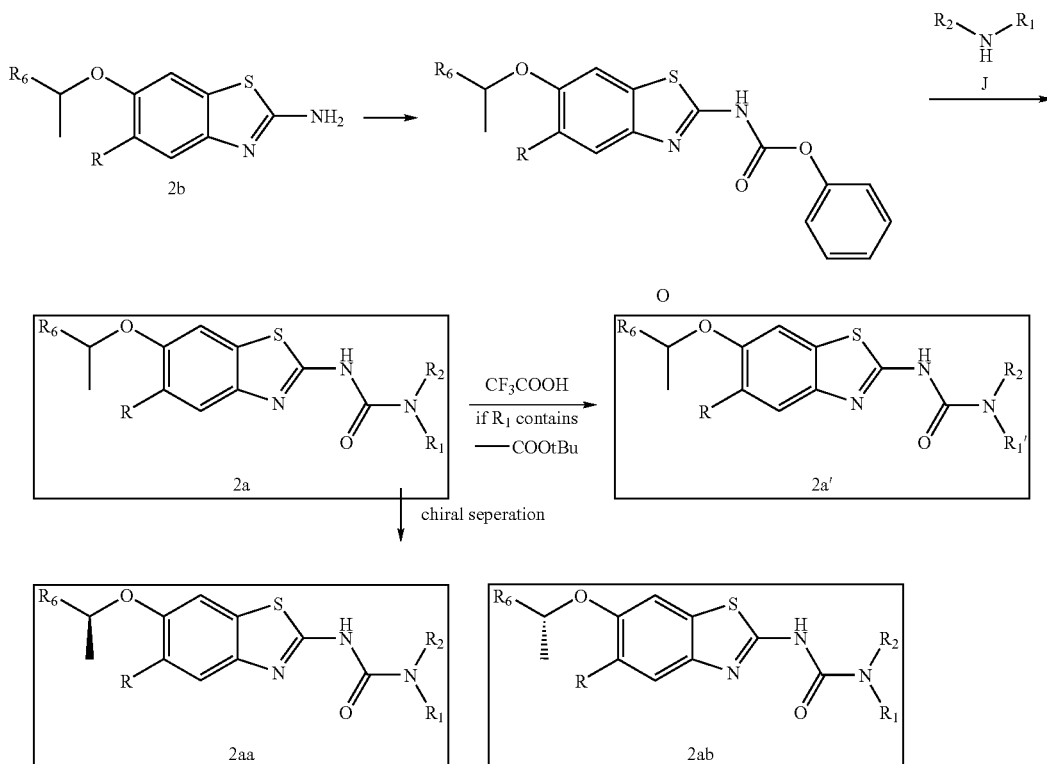

| Ex | 2a | 2a' | 2aa | 2ab | O | J |
|---|---|---|---|---|---|---|
| 75 | 1-{6-[1-(2,6-dichloro-3-fluorophenyl)ethoxy]-5-fluoro-1,3-benzothiazol-2-yl}-3-[2-(4-methylpiperazin-1-yl)ethyl]urea | | | | {6-[1-(2,6-dichloro-3-fluorophenyl)ethoxy]-5-fluoro-1,3-benzothiazol-2-yl}phenyl carbamate | 2-(4-methylpiperazin-1-yl)ethanamine |
| 76 | | | 1-{6-[(1R*)-1-(2,6-dichloro-3-fluorophenyl)ethoxy]-5-fluoro-1,3-benzothiazol-2-yl}-3-[2-(4-methylpiperazin-1-yl)ethyl]urea | | | |
| 77 | | | | 1-{6-[(1S*)-1-(2,6-dichloro-3-fluorophenyl)ethoxy]-5-fluoro-1,3-benzothiazol-2-yl}-3-[2-(4-methylpiperazin-1-yl)ethyl]urea | | |
| 78 | 1-{6-[1-(2,6-dichloro-3-fluorophenyl)ethoxy]-5-fluoro-1,3-benzothiazol-2-yl}-3-[3-(2-oxopyrrolidin-1-yl)propyl]urea | | | | {6-[1-(2,6-dichloro-3-fluorophenyl)ethoxy]-5-fluoro-1,3-benzothiazol-2-yl}phenyl carbamate | 1-(3-aminopropyl)pyrrolidin-2-one |
| 79 | 1-{6-[1-(2,6-dichloro-3-fluorophenyl)ethoxy]-5-fluoro-1,3-benzothiazol-2-yl}-3-[2-(1-methylpyrrolidin-2-yl)ethyl]urea | | | | {6-[1-(2,6-dichloro-3-fluorophenyl)ethoxy]-5-fluoro-1,3-benzothiazol-2-yl}phenyl carbamate | 2-(1-methylpyrrolidin-2-yl)ethanamine |

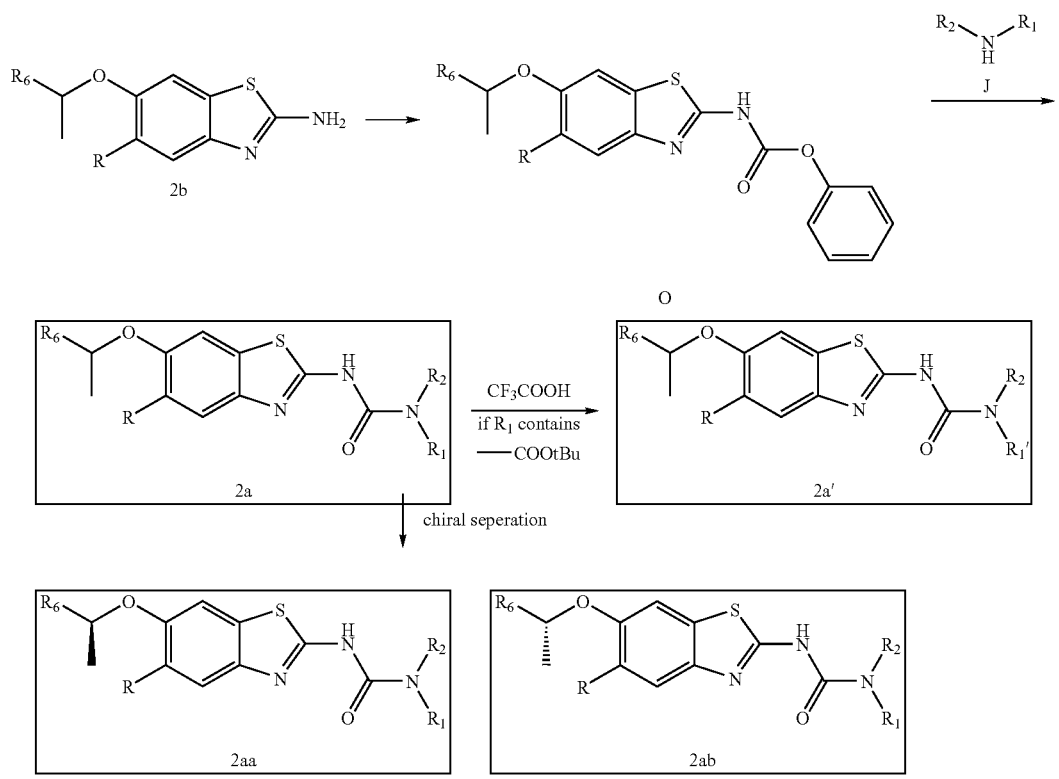

| Ex | 2a | 2a' | 2aa | 2ab | O | J |
|---|---|---|---|---|---|---|
| 80 | 1-{6-[1-(2,6-dichloro-3-fluorophenyl)ethoxy]-5-fluoro-1,3-benzothiazol-2-yl}-3-[2-(piperidin-1-yl)ethyl]urea | | | | {6-[1-(2,6-dichloro-3-fluorophenyl)ethoxy]-5-fluoro-1,3-benzothiazol-2-yl}phenyl carbamate | 2-(piperidin-1-yl)ethanamine |
| 81 | 1-{6-[1-(2,6-dichloro-3-fluorophenyl)ethoxy]-5-fluoro-1,3-benzothiazol-2-yl}-3-(2-methoxyethyl)urea | | | | {6-[1-(2,6-dichloro-3-fluorophenyl)ethoxy]-5-fluoro-1,3-benzothiazol-2-yl}phenyl carbamate | 2-methoxy ethanamine |
| 82 | 1-{6-[1-(2,6-dichloro-3-fluorophenyl)ethoxy]-1,3-benzothiazol-2-yl}-3-[2-(diethylamino)ethyl]urea | | | | {6-[1-(2,6-dichloro-3-fluorophenyl)ethoxy]-1,3-benzothiazol-2-yl}phenyl carbamate | N,N-diethylethane-1,2-diamine |
| 83 | 1-{6-[1-(2,6-dichloro-3-fluorophenyl)ethoxy]-1,3-benzothiazol-2-yl}-3-[3-(diethylamino)propyl]urea | | | | {6-[1-(2,6-dichloro-3-fluorophenyl)ethoxy]-1,3-benzothiazol-2-yl}phenyl carbamate | N,N-diethylpropane-1,3-diamine |
| 84 | 1-{6-[1-(2,6-dichloro-3-fluorophenyl)ethoxy]-5-fluoro-1,3-benzothiazol-2-yl}-3-[2-(pyrrolidin-1-yl)ethyl]urea | | | | {6-[1-(2,6-dichloro-3-fluorophenyl)ethoxy]-5-fluoro-1,3-benzothiazol-2-yl}phenyl carbamate | 2-(pyrrolidin-1-yl)ethanamine |
| 85 | | | 1-{6-[(1R*)1-(2,6-dichloro-3-fluorophenyl)ethoxy]-5-fluoro-1,3-benzothiazol-2-yl}-3-[2-(pyrrolidin-1-yl)ethyl]urea | | | |

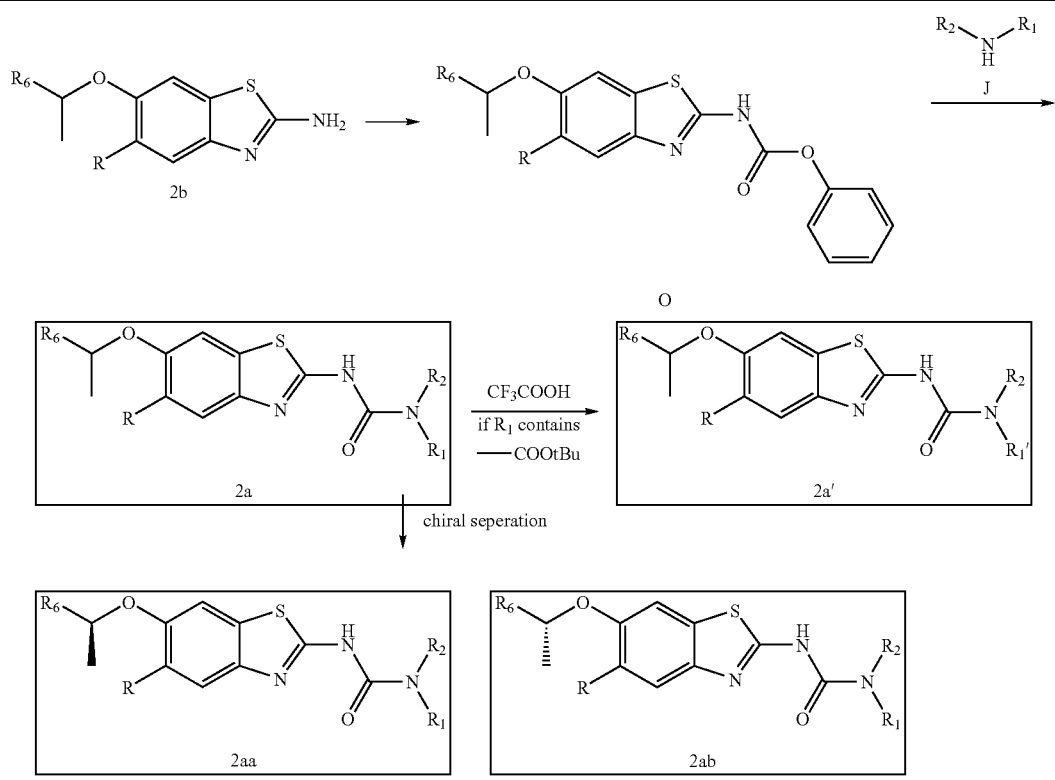

| Ex | 2a | 2a' | 2aa | 2ab | O | J |
|----|----|-----|-----|-----|---|---|
| 86 | 1-{6-[1-(2,6-dichloro-3-fluorophenyl)ethoxy]-5-fluoro-1,3-benzothiazol-2-yl}-3-(2-ethoxyethyl)urea | | | | {6-[1-(2,6-dichloro-3-fluorophenyl)ethoxy]-5-fluoro-1,3-benzothiazol-2-yl}phenyl carbamate | 2-ethoxyethanamine |
| 87 | {2-[({6-[1-(2,6-dichloro-3-fluorophenyl)ethoxy]-5-fluoro-1,3-benzothiazol-2-yl}carbamoyl)amino]ethyl}2-methylpropan-2-yl carbamate | | | | {6-[1-(2,6-dichloro-3-fluorophenyl)ethoxy]-5-fluoro-1,3-benzothiazol-2-yl}phenyl carbamate | (2-aminoethyl) 2-methylpropan-2-yl carbamate |
| 88 | | 1-(2-aminoethyl)-3-{6-[1-(2,6-dichloro-3-fluorophenyl)ethoxy]-5-fluoro-1,3-benzothiazol-2-yl}urea | | | {6-[1-(2,6-dichloro-3-fluorophenyl)ethoxy]-5-fluoro-1,3-benzothiazol-2-yl}phenyl carbamate | (2-aminoethyl) 2-methylpropan-2-yl carbamate |
| 89 | | | 1-(2-aminoethyl)-3-{6-[(1R*)-1-(2,6-dichloro-3-fluorophenyl)ethoxy]-5-fluoro-1,3-benzothiazol-2-yl}urea | | | |
| 90 | | | | 1-(2-aminoethyl)-3-{6-[(1S*)-1-(2,6-dichloro-3-fluorophenyl)ethoxy]-5-fluoro-1,3-benzothiazol-2-yl}urea | | |

-continued

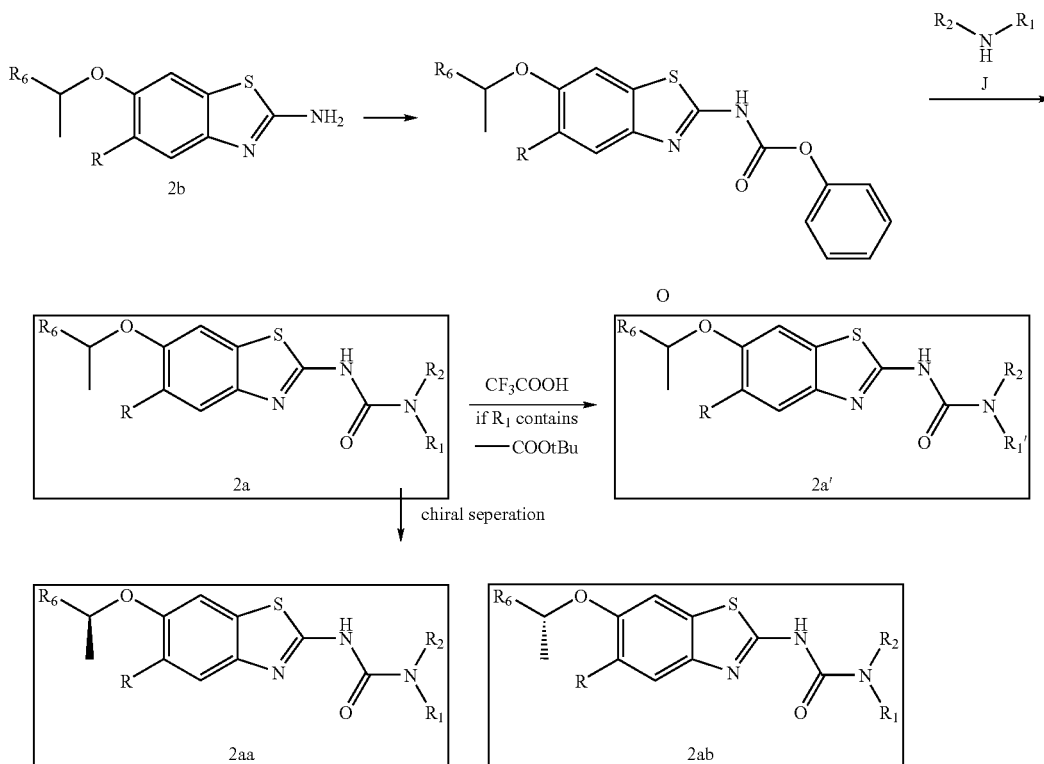

| Ex | 2a | 2a' | 2aa | 2ab | O | J |
|---|---|---|---|---|---|---|
| 91 | 1-{6-[1-(2,6-dichloro-3-fluorophenyl)ethoxy]-5-fluoro-1,3-benzothiazol-2-yl}-3-[2-(1H-pyrrol-1-yl)ethyl]urea | | | | {6-[1-(2,6-dichloro-3-fluorophenyl)ethoxy]-5-fluoro-1,3-benzothiazol-2-yl}phenyl carbamate | 2-(1H-pyrrol-1-yl)ethanamine |
| 92 | 1-{6-[1-(2,6-dichloro-3-fluorophenyl)ethoxy]-5-fluoro-1,3-benzothiazol-2-yl}-3-(2-isopropoxyethyl)urea | | | | {6-[1-(2,6-dichloro-3-fluorophenyl)ethoxy]-5-fluoro-1,3-benzothiazol-2-yl}phenyl carbamate | 2-isopropoxyethanamine |
| 93 | 3-{6-[1-(2,6-dichloro-3-fluorophenyl)ethoxy]-5-fluoro-1,3-benzothiazol-2-yl}-1-(2-methoxyethyl)-1-methylurea | | | | {6-[1-(2,6-dichloro-3-fluorophenyl)ethoxy]-5-fluoro-1,3-benzothiazol-2-yl}phenyl carbamate | 2-methoxy-N-methylethanamine |
| 94 | 1-{2-[benzyl(methyl)amino]ethyl}-3-{6-[1-(2,6-dichloro-3-fluorophenyl)ethoxy]-5-fluoro-1,3-benzothiazol-2-yl}urea | | | | {6-[1-(2,6-dichloro-3-fluorophenyl)ethoxy]-5-fluoro-1,3-benzothiazol-2-yl}phenyl carbamate | N-benzyl-N-methylethane-1,2-diamine |
| 95 | {2-[({6-[1-(2,6-dichloro-3-fluorophenyl)ethoxy]-5-fluoro-1,3-benzothiazol-2-yl}carbamoyl)amino]ethyl}2-methylpropan-2-yl methylcarbamate | | | | {6-[1-(2,6-dichloro-3-fluorophenyl)ethoxy]-5-fluoro-1,3-benzothiazol-2-yl}phenyl carbamate | (2-aminoethyl) 2-methylpropan-2-yl methylcarbamate |

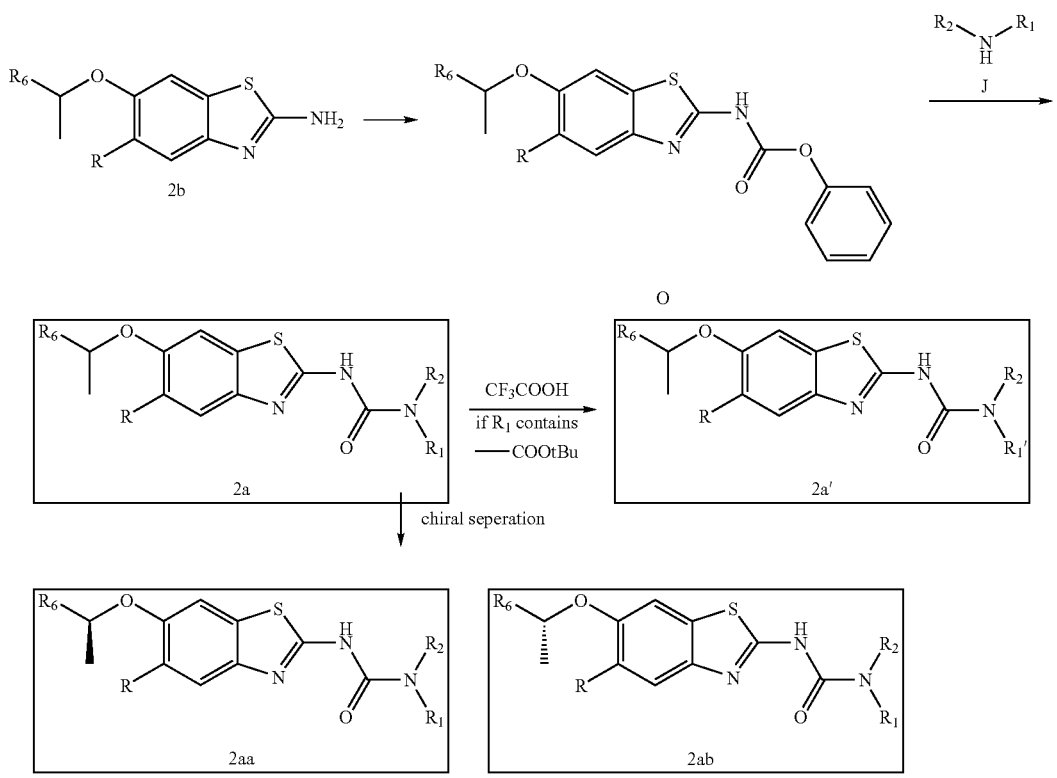

| Ex | 2a | 2a' | 2aa | 2ab | O | J |
|---|---|---|---|---|---|---|
| 96 |  | 1-{6-[1-(2,6-dichloro-3-fluorophenyl)ethoxy]-5-fluoro-1,3-benzothiazol-2-yl}-3-[2-(methylamino)ethyl]urea |  |  | {6-[1-(2,6-dichloro-3-fluorophenyl)ethoxy]-5-fluoro-1,3-benzothiazol-2-yl}phenyl carbamate | (2-aminoethyl) 2-methylpropan-2-yl methylcarbamate |
| 97 | 1-[2-(benzyloxy)ethyl]-3-{6-[1-(2,6-dichloro-3-fluorophenyl)ethoxy]-5-fluoro-1,3-benzothiazol-2-yl}urea |  |  |  | {6-[1-(2,6-dichloro-3-fluorophenyl)ethoxy]-5-fluoro-1,3-benzothiazol-2-yl}phenyl carbamate | 2-(benzyloxy)ethanamine |
| 98 | 1-{6-[1-(2,6-dichloro-3-fluorophenyl)ethoxy]-5-fluoro-1,3-benzothiazol-2-yl}-3-(2-hydroxyethyl)urea |  |  |  | {6-[1-(2,6-dichloro-3-fluorophenyl)ethoxy]-5-fluoro-1,3-benzothiazol-2-yl}phenyl carbamate | 2-aminoethanol |
| 99 |  |  | 1-{6-[(1R*)1-(2,6-dichloro-3-fluorophenyl)ethoxy]-5-fluoro-1,3-benzothiazol-2-yl}-3-(2-hydroxyethyl)urea |  |  |  |
| 100 | 1-{6-[1-(2,6-dichloro-3-fluorophenyl)ethoxy]-5-fluoro-1,3-benzothiazol-2-yl}-3-[2-(4-ethylpiperazin-1-yl)ethyl]urea |  |  |  | {6-[1-(2,6-dichloro-3-fluorophenyl)ethoxy]-5-fluoro-1,3-benzothiazol-2-yl}phenyl carbamate | 2-(4-ethylpiperazin-1-yl)ethanamine |

-continued

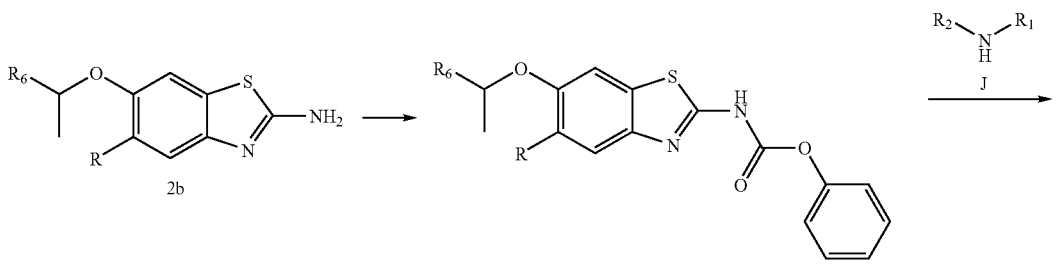

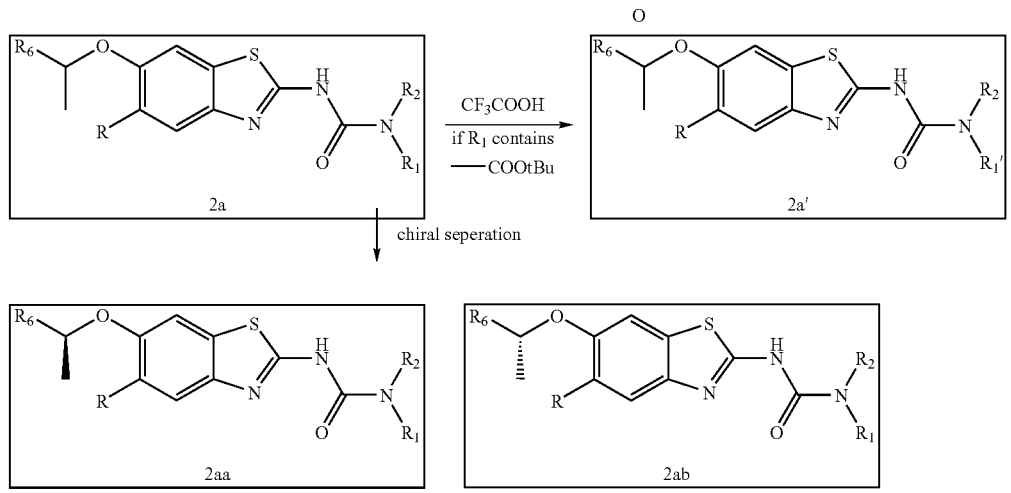

| Ex | 2a | 2a' | 2aa | 2ab | O | J |
|---|---|---|---|---|---|---|
| 101 | | | 1-{6-[(1R*)-1-(2,6-dichloro-3-fluorophenyl)ethoxy]-5-fluoro-1,3-benzothiazol-2-yl}-3-[2-(4-ethylpiperazin-1-yl)ethyl] urea | | | |
| 102 | | | | 1-{6-[(1S*)-1-(2,6-dichloro-3-fluorophenyl)ethoxy]-5-fluoro-1,3-benzothiazol-2-yl}-3-[2-(4-ethylpiperazin-1-yl)ethyl]urea | | |
| 103 | 1-[2-(cyclopropylmethoxy)ethyl]-3-{6-[1-(2,6-dichloro-3-fluorophenyl)ethoxy]-5-fluoro-1,3-benzothiazol-2-yl}urea | | | | {6-[1-(2,6-dichloro-3-fluorophenyl)ethoxy]-5-fluoro-1,3-benzothiazol-2-yl}phenyl carbamate | 2-(cyclopropylmethoxy)ethanamine |
| 104 | 1-{6-[1-(2,6-dichloro-3-fluorophenyl)ethoxy]-5-fluoro-1,3-benzothiazol-2-yl}-3-(3-methoxypropyl)urea | | | | {6-[1-(2,6-dichloro-3-fluorophenyl)ethoxy]-5-fluoro-1,3-benzothiazol-2-yl}phenyl carbamate | 3-methoxypropan-1-amine |
| 105 | 1-{6-[1-(2,6-dichloro-3-fluorophenyl)ethoxy]-5-fluoro-1,3-benzothiazol-2-yl}-3-(3-hydroxypropyl)urea | | | | {6-[1-(2,6-dichloro-3-fluorophenyl)ethoxy]-5-fluoro-1,3-benzothiazol-2-yl}phenyl carbamate | 3-aminopropan-1-ol |

-continued

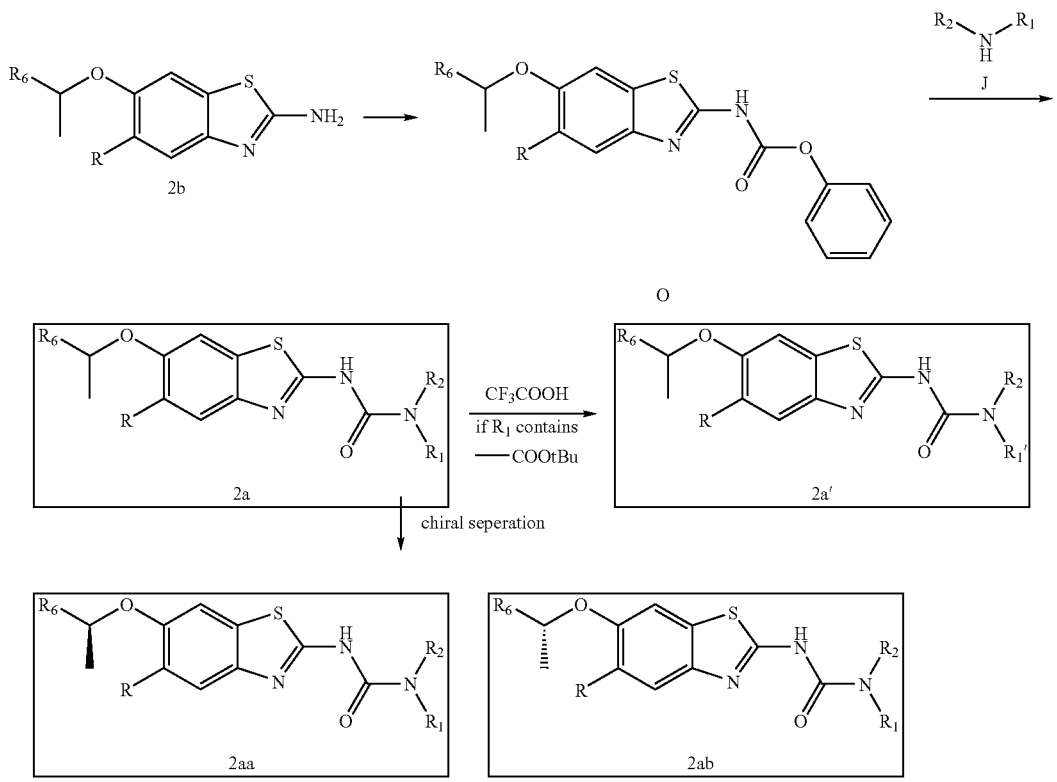

| Ex | 2a | 2a' | 2aa | 2ab | O | J |
|---|---|---|---|---|---|---|
| 108 | 1-{6-[1-(2,3-dichloro-6-fluorophenyl)ethoxy]-1,3-benzothiazol-2-yl}-3-[2-(4-methylpiperazin-1-yl)ethyl]urea | | | | {6-[1-(2,3-dichloro-6-fluorophenyl)ethoxy]-1,3-benzothiazol-2-yl}phenyl carbamate | 2-(4-methylpiperazin-1-yl)ethanamine |
| 109 | | | 1-{6-[(1R*)1-(2,3-dichloro-6-fluorophenyl)ethoxy]-1,3-benzothiazol-2-yl}-3-[2-(4-methylpiperazin-1-yl)ethyl]urea | | | |
| 110 | 1-{6-[1-(2,3-dichloro-6-fluorophenyl)ethoxy]-1,3-benzothiazol-2-yl}-3-[2-(1-methylpyrrolidin-2-yl)ethyl]urea | | | | {6-[1-(2,3-dichloro-6-fluorophenyl)ethoxy]-1,3-benzothiazol-2-yl}phenyl carbamate | 2-(1-methylpyrrolidin-2-yl)ethanamine |
| 111 | 1-{6-[1-(2,3-dichloro-6-fluorophenyl)ethoxy]-5-fluoro-1,3-benzothiazol-2-yl}-3-[2-(morpholin-4-yl)ethyl]urea | | | | {6-[1-(2,3-dichloro-6-fluorophenyl)ethoxy]-5-fluoro-1,3-benzothiazol-2-yl}phenyl carbamate | 2-(morpholin-4-yl)ethanamine |
| 112 | | | 1-{6-[(1R*)-1-(2,3-dichloro-6-fluorophenyl)ethoxy]-5-fluoro-1,3-benzothiazol-2-yl}-3-[2-(morpholin-4-yl)ethyl]urea | | | |

-continued

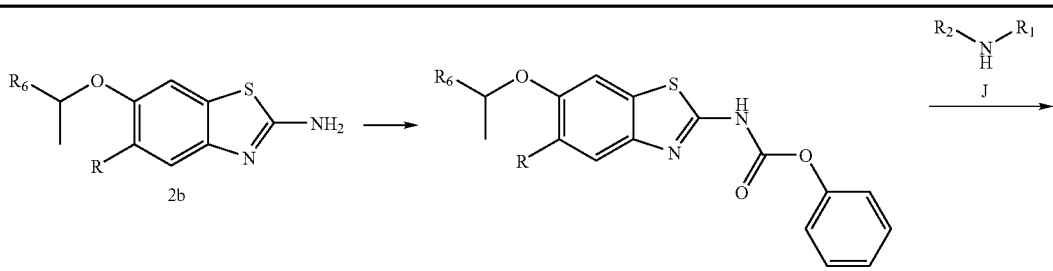

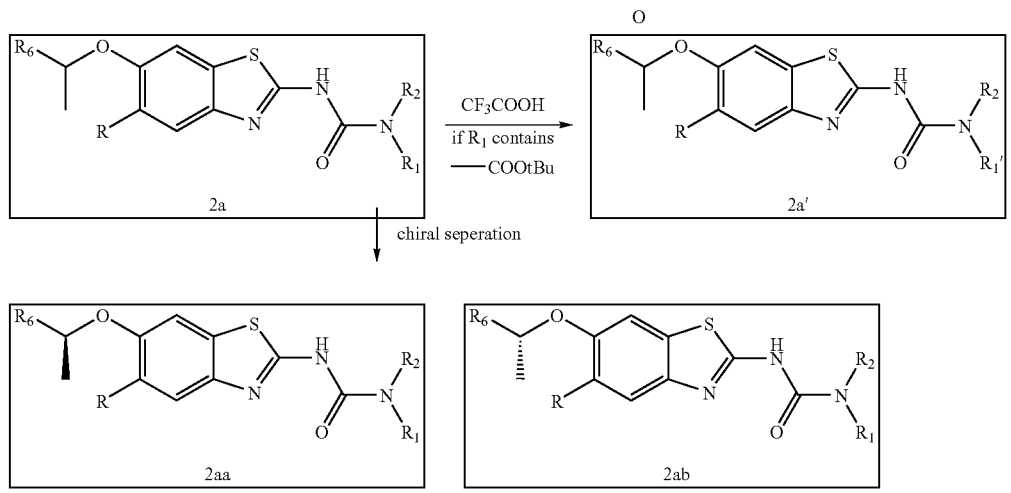

| Ex | 2a | 2a' | 2aa | 2ab | O | J |
|---|---|---|---|---|---|---|
| 113 | | | | 1-{6-[(1S*)-1-(2,3-dichloro-6-fluorophenyl)ethoxy]-5-fluoro-1,3-benzothiazol-2-yl}-3-[2-(morpholin-4-yl)ethyl]urea | | |
| 114 | 1-{6-[1-(2,3-dichloro-6-fluorophenyl)ethoxy]-5-fluoro-1,3-benzothiazol-2-yl}-3-[3-(2-oxopyrrolidin-1-yl)propyl]urea | | | | {6-[1-(2,3-dichloro-6-fluorophenyl)ethoxy]-5-fluoro-1,3-benzothiazol-2-yl}phenyl carbamate | 1-(3-aminopropyl)pyrrolidin-2-one |
| 115 | 1-{6-[1-(2,3-dichloro-6-fluorophenyl)ethoxy]-5-fluoro-1,3-benzothiazol-2-yl}-3-[2-(4-methylpiperazin-1-yl)ethyl]urea | | | | {6-[1-(2,3-dichloro-6-fluorophenyl)ethoxy]-5-fluoro-1,3-benzothiazol-2-yl}phenyl carbamate | 2-(4-methylpiperazin-1-yl)ethanamine |
| 116 | | | | 1-{6-[(1R*)-1-(2,3-dichloro-6-fluorophenyl)ethoxy]-5-fluoro-1,3-benzothiazol-2-yl}-3-[2-(4-methylpiperazin-1-yl)ethyl]urea | | |
| 117 | | | | 1-{6-[(1S*)-1-(2,3-dichloro-6-fluorophenyl)ethoxy]-5-fluoro-1,3-benzothiazol-2-yl}-3-[2-(4-methylpiperazin-1-yl)ethyl]urea | | |

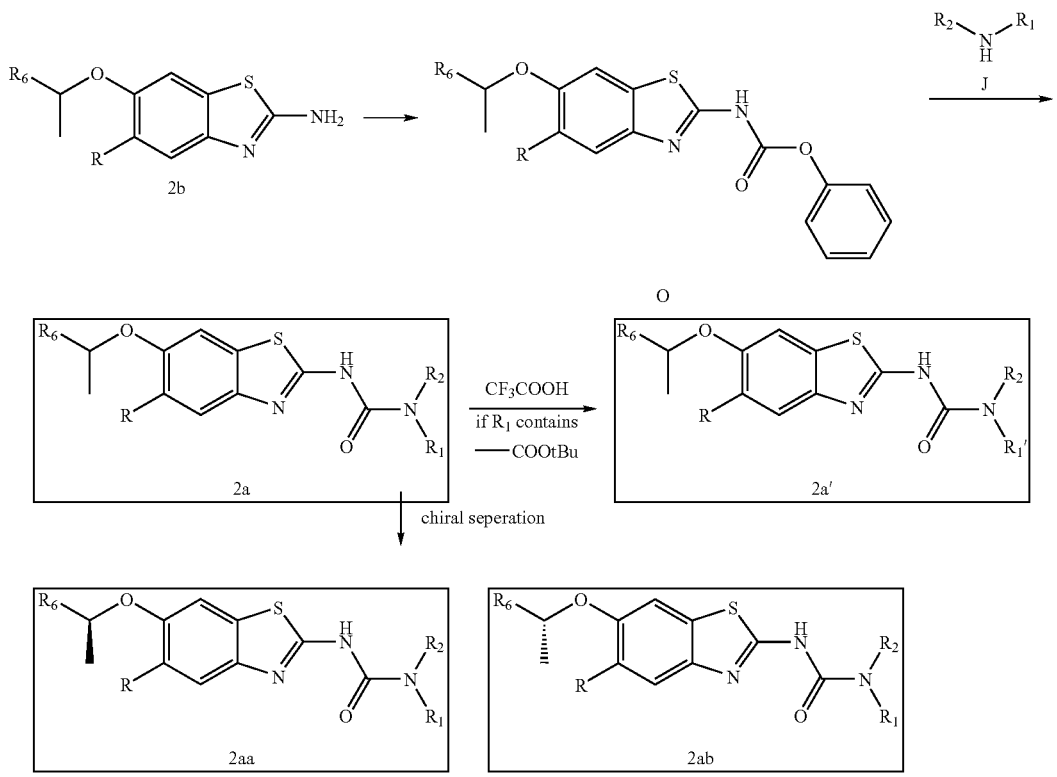

| Ex | 2a | 2a′ | 2aa | 2ab | O | J |
|---|---|---|---|---|---|---|
| 118 | 1-{6-[1-(2,3-dichloro-6-fluorophenyl)ethoxy]-5-fluoro-1,3-benzothiazol-2-yl}-3-[2-(pyrrolidin-1-yl)ethyl]urea | | | | {6-[1-(2,3-dichloro-6-fluorophenyl)ethoxy]-5-fluoro-1,3-benzothiazol-2-yl}phenyl carbamate | 2-(pyrrolidin-1-yl)ethanamine |
| 119 | | | 1-{6-[(1R*)-1-(2,3-dichloro-6-fluorophenyl)ethoxy]-5-fluoro-1,3-benzothiazol-2-yl}-3-[2-(pyrrolidin-1-yl)ethyl]urea | | | |
| 120 | 1-{6-[1-(2,3-dichloro-6-fluorophenyl)ethoxy]-1,3-benzothiazol-2-yl}-3-[2-(pyrrolidin-1-yl)ethyl]urea | | | | {6-[1-(2,3-dichloro-6-fluorophenyl)ethoxy]-1,3-benzothiazol-2-yl}phenyl carbamate | 2-(pyrrolidin-1-yl)ethanamine |
| 121 | | | 1-{6-[(1R*)-(2,3-dichloro-6-fluorophenyl)ethoxy]-1,3-benzothiazol-2-yl}-3-[2-(pyrrolidin-1-yl)ethyl]urea | | | |
| 124 | 1-[2-(morpholin-4-yl)ethyl]-3-{6-[1-(2,3,6-trichlorophenyl)ethoxy]-1,3-benzothiazol-2-yl}urea | | | | {6-[1-(2,3,6-trichlorophenyl)ethoxy]-1,3-benzothiazol-2-yl}phenyl carbamate | 2-(morpholin-4-yl)ethanamine |
| 125 | 1-[2-(pyrrolidin-1-yl)ethyl]-3-{6-[1-(2,3,6-trichlorophenyl)ethoxy]-1,3-benzothiazol-2-yl}urea | | | | {6-[1-(2,3,6-trichlorophenyl)ethoxy]-1,3-benzothiazol-2-yl}phenyl carbamate | 2-(pyrrolidin-1-yl)ethanamine |

-continued

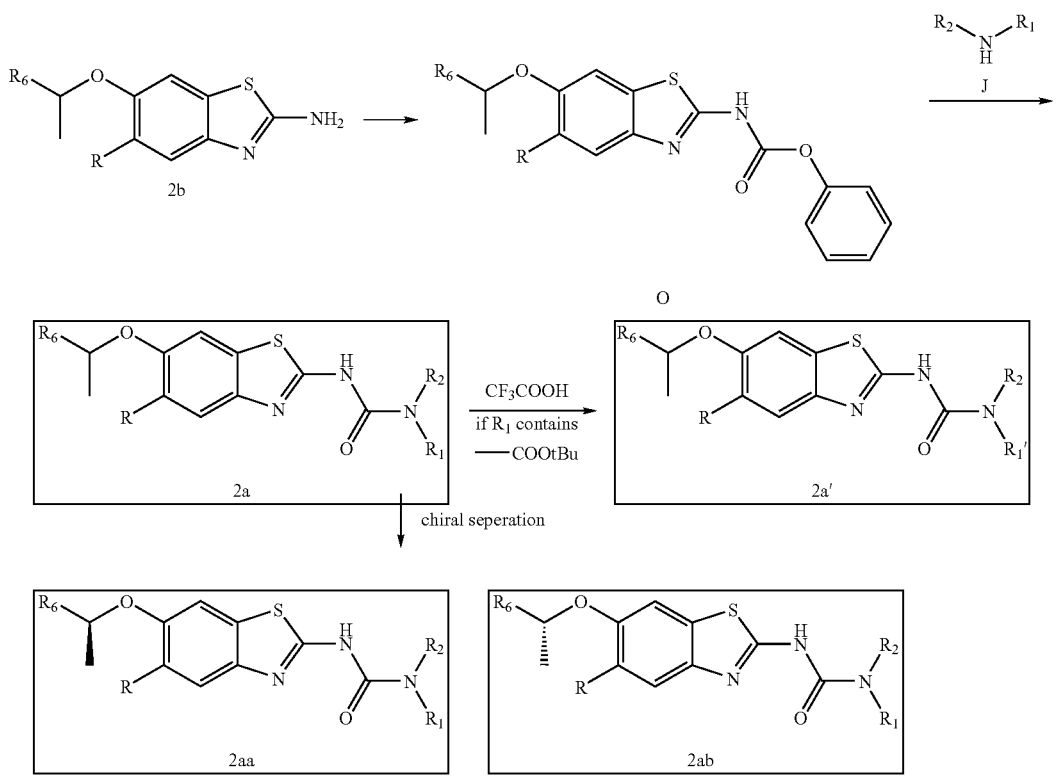

| Ex | 2a | 2a' | 2aa | 2ab | O | J |
|---|---|---|---|---|---|---|
| 126 | 1-{5-fluoro-6-[1-(2,3,6-trichlorophenyl)ethoxy]-1,3-benzothiazol-2-yl}-3-[2-(pyrrolidin-1-yl)ethyl]urea | | | | {6-[1-(2,3,6-trichlorophenyl)ethoxy]-5-fluoro-1,3-benzothiazol-2-yl}phenyl carbamate | 2-(pyrrolidin-1-yl)ethanamine |
| 127 | | 1-{6-[1-(2,6-dichloro-3-fluorophenyl)ethoxy]-5-fluoro-1,3-benzothiazol-2-yl}-3-[3-(methylamino)propyl]urea | | | {6-[1-(2,6-dichloro-3-fluorophenyl)ethoxy]-5-fluoro-1,3-benzothiazol-2-yl}phenyl carbamate | (3-aminopropyl) 2-methylpropan-2-ylmethyl carbamate |
| 128 | | 1-(3-aminopropyl)-3-{6-[1-(2,6-dichloro-3-fluorophenyl)ethoxy]-5-fluoro-1,3-benzothiazol-2-yl}urea | | | {6-[1-(2,6-dichloro-3-fluorophenyl)ethoxy]-5-fluoro-1,3-benzothiazol-2-yl}phenyl carbamate | (3-aminopropyl) 2-methylpropan-2-yl carbamate |
| 129 | 1-{6-[1-(2,6-dichloro-3-fluorophenyl)ethoxy]-5-fluoro-1,3-benzothiazol-2-yl}-3-[2-(4-methylpiperazin-1-yl)-2-oxoethyl]urea | | | | {6-[1-(2,6-dichloro-3-fluorophenyl)ethoxy]-5-fluoro-1,3-benzothiazol-2-yl}phenyl carbamate | 2-amino-1-(4-methylpiperazin-1-yl)ethanone |
| 130 | 1-{6-[1-(2,6-dichloro-3-fluorophenyl)ethoxy]-5-fluoro-1,3-benzothiazol-2-yl}-3-[2-(3-oxopiperazin-1-yl)ethyl]urea | | | | {6-[1-(2,6-dichloro-3-fluorophenyl)ethoxy]-5-fluoro-1,3-benzothiazol-2-yl}phenyl carbamate | 4-(2-aminoethyl)piperazin-2-one |

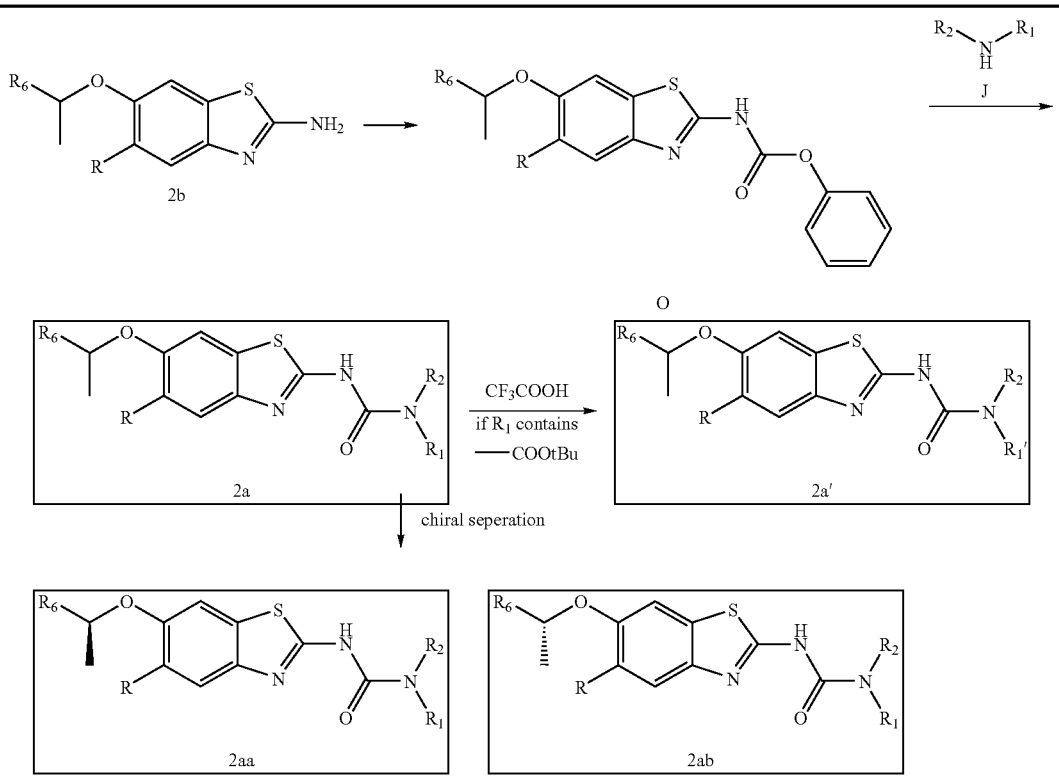

| Ex | 2a | 2a' | 2aa | 2ab | O | J |
|---|---|---|---|---|---|---|
| 131 | 1-cyclopropyl-3-{6-[1-(2,6-dichloro-3-fluorophenyl)ethoxy]-5-fluoro-1,3-benzothiazol-2-yl}urea | | | | {6-[1-(2,6-dichloro-3-fluorophenyl)ethoxy]-5-fluoro-1,3-benzothiazol-2-yl}phenyl carbamate | cyclopropanamine |

Examples 75, 78, 79, 80, 81, 84, 86, 87, 91, 92, 93, 94, 95, 97, 98, 100, 103, 104, 105, 129, 130, 131 were prepared according to the method described in Example 10a from {6-[1-(2,6-dichloro-3-fluorophenyl)ethoxy]-5-fluoro-1,3-benzothiazol-2-yl}phenyl carbamate and the corresponding amines (J) (table given above).

Examples 82 and 83 were prepared according to the method described in Example 24a from {6-[1-(2,6-dichloro-3-fluorophenyl)ethoxy]-1,3-benzothiazol-2-yl}phenyl carbamate and the corresponding amines (J) (table given above).

Examples 108, 110, 120 were prepared according to the method described in Example 61a from {6-[1-(2,3-dichloro-6-fluorophenyl)ethoxy]-1,3-benzothiazol-2-yl}phenyl carbamate and the corresponding amines (J) (table given above).

Examples 111, 114, 115, 118 were prepared according to the method described in Example 61a from {6-[1-(2,3-dichloro-6-fluorophenyl)ethoxy]-5-fluoro-1,3-benzothiazol-2-yl}phenyl carbamate and the corresponding amines (J).

a) {6-[1-(2,3-Dichloro-6-fluorophenyl)ethoxy]-5-fluoro-1,3-benzothiazol-2-yl}phenyl carbamate was prepared according to the method described in Example 10b but from 2.3 g of 6-[1-(2,3-dichloro-6-fluorophenyl)ethoxy]-5-fluoro-1,3-benzothiazol-2-amine and 3.84 g of phenyl chlorocarbonate. We thus obtain 2.3 g {6-[1-(2,3-dichloro-6-fluorophenyl)ethoxy]-5-fluoro-1,3-benzothiazol-2-yl}phenyl carbamate in the form of a cream-coloured powder, which has the following characteristics:

Melting point: 235-240° C. (Köfler)

Mass spectrum: HPLC-MS-DAD-ELSD: [M+H]$^+$: m/z=495 b) 6-[1-(2,3-Dichloro-6-fluorophenyl)ethoxy]-5-fluoro-1,3-benzothiazol-2-amine was prepared according to the method described in Example 20d but from 2 g of 4-[1-(2,3-dichloro-6-fluorophenyl)ethoxy]-3-fluoroaniline, 2.44 g of potassium thiocyanate and 0.322 cm$^3$ of dibromine. We obtain 2.3 g of 6-[1-(2,3-dichloro-6-fluorophenyl)ethoxy]-5-fluoro-1,3-benzothiazol-2-amine in the form of a cream-coloured powder, which has the following characteristics:

Melting point: 215-220° C. (Köfler)

Mass spectrum: HPLC-MS-DAD-ELSD: [M+H]$^+$: m/z 375 c) 4-[1-(2,3-Dichloro-6-fluorophenyl)ethoxy]-3-fluoroaniline was prepared according to the method described in Example 20e but from 0.143 g of platinum oxide and 2.2 g of 1,2-dichloro-4-fluoro-3-[1-(2-fluoro-4-nitrophenoxy)ethyl]benzene in 115 cm$^3$ of methanol. We thus obtain 2 g of 4-[1-(2,3-dichloro-6-fluorophenyl)ethoxy]-3-fluoroaniline in the form of an orange-coloured resin, which has the following characteristics:

Rf CCM silica=0.35 [eluent: dichloromethane]

Mass spectrum: LC-MS-DAD-ELSD: [M+H]$^+$: m/z 318 d) 1,2-Dichloro-4-fluoro-3-[1-(2-fluoro-4-nitrophenoxy)ethyl]benzene was prepared according to the method described in Example 20f but from 0.421 g of sodium hydride (at 60% in the oil), 2 g of 1-(2,3-dichloro-6-fluorophenyl)-ethanol and 1.67 g of 1,2-difluoro-4-nitrobenzene. We thus obtain 2.27 g of 1,2-dichloro-4-fluoro-3-[1-(2-fluoro-4-nitrophenoxy)ethyl]benzene in the form of a white powder, which has the following characteristics:

Melting point: 116-117° C. (Köfler)

Mass spectrum: SM-EI: [M]$^+$.: m/z 347; m/z 191 (base peak)

Examples 124 and 125 were prepared according to the method described in Example 61a from {6-[1-(2,3,6-trichlorophenyl)ethoxy]-1,3-benzothiazol-2-yl}phenyl carbamate and the corresponding amines (J) (table given above).

a) {6-[1-(2,3,6-Trichlorophenyl)ethoxy]-1,3-benzothiazol-2-yl}phenyl carbamate was prepared according to the method described in Example 10b but from 1.7 g of 6-[1-(2,3,6-trichlorophenyl)ethoxy]-1,3-benzothiazol-2-amine and 2.85 g of phenyl chlorocarbonate. We thus obtain 1.8 g {6-[1-(2,3,6-trichlorophenyl)ethoxy]-1,3-benzothiazol-2-yl}phenyl carbamate in the form of a cream-coloured powder, which has the following characteristics:

Melting point: 198-200° C. (Köfler)

Mass spectrum: HPLC-MS-DAD-ELSD: [M+H]$^+$: m/z 493 b) 6-[1-(2,3,6-Trichlorophenyl)ethoxy]-1,3-benzothiazol-2-amine was prepared according to the method described in Example 20d but from 1.5 g of 4-[1-(2,3,6-trichlorophenyl)ethoxy]aniline, 1.84 g of potassium thiocyanate and 0.243 cm$^3$ of dibromine. We obtain 1.77 g of 6-[1-(2,3,6-trichlorophenyl)ethoxy]-1,3-benzothiazol-2-amine in the form of an orange-coloured resin, which has the following characteristics:

Rf CCM silica=0.15 [eluent: dichloromethane/MeOH 98/2]

Mass spectrum: HPLC-MS-DAD-ELSD: [M+H]$^+$: m/z 373 c) 4-[1-(2,3,6-Trichlorophenyl)ethoxy]aniline was prepared according to the method described in Example 20e but from 0.111 g of platinum oxide and 1.7 g of 1,2,4-trichloro-3-[1-(4-nitrophenoxy)ethyl]benzene in 90 cm$^3$ of methanol. We thus obtain 1.5 g of 4-[1-(2,3,6-trichlorophenyl)ethoxy]aniline in the form of a green-coloured resin, which has the following characteristics:

Rf CCM silica=0.24 [eluent: dichloromethane]

Mass spectrum: LC-MS-DAD-ELSD: [M+H]$^+$: m/z 316 d) 1,2,4-Trichloro-3-[1-(4-nitrophenoxy)ethyl]benzene was prepared according to the method described in Example 20f but from 0.351 g of sodium hydride (at 60% in the oil), 1.8 g of 1-(2,3,6-trichlorophenyl)ethanol and 1.13 g of 1-fluoro-4-nitrobenzene. We thus obtain 1.74 g of 1,2,4-trichloro-3-[1-(4-nitrophenoxy)ethyl]benzene in the form of a white powder, which has the following characteristics:

Melting point: 151° C. (Köfler)

Mass spectrum: SM-EI: [M]$^+$: m/z 345; m/z 207 (base peak)

e) 1-(2,3,6-Trichlorophenyl)ethanol was prepared as follows:

a solution of 3 g of 2,3,6-trichlorobenzaldehyde and 0.376 g of triphenylphosphine in 40 cm$^3$ of tetrahydrofuran is added dropwise, while maintaining the temperature below 4-5° C., to a solution of 0.184 g of nickel(2+) bis[(2E)-4-oxopent-2-en-2-olate] in 30 cm$^3$ of tetrahydrofuran cooled to 0° C. After stirring the reaction mixture for about 15 min at 0° C., 28 cm$^3$ of a 1M solution of trimethylaluminium is added dropwise, while keeping the temperature below 4-5° C. The reaction mixture is stirred at 0° C. for 4 hours. Then slowly add 75 cm$^3$ of a 2N aqueous solution of hydrochloric acid. After stirring for 15 minutes the reaction mixture is extracted 3 times with 100 cm$^3$ of diethyl ether. The organic phases are dried over magnesium sulphate, then filtered and concentrated under reduced pressure (0.2 kPa). The oil obtained is purified by silica-column flash chromatography [eluent: dichloromethane]. We thus obtain 2.68 g of 1-(2,3,6-trichlorophenyl)ethanol in the form of a colorless oil, which has the following characteristics:

Rf CCM silica=0.51 (eluent: dichloromethane)

Mass spectrum: EI: [M]+.: m/z 224; m/z 209 (base peak)

Example 126 was prepared according to the method described in Example 61a from {5-fluoro-6-[1-(2,3,6-trichlorophenyl)ethoxy]-1,3-benzothiazol-2-yl}phenyl carbamate and 2-(pyrrolidin-1-yl)ethanamine (table given above).

a) {5-Fluoro-6-[1-(2,3,6-trichlorophenyl)ethoxy]-1,3-benzothiazol-2-yl}phenyl carbamate was prepared according to the method described in Example 10b but from 1.1 g of 5-fluoro-6-[1-(2,3,6-trichlorophenyl)ethoxy]-1,3-benzothiazol-2-amine and 1.76 g of phenyl chlorocarbonate. We thus obtain 1.4 g {5-fluoro-6-[1-(2,3,6-trichlorophenyl)ethoxy]-1,3-benzothiazol-2-yl}phenyl carbamate in the form of a cream-coloured powder, which has the following characteristics:

Melting point: 225-230° C. (Köfler)

Mass spectrum: HPLC-MS-DAD-ELSD: [M+H]$^+$: m/z 511 b) 5-Fluoro-6-[1-(2,3,6-trichlorophenyl)ethoxy]-1,3-benzothiazol-2-amine was prepared according to the method described in Example 20d but from 1.35 g of 3-fluoro-4-[1-(2,3,6-trichlorophenyl)ethoxy]aniline, 1.56 g of potassium thiocyanate and 0.207 cm$^3$ of dibromine. We obtain 1.18 g of 5-fluoro-6-[1-(2,3,6-trichlorophenyl)ethoxy]-1,3-benzothiazol-2-amine in the form of an orange-coloured powder, which has the following characteristics:

Melting point: 205-210° C. (Köfler)

Mass spectrum: HPLC-MS-DAD-ELSD: [M+H]$^+$: m/z 391 c) 3-Fluoro-4-[1-(2,3,6-trichlorophenyl)ethoxy]aniline was prepared according to the method described in Example 20e but from 0.093 g of platinum oxide and 1.5 g of 1,2,4-trichloro-3-[1-(2-fluoro-4-nitrophenoxy)ethyl]benzene in 100 cm$^3$ of methanol.

We thus obtain 1.35 g of 3-fluoro-4-[1-(2,3,6-trichlorophenyl)ethoxy]aniline in the form of an orange-coloured resin, which has the following characteristics:

Rf CCM silica=0.33 [eluent: dichloromethane]

Mass spectrum: LC-MS-DAD-ELSD: [M+H]$^+$: m/z 334 d) 1,2,4-Trichloro-3-[1-(2-fluoro-4-nitrophenoxy)ethyl]benzene was prepared according to the method described in Example 20f but from 0.254 g of sodium hydride (at 60% in the oil), 1.3 g of 1-(2,3,6-trichlorophenyl)ethanol and 0.917 g of 1,2-difluoro-4-nitrobenzene. We thus obtain 1.56 g of 1,2,4-trichloro-3-[1-(2-fluoro-4-nitrophenoxy)ethyl]benzene in the form of a beige-coloured powder, which has the following characteristics:

Melting point: 120° C. (Köfler)

Mass spectrum: SM-EI: [M]+.: m/z 363; m/z 207 (base peak)

Example 88

1-(2-aminoethyl)-3-{6-[1-(2,6-dichloro-3-fluorophenyl)ethoxy]-5-fluoro-1,3-benzothiazol-2-yl}urea a) 1-(2-Aminoethyl)-3-{6-[1-(2,6-dichloro-3-fluorophenyl)ethoxy]-5-fluoro-1,3-benzothiazol-2-yl}urea was prepared according to the method described in Example 69a but from 0.4 g of {2-[({6-[1-(2,6-dichloro-3-fluorophenyl)ethoxy]-5-fluoro-1,3-benzothiazol-2-yl}carbamoyl)amino]ethyl}2-methylpropan-2-yl carbamate and 1.22 g of trifluoroacetic acid. We thus obtain 0.298 g of 1-(2-aminoethyl)-3-{6-[1-(2,6-dichloro-3-fluorophenyl)ethoxy]-5-fluoro-1,3-benzothiazol-2-yl}urea in the form of a white powder, which has the following characteristics:

Melting point: 178° C. (Köfler)

1H NMR spectrum (400 MHz, DMSO-d6) δ ppm: 1.78 (d, J=6.4 Hz, 3H) 2.67 (t, J=6.1 Hz, 2H) 3.15 (m, 2H) 5.43 (m very spread-out, 2H) 6.04 (d, J=6.4 Hz, 1H) 6.78 (t broad, J=5.5 Hz, 1H) 7.39 (d, J=8.3 Hz, 1H) 7.40-7.50 (m, 2H) 7.53 (dd, J=9.3, 5.4 Hz, 1H) 12.44 (m very spread-out, 1H)

Mass spectrum: LC-MS-DAD-ELSD: [M+H]+m/z=461; [M−H]−m/z=459 b) {2-[({6-[1-(2,6-Dichloro-3-fluorophenyl)ethoxy]-5-fluoro-1,3-benzothiazol-2-yl}carbamoyl)amino]ethyl}2-methylpropan-2-yl carbamate was prepared according to the method described in Example 61a from 6-[1-(2,6-dichloro-3-fluorophenyl)ethoxy]-5-fluoro-1,3-benzothiazol-2-yl}phenyl carbamate and (2-aminoethyl) 2-methylpropan-2-yl carbamate (J) (Ex: 87)(table given above).

Example 96

1-{6-[1-(2,6-dichloro-3-fluorophenyl)ethoxy]-5-fluoro-1,3-benzothiazol-2-yl}-3-[2-(methylamino)ethyl]urea a) 1-{6-[1-(2,6-Dichloro-3-fluorophenyl)ethoxy]-5-fluoro-1,3-benzothiazol-2-yl}-3-[2-(methylamino)ethyl]urea was prepared according to the method described in Example 69a but from 0.158 g of {2-[({6-[1-(2,6-dichloro-3-fluorophenyl)ethoxy]-5-fluoro-1,3-benzothiazol-2-yl}carbamoyl)amino]ethyl}methyl 2-methylpropan-2-yl carbamate and 0.47 g of trifluoroacetic acid. We thus obtain 0.039 g of 1-{6-[1-(2,6-dichloro-3-fluorophenyl)ethoxy]-5-fluoro-1,3-benzothiazol-2-yl}-3-[2-(methylamino)ethyl]urea in the form of a white solid, which has the following characteristics:

Melting point: 173-188° C. (Büchi)

1H NMR spectrum (400 MHz, DMSO-d6) δ ppm: 1.78 (d, J=6.5 Hz, 3H) 2.30 (d, J=3.4 Hz, 3H) 2.59 (m, 2H) 3.20 (m, 2H) 6.04 (q, J=6.5 Hz, 1H) 6.75 (m broad, 1H) 7.35-7.49 (m, 3H) 7.53 (dd, J=9.3, 4.9 Hz, 1H)

Mass spectrum: LC-MS-DAD-ELSD: [M+H]+m/z=475; [M−H]−m/z=473 b) {2-[({6-[1-(2,6-Dichloro-3-fluorophenyl)ethoxy]-5-fluoro-1,3-benzothiazol-2-yl}carbamoyl)amino]ethyl}methyl 2-methylpropan-2-yl carbamate was prepared according to the method described in Example 61a from 6-[1-(2,6-dichloro-3-fluorophenyl)ethoxy]-5-fluoro-1,3-benzothiazol-2-yl}phenyl carbamate and (3-aminopropyl) methyl 2-methylpropan-2-yl carbamate (J) (Ex: 95 table given above).

Example 127

1-{6-[1-(2,6-dichloro-3-fluorophenyl)ethoxy]-5-fluoro-1,3-benzothiazol-2-yl}-3-[3-(methylamino)propyl]urea a) 1-{6-[1-(2,6-Dichloro-3-fluorophenyl)ethoxy]-5-fluoro-1,3-benzothiazol-2-yl}-3-[3-(methylamino)propyl]urea was prepared according to the method described in Example 61a from 0.55 g of 3-[({6-[1-(2,6-dichloro-3-fluorophenyl)ethoxy]-5-fluoro-1,3-benzothiazol-2-yl}carbamoyl)amino]propyl}2-methylpropan-2-yl carbamate and 1.59 g of trifluoroacetic acid. We thus obtain 0.296 g of 1-{6-[1-(2,6-dichloro-3-fluorophenyl)ethoxy]-5-fluoro-1,3-benzothiazol-2-yl}-3-[3-(methylamino)propyl]urea in the form of a cream-coloured powder, which has the following characteristics:

Melting point: 183° C. (Köfler)

1H NMR spectrum (400 MHz, DMSO-d6) δ ppm: 1.58 (m, 2H) 1.78 (d, J=6.8 Hz, 3H) 2.27 (s broad, 3H) 2.49 (m. 2H) 3.18 (m, 2H) 6.04 (q, J=6.8 Hz, 1H) 6.79 (m broad, 1H) 7.32-7.48 (m, 3H) 7.53 (dd, J=8.9, 5.0 Hz. 1H)

Mass spectrum: LC-MS-DAD-ELSD: [M+H]+m/z=489; [M−H]−m/z=487 b) 3-[({6-[1-(2,6-Dichloro-3-fluorophenyl)ethoxy]-5-fluoro-1,3-benzothiazol-2-yl}carbamoyl)amino]propyl}2-methylpropan-2-yl carbamate was prepared according to the method described in Example 61a from 6-[1-(2,6-dichloro-3-fluorophenyl)ethoxy]-5-fluoro-1,3-benzothiazol-2-yl}phenyl carbamate and (3-aminopropyl)methyl 2-methylpropan-2-yl carbamate (J) (table given above).

Example 128

1-(3-aminopropyl)-3-{6-[1-(2,6-dichloro-3-fluorophenyl)ethoxy]-5-fluoro-1,3-benzothiazol-2-yl}urea a) 1-(3-Aminopropyl)-3-{6-[1-(2,6-dichloro-3-fluorophenyl)ethoxy]-5-fluoro-1,3-benzothiazol-2-yl}urea was prepared according to the method described in Example 61a from 0.5 g of {3-[({6-[1-(2,6-dichloro-3-fluorophenyl)ethoxy]-5-fluoro-1,3-benzothiazol-2-yl}carbamoyl)amino]propyl}2-methylpropan-2-yl carbamate and 1.49 g of trifluoroacetic acid. We thus obtain 0.339 g of 1-(3-aminopropyl)-3-{6-[1-(2,6-dichloro-3-fluorophenyl)ethoxy]-5-fluoro-1,3-benzothiazol-2-yl}urea in the form of a cream-coloured powder, which has the following characteristics:

Melting point: 163° C. (Köfler)

1H NMR spectrum (400 MHz, DMSO-d6) δ ppm: 1.56 (m, 2H) 1.78 (d, J=6.7 Hz, 3H) 2.63 (t, J=6.7 Hz, 2H) 3.11-3.24 (m partially masked, 2H) 6.03 (q, J=6.7 Hz, 1H) 6.97 (m spread-out, 1H) 7.30-7.49 (m, 3H) 7.53 (dd, J=8.9, 5.0 Hz, 1H)

Mass spectrum: LC-MS-DAD-ELSD: [M+H]+m/z=475; [M−H]−m/z=473 b) {3-[({6-[1-(2,6-Dichloro-3-fluorophenyl)ethoxy]-5-fluoro-1,3-benzothiazol-2-yl}carbamoyl)amino]propyl}2-methylpropan-2-yl carbamate was prepared according to the method described in Example 61a from 6-[1-(2,6-dichloro-3-fluorophenyl)ethoxy]-5-fluoro-1,3-benzothiazol-2-yl}phenyl carbamate and (3-aminopropyl) 2-methylpropan-2-yl carbamate (J) (table given above).

Synoptic table of the characteristics of examples:
75, 76, 77, 78, 79, 80, 81, 82, 83, 84, 85, 86, 87, 89, 90, 91, 92, 93, 94, 95, 97, 98, 99, 100, 101, 102, 103, 104, 105, 108, 109, 110, 111, 112, 113, 114, 115, 116, 117, 118, 119, 120, 121, 124, 125, 126, 129, 130, 131

| Ex | Name | Chiral separation conditions | 1H NMR (400 MHz, DMSO-d6) δ ppm | Mass spectroscopy | m.p. ° C. |
|---|---|---|---|---|---|
| 75 | 1-{6-[1-(2,6-dichloro-3-fluorophenyl)ethoxy]-5-fluoro-1,3-benzothiazol-2-yl}-3-[2-(4-methylpiperazin-1-yl)ethyl]urea | | 1.78 (d, J = 6.8 Hz, 3 H) 2.15 (s, 3 H) 2.22-2.47 (m, 10 H) 3.24 (q, J = 5.9 Hz, 2 H) 6.04 (q, J = 6.8 Hz, 1 H) 6.72 (m broad, 1 H) 7.39 (d, J = 8.3 Hz, 1 H) 7.40-7.48 (m, 2 H) 7.53 (dd, J = 8.8, 4.9 Hz, 1 H) 10.82 (m, 1 H) | [M + H]+ m/z = 544; [M − H]− m/z = 542 | 131-134 |
| 76 | 1-{6-[(1R*)-1-(2,6-dichloro-3-fluorophenyl)ethoxy]-5-fluoro-1,3-benzothiazol-2-yl}-3-[2-(4-methylpiperazin-1-yl)ethyl]urea | Preparative separation on Chiralpak IC5 µm (25 × 2 cm). PR = + (dextrorotatory) 0.5 ml DMSO on 589 nM | 1.78 (d, J = 6.4 Hz, 3 H) 2.15 (s, 3 H) 2.24-2.45 (m, 10 H) 3.23 (q, J = 5.4 Hz, 2 H) 6.04 (q, J = 6.4 Hz, 1 H) 6.70 (m broad, 1 H) 7.37 (d, J = 8.3 Hz, 1 H) 7.40-7.48 (m, 2 H) 7.53 (dd, J = 8.8, 4.9 Hz, 1 H) 10.85 (m spread-out, 1 H) | [M + H]+ m/z = 544; [M + 2H]2+ m/z = 272.5 (base peak); [M + 2H + CH3CN]2+ m/z = 292.5 [M − H]− m/z = 542 | |
| 77 | 1-{6-[(1S*)-1-(2,6-dichloro-3-fluorophenyl)ethoxy]-5-fluoro-1,3-benzothiazol-2-yl}-3-[2-(4-methylpiperazin-1-yl)ethyl]urea | Preparative separation on Chiralpak IC5 µm (250 × 4.6 mm). PR = (−) (laevorotatory) 0.5 ml DMSO on 589 nM | 1.78 (d, J = 6.6 Hz, 3 H) 2.15 (s, 3 H) 2.24-2.45 (m, 10 H) 3.23 (q, J = 5.9 Hz, 2 H) 6.03 (q, J = 6.6 Hz, 1 H) 6.70 (m broad, 1 H) 7.37 (d, J = 8.4 Hz, 1 H) 7.39-7.47 (m, 2 H) 7.53 (dd, J = 9.0, 5.1 Hz, 1 H) 10.85 (m spread-out, 1 H) | [M + H]+ m/z = 544; [M + 2H]2+ m/z = 272.5 (base peak); [M + 2H + CH3CN]2+ m/z = 292.5 [M − H]− m/z = 542 | |
| 78 | 1-{6-[1-(2,6-dichloro-3-fluorophenyl)ethoxy]-5-fluoro-1,3-benzothiazol-2-yl}-3-[3-(2-oxopyrrolidin-1-yl)propyl]urea | | 1.63 (m, 2 H) 1.78 (d, J = 6.8 Hz, 3 H) 1.91 (m, 2 H) 2.21 (t, J = 8.1 Hz, 2 H) 3.09 (m, 2 H) 3.20 (t, J = 7.1 Hz, 2 H) 3.32 (d, J = 6.8 Hz, 2 H) 6.04 (q, J = 6.8 Hz, 1 H) 6.76 (m broad, 1 H) 7.37 (d, J = 8.3 Hz, 1 H) 7.40-7.47 (m, 2 H) 7.52 (dd, J = 9.3, 5.3 Hz, 1 H) 10.78 (m spread-out, 1 H) | [M + H]+ m/z = 543; [M − H]− m/z = 54 | 191-195 |
| 79 | 1-{6-[1-(2,6-dichloro-3-fluorophenyl)ethoxy]-5-fluoro-1,3-benzothiazol-2-yl}-3-[2-(1-methylpyrrolidin-2-yl)ethyl]urea | | 1.33-1.47 (m, 2 H) 1.57-1.65 (m, 2 H) 1.71-1.76 (m, 1 H) 1.78 (d, J = 6.8 Hz, 3 H) 1.88 (m, 1 H) 1.98-2.08 (m, 2 H) 2.19 (s, 3 H) 2.93 (m, 1 H) 3.16 (q, J = 6.8 Hz, 2H) 6.04 (q, J = 6.8 Hz, 1 H) 6.80 (m spread-out, 1 H) 7.37 (d, J = 8.3 Hz, 1 H) 7.39-7.47 (m, 2 H) 7.53 (dd, =9.1, 5.1 Hz, 1 H) 10.78 (m spread-out, 1 H) | [M + H]+ m/z = 529; [M + 2H]2+ m/z = 265; [M + 2H+ CH3CN]2+ m/z = 285; [C8H6FCl2]+ m/z = 191 (base peak); [M − H]− m/z = 527 | 78-89 |
| 80 | 1-{6-[1-(2,6-dichloro-3-fluorophenyl)ethoxy]-5-fluoro-1,3-benzothiazol-2-yl}-3-[2-(piperidin-1-yl)ethyl]urea | | 1.40 (m, 2 H) 1.53 (m, 4 H) 1.78 (d, J = 6.8 Hz, 3 H) 2.26-2.61 (m partially masked, 6 H) 3.25 (m partially masked, 2 H) 6.04 (q, J = 6.8 Hz, 1 H) 6.69 (m broad, 1H) 7.37-7.49 (m, 3 H) 7.53 (dd, J = 9.1, 5.1 Hz, 1 H) 10.78 (m spread-out, 1 H) | [M + H]+ m/z = 529; [M − H]− m/z = 527 | 186-195 |
| 81 | 1-{6-[1-(2,6-dichloro-3-fluorophenyl)ethoxy]-5-fluoro-1,3-benzothiazol-2-yl}-3-(2-methoxyethyl)urea | | 1.78 (d, J = 6.8 Hz, 3 H) 3.27 (s, 3 H) 3.29-3.33 (m partially masked, 2 H) 3.40 (t, J = 5.4 Hz, 2 H) 6.04 (q, J = 6.8 Hz, 1 H) 6.81 (m broad, 1 H) 7.39 (d, J = 8.3 Hz, 1 H) 7.40-7.48 (m, 2 H) 7.53 (dd, J = 9.0, 5.1 Hz, 1 H) 10.65 (m spread-out, 1 H) | [M + H]+ m/z = 476; [M − H]− m/z = 474 | 176-179 |
| 82 | 1-{6-[1-(2,6-dichloro-3-fluorophenyl)ethoxy]-1,3-benzothiazol-2-yl}-3-[2-(diethylamino)ethyl]urea | | 0.97 (t, J = 7.1 Hz, 6 H) 1.74 (d, J = 6.8 Hz, 3 H) 2.47-2.52 (m partially masked, 6 H) 3.19 (m, 2 H) 6.05 (q, J = 6.8 Hz, 1 H) 6.69 (m broad, 1 H) 6.89 (dd, J = 8.8, 2.7 Hz, 1 H) 7.34 (d, J = 2.7 Hz, 1 H) 7.40 (t, J = 8.8 Hz, 1 H) 7.44 (d, J = 8.8 Hz, 1 H) 7.51 (dd, | [M + H]+ m/z = 499; [M + 2H + CH3CN]2+ m/z = 270; [M − H]− m/z = 497 | 74-83 |

-continued

| Ex | Name | Chiral separation conditions | 1H NMR (400 MHz, DMSO-d6) δ ppm | Mass spectroscopy | m.p. ° C. |
|---|---|---|---|---|---|
| 83 | 1-{6-[1-(2,6-dichloro-3-fluorophenyl)ethoxy]-1,3-benzothiazol-2-yl}-3-[3-(diethylamino)propyl]urea | | J = 8.8, 4.9 Hz, 1H) 10.66 (m spread-out, 1 H) 0.94 (t, J = 7.2 Hz, 6 H) 1.56 (m, 2 H) 1.74 (d, J = 6.8 Hz, 3 H) 2.38 (t, J = 6.8 Hz, 2 H) 2.44 (q, J = 7.2 Hz, 4 H) 3.16 (m, 2 H) 6.05 (q, J = 6.8 Hz, 1 H) 6.77 (t broad, J = 5.9 Hz, 1 H) 6.88 (dd, J = 8.8, 2.4 Hz, 1 H) 7.34 (d, J = 2.4 Hz, 1 H) 7.40 (t, J = 9.0 Hz, 1 H) 7.44 (d, J = 8.8 Hz, 1H) 7.51 (dd, J = 9.0, 4.9 Hz, 1 H) 10.36 (m spread-out, 1 H) | [M + H]+ m/z = 513; [M + 2H]2+ m/z = 257 (base peak) [M + 2H + CH3CN]2+ m/z = 277; [M − H]− m/z = 511 | |
| 84 | 1-{6-[1-(2,6-dichloro-3-fluorophenyl)ethoxy]-5-fluoro-1,3-benzothiazol-2-yl}-3-[2-(pyrrolidin-1-yl)ethyl]urea | | 1.71 (m, 4 H) 1.78 (d, J = 6.8 Hz, 3 H) 2.46-2.57 (m partially masked, 6 H) 3.26 (m partially masked, 2 H) 6.04 (q, J = 6.8 Hz, 1 H) 6.75 (m broad, 1 H) 7.39 (d, J = 8.3 Hz, 1 H) 7.43 (t, J = 8.9 Hz, 1 H) 7.47 (d, J = 12.0 Hz, 1 H) 7.53 (dd, J = 8.9, 4.9 Hz, 1 H) 10.66 (m spread-out, 1 H) | [M + H]+ m/z = 515; [M − H]− m/z = 513 | 178-190 |
| 85 | 1-{6-[(1R*)-1-(2,6-dichloro-3-fluorophenyl)ethoxy]-5-fluoro-1,3-benzothiazol-2-yl}-3-[2-(pyrrolidin-1-yl)ethyl]urea | Preparative separation on Chiralpak T304 20 μm (6 × 35 cm). PR = +83.8 (dextrorotatory) C = 1.994 mg/0.5 ml DMSO on 589 nM | 1.75 (m spread-out, 4 H) 1.78 (d, J = 6.8 Hz, 3 H) 2.39-2.68 (m spread-out, partially masked, 6 H) 3.29 (m spread-out, partially masked, 2 H) 6.04 (q, J = 6.8 Hz, 1 H) 6.79 (m broad, 1 H) 7.38-7.49 (m, 3 H) 7.53 (dd, J = 9.0, 5.1 Hz, 1 H) 10.74 (m spread-out, 1 H) | [M + H]+ m/z = 515; [M − H]− m/z = 513 | |
| 86 | 1-{6-[1-(2,6-dichloro-3-fluorophenyl)ethoxy]-5-fluoro-1,3-benzothiazol-2-yl}-3-(2-ethoxyethyl)urea | | 1.13 (t, J = 7.0 Hz, 3 H) 1.78 (d, J = 6.8 Hz, 3 H) 3.32 (m partially masked, 2 H) 3.40-3.49 (m, 4 H) 6.04 (q, J = 6.8 Hz, 1 H) 6.75 (t broad, J = 5.8 Hz, 1 H) 7.37-7.50 (m, 3 H) 7.53 (dd, J = 8.9, 5.0 Hz, 1 H) 10.61 (s broad, 1 H) | [M + H]+ m/z = 490; [M − H]− m/z = 488 | 166-167 |
| 87 | {2-[({6-[1-(2,6-dichloro-3-fluorophenyl)ethoxy]-5-fluoro-1,3-benzothiazol-2-yl}carbamoyl)amino]ethyl}2-methylpropan-2-yl carbamate | | 1.36 (s, 9 H) 1.78 (d, J = 6.8 Hz, 3 H) 3.02 (q, J = 6.2 Hz, 2 H) 3.18 (d, J = 6.2 Hz, 2 H) 6.04 (q, J = 6.8 Hz, 1 H) 6.73 (m broad, 1 H) 6.86 (m broad, 1 H) 7.36-7.50 (m, 3 H) 7.53 (dd, J = 8.9, 5.0 Hz, 1 H) 9.73 (m spread-out, 1 H) | [M + H]+ m/z = 561; [M − H]− m/z = 559 | 230 |
| 89 | 1-(2-aminoethyl)-3-{6-[(1R*)-1-(2,6-dichloro-3-fluorophenyl)ethoxy]-5-fluoro-1,3-benzothiazol-2-yl}urea | Preparative separation on Chiralpak AD (lot FB03)20 μm (5 × 35 cm). PR = +164(dextrorotatory) C = 0.616 mg/0.5 ml DMSO on 589 nM | 1.78 (d, J = 6.8 Hz, 3 H) 2.66 (t, J = 6.0 Hz, 2 H) 3.14 (m, 2 H) 5.16 (m very spread-out, 2 H) 6.04 (q, J = 6.8 Hz, 1 H) 6.82 (t broad, J = 5.6 Hz, 1 H) 7.39 (d, J = 8.3 Hz, 1 H) 7.41-7.49 (m, 2 H) 7.54 (dd, J = 9.0, 5.1 Hz, 1 H) 10.40-13.97 (m very spread-out, 1 H) | [M + H]+ m/z = 461; [M − H]− m/z = 459 | |
| 90 | 1-(2-aminoethyl)-3-{6-[(1S*)-1-(2,6-dichloro-3-fluorophenyl)ethoxy]-5-fluoro-1,3-benzothiazol-2-yl}urea | Preparative separation on Chiralpak AD (lot FB03)20 μm (5 × 35 cm). PR = −114 laevorotatory) C = 1.057 mg/0.5 ml DMSO on 589 nM | 1.78 (d, J = 6.7 Hz, 3 H) 2.66 (t, J = 6.1 Hz, 2 H) 3.14 (m, 2 H) 4.57-5.83 (m very spread-out, 2 H) 6.04 (q, J = 6.7 Hz, 1 H) 6.80 (t broad, J = 5.5 Hz, 1 H) 7.39 (d, J = 8.1 Hz, 1 H) 7.41-7.49 (m, 2 H) 7.54 (dd, J = 8.9, 5.0 Hz, 1 H) 11.20-13.50 (m very spread-out, 1 H) | [M + H]+ m/z = 461; [M − H]− m/z = 459 | |
| 91 | 1-{6-[1-(2,6-dichloro-3-fluorophenyl)ethoxy]-5-fluoro-1,3-benzothiazol-2- | | 1.78 (d, J = 6.5 Hz, 3 H) 3.46 (m, 2 H) 3.99 (t, J = 6.1 Hz, 2 H) 6.00 (t, J = 2.2 Hz, 2 H) | [M + H]+ m/z = 511; [M − H]− m/z = 509 | 178-198 |

| Ex | Name | Chiral separation conditions | 1H NMR (400 MHz, DMSO-d6) δ ppm | Mass spectroscopy | m.p. ° C. |
|---|---|---|---|---|---|
| | yl}-3-[2-(1H-pyrrol-1-yl)ethyl]urea | | 6.05 (q, J = 6.5 Hz, 1 H) 6.70 (m broad, 1 H) 6.75 (t, J = 2.2 Hz, 2 H) 7.38-7.49 (m, 3H) 7.53 (dd, J = 8.8, 4.9 Hz, 1 H) 10.72 (m spread-out, 1 H) | | |
| 92 | 1-{6-[1-(2,6-dichloro-3-fluorophenyl)ethoxy]-5-fluoro-1,3-benzothiazol-2-yl}-3-(2-isopropoxyethyl)urea | | 1.10 (d, J = 6.5 Hz, 6 H) 1.78 (d, J = 6.4 Hz, 3 H) 3.28 (m partially masked, 2 H) 3.43 (t, J = 5.4 Hz, 2 H) 3.57 (m, 1 H) 6.04 (q, J = 6.5 Hz, 1 H) 6.72 (m broad, 1H) 7.38-7.49 (m, 3 H) 7.53 (dd, J = 9.3, 5.4 Hz, 1 H) 10.67 (m spread-out, 1 H) | [M + H]+ m/z = 504; [M − H]− m/z = 502 | 177-184 |
| 93 | 3-{6-[1-(2,6-dichloro-3-fluorophenyl)ethoxy]-5-fluoro-1,3-benzothiazol-2-yl}-1-(2-methoxyethyl)-1-methylurea | | 1.78 (d, J = 6.6 Hz, 3 H) 2.99 (s, 3 H) 3.23 (s, 3 H) 3.47 (m, 2 H) 3.54 (m, 2 H) 6.05 (q, J = 6.6 Hz, 1 H) 7.33-7.51 (m, 3 H) 7.53 (dd, J = 8.9, 5.0 Hz, 1 H) 10.91 (m broad, 1 (H) | [M + H]+ m/z = 490; [M − H]− m/z = 488 | 62-67 |
| 94 | 1-{2-[benzyl(methyl)amino]ethyl}-3-{6-[1-(2,6-dichloro-3-fluorophenyl)ethoxy]-5-fluoro-1,3-benzothiazol-2-yl}urea | | 1.78 (d, J = 6.6 Hz, 3 H) 2.14 (s, 3 H) 2.46 (t, J = 6.1 Hz, 2 H) 3.27 (m partially masked, 2 H) 3.50 (s, 2 H) 6.05 (q, J = 6.6 Hz, 1 H) 6.72 (t broad, J = 5.6 Hz, 1 H) 7.21 (tt, J = 7.5, 1.5 Hz, 1 H) 7.28 (t, J = 7.5 Hz, 2 H) 7.34 (d broad, J = 7.5 Hz, 2 H) 7.37-7.50 (m, 3 H) 7.53 (dd, J = 8.9, 5.0 Hz, 1 H) 10.82 (m spread-out, 1 H) | [M + H]+ m/z = 565 | 142-146 |
| 95 | {2-[({6-[1-(2,6-dichloro-3-fluorophenyl)ethoxy]-5-fluoro-1,3-benzothiazol-2-yl}carbamoyl)amino]ethyl}2-methylpropan-2-yl methylcarbamate | | 1.33 (s, 9 H) 1.78 (d, J = 6.6 Hz, 3 H) 2.50 (m masked, 2 H) 2.79 (s broad, 3 H) 3.27 (m partially masked, 2 H) 6.04 (q, J = 6.6 Hz, 1 H) 6.71 (m spread-out, 1 H) 7.36-7.51 (m, 3 H) 7.53 (dd, J = 8.9, 5.0 Hz, 1 H) 10.69 (m broad, 1 H) | [M + H]+ m/z = 575; [M − H]− m/z = 573 | 151-193 |
| 97 | 1-[2-(benzyloxy)ethyl]-3-{6-[1-(2,6-dichloro-3-fluorophenyl)ethoxy]-5-fluoro-1,3-benzothiazol-2-yl}urea | | 1.78 (d, J = 6.8 Hz, 3 H) 3.36 (q, J = 5.4 Hz, 2 H) 3.52 (t, J = 5.4 Hz, 2 H) 4.51 (s, 2 H) 6.04 (q, J = 6.8 Hz, 1 H) 6.82 (t broad, J = 5.4 Hz, 1 H) 7.28 (m, 1 H) 7.31-7.37 (m, 4H) 7.38-7.49 (m, 3 H) 7.53 (dd, J = 8.8, 4.9 Hz, 1 H) 10.52 (m spread-out, 1 H) | [M + H]+ m/z = 552; [M − H]− m/z = 550 | 170 |
| 98 | 1-{6-[1-(2,6-dichloro-3-fluorophenyl)ethoxy]-5-fluoro-1,3-benzothiazol-2-yl}-3-(2-hydroxyethyl)urea | | 1.78 (d, J = 6.7 Hz, 3 H) 3.21 (q, J = 5.6 Hz, 2 H) 3.46 (m, 2 H) 4.79 (m broad, 1 H) 6.04 (q, J = 6.7 Hz, 1 H) 6.76 (t, J = 5.6 Hz, 1 H) 7.36-7.50 (m, 3 H) 7.53 (dd, J = 8.8, 4.9 Hz, 1 H) 10.32 (m spread-out, 1 H) | [M + H]+ m/z = 462; [M − H]− m/z = 460 | 198 |
| 99 | 1-{6-[(1R*)-1-(2,6-dichloro-3-fluorophenyl)ethoxy]-5-fluoro-1,3-benzothiazol-2-yl}-3-(2-hydroxyethyl)urea | Semi-preparative separation on Chiralpak IA 5 μm (2 × 25 cm). PR = +108.7(dextrorotatory) C = 1.518 mg/0.5 ml DMSO on 589 nM | 1.78 (d, J = 6.6 Hz, 3 H) 3.20 (m, 2 H) 3.46 (m, 2 H) 4.79 (m broad, 1 H) 6.04 (q, J = 6.6 Hz, 1 H) 6.77 (t broad, J = 5.6 Hz, 1 H) 7.39 (d, J = 8.3 Hz, 1 H) 7.41-7.49 (m, 2H) 7.53 (dd, J = 8.9, 5.0 Hz, 1 H) 10.60 (m spread-out, 1 H) | [M + H]+ m/z = 462; [M − H]− m/z = 460 | |
| 100 | 1-{6-[1-(2,6-dichloro-3-fluorophenyl)ethoxy]-5-fluoro-1,3-benzothiazol-2-yl}-3-[2-(4-ethylpiperazin-1-yl)ethyl]urea | | 0.99 (t, J = 7.2 Hz, 3 H) 1.78 (d, J = 6.8 Hz, 3 H) 2.25-2.46 (m.10 H) 3.22-3.44 (m partially masked, 4 H) 6.04 (q, J = 6.8 Hz, 1 H) 6.69 (m, 1 H) 7.39 (d, J = 8.1 Hz, 1H) 7.40-7.49 (m, 2 H) 7.53 (dd, | [M + H]+ m/z = 558; [M + 2H]2+ m/z = 279.5 (base peak); [M − H]− m/z = 556 | 150-152 |

-continued

| Ex | Name | Chiral separation conditions | 1H NMR (400 MHz, DMSO-d6) δ ppm | Mass spectroscopy | m.p. ° C. |
|---|---|---|---|---|---|
| | | | J = 8.9, 5.0 Hz, 1 H) 10.75 (m spread-out, 1 H) | | |
| 101 | 1-{6-[(1R*)-1-(2,6-dichloro-3-fluorophenyl)ethoxy]-5-fluoro-1,3-benzothiazol-2-yl}-3-[2-(4-ethylpiperazin-1-yl)ethyl]urea | Preparative separation on Chiralpak IC 20 μm (6 × 35 cm). PR = +(dextrorotatory) 0.5 ml DMSO on 589 nM | 0.98 (t, J = 7.2 Hz, 3 H) 1.78 (d, J = 6.7 Hz, 3 H) 2.25-2.47 (m.10 H) 2.31 (q, J = 7.2 Hz, 2 H) 3.19-3.28 (m, 2 H) 6.05 (q, J = 6.7 Hz, 1 H) 6.70 (m broad, 1 H) 7.40 (d, J = 8.1 Hz, 1 H) 7.38-7.48 (m, 3 H) 7.53 (dd, J = 9.0, 4.9 Hz, 1 H) 10.78 (m spread-out, 1 H) | [M + H]+ m/z = 558; [M + 2H]2+ m/z = 279.5 (base peak) [M − H]− m/z = 556 | |
| 102 | 1-{6-[(1S*)-1-(2,6-dichloro-3-fluorophenyl)ethoxy]-5-fluoro-1,3-benzothiazol-2-yl}-3-[2-(4-ethylpiperazin-1-yl)ethyl]urea | Preparative separation on Chiralpak IC 20 μm (6 × 35 cm). PR = −(laevorotatory) 0.5 ml DMSO on 589 nM | 0.98 (t, J = 7.2 Hz, 3 H) 1.78 (d, J = 6.8 Hz, 3 H) 2.25-2.46 (m.10 H) 2.31 (q, J = 7.2 Hz, 2 H) 3.22-3.27 (m, 2 H) 6.05 (q, J = 6.8 Hz, 1 H) 6.69 (m broad, 1 H) 7.40 (d, J = 8.3 Hz, 1 H) 7.41-7.48 (m, 2 H) 7.54 (dd, J = 9.0, 5.1 Hz, 1 H) 10.75 (m spread-out, 1 H) | [M + H]+ m/z = 558; [M + 2H]2+ m/z = 279.5 (base peak) [M − H]− m/z = 556 | |
| 103 | 1-[2-(cyclopropylmethoxy)ethyl]-3-{6-[1-(2,6-dichloro-3-fluorophenyl)ethoxy]-5-fluoro-1,3-benzothiazol-2-yl}urea | | 0.17 (m, 2 H) 0.46 (m, 2 H) 0.99 (m, 1 H) 1.78 (d, J = 6.6 Hz, 3H) 3.26 (d, J = 6.8 Hz, 2 H) 3.32 (m, 2 H) 3.46 (t, J = 5.5 Hz, 2 H) 6.04 (q, J = 6.6 Hz, 1 H) 6.78 (m, 1 H) 7.39 (d, J = 8.3 Hz, 1 H) 7.43 (t, J = 8.9 Hz, 1 H) 7.46 (d, J = 12.2 Hz, 1 H) 7.53 (dd, J = 8.9, 5.0 Hz, 1 H) 10.67 (m spread-out, 1 H) | [M + H]+ m/z = 516; [M − H]− m/z = 514 | 178-184 |
| 104 | 1-{6-[1-(2,6-dichloro-3-fluorophenyl)ethoxy]-5-fluoro-1,3-benzothiazol-2-yl}-3-(3-methoxypropyl)urea | | 1.68 (m, 2 H) 1.78 (d, J = 6.6 Hz, 3 H) 3.19 (m, 2 H) 3.23 (s, 3 H) 3.36 (t, J = 6.2 Hz, 2 H) 6.04 (q, J = 6.8 Hz, 1 H) 6.71 (t broad, J = 6.1 Hz, 1 H) 7.39 (d, J = 8.1 Hz, 1 H) 7.41-7.49 (m, 2 H) 7.53 (dd, J = 9.0, 5.1 Hz, 1 H) 10.67 (m spread-out, 1 H) | [M + H]+ m/z = 490; [M − H]− m/z = 488 | 175 |
| 105 | 1-{6-[1-(2,6-dichloro-3-fluorophenyl)ethoxy]-5-fluoro-1,3-benzothiazol-2-yl}-3-(3-hydroxypropyl)urea | | 1.60 (m, 2 H) 1.78 (d, J = 6.7 Hz, 3 H) 3.20 (m, 2 H) 3.45 (t, J = 6.1 Hz, 2 H) 4.50 (m broad, 1 H) 6.04 (q, J = 6.7 Hz, 1 H) 6.72 (t broad, J = 6.1 Hz, 1 H) 7.39 (d, J = 8.1 Hz.1 H) 7.42 (t, J = 8.9 Hz, 1 H) 7.46 (d, J = 12.0 Hz, 1 H) 7.53 (dd, J = 8.9, 5.0 Hz, 1 H) 10.16 (m spread-out, 1 H) | [M + H]+ m/z = 476; [M − H]− m/z = 474 | 158 |
| 108 | 1-{6-[1-(2,3-dichloro-6-fluorophenyl)ethoxy]-1,3-benzothiazol-2-yl}-3-[2-(4-methylpiperazin-1-yl)ethyl]urea | | 1.74 (d, J = 6.7 Hz, 3 H) 2.15 (s, 3 H) 2.27-2.47 (m, 10 H) 3.24 (q, J = 5.9 Hz, 2 H) 6.05 (q, J = 6.7 Hz, 1 H) 6.70 (m broad, 1 H) 6.89 (dd, J = 8.7, 2.8 Hz, 1 H) 7.34 (d, J = 2.8 Hz, 1 H) 7.40 (t, J = 8.9 Hz, 1 H) 7.45 (d, J = 8.7 Hz, 1 H) 7.51 (dd, J = 8.9, 5.3 Hz, 1 H) 10.65 (m spread-out, 1 H) | [M + H]+ m/z = 526; [M + 2H + CH3CN]2+ m/z = 284 (base peak) [M − H]− m/z = 524 | 105-110 |
| 109 | 1-{6-[(1R*)-1-(2,3-dichloro-6-fluorophenyl)ethoxy]-1,3-benzothiazol-2-yl}-3-[2-(4-methylpiperazin-1-yl)ethyl]urea | Semi-preparative separation on Chiralpak IC 5 μm (2 × 25 cm). PR = +6.2(dextrorotatory) C = 2.618 mg/0.5 ml DMSO on 589 nM | 1.74 (d, J = 6.6 Hz, 3 H) 2.15 (s, 3 H) 2.24-2.46 (m, 10 H) 3.24 (q, J = 6.1 Hz, 2 H) 6.05 (q, J = 6.6 Hz, 1 H) 6.72 (t, J = 6.1 Hz, 1 H) 6.89 (dd, J = 8.8, 2.6 Hz, 1 H) 7.34 (d, J = 2.6 Hz, 1 H) 7.40 (t, J = 8.9 Hz, 1 H) 7.45 (d, J = 8.8 Hz, 1 H) 7.51 (dd, J = 8.9, 5.1 Hz, 1 H) 10.67 (m spread-out, 1 H) | [M + H]+ m/z = 526; [M + 2H]2+ m/z = 263.5 (base peak) [M − H]− m/z = 524 | |

-continued

| Ex | Name | Chiral separation conditions | 1H NMR (400 MHz, DMSO-d6) δ ppm | Mass spectroscopy | m.p. ° C. |
|---|---|---|---|---|---|
| 110 | 1-{6-[1-(2,3-dichloro-6-fluorophenyl)ethoxy]-1,3-benzothiazol-2-yl}-3-[2-(1-methylpyrrolidin-2-yl)ethyl]urea | | 1.32-1.50 (m, 2 H) 1.56-1.67 (m, 2 H) 1.74 (d, J = 6.7 Hz, 3 H) 1.75 (m, 1 H) 1.82-1.94 (m, 1 H) 1.99-2.09 (m, 2 H) 2.20 (s, 3 H) 2.93 (m, 1 H) 3.17 (m, 1 H) 6.05 (q, J = 6.7 Hz, 1 H) 6.77 (t, J = 5.9 Hz, 1 H) 6.89 (dd, J = 8.8, 2.7 Hz, 1 H) 7.34 (d, J = 2.7 Hz, 1 H) 7.40 (t, J = 8.8 Hz, 1 H) 7.44 (d, J = 8.8 Hz, 1 H) 7.51 (dd, J = 8.8, 4.9 Hz, 1 H) 10.57 (m spread-out, 1 H) | [M + H]+ m/z = 511; [M − H]− m/z = 509 | 102-105 |
| 111 | 1-{6-[1-(2,3-dichloro-6-fluorophenyl)ethoxy]-5-fluoro-1,3-benzothiazol-2-yl}-3-[2-(morpholin-4-yl)ethyl]urea | | 1.78 (d, J = 6.8 Hz, 3 H) 2.37-2.43 (m, 6 H) 3.26 (m, 2 H) 3.58 (m, 4 H) 6.04 (q, J = 6.8 Hz, 1 H) 6.72 (m broad, 1 H) 7.38 (d, J = 8.3 Hz, 1 H) 7.40-7.48 (m, 2 H) 7.53 (dd, J = 8.8, 4.9 Hz, 1 H) 10.74 (m spread-out, 1 H) | [M + H]+ m/z = 531; [M − H]− m/z = 529 | 220-225 |
| 112 | 1-{6-[(1R*)-1-(2,3-dichloro-6-fluorophenyl)ethoxy]-5-fluoro-1,3-benzothiazol-2-yl}-3-[2-(morpholin-4-yl)ethyl]urea | Preparative separation on Chiralpak IC 20 μm (6 × 35 cm). PR = +109.3(dextrorotatory) C = 1.781 mg/0.5 ml DMSO on 589 nM | 1.78 (d, J = 6.7 Hz, 3 H) 2.35-2.44 (m, 6 H) 3.26 (q, J = 5.9 Hz, 2H) 3.58 (m, 4 H) 6.04 (q, J = 6.7 Hz, 1 H) 6.71 (m broad, 1 H) 7.38 (d, J = 8.1 Hz, 1 H) 7.40-7.47 (m, 2 H) 7.53 (dd, J = 9.0, 5.1 Hz, 1 H) 10.81 (m spread-out, 1 H) | [M + H]+ m/z = 531; [M − H]− m/z = 529 | |
| 113 | 1-{6-[(1S*)-1-(2,3-dichloro-6-fluorophenyl)ethoxy]-5-fluoro-1,3-benzothiazol-2-yl}-3-[2-(morpholin-4-yl)ethyl]urea | Preparative separation on Chiralpak IC 20 μm (6 × 35 cm). PR = −105.3 (laevorotatory) C = 1.718 mg/0.5 ml DMSO on 589 nM | 1.78 (d, J = 6.6 Hz, 3 H) 2.36-2.43 (m, 6 H) 3.25 (q, J = 5.9 Hz, 2H) 3.58 (m, 4 H) 6.03 (q, J = 6.6 Hz, 1 H) 6.71 (m broad, 1 H) 7.36 (d, J = 8.5 Hz, 1 H) 7.39-7.46 (m, 2 H) 7.53 (dd, J = 8.8, 5.1 Hz, 1 H) 10.81 (m spread-out, 1 H) | [M + H]+ m/z = 531; [M − H]− m/z = 529 | |
| 114 | 1-{6-[1-(2,3-dichloro-6-fluorophenyl)ethoxy]-5-fluoro-1,3-benzothiazol-2-yl}-3-[3-(2-oxopyrrolidin-1-yl)propyl]urea | | 1.62 (m, 2 H) 1.78 (d, J = 6.8 Hz, 3 H) 1.91 (m, 2 H) 2.21 (t, J = 8.1 Hz, 2 H) 3.09 (m, 2 H) 3.19 (t, J = 7.1 Hz, 2 H) 3.32 (t, J = 7.1 Hz, 2 H) 6.03 (q, J = 6.8 Hz, 1 H) 6.83 (m broad, 1 H) 7.36 (d, J = 8.5 Hz, 1 H) 7.38-7.47 (m, 2 H) 7.53 (dd, J = 9.2, 5.2 Hz, 1 H) 10.53 (m spread-out, 1 H) | [M + H]+ m/z = 543; [M − H]− m/z = 541 | 195 |
| 115 | 1-{6-[1-(2,3-dichloro-6-fluorophenyl)ethoxy]-5-fluoro-1,3-benzothiazol-2-yl}-3-[2-(4-methylpiperazin-1-yl)ethyl]urea | | 1.78 (d, J = 6.7 Hz, 3 H) 2.15 (s, 3 H) 2.20-2.47 (m, 10 H) 3.24 (q, J = 6.0 Hz, 2 H) 6.04 (q, J = 6.7 Hz, 1 H) 6.68 (m broad, 1 H) 7.39 (d, J = 8.3 Hz, 1 H) 7.41-7.49 (m, 2 H) 7.53 (dd, J = 9.0, 5.1 Hz, 1 H) 10.76 (m spread-out, 1 H) | [M + H]+ m/z = 544; [M + 2H]2+ m/z = 272.5 (base peak); [M − H]− m/z = 542 | 120 |
| 116 | 1-{6-[(1R*)-1-(2,3-dichloro-6-fluorophenyl)ethoxy]-5-fluoro-1,3-benzothiazol-2-yl}-3-[2-(morpholin-4-yl)ethyl]urea | Preparative separation on Chiralpak IC 20 μm (6 × 35 cm). PR = +94.9(dextrorotatory) C = 2.185 mg/0.5 ml DMSO on 589 nM | 1.78 (d, J = 6.6 Hz, 3 H) 2.15 (s, 3 H) 2.25-2.48 (m, 10 H) 3.25 (m, 2 H) 6.04 (q, J = 6.6 Hz, 1 H) 6.69 (t, J = 5.9 Hz, 1 H) 7.39 (d, J = 8.3 Hz, 1 H) 7.41-7.49 (m, 2 H) 7.53 (dd, J = 8.9, 5.0 Hz, 1 H) 10.18 (m spread-out, 1 H) | [M + H]+ m/z = 544; [M + 2H]2+ m/z = 272.5 (base peak); [M − H]− m/z = 542 | |
| 117 | 1-{6-[(1S*)-1-(2,3-dichloro-6-fluorophenyl)ethoxy]-5-fluoro-1,3-benzothiazol-2-yl}-3-[2-(morpholin-4-yl)ethyl]urea | Preparative separation on Chiralpak IC 20 μm (6 × 35 cm). PR = −98.1 (laevorotatory) C = 2.086 mg/0.5 ml DMSO on 589 nM | 1.78 (d, J = 6.6 Hz, 3 H) 2.15 (s, 3 H) 2.22-2.47 (m, 10 H) 3.24 (q, J = 6.1 Hz, 2 H) 6.04 (q, J = 6.8 Hz, 1 H) 6.66 (m broad, 1 H) 7.38 (d, J = 8.3 Hz, 1 H) 7.41-7.47 (m, 2 H) 7.53 (dd, J = 9.0, 5.1 Hz, 1 H) 10.50 (m very spread-out, 1 H) | [M + H]+ m/z = 544; [M + 2H]2+ m/z = 272.5; [M + 2H + CH3CN]2+ m/z = peak); 292.5 (base [M − H]− m/z = 542 | |
| 118 | 1-{6-[1-(2,3-dichloro-6-fluorophenyl)ethoxy]-5-fluoro-1,3-benzothiazol-2- | | 1.70 (m, 4 H) 1.78 (d, J = 6.8 Hz, 3 H) 2.43-2.55 (m partially masked, 6 H) | [M + H]+ m/z = 515; [M − H]− m/z = 513 | 191 |

| Ex | Name | Chiral separation conditions | 1H NMR (400 MHz, DMSO-d6) δ ppm | Mass spectroscopy | m.p. ° C. |
|---|---|---|---|---|---|
| | yl}-3-[2-(pyrrolidin-1-yl)ethyl]urea | | 3.25 (m, 2 H) 6.04 (q, J = 6.8 Hz, 1 H) 6.74 (t broad, J = 6.0 Hz, 1 H) 7.39 (d, J = 8.3 Hz, 1 H) 7.43 (t, J = 8.9 Hz, 1 H) 7.46 (d, J = 12.0 Hz, 1 H) 7.53 (dd, J = 8.9, 5.0 Hz, 1 H) 10.63 (m spread-out, 1 H) | | |
| 119 | 1-{6-[(1R*)-1-(2,3-dichloro-6-fluorophenyl)ethoxy]-5-fluoro-1,3-benzothiazol-2-yl}-3-[2-(pyrrolidin-1-yl)ethyl]urea | Preparative separation on Chiralpak T304 10 µm (6 × 35 cm). PR = +104.6 (dextrorotatory) C = 1.917 mg/0.5 ml DMSO on 589 nM | 1.75 (m, 4 H) 1.78 (d, J = 6.5 Hz, 3 H) 2.48-2.80 (m, 6 H) 3.27-3.33 (m masked, 2 H) 6.04 (q, J = 6.8 Hz, 1 H) 6.77 (m broad, 1 H) 7.40 (d, J = 8.2 Hz, 1 H) 7.41-7.49 (m, 2H) 7.53 (dd, J = 8.8, 4.9 Hz, 1 H) 10.75 (m spread-out, 1 H) | [M + H]+ m/z = 515; [M − H]− m/z = 513 | |
| 120 | 1-{6-[1-(2,3-dichloro-6-fluorophenyl)ethoxy]-1,3-benzothiazol-2-yl}-3-[2-(pyrrolidin-1-yl)ethyl]urea | | 1.69 (m, 4 H) 1.74 (d, J = 6.6 Hz, 3 H) 2.42-2.53 (m partially masked, 6 H) 3.25 (m, 2 H) 6.05 (q, J = 6.6 Hz, 1 H) 6.82 (m broad, 1 H) 6.88 (dd, J = 8.8, 2.7 Hz, 1 H) 7.34 (d, J = 2.7 Hz, 1 H) 7.41-7.49 (m, 2 H) 7.52 (dd, J = 8.9, 5.0 Hz, 1 H) 10.61 (m spread-out, 1 H) | [M + H]+ m/z = 497; [M − H]− m/z = 495 | 110-115 |
| 121 | 1-{6-[(1R*)-(2,3-dichloro-6-fluorophenyl)ethoxy]-1,3-benzothiazol-2-yl}-3-[2-(pyrrolidin-1-yl)ethyl]urea | Preparative separation on Chiralpak T304 20 µm (6 × 35 cm). PR = +11.5 (dextrorotatory) C = 2.433 mg/0.5 ml DMSO on 589 nM | 1.68-1.85 (m spread-out, partially masked, 4 H) 1.75 (d, J = 6.7 Hz, 3 H) 2.35-2.75 (m spread-out, partially masked, 6 H) 3.25-3.37 (m partially masked, 2 H) 6.06 (q, J = 6.7 Hz, 1 H) 6.79 (m broad, 1 H) 6.89 (dd, J = 8.7, 2.8 Hz, 1 H) 7.35 (d, J = 2.8 Hz, 1 H) 7.41 (t, J = 8.9 Hz.1 H) 7.46 (d, J = 8.7 Hz, 1 H) 7.52 (dd, J = 8.9, 5.1 Hz, 1 H) 10.63 (m spread-out, 1 H) | [M + H]+ m/z = 497; [M − H]− m/z = 495 | |
| 124 | 1-[2-(morpholin-4-yl)ethyl]-3-{6-[1-(2,3,6-trichlorophenyl)ethoxy]-1,3-benzothiazol-2-yl}urea | | 1.74 (d, J = 6.7 Hz, 3 H) 2.35-2.45 (m, 6 H) 3.26 (q, J = 5.9 Hz, 2H) 3.59 (m, 4 H) 6.10 (q, J = 6.7 Hz, 1 H) 6.74 (t broad, J = 5.9 Hz, 1 H) 6.88 (dd, J = 8.8, 2.9 Hz, 1 H) 7.34 (d, J = 2.9 Hz, 1 H) 7.45 (d, J = 8.8 Hz, 1 H) 7.48 (d, J = 8.8 Hz, 1 H) 7.61 (d, J = 8.8 Hz, 1 H) 10.48 (m spread-out, 1 H) | [M + H]+ m/z = 529; [M + 2H + CH3CN]2+ m/z = 285 (base peak) | 189 |
| 125 | 1[2-(pyrrolidin-1-yl)ethyl]-3-{6-[1-(2,3,6-trichlorophenyl)ethoxy]-1,3-benzothiazol-2-yl}urea | | 1.69 (m, 4 H) 1.74 (d, J = 6.8 Hz, 3 H) 2.43-2.53 (m partially masked, 6 H) 3.25 (q, J = 5.9 Hz, 2 H) 6.10 (q, J = 6.8 Hz, 1 H) 6.78 (t broad, J = 5.9 Hz, 1 H) 6.87 (dd, J = 8.8.2.7 Hz, 1 H) 7.33 (d, J = 2.7 Hz, 1 H) 7.44 (d, J = 8.8 Hz, 1 H) 7.48 (d, J = 8.8 Hz, 1 H) 7.60 (d, J = 8.8 Hz, 1H) 10.56 (m spread-out, 1 H) | [M + H]+ m/z = 513; [M − H]− m/z = 511 | 189 |
| 126 | 1-{5-fluoro-6-[1-(2,3,6-trichlorophenyl)ethoxy]-1,3-benzothiazol-2-yl}-3-[2-(pyrrolidin-1-yl)ethyl]urea | | 1.57-1.73 (m, 4 H) 1.77 (d, J = 6.8 Hz, 3 H) 2.36-2.53 (m partially masked, 6 H) 3.24 (q, J = 5.9 Hz, 2 H) 6.09 (q, J = 6.8 Hz, 1 H) 6.48 (m spread-out, 1 H) 6.79 (m broad, 1 H) 7.37 (d, J = 8.3 Hz, 1 H) 7.46 (d, J = 12.3 Hz, 1 H) 7.51 (d, J = 8.8 Hz, 1 H) 7.64 (d, J = 8.8 Hz, 1H) | [M + H]+ m/z = 531; [M − H]− m/z = 529 | 103-107 |
| 129 | 1-{6-[1-(2,6-dichloro-3-fluorophenyl)ethoxy]-5-fluoro-1,3-benzothiazol-2- | | 1.78 (d, J = 6.8 Hz, 3 H) 2.19 (s, 3 H) 2.27 (m, 2 H) 2.32 (m, 2 H) | [M + H]+ m/z = 558; [M − H]− m/z = 556 | 235-238 |

| Ex | Name | Chiral separation conditions | 1H NMR (400 MHz, DMSO-d6) δ ppm | Mass spectroscopy | m.p. ° C. |
|---|---|---|---|---|---|
| | yl}-3-[2-(4-methylpiperazin-1-yl)-2-oxoethyl]urea | | 3.38 (m, 2 H) 3.47 m, 2 H) 4.06 (d, J = 5.0 Hz, 2 H) 6.04 (q, J = 6.8 Hz, 1 H) 6.95 (t, J = 5.0 Hz, 1 H) 7.38-7.46 (m, 2 H) 7.48 (d, J = 12.0 Hz, 1 H) 7.53 (dd, J = 9.2, 5.3 Hz, 1 H) 10.91 (s, 1 H) | | |
| 130 | 1-{6-[1-(2,6-dichloro-3-fluorophenyl)ethoxy]-5-fluoro-1,3-benzothiazol-2-yl}-3-[2-(3-oxopiperazin-1-yl)ethyl]urea | | 1.78 (d, J = 6.6 Hz, 3 H) 2.49 (m, 2 H) 2.59 (m, 2 H) 2.97 (s, 2 H) 3.16 (m, 2 H) 3.24-3.33 (m partially masked, 2 H) 6.04 (q, J = 6.6 Hz, 1 H) 6.74 (t broad, J = 6.0 Hz, 1H) 7.39 (d, J = 8.3 Hz, 1 H) 7.41-7.49 (m, 2 H) 7.53 (dd, J = 9.0, 5.0 Hz, 1 H) 7.71 (s broad, 1 H) 10.75 (m spread-out, 1 H) | [M + H]+ m/z = 544; [M − H]− m/z = 542 | |
| 131 | 1-cyclopropyl-3-{6-[1-(2,6-dichloro-3-fluorophenyl)ethoxy]-5-fluoro-1,3-benzothiazol-2-yl}urea | | 0.46 (m, 2 H) 067 (m, 2 H) 1.78 (d, J = 6.8 Hz, 3 H) 2.59 (m, 1 H) 6.05 (q, J = 6.8 Hz, 1 H) 6.92 (m broad, 1 H) 7.39-7.46 (m, 2 H) 7.47 (d, J = 11.7 Hz, 1 H) 7.53 (dd, J = 9.0, 5.0 Hz, 1 H) 10.53 (m spread-out, 1 H) | [M + H]+ m/z = 458; [M − H]− m/z = 456 | |

Example 106

1-{5-chloro-6-[1-(2,6-dichloro-3-fluorophenyl)ethoxy]-1,3-benzothiazol-2-yl}-3-[2-(morpholin-4-yl)ethyl]urea a) 1-{5-Chloro-6-[1-(2,6-dichloro-3-fluorophenyl)ethoxy]-1,3-benzothiazol-2-yl}-3-[2-(morpholin-4-yl)ethyl]urea can be prepared as in Example 10a but from 0.4 g of {5-chloro-6-[1-(2,6-dichloro-3-fluorophenyl)ethoxy]-1,3-benzothiazol-2-yl}phenyl carbamate and 0.203 g of 2-morpholin-4-ylethanamine. After silica-column chromatography [eluent: dichloromethane/methanol 95/5], we obtain 0.348 g of 1-{5-chloro-6-[1-(2,6-dichloro-3-fluorophenyl)ethoxy]-1,3-benzothiazol-2-yl}-3-[2-(morpholin-4-yl)ethyl]urea in the form of a white solid, which has the following characteristics:

Melting point: 196-198° C. (Büchi)

1H NMR spectrum (400 MHz, DMSO-d$_6$) δ ppm: 1.79 (d, J=6.6 Hz, 3H) 2.40 (m, 6H) 3.27 (m partially masked, 2H) 3.58 (m, 4H) 6.03 (q, J=6.6 Hz, 1H) 6.69 (m broad, 1H) 7.31 (s, 1H) 7.45 (t, J=8.9 Hz, 1H) 7.55 (dd, J=8.9, 5.1 Hz, 1H) 7.65 (s, 1H) 10.84 (m spread-out, 1H)

Mass spectrum: LC-MS-DAD-ELSD: [M+H]+m/z=547; [M−H]−m/z=545 b) {5-Chloro-6-[1-(2,6-dichloro-3-fluorophenyl)ethoxy]-1,3-benzothiazol-2-yl}phenyl carbamate was prepared according to the method described in Example 10b but from 0.85 g of 5-chloro-6-[1-(2,6-dichloro-3-fluorophenyl)ethoxy]-1,3-benzothiazol-2-amine and 1.35 g of phenyl chlorocarbonate. We thus obtain 0.83 g of {5-chloro-6-[1-(2,6-dichloro-3-fluorophenyl)ethoxy]-1,3-benzothiazol-2-yl}phenyl carbamate in the form of a cream-coloured solid, which has the following characteristics:

1H NMR spectrum (400 MHz, DMSO-d$_6$) δ ppm: 1.79 (d, J=6.4 Hz, 3H) 6.06 (q, J=6.4 Hz, 1H) 7.24-7.33 (m, 3H) 7.42-7.48 (m, 4H) 7.55 (dd, J=9.0, 5.1 Hz, 1H) 7.82 (s, 1H) 12.60 (m spread-out, 1H)

Mass spectrum: HPLC-MS-DAD-ELSD: [M+H]+m/z=511; [M−H]−m/z=509 c) 5-Chloro-6-[1-(2,6-dichloro-3-fluorophenyl)ethoxy]-1,3-benzothiazol-2-amine was prepared according to the method described in Example 20d but from 1.19 g of 3-chloro-4-[1-(2,6-dichloro-3-fluorophenyl)ethoxy]aniline, 1.38 g of potassium thiocyanate and 0.182 cm$^3$ of dibromine. We obtain 0.85 g of 5-chloro-6-[1-(2,6-dichloro-3-fluorophenyl)ethoxy]-1,3-benzothiazol-2-amine in the form of a yellow-coloured solid, which has the following characteristics:

Rf CCM silica=0.33 [eluent: dichloromethane/methanol 95/5]

Mass spectrum: HPLC-MS-DAD-ELSD: [M+H]+: m/z=391 d) 3-Chloro-4-[1-(2,6-dichloro-3-fluorophenyl)ethoxy]aniline was prepared according to the following method:

1.34 g of 1,3-dichloro-2-[1-(2-chloro-4-nitrophenoxy)ethyl]-4-fluorobenzene is dissolved in 370 cm$^3$ of ethyl acetate. The solution is passed over an H-cube with a Pt/C cartridge at 1 ml/min at atmospheric pressure. The solution obtained is evaporated to dryness under reduced pressure (2 kPa). We thus obtain 1.19 g of 3-chloro-4-[1-(2,6-dichloro-3-fluorophenyl)ethoxy]aniline in the form of a yellow-coloured oil, which has the following characteristics:

Rf CCM silica=0.35 [eluent: cyclohexane/ethyl acetate 75/25]

Mass spectrum: LC-MS-DAD-ELSD: [M+H]+: m/z=334; [M+CH$_3$CN+H]+: m/z=375 e) 1,3-Dichloro-2-[1-(2-chloro-4-nitrophenoxy)ethyl]-4-fluorobenzene was prepared according to the method described in Example 20f but from 0.211 g of sodium hydride (at 60% in the oil), 1 g of 1-(2,6-dichloro-3-fluorophenyl)ethanol and 0.843 g of 2-chloro-1-fluoro-4-nitrobenzene. We thus obtain 1.35 g of 1,3-dichloro-2-[1-(2-chloro-4-nitrophenoxy)ethyl]-4-fluorobenzene in the form of a yellow-coloured solid, which has the following characteristics:

Rf CCM silica=0.69 [eluent: cyclohexane/ethyl acetate 75/25]

Mass spectrum: SM-EI: EI: [M]+.: m/z 363; m/z 191 (base peak)

Example 107

1-{6-[1-(2,6-dichloro-3-fluorophenyl)ethoxy]-5-methyl-1,3-benzothiazol-2-yl}-3-[2-(morpholin-4-yl)ethyl]urea a) 1-{6-[1-(2,6-Dichloro-3-fluorophenyl)ethoxy]-5-methyl-1,3-benzothiazol-2-yl}-3-[2-(morpholin-4-yl)ethyl]urea can be prepared as in Example 10a but from 0.765 g of {5-chloro-6-[1-(2,6-dichloro-3-fluorophenyl)ethoxy]-1,3-benzothiazol-2-yl}phenyl carbamate and 0.402 g of 2-morpholin-4-ylethanamine. After silica-column chromatography [eluent: dichloromethane/methanol 95/5], we obtain 0.49 g of 1-{6-[1-(2,6-dichloro-3-fluorophenyl)ethoxy]-5-methyl-1,3-benzothiazol-2-yl}-3-[2-(morpholin-4-yl)ethyl]urea in the form of a white solid, which has the following characteristics:

Melting point: 270-276° C. (Büchi)

1H NMR spectrum (400 MHz, DMSO-$d_6$) δ ppm: 1.76 (d, J=6.6 Hz, 3H) 2.32 (s, 3H) 2.36-2.43 (m, 6H) 3.25 (q, J=6.3 Hz, 2H) 3.59 (m, 4H) 6.00 (q, J=6.6 Hz, 1H) 6.72 (m broad, 1H) 7.06 (s, 1H) 7.40 (s, 1H) 7.43 (t, J=8.9 Hz, 1H) 7.55 (dd, J=8.9, 5.0 Hz, 1H) 10.63 (m spread-out, 1H)

Mass spectrum: LC-MS-DAD-ELSD: [M+H]+m/z=527; [M−H]−m/z=525 b) {6-[1-(2,6-Dichloro-3-fluorophenyl)ethoxy]-5-methyl-1,3-benzothiazol-2-yl}phenyl carbamate was prepared according to the method described in Example 10b but from 0.85 g of 6-[1-(2,6-dichloro-3-fluorophenyl)ethoxy]-5-methyl-1,3-benzothiazol-2-amine and 1.35 g of phenyl chlorocarbonate. We thus obtain 0.765 g of {6-[1-(2,6-dichloro-3-fluorophenyl)ethoxy]-5-methyl-1,3-benzothiazol-2-yl}phenyl carbamate in the form of a cream-coloured solid, which has the following characteristics:

1H NMR spectrum (400 MHz, DMSO-$d_6$) δ ppm: 1.77 (d, J=6.8 Hz, 3H) 2.35 (s, 3H) 6.03 (q, J=6.8 Hz, 1H) 7.16 (s, 1H) 7.25-7.34 (m, 3H) 7.42-7.49 (m, 3H) 7.52-7.59 (m, 2H) 12.15-12.54 (s broad, 1H)

Mass spectrum: HPLC-MS-DAD-ELSD: [M+H]+m/z=491 c) 6-[1-(2,6-Dichloro-3-fluorophenyl)ethoxy]-5-methyl-1,3-benzothiazol-2-amine was prepared according to the method described in Example 20d but from 3.12 g of 4-[1-(2,6-dichloro-3-fluorophenyl)ethoxy]-3-methylaniline, 3.86 g of potassium thiocyanate and 0.509 cm³ of dibromine. We obtain 0.644 g of 6-[1-(2,6-dichloro-3-fluorophenyl)ethoxy]-5-methyl-1,3-benzothiazol-2-amine in the form of a yellow-coloured solid, which has the following characteristics:

Rf CCM silica=0.20 [eluent: dichloromethane/methanol 95/5]

Mass spectrum: HPLC-MS-DAD-ELSD: [M+H]+: m/z 371 d) 4-[1-(2,6-Dichloro-3-fluorophenyl)ethoxy]-3-methylaniline was prepared according to the method described in Example 106d but from 3.5 g of 1,3-dichloro-4-fluoro-2-[1-(2-methyl-4-nitrophenoxy)ethyl]benzene. We thus obtain 3.12 g of 4-[1-(2,6-dichloro-3-fluorophenyl)ethoxy]-3-methylaniline in the form of a brown-coloured oil, which has the following characteristics:

Rf CCM silica=0.22 [eluent: cyclohexane/ethyl acetate 75/25]

Mass spectrum: LC-MS-DAD-ELSD: [M+H]+: m/z 314; m/z 355 (base peak)

e) 1,3-Dichloro-4-fluoro-2-[1-(2-methyl-4-nitrophenoxy)ethyl]benzene was prepared according to the method described in Example 20f but from 0.422 g of sodium hydride (at 60% in the oil), 2 g of 1-(2,6-dichloro-3-fluorophenyl)-ethanol and 1.49 g of 2-methyl-1-fluoro-4-nitrobenzene. We thus obtain 3.5 g of 1,3-dichloro-4-fluoro-2-[1-(2-methyl-4-nitrophenoxy)ethyl]benzene in the form of an orange-coloured solid, which has the following characteristics:

Rf CCM silica=0.65 [eluent: cyclohexane/ethyl acetate 75/25]

Mass spectrum: SM-EI: EI: [M]+.: m/z 343; m/z 191 (base peak)

Example 122

1-{6-[1-(2,6-dichlorophenyl)propoxy]-1,3-benzothiazol-2-yl}-3-[2-(morpholin-4-yl)ethyl]urea 1-{6-[1-(2,6-Dichlorophenyl)propoxy]-1,3-benzothiazol-2-yl}-3-[2-(morpholin-4-yl)ethyl]urea can be prepared as in Example 10a but from 0.3 g of {6-[1-(2,6-dichlorophenyl)propoxy]-1,3-benzothiazol-2-yl}phenyl carbamate and 0.165 g of 2-morpholin-4-ylethanamine. We obtain 0.235 g of 1-{6-[1-(2,6-dichlorophenyl)propoxy]-1,3-benzothiazol-2-yl}-3-[2-(morpholin-4-yl)ethyl]urea in the form of a cream-coloured powder with the following characteristics:

Melting point: 200° C. (Köfler)

1H NMR spectrum (400 MHz, DMSO-$d_6$) δ ppm: 1.00 (t, J=7.3 Hz, 3H) 2.05 (m, 1H) 2.29 (m, 1H) 2.35-2.44 (m, 6H) 3.26 (q, J=5.8 Hz, 2H) 3.59 (m, 4H) 5.82 (dd, J=7.6, 6.6 Hz, 1H) 6.75 (t broad, J=5.8 Hz, 1H) 6.89 (dd, J=8.8, 2.9 Hz, 1H) 7.30 (t, J=7.8 Hz, 1H) 7.33 (d, J=2.9 Hz, 1H) 7.42-7.45 (m, 3H) 10.58 (m spread-out, 1H)

Mass spectrum: LC-MS-DAD-ELSD: [M+H]+m/z=509; [M−H]−m/z=507 b) {6-[1-(2,6-Dichlorophenyl)propoxy]-1,3-benzothiazol-2-yl}phenyl carbamate was prepared according to the method described in Example 10b but from 1.1 g of 6-[1-(2,6-dichlorophenyl)propoxy]-1,3-benzothiazol-2-amine and 1.95 g of phenyl chlorocarbonate. We thus obtain 1.35 g of {6-[1-(2,6-dichlorophenyl)propoxy]-1,3-benzothiazol-2-yl}phenyl carbamate in the form of a cream-coloured powder, which has the following characteristics:

Melting point: 185-190° C. (Köfler)

Mass spectrum: HPLC-MS-DAD-ELSD: [M+H]+: m/z 473 c) 6-[1-(2,6-Dichlorophenyl)propoxy]-1,3-benzothiazol-2-amine was prepared according to the method described in Example 20d but from 1 g of 4-[1-(2,6-dichlorophenyl)propoxy]aniline, 1.31 g of potassium thiocyanate and 0.173 cm³ of dibromine. We thus obtain 1.2 g of 6-[1-(2,6-dichlorophenyl)propoxy]-1,3-benzothiazol-2-amine in the form of an orange-coloured resin, which has the following characteristics:

Rf CCM silica=0.14 [eluent: dichloromethane/methanol 98/2]

Mass spectrum: UPLC-MS-DAD-ELSD: [M+H]+: m/z 353 d) 4-[1-(2,6-Dichlorophenyl)propoxy]aniline was prepared according to the method described in Example 20e but from 1.1 g of 1,3-dichloro-2-[1-(4-nitrophenoxy)propyl]benzene and 0.076 g of platinum oxide in 150 cm³ of methanol. We thus obtain 1 g of 4-[1-(2,6-dichlorophenyl)propoxy]aniline in the form of an orange-coloured oil, which has the following characteristics:

Rf CCM silica=0.23 [eluent: dichloromethane

Mass spectrum: LC-MS-DAD-ELSD: [M+H]+: m/z 296 e) 1,3-Dichloro-2-[1-(4-nitrophenoxy)propyl]benzene was prepared according to the method described in Example 20f but from 0.236 g of sodium hydride (at 60% in the oil), 1.1 g of 1-(2,6-dichlorophenyl)propan-1-ol and 0.832 g of 1-fluoro-4-nitrobenzene. We thus obtain 1.18 g of 1,3-dichloro-2-[1-(4-nitrophenoxy)propyl]benzene in the form of a colorless oil which crystallizes, having the following characteristics:

Rf CCM silica=0.41 [eluent: petroleum ether/ethyl acetate 95/5]

Mass spectrum: LC-MS-DAD-ELSD: [M+H]$^+$: m/z 326

1-(2,6-Dichlorophenyl)propan-1-ol was prepared according to the method described in Example 124-125e but from 0.123 g of nickel(2+) bis[(2E)-4-oxopent-2-en-2-olate], 1.67 g of 2,6-dichlorobenzaldehyde, 0.25 g of triphenylphosphine and 19 cm$^3$ of a 1M solution of trimethylaluminium. After silica-column chromatography [eluent: cyclohexane/ethyl acetate 75/25], we thus obtain 1.28 g of 1-(2,6-dichlorophenyl)propan-1-ol in the form of a yellow oil, which has the following characteristics:

Rf CCM silica=0.68 (eluent: dichloromethane/methanol 98/2)

Mass spectrum: LC-MS-DAD-ELSD: [M+H–H2O]$^+$: m/z 187 [M+H–H2O—C2H4]$^+$: m/z 159; m/z 200 (base peak)

Example 123

1-{6-[1-(2,6-difluoro-3-methylphenyl)ethoxy]-1,3-benzothiazol-2-yl}-3-[2-(morpholin-4-yl)ethyl]urea 1-{6-[1-(2,6-Difluoro-3-methylphenyl)ethoxy]-1,3-benzothiazol-2-yl}-3-[2-(morpholin-4-yl)ethyl]urea can be prepared as in Example 10a but from 1 g of {6-[1-(2,6-difluoro-3-methylphenyl)ethoxy]-1,3-benzothiazol-2-yl}phenyl carbamate and 0.591 g of 2-morpholin-4-ylethanamine. We obtain 0.5 g of 1-{6-[1-(2,6-difluoro-3-methylphenyl)ethoxy]-1,3-benzothiazol-2-yl}-3-[2-(morpholin-4-yl)ethyl]urea in the form of a white powder, which has the following characteristics:

Melting point: 92-95° C. (Köfler)

1H NMR spectrum (400 MHz, DMSO-d$_6$) δ ppm: 1.70 (d, J=6.7 Hz, 3H) 2.17 (s broad, 3H) 2.37-2.46 (m, 6H) 3.27 (m, 2H) 3.59 (m, 4H) 5.78 (q, J=6.7 Hz, 1H) 6.78 (m broad, 1H) 6.90-7.00 (m, 2H) 7.24 (m, 1H) 7.42 (d, J=2.4 Hz, 1H) 7.44 (d, J=8.8 Hz, 1H) 10.67 (m spread-out, 1H)

Mass spectrum: LC-MS-DAD-ELSD: [M+H]+m/z=477; [M−H]−m/z=475 b) {6-[1-(2,6-Difluoro-3-methylphenyl)ethoxy]-1,3-benzothiazol-2-yl}phenyl carbamate was prepared according to the method described in Example 10b but from 2 g of 6-[1-(2,6-difluoro-3-methylphenyl)ethoxy]-1,3-benzothiazol-2-amine and 3.91 g of phenyl chlorocarbonate. We thus obtain 2.1 g of {6-[1-(2,6-difluoro-3-methylphenyl)ethoxy]-1,3-benzothiazol-2-yl}phenyl carbamate in the form of a cream-coloured powder, which has the following characteristics:

Rf CCM silica=0.23 [eluent: dichloromethane]

Mass spectrum: HPLC-MS-DAD-ELSD: [M+H]$^+$: m/z 441 c) 6-[1-(2,6-Difluoro-3-methylphenyl)ethoxy]-1,3-benzothiazol-2-amine was prepared according to the method described in Example 20d but from 3.5 g of 4-[1-(2,6-difluoro-3-methylphenyl)ethoxy]aniline, 5.2 g of potassium thiocyanate and 0.681 cm$^3$ of dibromine. We obtain 4.2 g of 6-[1-(2,6-difluoro-3-methylphenyl)ethoxy]-1,3-benzothiazol-2-amine in the form of a brown-coloured solid, which has the following characteristics:

Rf CCM silica=0.14 [eluent: dichloromethane/methanol 98/2]

Mass spectrum: HPLC-MS-DAD-ELSD: [M+H]$^+$: m/z=321 d) 4-[1-(2,6-Difluoro-3-methylphenyl)ethoxy]aniline was prepared according to the method described in Example 20e but from 0.31 g of platinum oxide and 4 g of 1,3-difluoro-4-methyl-2-[1-(4-nitrophenoxy)ethyl]benzene. We thus obtain 3.6 g of 4-[1-(2,6-difluoro-3-methylphenyl)ethoxy]aniline in the form of a brown-coloured oil, which has the following characteristics:

Rf CCM silica=0.22 [eluent: cyclohexane/ethyl acetate 75/25]

Mass spectrum: LC-MS-DAD-ELSD: [M+H]$^+$: m/z 264; [M+CH$_3$CN+H]$^+$: m/z 305 (base peak)

e) 1,3-Difluoro-4-methyl-2-[1-(4-nitrophenoxy)ethyl]benzene was prepared according to the method described in Example 20f but from 1.28 g of sodium hydride (at 60% in the oil), 5 g of 1-(2,6-difluoro-3-methylphenyl)ethanol and 1.49 g of 2-methyl-1-fluoro-4-nitrobenzene. We thus obtain 4.63 g of 1,3-difluoro-4-methyl-2-[1-(4-nitrophenoxy)ethyl]benzene in the form of a cream-coloured powder, which has the following characteristics:

Rf CCM silica=0.38 [eluent: diethyl oxide/ethyl acetate 95/5]

Mass spectrum: SM-EI: EI: [M]$^+$.: m/z 293; m/z 155 (base peak)

f) 1-(2,6-Difluoro-3-methylphenyl)ethanol was prepared according to the method described in Example 3e but from 5 g of 1-(2,6-difluoro-3-methyphenyl)-ethanone and 30.4 cm$^3$ of a 1M solution of aluminium lithium hydride in tetrahydrofuran. We thus obtain 5 g of 1-(2,6-difluoro-3-methylphenyl)ethanol in the form of an oil, which has the following characteristics:

Rf CCM silica=0.54 [eluent: dichloromethane/methanol 98/2]

Mass spectrum: SM-EI: EI: [M]$^+$.: m/z 172; m/z: 157 (base peak)

Example 132

Pharmaceutical Composition

Tablets were prepared corresponding to the following formula:

Product from Example 1 . . . 0.2 g

Excipient for one tablet, to . . . 1 g (details of the excipient: lactose, talc, starch, magnesium stearate).

Example 133

Pharmaceutical Composition

Tablets were prepared corresponding to the following formula:

Product from Example 4 . . . 0.2 g

Excipient for one tablet, to . . . 1 g (details of the excipient: lactose, talc, starch, magnesium stearate).

Examples 1 and 4 are taken as examples of pharmaceutical preparation, and said preparation can be performed if desired with other products given in the examples in the present application.

Pharmacological Section:
Experimental Protocols
I) Expression and Purification of MET, Cytoplasmic Domain
Expression in Baculovirus:

The recombinant DNA His-Tev-MET (956-1390) in pFast-Bac(Invitrogen) is transfected in insect cells and after several stages of viral amplification, the final stock of baculovirus is tested for expression of the protein of interest.

After infection for 72 h at 27° C. with the recombinant virus, the SF21 cell cultures are harvested by centrifugation and the cellular deposits are stored at −80° C.

Purification:

The cellular deposits are resuspended in the lysis buffer (buffer A [50 mM HEPES, pH 7.5, 250 mM NaCl, Glycerol 10%, TECP 1 mM]; +cocktail of protease inhibitors Roche Diagnostics without EDTA, ref 1873580), stirred at 4° C. until homogeneous, then lysed mechanically using apparatus of the "Dounce" type.

After centrifugation, the lysis supernatant is incubated for 2 h at 4° C. with Nickel Chelate resin (His-Trap 6 Fast Flow™, GE HealthCare). After washing with 20 volumes of Tp A, the suspension is packed in a column, and the proteins are eluted with a gradient of buffer B (TpA+290 mM imidazole).

The fractions containing the protein of interest with a view to electrophoretic analysis (SDS PAGE) are collected, concentrated by ultrafiltration (cut-off 10 kDa) and injected in an exclusion chromatography column (Superdex™ 200, GE HealthCare) equilibrated with buffer A.

After enzymatic cleavage of the tag Histidine, the protein is reinjected in a new IMAC Nickel Chelate chromatography column (His-Trap 6 Fast Flow™, GE HealthCare) equilibrated with Buffer A. The fractions eluted with a gradient of buffer B and containing the protein of interest after electrophoresis (SDS PAGE), are finally collected and stored at −80° C.

For the production of autophosphorylated protein, the preceding fractions are incubated for 1 h at room temperature after adding ATP 2 mM, MgCl2 2 mM, and Na₃VO4 4 mM. After stopping the reaction with 5 mM of EDTA, the reaction mixture is injected in a HiPrep desalting column (GE HealthCare) equilibrated beforehand with buffer A+Na3VO4 4 mM; the fractions containing the protein of interest (SDS PAGE analysis) are collected and stored at −80° C. The degree of phosphorylation is verified by mass spectrometry (LC-MS), and by peptide mapping.

II) Tests A, B, C, D

A) HTRF Met test in 96-well format

In a final volume of 50 µl of enzymatic reaction mixture, final c-MET 5 nM is incubated in the presence of the molecule to be tested (for a final concentration range from 0.17 nM to 10 µM, final DMSO 3%) in buffer MOPS 10 mM pH 7.4, DTT 1 mM, Tween 20 0.01%. The reaction is initiated by the substrate solution to obtain the final concentrations of poly-(GAT) 1 µg/ml, ATP 10 µM and MgCl2 5 mM. After incubation for 10 min at room temperature, the reaction is stopped with a mix of 30 µl to obtain a final solution of Hepes 50 mM pH 7.5, potassium fluoride 500 mM, BSA 0.1% and EDTA 133 mM in the presence of 80 ng Streptavidin 61SAXLB Cis-Bio Int. and 18 ng anti-phosphotyrosine Mab PT66-Europium Cryptate per well. After 2 hours of incubation at room temperature, reading is carried out at 2 wavelengths 620 nm and 665 nm in a reader for the TRACE/HTRF technique and the percentage inhibition is calculated according to the 665/620 ratios.

The results obtained by this test A for the products of formula (I) in the examples in the experimental section are such that IC50 is below 5 µM.

B) HTRF RON Test in 96-Well Format

The inhibitory potency (IC50) of molecules on the enzymatic activity of kinase phosphorylation RON is determined by the HTRF technique. The activity of the kinase is evaluated by measuring the phosphorylation of the substrate polyGAT by the enzyme, in the presence of ATP.

Final RON 5 nM is incubated in the presence of the molecule to be tested (for a final concentration range from 0.17 nM to 10 µM, final DMSO 3%) in buffer MOPS 10 mM pH 7, DTT 1 mM, Tween 20 0.01%. This pre-incubation is performed in 96 half-well black plates in a volume of 35 µl for 30 minutes at room temperature.

The reaction is initiated by adding 15 µl of a mixture of substrates constituted of biotinylated poly-(GAT) 1 µg/ml final and ATP 10 µM final in the presence of MgCl2 5 mM final for a final volume of 50 µl.

After incubation for 30 min at room temperature, the reaction is stopped with 30 µl of a mixture of Hepes 100 mM final pH 7, potassium fluoride 400 mM final, BSA 0.1% and EDTA 133 mM in the presence of 80 ng per well of antibodies Streptavidin ITS-XL665 Cis-Bio Int. and 18 ng per well of anti-phosphotyrosine PT66 labelled with europium cryptate.

After incubation for 2 hours at room temperature, reading is carried out at 2 wavelengths 620 nm and 665 nm in a Genios TECAN reader for the TRACE/HTRF technique and the percentage inhibition is calculated according to the 665/620 ratios.

C) Inhibition of the Autophosphorylation of MET; ELISA Technique (pppY1230, 1234, 1235)

a) Cellular lysates: Sow the MKN45 cells in a 96-well plate (Cell coat BD polylysine) at 20 000 cells/well under 200 µl of medium RPMI+10% FCS+1% L-glutamine. Leave to adhere to the incubator for 24 h.

The cells are treated on the day after sowing with the products at 6 concentrations in duplicate for 1 h. At least 3 control wells are treated with the same amount of final DMSO.

Dilution of the products: Stock at 10 mM in pure DMSO—range from 10 mM to 30 µM with steps of 3 of pure DMSO—Intermediate dilutions to 1/50 in culture medium then taking of 10 µl added directly to the cells (200 µl): final range from 10000 to 30 nM.

At the end of incubation, carefully remove the supernatant and rinse with 200 µl of PBS. Then put 100 µl of lysis buffer directly in the wells on ice and incubate at 4° C. for 30 minutes. Lysis buffer: 10 mM Tris, HCl pH7.4, 100 mM NaCl, 1 mM EDTA, 1 mM EGTA, 1% Triton X-100, 10% glycerol, 0.1% SDS, 0.5% deoxycholate, 20 mM NaF, 2 mM Na₃VO4, 1 mM PMSF and antiprotease cocktail.

The 100 µl of lysates are transferred to a V-bottomed polypropylene plate and ELISA is performed next or the plate is frozen at −80° C.

b) ELISA PhosphoMET BioSource Kit KH00281

In each well of the plate from the kit, add 70 µl of dilution buffer from the kit+30 µL of cell lysate or 30 µl of lysis buffer for the blank. Incubate for 2 h at room temperature, stirring gently.

Rinse the wells 4 times with 400 µl of washing buffer from the kit. Incubate with 100 µl of anti-phospho MET antibodies for 1 h at room temperature.

Rinse the wells 4 times with 400 µl of washing buffer from the kit. Incubate with 100 µl of anti-rabbit HRP antibodies for 30 minutes at room temperature (except for the wells with chromogen only).

Rinse the wells 4 times with 400 µl of washing buffer from the kit. Add 100 µL of chromogen and incubate for 30 minutes in the dark at room temperature.

Stop the reaction with 100 µl of stop solution. Read at once at 450 nM 0.1 second in the Wallac Victor plate reader.

The products of formula (I) as defined above show cellular activity in this test between 10 nM and 10 µM.

D) Measurement of Cellular Proliferation by 14C-Thymidine Pulse

The cells are sown in Cytostar 96-well plates under 180 µl for 4 hours at 37° C. and 5% CO2: The HCT116 cells at a rate of 2500 cells per well in DMEM medium+10% foetal calf serum+1% of L-glutamine and the MKN45 cells at a rate of 7500 cells per well in RPMI medium+10% foetal calf serum+ 1% of L-glutamine. After said incubation for 4 hours, the products are added under 10 µl in 20-times concentrated solution according to the method of dilution stated for ELISA. The products are tested at 10 concentrations in duplicate from 10000 nM to 0.3 nM in steps of 3.

After treatment for 72 h, add 10 µl of 14C-thymidine at 10 µCi/ml to obtain 0.1 µCi per well. The incorporation of 14C-thymidine is measured on a Micro-Beta (Perkin-Elmer) after 24 hours of pulse and 96 h of treatment.

All the stages of the test are automated on the BIOMEK 2000 or TECAN stations.

The results obtained for the products in the examples in the experimental section are given in the table of pharmacological results presented below, as follows: for test A, the sign + corresponds to less than 10 µM and the sign ++ corresponds to less than 100 nM.

for tests B, C and D, the sign + corresponds to less than 10 µM and the sign ++ corresponds to less than 500 nM.

Table of Pharmacological Results:

| Ex No. | test A | test B | test C | test D |
|---|---|---|---|---|
| 1 | ++ | + | − | − |
| 2 | ++ | + | + | + |
| 3 | ++ | + | + | + |
| 4 | ++ | ++ | + | + |
| 5 | ++ | ++ | + | + |
| 6 | ++ | ++ | ++ | + |
| 7 | ++ | + | + | ++ |
| 8 | + | − | − | − |
| 9 | ++ | − | − | ++ |
| 10 | ++ | + | + | + |
| 11 | ++ | + | − | − |
| 12 | − | − | − | − |
| 13 | ++ | + | − | − |
| 14 | + | + | − | − |
| 15 | ++ | + | − | + |
| 16 | + | − | − | − |
| 17 | ++ | ++ | + | + |
| 18 | ++ | + | + | + |
| 19 | ++ | + | + | − |
| 20 | + | − | − | − |
| 21 | ++ | + | + | + |
| 22 | ++ | − | + | − |
| 23 | + | − | − | − |
| 24 | ++ | ++ | ++ | ++ |
| 25 | ++ | ++ | ++ | ++ |
| 26 | + | − | + | − |
| 27 | + | − | − | − |
| 28 | ++ | + | + | − |
| 29 | ++ | ++ | ++ | + |
| 30 | ++ | + | − | − |
| 31 | ++ | ++ | ++ | + |
| 32 | ++ | ++ | ++ | + |
| 33 | ++ | ++ | + | + |
| 34 | ++ | + | + | − |
| 35 | ++ | + | + | − |
| 36 | ++ | + | + | − |
| 37 | + | ++ | ++ | + |
| 38 | − | − | − | − |
| 39 | ++ | ++ | ++ | + |
| 40 | ++ | + | + | − |
| 41 | ++ | + | + | − |
| 42 | ++ | + | ++ | + |
| 43 | ++ | ++ | ++ | − |
| 44 | ++ | + | ++ | ++ |
| 45 | ++ | + | ++ | + |
| 46 | ++ | + | + | − |
| 47 | ++ | + | + | + |
| 48 | ++ | ++ | ++ | − |
| 49 | ++ | + | ++ | + |
| 50 | ++ | + | ++ | + |
| 51 | ++ | + | ++ | + |
| 52 | ++ | − | ++ | + |
| 53 | ++ | ++ | ++ | ++ |
| 54 | ++ | + | ++ | + |
| 55 | ++ | ++ | ++ | ++ |
| 56 | ++ | + | ++ | ++ |
| 57 | ++ | + | + | − |
| 58 | ++ | + | + | − |
| 59 | ++ | + | + | + |
| 60 | ++ | + | + | − |
| 61 | ++ | ++ | ++ | ++ |
| 62 | + | + | − | − |
| 63 | + | − | + | − |
| 64 | ++ | + | + | − |
| 65 | ++ | + | + | + |
| 66 | ++ | + | ++ | + |
| 67 | ++ | − | ++ | ++ |
| 68 | ++ | + | ++ | + |
| 69 | ++ | + | ++ | + |
| 70 | ++ | + | + | + |
| 71 | ++ | − | + | + |
| 72 | ++ | − | + | + |
| 73 | ++ | + | + | + |
| 74 | ++ | + | ++ | + |
| 75 | ++ | ++ | ++ | ++ |
| 76 | ++ | ++ | ++ | ++ |
| 77 | ++ | + | + | + |
| 78 | ++ | ++ | ++ | + |
| 79 | ++ | ++ | ++ | + |
| 80 | ++ | + | −+ | + |
| 81 | ++ | ++ | ++ | + |
| 82 | ++ | + | ++ | + |
| 83 | ++ | + | ++ | + |
| 84 | ++ | + | ++ | ++ |
| 85 | ++ | ++ | ++ | ++ |
| 86 | ++ | − | ++ | + |
| 87 | ++ | − | + | + |
| 88 | ++ | + | ++ | + |
| 89 | ++ | + | ++ | + |
| 90 | ++ | − | − | + |
| 91 | ++ | − | + | + |
| 92 | ++ | − | ++ | + |
| 93 | ++ | − | + | + |
| 94 | ++ | + | + | + |
| 95 | ++ | + | + | + |
| 96 | ++ | ++ | ++ | + |
| 97 | ++ | + | + | + |
| 98 | ++ | ++ | ++ | + |
| 99 | ++ | ++ | ++ | ++ |
| 100 | ++ | ++ | ++ | ++ |
| 101 | ++ | ++ | ++ | ++ |
| 102 | ++ | + | + | + |
| 103 | ++ | + | + | + |
| 104 | ++ | ++ | ++ | + |
| 105 | ++ | ++ | ++ | + |
| 106 | ++ | + | + | + |
| 107 | ++ | − | ++ | + |
| 108 | ++ | ++ | ++ | + |
| 109 | ++ | ++ | ++ | ++ |
| 110 | ++ | ++ | ++ | + |
| 111 | ++ | + | + | + |
| 112 | ++ | ++ | ++ | ++ |
| 113 | ++ | + | ++ | + |

-continued

| Ex No. | test A | test B | test C | test D |
|---|---|---|---|---|
| 114 | ++ | ++ | ++ | + |
| 115 | ++ | ++ | ++ | ++ |
| 116 | ++ | ++ | ++ | ++ |
| 117 | ++ | + | + | + |
| 118 | ++ | ++ | ++ | + |
| 119 | ++ | + | ++ | ++ |
| 120 | ++ | ++ | ++ | ++ |
| 121 | ++ | ++ | ++ | ++ |
| 122 | ++ | − | + | + |
| 123 | ++ | + | + | + |
| 124 | ++ | + | ++ | + |
| 125 | ++ | + | + | + |
| 126 | ++ | + | + | + |
| 127 | ++ | + | ++ | + |
| 128 | ++ | + | ++ | + |
| 129 | ++ | + | ++ | + |
| 130 | ++ | += | ++ | + |
| 131 | ++ | − | ++ | ++ |

What is claimed is:
1. A compound of formula (Ia):

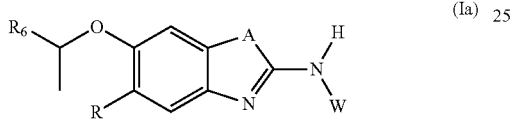

Wherein:
R represents a hydrogen atom, a halogen atom or an alkyl radical,
A represents NH or S;
R6 represents an aryl or heteroaryl radical optionally substituted with one or more radicals, which may be identical or different, selected from halogen atoms, hydroxyl, alkoxy, NR3R4 radicals, and alkyl, phenyl and phenylalkyl radicals, these last three radicals themselves are optionally substituted with one or more radicals selected from halogen atoms and hydroxyl, alkyl, alkoxy, NH2, NHalk and N(alk)2 radicals; and
W represents a hydrogen atom or the radical COR7 in which R7 represents:
a cycloalkyl radical or an alkyl radical optionally substituted with an alkoxy, hydroxyl, phenyl, heteroaryl, NR3R4, CONR3R4 or heterocycloalkyl radical, themselves optionally substituted as indicated below;
an alkoxy radical optionally substituted with a hydroxyl, alkoxy, phenyl, heteroaryl, NR3R4, CONR3R4 or heterocycloalkyl radical, themselves optionally substituted as indicated below;
or the radical NR1R2 in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, selected from hydroxyl, alkoxy, phenylalkoxy, cycloalkylalkoxy radicals, and heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains are optionally substituted as indicated below;

wherein R3 and R4, identical or different, are such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from hydroxyl, alkoxy, NH2, NHalk, N(alk)2 radicals and heteroaryl, heterocycloalkyl, and phenyl radicals optionally substituted with one or more radicals selected from halogen atoms and hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains are optionally substituted as indicated below;
the heterocycloalkyl, heteroaryl, aryl and phenyl radicals defined above as well as the cyclic radicals that R1 and R2 or R3 and R4 can form with the nitrogen atom to which they are attached, are optionally substituted with one or more radicals selected from halogen atoms, hydroxyl, oxo, alkoxy, NH2, NHalk, N(alk)2, free or esterified carboxyl radicals and alkyl, cycloalkyl, heterocycloalkyl, phenyl, heteroaryl, (heterocycloalkyl)alkyl, (phenyl)alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from halogen atoms and hydroxyl, oxo, alkyl and alkoxy radicals containing from 1 to 4 carbon atoms, NH2, NHalk and N(alk)2;
and wherein:
-R6 bears at least one halogen atom;
-R7 does not represent a methoxy radical;
or an addition salt thereof with a mineral or organic acid or with a mineral or organic base.
2. A compound of formula (Ia) according to claim 1:

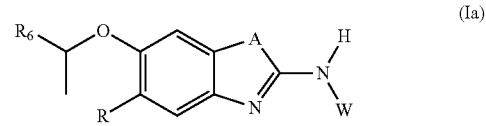

wherein:
R represents a hydrogen atom, a halogen atom or an alkyl radical;
A represents NH or S;
R6 represents an aryl or heteroaryl radical optionally substituted with one or more radicals, which may be identical or different, selected from halogen atoms, hydroxyl, alkoxy, NR3R4 radicals and alkyl, phenyl and phenylalkyl radicals, these last three radicals themselves are optionally substituted with one or more radicals selected from halogen atoms and hydroxyl, alkyl, alkoxy, NH2, NHalk and N(alk)2 radicals; and
W represents a hydrogen atom or the radical COR7 in which R7 represents:
a cycloalkyl radical or an alkyl radical optionally substituted with an alkoxy, hydroxyl, phenyl, heteroaryl, NR3R4 or heterocycloalkyl radical, themselves optionally substituted as indicated below;

an alkoxy radical optionally substituted with an alkoxy, phenyl, heteroaryl, NR3R4 or heterocycloalkyl radical, themselves optionally substituted as indicated below;

or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from hydroxyl, alkoxy, phenylalkoxy, cycloalkylalkoxy radicals, and heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains are optionally substituted as indicated below;

wherein R3 and R4, identical or different, are such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from hydroxyl, alkoxy, NH2, NHalk, N(alk)2 radicals and heteroaryl, heterocycloalkyl, and phenyl radicals optionally substituted with one or more radicals selected from halogen atoms and hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains are optionally substituted as indicated below;

the heterocycloalkyl, heteroaryl, aryl and phenyl radicals defined above as well as the cyclic radicals that R1 and R2 or R3 and R4 can form with the nitrogen atom to which they are attached, are optionally substituted with one or more radicals selected from halogen atoms, hydroxyl, oxo, alkoxy, NH2, NHalk, N(alk)2, free or esterified carboxyl radicals and alkyl, cycloalkyl, heterocycloalkyl, phenyl, heteroaryl, (hetero cycloalkyl) alkyl, (phenyl) alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from halogen atoms and hydroxyl, oxo, alkyl and alkoxy radicals containing from 1 to 4 carbon atoms, NH2, NHalk and N(alk)2;

and wherein:
R6 bears at least one halogen atom;
R7 does not represent a methoxy radical;
or an addition salt thereof with a mineral or organic acid or with a mineral or organic base.

3. The compound of formula (Ia) according to claim 1, wherein:

R represents a hydrogen atom, a halogen atom or an alkyl radical;
A represents NH or S;
R6 represents an aryl or heteroaryl radical optionally substituted with one or more radicals, which may be identical or different, selected from halogen atoms, hydroxyl, alkoxy, NR3R4 radicals and alkyl, phenyl and phenylalkyl radicals, these last three radicals themselves are optionally substituted with one or more radicals selected from halogen atoms and hydroxyl, alkyl, alkoxy, NH2, NHalk and N(alk)2 radicals;

W represents a hydrogen atom or the radical COR7 in which R7 represents:
a cycloalkyl radical or an alkyl radical optionally substituted with an alkoxy, hydroxyl, phenyl, heteroaryl, NR3R4 or heterocycloalkyl radical, themselves optionally substituted as indicated below;
an alkoxy radical optionally substituted with a phenyl, heteroaryl, NR3R4 or heterocycloalkyl radical, themselves optionally substituted as indicated below;
or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from hydroxyl, alkoxy, phenylalkoxy, cycloalkylalkoxy radicals, and heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains are optionally substituted as indicated below;

wherein R3 and R4, identical or different, are such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from hydroxyl, alkoxy, NH2, NHalk, N(alk)2 radicals and heteroaryl, heterocycloalkyl, and phenyl radicals optionally substituted with one or more radicals selected from halogen atoms and hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains are optionally substituted as indicated below;

the heterocycloalkyl, heteroaryl, aryl and phenyl radicals defined above as well as the cyclic radicals that R1 and R2 or R3 and R4 can form with the nitrogen atom to which they are attached, are optionally substituted with one or more radicals selected from halogen atoms, hydroxyl, oxo, alkoxy, NH2, NHalk, N(alk)2, free or esterified carboxyl radicals and alkyl, cycloalkyl, heterocycloalkyl, phenyl, heteroaryl, (heterocycloalkyl)alkyl, (phenyl)alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from halogen atoms and hydroxyl, oxo, alkyl and alkoxy radicals containing from 1 to 4 carbon atoms, NH2, NHalk and N(alk)2;

and wherein:
R6 bears at least one halogen atom;
R7 does not represent a methoxy radical;
or an addition salt thereof with a mineral or organic acid or with a mineral or organic base.

4. The compound of formula (Ia) according to claim 1, wherein:

R represents a hydrogen atom, a halogen atom or an alkyl radical;

A represents NH or S;

R6 represents a phenyl or heteroaryl radical optionally substituted with one or more radicals, which may be identical or different, selected from halogen atoms, hydroxyl, alkoxy, NR3R4 radicals and alkyl, phenyl and phenylalkyl radicals, these last three radicals themselves are optionally substituted with one or more radicals selected from halogen atoms and hydroxyl, alkyl, alkoxy, NH2, NHalk and N(alk)2 radicals; and W represents a hydrogen atom or the radical COR7 in which R7 represents:
- a cycloalkyl radical or an alkyl radical optionally substituted with a phenyl, heteroaryl, NR3R4 or heterocycloalkyl radical, themselves optionally substituted as indicated below;
- an alkoxy radical optionally substituted with NR3R4;
- or the radical NR1R2 in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, selected from hydroxyl, alkoxy, phenylalkoxy, cycloalkylalkoxy, heteroaryl, heterocycloalkyl, NR3R4, CONR3R4 and phenyl radicals optionally substituted as indicated below; or alternatively R1 and R2 form with the nitrogen atom to which they are attached a cyclic radical optionally containing one or more other heteroatoms selected from O and NH, said radical including the NH that it possibly contains are optionally substituted as indicated below;

wherein R3 and R4, identical or different, are such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from hydroxyl, alkoxy, NH2, NHalk, N(alk)2 and phenyl radical itself optionally substituted with one or more radicals selected from halogen atoms and hydroxyl, alkyl and alkoxy radicals; or alternatively R3 and R4 form with the nitrogen atom to which they are attached a cyclic radical optionally containing one or more other heteroatoms selected from O and NH, said radical including the NH that it possibly contains are optionally substituted as indicated below;

the heterocycloalkyl, heteroaryl and phenyl radicals defined above as well as the cyclic radicals that R1 and R2 or R3 and R4 can form with the nitrogen atom to which they are attached, are optionally substituted with one or more radicals selected from halogen atoms, hydroxyl, oxo, alkoxy, NH2, NHalk, N(alk)2, free or esterified carboxyl radicals and alkyl, cycloalkyl, heterocycloalkyl, phenyl, phenylalkyl and heteroaryl radicals, these last-mentioned heterocycloalkyl, phenyl, phenylalkyl and heteroaryl radicals themselves are optionally substituted with one or more radicals selected from halogen atoms and hydroxyl, oxo, alkyl and alkoxy radicals containing from 1 to 4 carbon atoms, NH2, NHalk and N(alk)2;

or an addition salt thereof with a mineral or organic acid or with a mineral or organic base.

5. The compound of formula (Ia) according to claim 1, wherein:

R represents a hydrogen atom, a halogen atom or an alkyl radical;

A represents NH or S;

R6 represents a phenyl or pyridyl radical optionally substituted with one or more radicals, which may be identical or different, selected from halogen atoms and hydroxyl, alkoxy, NH2, NHalk, N(alk)2, alkyl and phenyl radicals optionally substituted with one or more radicals selected from halogen atoms and hydroxyl, alkyl, alkoxy, NH2, NHalk and N(alk)2 radicals;

W represents a hydrogen atom or the radical COR7 in which R7 represents a cycloalkyl radical or the radical NR1R2 in which R1 and R2 are such that one of R1 and R2 represents a hydrogen atom or an alkyl radical and the other of R1 and R2 represents an alkyl radical optionally substituted with one or more radicals, which may be identical or different, selected from hydroxyl, alkoxy, phenylalkoxy, cycloalkylalkoxy, heteroaryl, heterocycloalkyl, NR3R4, CONR3R4 and phenyl radicals optionally substituted as indicated below; or alternatively R1 and R2 form with the nitrogen atom to which they are attached a radical selected from pyrrolidinyl, pyrazolidinyl, pyrazolinyl, piperidyl, azepinyl, morpholino and piperazinyl radicals, optionally substituted as indicated below;

wherein R3 and R4, identical or different, are such that one of R3 and R4 represents a hydrogen atom or an alkyl radical and the other of R3 and R4 represents a hydrogen atom, a CO2Alk radical or an alkyl radical optionally substituted with one or more radicals, which may be identical or different, selected from hydroxyl, alkoxy, NH2, NHalk, N(alk)2 and phenyl radicals optionally substituted as indicated below; or alternatively R3 and R4 form with the nitrogen atom to which they are attached a radical selected from pyrrolidinyl, pyrazolidinyl, pyrazolinyl, piperidyl, azepinyl, morpholino and piperazinyl radicals, optionally substituted as indicated below;

the heterocycloalkyl, heteroaryl and phenyl radicals defined above as well as the cyclic radicals that R1 and R2 or R3 and R4 can form with the nitrogen atom to which they are attached, are optionally substituted with one or more radicals selected from halogen atoms, hydroxyl, oxo, alkoxy, NH2, NHalk, N(alk)2, free or esterified carboxyl, alkyl, phenyl and phenylalkyl radicals in which the phenyl radical is itself optionally substituted with one or more radicals selected from halogen atoms, hydroxyl, alkyl, alkoxy, NH2, NHalk and N(alk)2 radicals;

or an addition salt thereof with a mineral or organic acid or with a mineral or organic base.

6. A compound of formula (Ia) according to claim 1, wherein:

R represents a hydrogen atom, a fluorine atom or a methyl radical;

A represents NH or S;

R6 represents a phenyl or pyridyl radical optionally substituted with 1 to 3 substituents, which may be identical or different, selected from halogen atoms and alkyl radicals themselves optionally substituted with one or more halogen atoms;

W represents a hydrogen atom or the radical COR7 in which R7 represents:
  a cycloalkyl radical or an alkyl radical optionally substituted with NR3R4;
  an alkoxy radical optionally substituted with an alkoxy radical, or NR3R4;
  or the radical NR1R2 in which R1 and R2 are such that one of R1 and R2 represents a hydrogen atom or an alkyl radical and the other of R1 and R2 represents an alkyl radical optionally substituted with a radical selected from the hydroxyl radical; alkoxy; phenylalkoxy optionally substituted on phenyl; cycloalkylalkoxy; CONR3R4; and pyrrolyl, pyridyl, morpholinyl, piperazinyl, pyrrolidinyl, piperidyl, and azepanyl radicals, these radicals themselves are optionally substituted on carbon or nitrogen atoms with one or more radicals selected from the radicals oxo =O, free or esterified carboxyl, alkyl or phenylalkyl with phenyl optionally substituted;
  wherein R3 and R4, identical or different, are such that one of R3 and R4 represents a hydrogen atom or an alkyl radical and the other of R3 and R4 represents a hydrogen atom, a CO2Alk radical or an alkyl radical optionally substituted with a phenyl radical itself optionally substituted; or alternatively R3 and R4 form with the nitrogen atom to which they are attached a radical selected from pyrrolidinyl, pyrazolidinyl, pyrazolinyl, piperidyl, azepinyl, morpholino and piperazinyl radicals, these radicals themselves are optionally substituted on carbon or nitrogen atoms with one or more radicals selected from the radicals oxo =O, free or esterified carboxyl, alkyl or phenylalkyl with phenyl optionally substituted;
  the phenyl radicals defined above are optionally substituted with one or more radicals selected from halogen atoms and hydroxyl, alkoxy, alkyl; NH2, NHalk, N(alk)2 and free or esterified carboxyl radicals;
or an addition salt thereof with a mineral or organic acid or with a mineral or organic base.

7. The compound of formula (Ia) according to claim 1, wherein:
R represents a hydrogen atom or a fluorine atom;
A represents NH or S;
R6 represents a phenyl or pyridyl radical optionally substituted with 1 to 3 substituents, which may be identical or different, selected from halogen atoms and alkyl radicals themselves optionally substituted with one or more halogen atoms;
W represents a hydrogen atom or the radical COR7 in which R7 represents a cycloalkyl radical or a radical NR1R2 in which R1 and R2 are such that one of R1 and R2 represents a hydrogen atom or an alkyl radical and the other of R1 and R2 represents an alkyl radical optionally substituted with a pyrrolyl, pyridyl, morpholinyl, piperazinyl, pyrrolidinyl, piperidyl, or azepanyl radical, these radicals themselves are optionally substituted on carbon or nitrogen atoms with one or more radicals selected from the radicals oxo =O, free or esterified carboxyl, alkyl or phenylalkyl with phenyl optionally substituted with one or more radicals selected from halogen atoms and hydroxyl, alkyl, alkoxy, NH2, NHalk and N(alk)2 radicals;
or an addition salt thereof with a mineral or organic acid or with a mineral or organic base.

8. A compound of formula (Ib):

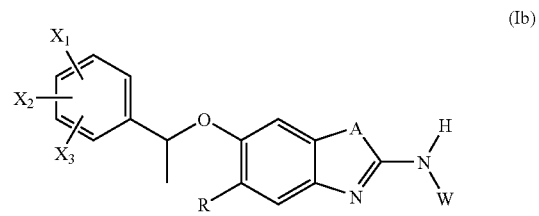

wherein
R represents a hydrogen atom, a halogen atom or an alkyl radical,
A represents NH or S;
W represents a hydrogen atom or the radical COR7 in which R7 represents:
  a cycloalkyl radical or an alkyl radical optionally substituted with an alkoxy, hydroxyl, phenyl, heteroaryl, NR3R4, CONR3R4 or heterocycloalkyl radical, themselves optionally substituted as indicated below;
  an alkoxy radical optionally substituted with a hydroxyl, alkoxy, phenyl, heteroaryl, NR3R4, CONR3R4 or heterocycloalkyl radical, themselves optionally substituted as indicated below;
  or the radical NR1R2 in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, selected from hydroxyl, alkoxy, phenylalkoxy, cycloalkylalkoxy radicals, and heteroaryl heteroalkyl, NR3R4 CONR3R4 and phenyl radicals optionally substituted as indicated below; or alternatively R1 and R2 form with the nitrogen atom to which they are attached a cyclic radical optionally containing one or more other heteroatoms selected from O, S, N and NH, said radical including the NH that it possibly contains are optionally substituted as indicated below;
  wherein R3 and R4, identical or different, are such that one of R3 and R4 represents a hydrogen atom or an alkyl radical and the other of R3 and R4 represents a hydrogen atom, a cycloalkyl, CO2Alk radical or an alkyl radical optionally substituted with one or more radicals, which may be identical or different, selected from hydroxyl, alkoxy, NH2, NHalk, N(alk)2 radicals and heteroaryl, heterocycloalkyl, and phenyl radicals optionally substituted with one or more radicals selected from halogen atoms and hydroxyl, alkyl and alkoxy radicals; or alternatively R3 and R4 form with the nitrogen atom to which they are attached a cyclic radical optionally containing one or more other heteroatoms selected from O, S, N and NH, said radical including the NH that it possibly contains are optionally substituted as indicated below;
  the heterocycloalkyl, heteroaryl, aryl and phenyl radicals defined above as well as the cyclic radicals that R1 and R2 or R3 and R4 can form with the nitrogen atom to which they are attached, are optionally substituted with one or more radicals selected from halogen atoms, hydroxyl, oxo, alkoxy, NH2, NHalk, N(alk)2, free or esterified carboxyl radicals and alkyl, cycloalkyl, heterocycloalkyl, phenyl, heteroaryl, (heterocycloalkyl)alkyl, (phenyl) alkyl, (heteroaryl)alkyl, —CO-heterocycloalkyl, —CO-phenyl, —CO-heteroaryl, —S-heterocycloalkyl, —S-aryl, —S-heteroaryl, —O-heterocycloalkyl, —O-aryl and —O-heteroaryl radicals, such that in these last-mentioned radicals, the heterocycloalkyl, phenyl and heteroaryl radicals are themselves optionally substituted with one or more radicals selected from halogen atoms and hydroxyl, oxo, alkyl and alkoxy radicals containing from 1 to 4 carbon atoms, NH2, NHalk and N(alk)2; and X1, X2 and X3, which may be identical or different, are such that one represents a halogen atom and the other two, identical or different, are selected from hydrogen atom, halogen atoms, hydroxyl, alkoxy, NR3R4 radicals, and alkyl, phenyl and phenylalkyl radicals, these last three radicals themselves are optionally substituted with one or more radicals selected from halogen atoms and hydroxyl, alkyl, alkoxy, NH2, NHalk and N(alk)2 radicals;

or an addition salt thereof with a mineral or organic acid or with a mineral or organic base.

9. A compound selected from the group consisting of:
1-{6-[1-(2,6-dichlorophenyl)ethoxy]-1H-benzimidazol-2-yl}-3-(2-morpholin-4-ylethyl)urea;
1-{6-[1-(2,6-dichloro-3-fluorophenyl)ethoxy]-1H-benzimidazol-2-yl}-3-(2-morpholin-4-ylethyl)urea trifluoroacetate;
1-{6-[1-(2,6-dichloro-3-fluorophenyl)ethoxy]-5-fluoro-1H-benzimidazol-2-yl}-3-(2-morpholin-4-ylethyl)urea;
1-{6-[1-(2,6-dichlorophenyl)ethoxy]-1,3-benzothiazol-2-yl}-3-(2-morpholin-4-ylethyl)urea;
1-{6-[1-(2,6-dichloro-3-fluorophenyl)ethoxy]-1,3-benzothiazol-2-yl}-3-(2-morpholin-4-ylethyl)urea;
1-{6-[(1R*)-(2,6-dichloro-3-fluorophenyl)ethoxy]-1,3-benzothiazol-2-yl}-3-(2-morpholin-4-ylethyl)urea;
1-{6-[1-(2,6-dichlorophenyl)ethoxy]-5-fluoro-1,3-benzothiazol-2-yl}-3-(2-morpholin-4-ylethyl)urea;
1-{6-[1-(2,6-dichloro-3-fluorophenyl)ethoxy]-5-fluoro-1,3-benzothiazol-2-yl}-3-(2-morpholin-4-ylethyl)urea;
1-{6-[(1R*)-(2,6-dichloro-3-fluorophenyl)ethoxy]-5-fluoro-1,3-benzothiazol-2-yl}-3-(2-morpholin-4-ylethyl)urea;
1-{6-[1-(2,6-dichloro-3-fluorophenyl)ethoxy]-1,3-benzothiazol-2-yl}-3-(3-morpholin-4-ylpropyl)urea;
1-{6-[1-(2,6-dichloro-3-fluorophenyl)ethoxy]-1,3-benzothiazol-2-yl}-3-[3-(dimethylamino)propyl]urea;
1-{6-[1-(2,6-dichloro-3-fluorophenyl)ethoxy]-1,3-benzothiazol-2-yl}-3-(3-piperidin-1-ylpropyl)urea;
1-{3-[4-(2-chloro-6-fluorobenzyl)piperazin-1-yl]propyl}-3-{6-[1-(2,6-dichloro-3-fluorophenyl)ethoxy]-1,3-benzothiazol-2-yl}urea;
1-(3-azepan-1-ylpropyl)-3-{6-[1-(2,6-dichloro-3-fluorophenyl)ethoxy]-1,3-benzothiazol-2-yl}urea;
1-{6-[1-(2,6-dichloro-3-fluorophenyl)ethoxy]-1,3-benzothiazol-2-yl}-3-(2-piperidin-1-ylethyl)urea;
1-{6-[1-(2,6-dichloro-3-fluorophenyl)ethoxy]-1,3-benzothiazol-2-yl}-3-(2-pyrrolidin-1-ylethyl)urea;
1-[2-(1-benzylpiperidin-4-yl)ethyl]-3-{6-[1-(2,6-dichloro-3-fluorophenyl)ethoxy]-1,3-benzothiazol-2-yl}urea;
1-{6-[1-(2,6-dichloro-3-fluorophenyl)ethoxy]-1,3-benzothiazol-2-yl}-3-[2-(1-methylpyrrolidin-2-yl)ethyl]urea;
1-{6-[1-(2,6-dichloro-3-fluorophenyl)ethoxy]-1,3-benzothiazol-2-yl}-3-[2-(4-methylpiperazin-1-yl)ethyl]urea;
1-{6-[1-(2,6-dichloro-3-fluorophenyl)ethoxy]-1,3-benzothiazol-2-yl}-3-[2-(2,6-dimethylpiperidin-1-yl)ethyl]urea;
1-{6-[1-(2,3-dichloro-6-fluorophenyl)ethoxy]-1,3-benzothiazol-2-yl}-3-(2-morpholin-4-ylethyl)urea;
1-{6-[(1R*)-1-(2,6-dichloro-3-fluorophenyl)ethoxy]-5-fluoro-1,3-benzothiazol-2-yl}-3-[2-(4-methylpiperazin-1-yl)ethyl]urea;
1-{6-[(1R*)-1-(2,6-dichloro-3-fluorophenyl)ethoxy]-5-fluoro-1,3-benzothiazol-2-yl}-3-[2-(pyrrolidin-1-yl)ethyl]urea;
1-{6-[1-(2,6-dichloro-3-fluorophenyl)ethoxy]-5-fluoro-1,3-benzothiazol-2-yl}-3-(2-hydroxyethyl)urea;
1-{6-[(1R*)-1-(2,6-dichloro-3-fluorophenyl)ethoxy]-5-fluoro-1,3-benzothiazol-2-yl}-3-(2-hydroxyethyl)urea;
1-{6-[1-(2,6-dichloro-3-fluorophenyl)ethoxy]-5-fluoro-1,3-benzothiazol-2-yl}-3-[2-(4-ethylpiperazin-1-yl)ethyl]urea;
1-{6-[(1R*)-1-(2,6-dichloro-3-fluorophenyl)ethoxy]-5-fluoro-1,3-benzothiazol-2-yl}-3-[2-(4-ethylpiperazin-1-yl)ethyl]urea;
1-{6-[(1R*)-1-(2,3-dichloro-6-fluorophenyl)ethoxy]-1,3-benzothiazol-2-yl}-3-[2-(4-methylpiperazin-1-yl)ethyl]urea;
1-{6-[1-(2,3-dichloro-6-fluorophenyl)ethoxy]-5-fluoro-1,3-benzothiazol-2-yl}-3-[2-(morpholin-4-yl)ethyl]urea;
1-{6-[(1R*)-1-(2,3-dichloro-6-fluorophenyl)ethoxy]-5-fluoro-1,3-benzothiazol-2-yl}-3-[2-(morpholin-4-yl)ethyl]urea;
1-{6-[1-(2,3-dichloro-6-fluorophenyl)ethoxy]-5-fluoro-1,3-benzothiazol-2-yl}-3-[2-(4-methylpiperazin-1-yl)ethyl]urea;
1-{6-[(1R*)-1-(2,3-dichloro-6-fluorophenyl)ethoxy]-5-fluoro-1,3-benzothiazol-2-yl}-3-[2-(4-methylpiperazin-1-yl)ethyl]urea; and
1-{6-[(1R*)-1-(2,3-dichloro-6-fluorophenyl)ethoxy]-5-fluoro-1,3-benzothiazol-2-yl}-3-[2-(pyrrolidin-1-yl)ethyl]urea;

or an addition salt thereof with a mineral or organic acid or with a mineral or organic base.

10. A pharmaceutical composition comprising a compound of formula (Ia) according to claim 1, or a pharmaceutically acceptable salt thereof, and a pharmaceutically acceptable support.

11. A pharmaceutical composition comprising a compound of formula (I) according to claim 9, or a pharmaceutically acceptable salt thereof, and a pharmaceutically acceptable support.

12. A method of inhibiting the activity of protein kinase MET which comprises contacting said protein kinase with a compound of formula (Ia) according to claim 1 or a pharmaceutically acceptable salt thereof.

13. The method according to claim 12 wherein the protein kinase is in a cell culture.

14. The method according to claim 12 wherein the protein kinase is in a mammal.

15. A pharmaceutical composition comprising a compound of formula Ib according to claim 8 or a pharmaceutically acceptable salt thereof and a pharmaceutically acceptable support.

* * * * *